US011959144B2

(12) United States Patent
Kondou et al.

(10) Patent No.: US 11,959,144 B2
(45) Date of Patent: Apr. 16, 2024

(54) PROSTATE CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Takahiro Ochiya, Tokyo (JP); Nobuyoshi Kosaka, Tokyo (JP)

(73) Assignees: Toray Industries, Inc., Tokyo (JP); National Cancer Center, Tokyo (JP)

( * ) Notice: Subject to any disclaimer, the term of this patent is extended or adjusted under 35 U.S.C. 154(b) by 0 days.

(21) Appl. No.: 17/977,451

(22) Filed: Oct. 31, 2022

(65) Prior Publication Data

US 2023/0137844 A1 May 4, 2023

Related U.S. Application Data

(62) Division of application No. 16/808,095, filed on Mar. 3, 2020, now Pat. No. 11,519,038, which is a division of application No. 15/317,882, filed as application No. PCT/JP2015/066964 on Jun. 12, 2015, now Pat. No. 10,619,213.

(30) Foreign Application Priority Data

Jun. 12, 2014 (JP) ................................ 2014-121377
Mar. 31, 2015 (JP) ................................ 2015-071756

(51) Int. Cl.

| | |
|---|---|
| ***C12P 19/34*** | (2006.01) |
| ***C12M 1/00*** | (2006.01) |
| ***C12M 1/34*** | (2006.01) |
| ***C12N 15/09*** | (2006.01) |
| ***C12Q 1/68*** | (2018.01) |
| ***C12Q 1/6886*** | (2018.01) |
| ***G01N 33/53*** | (2006.01) |
| ***G01N 33/574*** | (2006.01) |
| ***G01N 37/00*** | (2006.01) |

(52) U.S. Cl.
CPC ............. *C12Q 1/6886* (2013.01); *C12M 1/00* (2013.01); *C12M 1/34* (2013.01); *C12N 15/09* (2013.01); *C12Q 1/68* (2013.01); *G01N 33/53* (2013.01); *G01N 33/574* (2013.01); *G01N 37/00* (2013.01); *C12Q 2600/156* (2013.01); *C12Q 2600/158* (2013.01); *C12Q 2600/16* (2013.01); *C12Q 2600/178* (2013.01)

(58) Field of Classification Search
CPC ................ C12Q 1/6886; C12Q 1/6837; C12Q 2600/158; C12Q 2600/178
See application file for complete search history.

(56) References Cited

U.S. PATENT DOCUMENTS

| | | | |
|---|---|---|---|
| 2012/0214697 A1 | 8/2012 | Croce et al. | |
| 2015/0337332 A1 | 11/2015 | Ruohoa-Baker et al. | |
| 2017/0121779 A1 | 5/2017 | Kondou et al. | |
| 2017/0356903 A1 | 12/2017 | Domenyuk et al. | |
| 2018/0030440 A1 | 2/2018 | Lee et al. | |

FOREIGN PATENT DOCUMENTS

| | | | |
|---|---|---|---|
| EP | 2 341 145 | A1 | 7/2011 |
| JP | 2013-535982 | A | 9/2013 |
| JP | 2015-39365 | A | 3/2015 |
| WO | WO 2009/108860 | A2 | 9/2009 |
| WO | WO 2010/054386 | A2 | 5/2010 |
| WO | WO 2010/062706 | A2 | 6/2010 |
| WO | WO 2011/080315 | A1 | 7/2011 |
| WO | WO 2012/027206 | A1 | 3/2012 |
| WO | WO 2013/022995 | A2 | 2/2013 |
| WO | WO 2014/071205 | A1 | 5/2014 |
| WO | WO 2014/071226 | A1 | 5/2014 |
| WO | WO 2015/190584 | A1 | 12/2015 |

OTHER PUBLICATIONS

Hart, Martin, et al. "Comparative microRNA profiling of prostate carcinomas with increasing tumor stage by deep sequencing." Molecular cancer research 12.2 (Feb. 2014): 250-263. (Epub Dec. 13, 2013) (Year: 2014).*
Christa Haldrup, et al. "Profiling of circulating microRNAs for prostate cancer biomarker discovery" Drug Delivery and Translational Research vol. 4, pp. 19-30 (2014) (Published: Aug. 17, 2013) (Year: 2014).*
Watahiki et al., "Plasma miRNAs as Biomarkers to Identify Patients with Castration-Resistant Metastatic Prostrate Cancer," Int. J. Mol. Sci. (2013), vol. 14, pp. 7757-7770.
Wolf et al., "American Cancer Society Guideline for the Early Detection of Prostate Cancer", A Cancer Journal for Clinicians, vol. 60, 2010, pp. 70-98.
Written Opinion of the International Searching Authority for PCT/JP2015/066964 (PCT/ISA/237) dated Sep. 1, 2015.
Written Opinion of the International Searching Authority, issued in PCT/JP2019/031550, dated Sep. 10, 2019.
Xu et al., "Down-Regulation of miR-3928 Promoted Osteosarcoma Growth" Cell Physiol. Biochem. (2014), vol. 33 pp. 1547-1556.
American Cancer Society, "Prostate Cancer", 2013, pp. 5, 14-26, 32-54, and 68-70.

(Continued)

*Primary Examiner* — Stephen T Kapushoc
(74) *Attorney, Agent, or Firm* — Birch, Stewart, Kolasch & Birch, LLP

(57) ABSTRACT

An object of the present invention is to provide a kit or a device for the detection of prostate cancer and a method for detecting prostate cancer. The present invention provides a kit or a device for the detection of prostate cancer, comprising a nucleic acid capable of specifically binding to a miRNA in a sample of a subject, and a method for detecting prostate cancer, comprising measuring the miRNA in vitro.

6 Claims, 4 Drawing Sheets

Specification includes a Sequence Listing.

(56) References Cited

OTHER PUBLICATIONS

Berillo et al., "Binding of intronic miRNAs to the mRNAs of host genes encoding intronic miRNAs and proteins that participate in tumourigenesis." Computers in Biology and Medicine, vol. 43, 2013, pp. 1374-1381.
Cheung et al., "Natural variation in human gene expression assesed in lymphoblastoid cells," Nature Genetics, vol. 33, Mar. 2003, pp. 422-425.
Chinese Office Action and Search Report for Chinese Application No. 201580030849.6, dated Apr. 1, 2019.
Cobb et al., Sepsis gene expression profiling: Murine splenic compared with hepatic responses determined by using complementary DNA microarrays; Crit. Care. Med. (2002), vol. 30, pp. 2711-2721.
Enard e al., "Intra- and Interspecific Variation in Primate Gene Expression Patterns," Science (2002), vol. 296, pp. 340-343.
Eto et al., "Prospect of microRNA toward laboratory medicine gastrointestinal cancer and microRNA" Clinical Chemistry, vol. 43, 2014, pp. 99-105.
Extended European Search Report for corresponding European Application No. 19847308.4, dated May 9, 2022.
Feng et al., "Combinations of elevated tissue miRNA-17-92 cluster expression and serum prostate-specific antigen as potential diagnostic biomarkers for prostate cancer", Oncology Letters, 2017, vol. 14, pp. 6943-6949.
GenBank "*Homo sapiens* microRNA 4443 (MIR4443), MicroRNA," NCBI, Locus: NR_039645, Accession No. NR_039645, Jul. 17, 2013, pp. 1-2.
Gordanpour et al., "MicroRNAs in prostate cancer: from biomarkers to molecularly-based therapeutics," Prostate Cancer and Prostatic Diseases (2012), vol. 15, pp. 314-319.
Hibino et al., "Inhibitors of enhancer of zeste homolog 2 (EZH2) activate tumor-suppressor micro-RNAs in human cancer cells," Oncogenesis (2014), vol. 3, e104, pp. 1-10.
Hoshikawa et al., "Hypoxia induces different genes in the lungs of rats compared with mice," Physiol Genomics, vol. 12, Dec. 3, 2002, pp. 209-219.
Huang, et al., "Extracellular MicroRNAs in Urologic Malignancies: Chances and Challenges", International Journal of Molecular Sciences, vol. 14, No. 7, 2013, pp. 14785-14799.
International Search Report for PCT/JP2015/066964 (PCT/ISA/210) dated Sep. 1, 2015.
International Search Report, issued in PCT/JP2019/031550, dated Sep. 10, 2019.
Japanese Office Action dated Jul. 2, 2019 for Application No. 2016-527882.
Jima et al., "Deep sequencing of the small RNA transcriptome of normal and malignant human B cells identifies hundreds of novel microRNAs," Blood, vol. 116, No. 23, Dec. 2, 2010 (published online Aug. 23, 2010), pp. 118-127 (11 pages total).
Kobayashi et al., "Identification of miR-30d as a novel prognostic maker of prostate cancer," Oncotarget, vol. 3, No. 11, Nov. 2012, pp. 1455-1471.
Kozomara et al., "miRBase: annotating high confidence microRNAs using deep sequencing data", Nucleic Acids Research, vol. 42, 2014, Database issue, pp. D68-D73.
Lee et al., "MicroRNA-Regulated Protein-Protein Interaction Networks and Their functions in Breast Cancer" Int. J. Mol. Sci. (2013), vol. 14, pp. 11560-11606.
Lieb et al., "Serum levels of miR-320 family members are associated with clinical parameters and diagnosis in prostate cancer patients", Oncotarget, 2018, vol. 9, No. 12, pp. 10402-10416.
Liu et al., "MicroRNA expression profile of gastric cancer stem cells in the MKN-45 cancer cell line," Acta Biochim. Biophys, Sin., vol. 46, No. 2, 2014 (Advance Access Publication Jan. 2, 2014), pp. 92-99.
Mahn, et al., "Circulating microRNAs (miRNA) in Serum of Patients with Prostate Cancer", Urology, vol. 77, No. 5, 2011, pp. 1265.e9-1265.e16.
Mitchell et al., "Circulating microRNAs as stable blood-based markers for cancer detection", Proceedings of the National Academy of Sciences of the United States of America, vol. 105, No. 30, 2008, pp. 10513-10518.
Non-Final Office Action dated May 17, 2022, in U.S. Appl. No. 17/265,060.
Office Action dated Aug. 23, 2021, in Republic of Korea Patent Application No. 10-2017-7000938.
Office Action dated Jan. 4, 2022, in Japanese Patent Application No. 2020-075338 .
Partial European Search Report dated Mar. 4, 2021, in European Patent Application No. 20207829.1.
Partial Supplementary European Search Report for European Application No. 15806052.5, dated Dec. 15, 2017.
Qiagen, "miScript miRNA PCR Array (384-well, 384HC) Human miRBase Profiler HC Plate 4," Sample & Assay Technologies, 2012, 10 pages.
Restriction Requirement dated Apr. 1, 2022, in U.S. Appl. No. 17/265,060.
Shen et al., "Exploration of Genome-Wide Circulating MicroRNA in Hepatocellular Carcinoma: MIR-483-5p as a Potential Biomarker," Cancer Epidemiol Biomarkers Prev., vol. 22, No. 12, Dec. 2013, pp. 2364-2373 (11 pages).
Sobin, et al., "TNM Classification of Malignant Tumours", International Union Against Cancer, 7th edition, 2010, pp. 230 to 234.
Takizawa et al., "miRNA Profiling in Serum Samples Using DNA Chip 3D-Gene", BIO Clinica, vol. 29, No. 6, 2014, pp. 588 to 589.
Technical Document "miScript™ miRNA PCR Array (384-well, 384HC) Human miRBase Profiler HC Plate 5". Document No. 1073798, Aug. 2012, QIAGEN, from https://b2b.qiagen.com/-/media/genetable/mi/hs/34/mi hs-3405z (Year: 2012).
Toray Industries, Inc., "Kyoto Univ. 3D-Gene Human miRNA Oligo chip v11.0," NCBI, GEO Accession: GPL7766, May 14, 2009, 12 pages.
Urabe et al., "Large-scale Circulating microRNA Profiling for the Liquid Biopsy of Prostate Cancer", Clinical Cancer Research, May 15, 2019, vol. 25, No. 10, pp. 3016-3025.
Walter et al., "Comprehensive micro RNA Profiling of Prostate Cancer" Journal of Cancer (2013) vol. 4, No. 5, pp. 350-357.
Wang et al., Tumor-Associated Circulating MicroRNAs as Biomarkers of Cancer, Molecules, vol. 19, No. 2, 2014, pp. 1912-1938.
Watahiki et al., "Plasma miRNAs as Biomarkers to Identify Patients with Castration-Resistant Metastatic Prostate Cancer," Int. J. Mol. Sci. (2013), vol. 14, pp. 7757-7770.

* cited by examiner

SEQUENCE LISTING

```
Sequence total quantity: 684
SEQ ID NO: 1            moltype = RNA  length = 17
FEATURE                 Location/Qualifiers
source                  1..17
                        mol_type = transcribed RNA
                        organism = Homo sapiens
SEQUENCE: 1
ttggaggcgt gggtttt                                                  17

SEQ ID NO: 2            moltype = RNA  length = 21
FEATURE                 Location/Qualifiers
source                  1..21
                        mol_type = transcribed RNA
                        organism = Homo sapiens
SEQUENCE: 2
cggcggggac ggcgattggt c                                             21

SEQ ID NO: 3            moltype = RNA  length = 18
FEATURE                 Location/Qualifiers
source                  1..18
                        mol_type = transcribed RNA
                        organism = Homo sapiens
SEQUENCE: 3
ccagaggtgg ggactgag                                                 18

SEQ ID NO: 4            moltype = RNA  length = 23
FEATURE                 Location/Qualifiers
source                  1..23
                        mol_type = transcribed RNA
                        organism = Homo sapiens
SEQUENCE: 4
ggaggcgcag gctcggaaag gcg                                           23

SEQ ID NO: 5            moltype = RNA  length = 23
FEATURE                 Location/Qualifiers
source                  1..23
                        mol_type = transcribed RNA
                        organism = Homo sapiens
SEQUENCE: 5
agaggctttg tgcggatacg ggg                                           23

SEQ ID NO: 6            moltype = RNA  length = 24
FEATURE                 Location/Qualifiers
source                  1..24
                        mol_type = transcribed RNA
                        organism = Homo sapiens
SEQUENCE: 6
tgggcgaggg gtgggctctc agag                                          24

SEQ ID NO: 7            moltype = RNA  length = 22
FEATURE                 Location/Qualifiers
source                  1..22
                        mol_type = transcribed RNA
                        organism = Homo sapiens
```

```
SEQUENCE: 7
ctcctggggc ccgcactctc gc                                            22

SEQ ID NO: 8            moltype = RNA  length = 22
FEATURE                 Location/Qualifiers
source                  1..22
                        mol_type = transcribed RNA
                        organism = Homo sapiens
SEQUENCE: 8
actgggtagg tggggctcca gg                                            22

SEQ ID NO: 9            moltype = RNA  length = 22
FEATURE                 Location/Qualifiers
source                  1..22
                        mol_type = transcribed RNA
                        organism = Homo sapiens
SEQUENCE: 9
tggggagcgg cccccgggtg gg                                            22

SEQ ID NO: 10           moltype = RNA  length = 22
FEATURE                 Location/Qualifiers
source                  1..22
                        mol_type = transcribed RNA
                        organism = Homo sapiens
SEQUENCE: 10
agacacattt ggagagggac cc                                            22

SEQ ID NO: 11           moltype = RNA  length = 22
FEATURE                 Location/Qualifiers
source                  1..22
                        mol_type = transcribed RNA
                        organism = Homo sapiens
SEQUENCE: 11
gtgggtgctg gtgggagccg tg                                            22

SEQ ID NO: 12           moltype = RNA  length = 23
FEATURE                 Location/Qualifiers
source                  1..23
                        mol_type = transcribed RNA
                        organism = Homo sapiens
SEQUENCE: 12
tgagtggggc tcccgggacg gcg                                           23

SEQ ID NO: 13           moltype = RNA  length = 23
FEATURE                 Location/Qualifiers
source                  1..23
                        mol_type = transcribed RNA
                        organism = Homo sapiens
SEQUENCE: 13
tcaataggaa agaggtggga cct                                           23

SEQ ID NO: 14           moltype = RNA  length = 23
FEATURE                 Location/Qualifiers
source                  1..23
                        mol_type = transcribed RNA
                        organism = Homo sapiens
SEQUENCE: 14
tgagcaccac acaggccggg cgc                                           23

SEQ ID NO: 15           moltype = RNA  length = 23
FEATURE                 Location/Qualifiers
source                  1..23
                        mol_type = transcribed RNA
                        organism = Homo sapiens
SEQUENCE: 15
tcgaggactg gtggaagggc ctt                                           23

SEQ ID NO: 16           moltype = RNA  length = 22
FEATURE                 Location/Qualifiers
source                  1..22
                        mol_type = transcribed RNA
                        organism = Homo sapiens
SEQUENCE: 16
gggtggggat ttgttgcatt ac                                            22

SEQ ID NO: 17           moltype = RNA  length = 17
FEATURE                 Location/Qualifiers
source                  1..17
                        mol_type = transcribed RNA
```

-continued

```
                        organism = Homo sapiens
SEQUENCE: 17
ccccgccacc gccttgg                                              17

SEQ ID NO: 18           moltype = RNA  length = 20
FEATURE                 Location/Qualifiers
source                  1..20
                        mol_type = transcribed RNA
                        organism = Homo sapiens
SEQUENCE: 18
ggctccttgg tctaggggta                                           20

SEQ ID NO: 19           moltype = RNA  length = 20
FEATURE                 Location/Qualifiers
source                  1..20
                        mol_type = transcribed RNA
                        organism = Homo sapiens
SEQUENCE: 19
gcggaaggcg gagcggcgga                                           20

SEQ ID NO: 20           moltype = RNA  length = 22
FEATURE                 Location/Qualifiers
source                  1..22
                        mol_type = transcribed RNA
                        organism = Homo sapiens
SEQUENCE: 20
tggtggagga agagggcagc tc                                        22

SEQ ID NO: 21           moltype = RNA  length = 19
FEATURE                 Location/Qualifiers
source                  1..19
                        mol_type = transcribed RNA
                        organism = Homo sapiens
SEQUENCE: 21
agcagggctg gggattgca                                            19

SEQ ID NO: 22           moltype = RNA  length = 22
FEATURE                 Location/Qualifiers
source                  1..22
                        mol_type = transcribed RNA
                        organism = Homo sapiens
SEQUENCE: 22
tggcggcggt agttatgggc tt                                        22

SEQ ID NO: 23           moltype = RNA  length = 22
FEATURE                 Location/Qualifiers
source                  1..22
                        mol_type = transcribed RNA
                        organism = Homo sapiens
SEQUENCE: 23
tcgggcctgg ggttggggga gc                                        22

SEQ ID NO: 24           moltype = RNA  length = 20
FEATURE                 Location/Qualifiers
source                  1..20
                        mol_type = transcribed RNA
                        organism = Homo sapiens
SEQUENCE: 24
taggatgggg gtgagaggtg                                           20

SEQ ID NO: 25           moltype = RNA  length = 21
FEATURE                 Location/Qualifiers
source                  1..21
                        mol_type = transcribed RNA
                        organism = Homo sapiens
SEQUENCE: 25
accactgcac tccagcctga g                                         21

SEQ ID NO: 26           moltype = RNA  length = 21
FEATURE                 Location/Qualifiers
source                  1..21
                        mol_type = transcribed RNA
                        organism = Homo sapiens
SEQUENCE: 26
agcggtgctc ctgcgggccg a                                         21

SEQ ID NO: 27           moltype = RNA  length = 22
FEATURE                 Location/Qualifiers
source                  1..22
```

```
                        mol_type = transcribed RNA
                        organism = Homo sapiens
SEQUENCE: 27
ggaggggtcc cgcactggga gg                                                22

SEQ ID NO: 28           moltype = RNA  length = 21
FEATURE                 Location/Qualifiers
source                  1..21
                        mol_type = transcribed RNA
                        organism = Homo sapiens
SEQUENCE: 28
aagggacagg gagggtcgtg g                                                 21

SEQ ID NO: 29           moltype = RNA  length = 21
FEATURE                 Location/Qualifiers
source                  1..21
                        mol_type = transcribed RNA
                        organism = Homo sapiens
SEQUENCE: 29
cgggagctgg ggtctgcagg t                                                 21

SEQ ID NO: 30           moltype = RNA  length = 23
FEATURE                 Location/Qualifiers
source                  1..23
                        mol_type = transcribed RNA
                        organism = Homo sapiens
SEQUENCE: 30
gggggccgat acactgtacg aga                                               23

SEQ ID NO: 31           moltype = RNA  length = 20
FEATURE                 Location/Qualifiers
source                  1..20
                        mol_type = transcribed RNA
                        organism = Homo sapiens
SEQUENCE: 31
cggggtgggt gaggtcgggc                                                   20

SEQ ID NO: 32           moltype = RNA  length = 21
FEATURE                 Location/Qualifiers
source                  1..21
                        mol_type = transcribed RNA
                        organism = Homo sapiens
SEQUENCE: 32
tcacctggct ggcccgccca g                                                 21

SEQ ID NO: 33           moltype = RNA  length = 23
FEATURE                 Location/Qualifiers
source                  1..23
                        mol_type = transcribed RNA
                        organism = Homo sapiens
SEQUENCE: 33
agaagaaggc ggtcggtctg cgg                                               23

SEQ ID NO: 34           moltype = RNA  length = 18
FEATURE                 Location/Qualifiers
source                  1..18
                        mol_type = transcribed RNA
                        organism = Homo sapiens
SEQUENCE: 34
cggtgagcgc tcgctggc                                                     18

SEQ ID NO: 35           moltype = RNA  length = 23
FEATURE                 Location/Qualifiers
source                  1..23
                        mol_type = transcribed RNA
                        organism = Homo sapiens
SEQUENCE: 35
tggggggaca gatggagagg aca                                               23

SEQ ID NO: 36           moltype = RNA  length = 21
FEATURE                 Location/Qualifiers
source                  1..21
                        mol_type = transcribed RNA
                        organism = Homo sapiens
SEQUENCE: 36
gttggggtgc aggggtctgc t                                                 21

SEQ ID NO: 37           moltype = RNA  length = 22
FEATURE                 Location/Qualifiers
```

```
source                  1..22
                        mol_type = transcribed RNA
                        organism = Homo sapiens
SEQUENCE: 37
gggaccatcc tgcctgctgt gg                                            22

SEQ ID NO: 38           moltype = RNA  length = 23
FEATURE                 Location/Qualifiers
source                  1..23
                        mol_type = transcribed RNA
                        organism = Homo sapiens
SEQUENCE: 38
tggggaaggc ttggcaggga aga                                           23

SEQ ID NO: 39           moltype = RNA  length = 23
FEATURE                 Location/Qualifiers
source                  1..23
                        mol_type = transcribed RNA
                        organism = Homo sapiens
SEQUENCE: 39
gccccggcgc gggcgggttc tgg                                           23

SEQ ID NO: 40           moltype = RNA  length = 22
FEATURE                 Location/Qualifiers
source                  1..22
                        mol_type = transcribed RNA
                        organism = Homo sapiens
SEQUENCE: 40
tcaaaatcag gagtcggggc tt                                            22

SEQ ID NO: 41           moltype = RNA  length = 20
FEATURE                 Location/Qualifiers
source                  1..20
                        mol_type = transcribed RNA
                        organism = Homo sapiens
SEQUENCE: 41
ggatccgagt cacggcacca                                               20

SEQ ID NO: 42           moltype = RNA  length = 21
FEATURE                 Location/Qualifiers
source                  1..21
                        mol_type = transcribed RNA
                        organism = Homo sapiens
SEQUENCE: 42
ggggggatgt gcatgctggt t                                             21

SEQ ID NO: 43           moltype = RNA  length = 18
FEATURE                 Location/Qualifiers
source                  1..18
                        mol_type = transcribed RNA
                        organism = Homo sapiens
SEQUENCE: 43
atcctagtca cggcacca                                                 18

SEQ ID NO: 44           moltype = RNA  length = 22
FEATURE                 Location/Qualifiers
source                  1..22
                        mol_type = transcribed RNA
                        organism = Homo sapiens
SEQUENCE: 44
tgcggggcta gggctaacag ca                                            22

SEQ ID NO: 45           moltype = RNA  length = 22
FEATURE                 Location/Qualifiers
source                  1..22
                        mol_type = transcribed RNA
                        organism = Homo sapiens
SEQUENCE: 45
ggctggagcg agtgcagtgg tg                                            22

SEQ ID NO: 46           moltype = RNA  length = 20
FEATURE                 Location/Qualifiers
source                  1..20
                        mol_type = transcribed RNA
                        organism = Homo sapiens
SEQUENCE: 46
tgtgggactg caaatgggag                                               20

SEQ ID NO: 47           moltype = RNA  length = 21
```

```
FEATURE                Location/Qualifiers
source                 1..21
                       mol_type = transcribed RNA
                       organism = Homo sapiens
SEQUENCE: 47
tggggcgggg caggtccctg c                                         21

SEQ ID NO: 48          moltype = RNA  length = 23
FEATURE                Location/Qualifiers
source                 1..23
                       mol_type = transcribed RNA
                       organism = Homo sapiens
SEQUENCE: 48
cgggctgtcc ggaggggtcg gct                                       23

SEQ ID NO: 49          moltype = RNA  length = 18
FEATURE                Location/Qualifiers
source                 1..18
                       mol_type = transcribed RNA
                       organism = Homo sapiens
SEQUENCE: 49
ctggcagggg gagaggta                                             18

SEQ ID NO: 50          moltype = RNA  length = 22
FEATURE                Location/Qualifiers
source                 1..22
                       mol_type = transcribed RNA
                       organism = Homo sapiens
SEQUENCE: 50
cccctggggc tgggcaggcg ga                                        22

SEQ ID NO: 51          moltype = RNA  length = 24
FEATURE                Location/Qualifiers
source                 1..24
                       mol_type = transcribed RNA
                       organism = Homo sapiens
SEQUENCE: 51
ccccgggaac gtcgagactg gagc                                      24

SEQ ID NO: 52          moltype = RNA  length = 18
FEATURE                Location/Qualifiers
source                 1..18
                       mol_type = transcribed RNA
                       organism = Homo sapiens
SEQUENCE: 52
ttcccagcca acgcacca                                             18

SEQ ID NO: 53          moltype = RNA  length = 17
FEATURE                Location/Qualifiers
source                 1..17
                       mol_type = transcribed RNA
                       organism = Homo sapiens
SEQUENCE: 53
ctccgggacg gctgggc                                              17

SEQ ID NO: 54          moltype = RNA  length = 19
FEATURE                Location/Qualifiers
source                 1..19
                       mol_type = transcribed RNA
                       organism = Homo sapiens
SEQUENCE: 54
ggggagcgag gggcggggc                                            19

SEQ ID NO: 55          moltype = RNA  length = 21
FEATURE                Location/Qualifiers
source                 1..21
                       mol_type = transcribed RNA
                       organism = Homo sapiens
SEQUENCE: 55
cgggccggag gtcaagggcg t                                         21

SEQ ID NO: 56          moltype = RNA  length = 19
FEATURE                Location/Qualifiers
source                 1..19
                       mol_type = transcribed RNA
                       organism = Homo sapiens
SEQUENCE: 56
tgggggagat gggggttga                                            19
```

```
SEQ ID NO: 57          moltype = RNA  length = 22
FEATURE                Location/Qualifiers
source                 1..22
                       mol_type = transcribed RNA
                       organism = Homo sapiens
SEQUENCE: 57
tgggcgaggg cggctgagcg gc                                            22

SEQ ID NO: 58          moltype = RNA  length = 18
FEATURE                Location/Qualifiers
source                 1..18
                       mol_type = transcribed RNA
                       organism = Homo sapiens
SEQUENCE: 58
cccagcagga cgggagcg                                                 18

SEQ ID NO: 59          moltype = RNA  length = 21
FEATURE                Location/Qualifiers
source                 1..21
                       mol_type = transcribed RNA
                       organism = Homo sapiens
SEQUENCE: 59
cgtggaggac gaggaggagg c                                             21

SEQ ID NO: 60          moltype = RNA  length = 22
FEATURE                Location/Qualifiers
source                 1..22
                       mol_type = transcribed RNA
                       organism = Homo sapiens
SEQUENCE: 60
tggggaggtg tggagtcagc at                                            22

SEQ ID NO: 61          moltype = RNA  length = 21
FEATURE                Location/Qualifiers
source                 1..21
                       mol_type = transcribed RNA
                       organism = Homo sapiens
SEQUENCE: 61
ctgggctcgg gacgcgcggc t                                             21

SEQ ID NO: 62          moltype = RNA  length = 20
FEATURE                Location/Qualifiers
source                 1..20
                       mol_type = transcribed RNA
                       organism = Homo sapiens
SEQUENCE: 62
gctcggactg agcaggtggg                                               20

SEQ ID NO: 63          moltype = RNA  length = 22
FEATURE                Location/Qualifiers
source                 1..22
                       mol_type = transcribed RNA
                       organism = Homo sapiens
SEQUENCE: 63
agcccgcccc agccgaggtt ct                                            22

SEQ ID NO: 64          moltype = RNA  length = 25
FEATURE                Location/Qualifiers
source                 1..25
                       mol_type = transcribed RNA
                       organism = Homo sapiens
SEQUENCE: 64
aggggggcac tgcgcaagca aagcc                                         25

SEQ ID NO: 65          moltype = RNA  length = 22
FEATURE                Location/Qualifiers
source                 1..22
                       mol_type = transcribed RNA
                       organism = Homo sapiens
SEQUENCE: 65
tgcaggggtc gggtgggcca gg                                            22

SEQ ID NO: 66          moltype = RNA  length = 17
FEATURE                Location/Qualifiers
source                 1..17
                       mol_type = transcribed RNA
                       organism = Homo sapiens
SEQUENCE: 66
gggagaaggg tcggggc                                                  17
```

```
SEQ ID NO: 67          moltype = RNA  length = 22
FEATURE                Location/Qualifiers
source                 1..22
                       mol_type = transcribed RNA
                       organism = Homo sapiens
SEQUENCE: 67
tagggatggg aggccaggat ga                                            22

SEQ ID NO: 68          moltype = RNA  length = 22
FEATURE                Location/Qualifiers
source                 1..22
                       mol_type = transcribed RNA
                       organism = Homo sapiens
SEQUENCE: 68
gcccaggact ttgtgcgggg tg                                            22

SEQ ID NO: 69          moltype = RNA  length = 21
FEATURE                Location/Qualifiers
source                 1..21
                       mol_type = transcribed RNA
                       organism = Homo sapiens
SEQUENCE: 69
atccagttct ctgagggggc t                                             21

SEQ ID NO: 70          moltype = RNA  length = 23
FEATURE                Location/Qualifiers
source                 1..23
                       mol_type = transcribed RNA
                       organism = Homo sapiens
SEQUENCE: 70
agggtggggc tggaggtggg gct                                           23

SEQ ID NO: 71          moltype = RNA  length = 21
FEATURE                Location/Qualifiers
source                 1..21
                       mol_type = transcribed RNA
                       organism = Homo sapiens
SEQUENCE: 71
gtaggtgaca gtcaggggcg g                                             21

SEQ ID NO: 72          moltype = RNA  length = 23
FEATURE                Location/Qualifiers
source                 1..23
                       mol_type = transcribed RNA
                       organism = Homo sapiens
SEQUENCE: 72
ctcggggcag gcggctggga gcg                                           23

SEQ ID NO: 73          moltype = RNA  length = 18
FEATURE                Location/Qualifiers
source                 1..18
                       mol_type = transcribed RNA
                       organism = Homo sapiens
SEQUENCE: 73
gtgaaggccc ggcggaga                                                 18

SEQ ID NO: 74          moltype = RNA  length = 21
FEATURE                Location/Qualifiers
source                 1..21
                       mol_type = transcribed RNA
                       organism = Homo sapiens
SEQUENCE: 74
cccatgcctc ctgccgcggt c                                             21

SEQ ID NO: 75          moltype = RNA  length = 22
FEATURE                Location/Qualifiers
source                 1..22
                       mol_type = transcribed RNA
                       organism = Homo sapiens
SEQUENCE: 75
cagggctggc agtgacatgg gt                                            22

SEQ ID NO: 76          moltype = RNA  length = 18
FEATURE                Location/Qualifiers
source                 1..18
                       mol_type = transcribed RNA
                       organism = Homo sapiens
SEQUENCE: 76
```

```
cgggcgtggt ggtggggg                                                18

SEQ ID NO: 77          moltype = RNA  length = 21
FEATURE                Location/Qualifiers
source                 1..21
                       mol_type = transcribed RNA
                       organism = Homo sapiens
SEQUENCE: 77
ccggccgccg gctccgcccc g                                            21

SEQ ID NO: 78          moltype = RNA  length = 23
FEATURE                Location/Qualifiers
source                 1..23
                       mol_type = transcribed RNA
                       organism = Homo sapiens
SEQUENCE: 78
tgaggatatg gcagggaagg gga                                          23

SEQ ID NO: 79          moltype = RNA  length = 17
FEATURE                Location/Qualifiers
source                 1..17
                       mol_type = transcribed RNA
                       organism = Homo sapiens
SEQUENCE: 79
ggatggagga ggggtct                                                 17

SEQ ID NO: 80          moltype = RNA  length = 22
FEATURE                Location/Qualifiers
source                 1..22
                       mol_type = transcribed RNA
                       organism = Homo sapiens
SEQUENCE: 80
ggggctgtga ttgaccagca gg                                           22

SEQ ID NO: 81          moltype = RNA  length = 21
FEATURE                Location/Qualifiers
source                 1..21
                       mol_type = transcribed RNA
                       organism = Homo sapiens
SEQUENCE: 81
gtgtggccgg caggcgggtg g                                            21

SEQ ID NO: 82          moltype = RNA  length = 20
FEATURE                Location/Qualifiers
source                 1..20
                       mol_type = transcribed RNA
                       organism = Homo sapiens
SEQUENCE: 82
ggggaggtgt gcagggctgg                                              20

SEQ ID NO: 83          moltype = RNA  length = 22
FEATURE                Location/Qualifiers
source                 1..22
                       mol_type = transcribed RNA
                       organism = Homo sapiens
SEQUENCE: 83
caggaggcag tgggcgagca gg                                           22

SEQ ID NO: 84          moltype = RNA  length = 17
FEATURE                Location/Qualifiers
source                 1..17
                       mol_type = transcribed RNA
                       organism = Homo sapiens
SEQUENCE: 84
ggggcgcggc cggatcg                                                 17

SEQ ID NO: 85          moltype = RNA  length = 23
FEATURE                Location/Qualifiers
source                 1..23
                       mol_type = transcribed RNA
                       organism = Homo sapiens
SEQUENCE: 85
ccggggcaga ttggtgtagg gtg                                          23

SEQ ID NO: 86          moltype = RNA  length = 19
FEATURE                Location/Qualifiers
source                 1..19
                       mol_type = transcribed RNA
                       organism = Homo sapiens
```

```
SEQUENCE: 86
tggggcggag cttccggag                                                19

SEQ ID NO: 87          moltype = RNA  length = 21
FEATURE                Location/Qualifiers
source                 1..21
                       mol_type = transcribed RNA
                       organism = Homo sapiens
SEQUENCE: 87
cgggggcggg gccgaagcgc g                                             21

SEQ ID NO: 88          moltype = RNA  length = 23
FEATURE                Location/Qualifiers
source                 1..23
                       mol_type = transcribed RNA
                       organism = Homo sapiens
SEQUENCE: 88
gtgagtggga gccggtgggg ctg                                           23

SEQ ID NO: 89          moltype = RNA  length = 24
FEATURE                Location/Qualifiers
source                 1..24
                       mol_type = transcribed RNA
                       organism = Homo sapiens
SEQUENCE: 89
tgaggggcct cagaccgagc tttt                                          24

SEQ ID NO: 90          moltype = RNA  length = 17
FEATURE                Location/Qualifiers
source                 1..17
                       mol_type = transcribed RNA
                       organism = Homo sapiens
SEQUENCE: 90
accccactcc tggtacc                                                  17

SEQ ID NO: 91          moltype = RNA  length = 20
FEATURE                Location/Qualifiers
source                 1..20
                       mol_type = transcribed RNA
                       organism = Homo sapiens
SEQUENCE: 91
gccggggctt tgggtgaggg                                               20

SEQ ID NO: 92          moltype = RNA  length = 23
FEATURE                Location/Qualifiers
source                 1..23
                       mol_type = transcribed RNA
                       organism = Homo sapiens
SEQUENCE: 92
cacacaggaa aagcggggcc ctg                                           23

SEQ ID NO: 93          moltype = RNA  length = 22
FEATURE                Location/Qualifiers
source                 1..22
                       mol_type = transcribed RNA
                       organism = Homo sapiens
SEQUENCE: 93
tgggagggcg tggatgatgg tg                                            22

SEQ ID NO: 94          moltype = RNA  length = 25
FEATURE                Location/Qualifiers
source                 1..25
                       mol_type = transcribed RNA
                       organism = Homo sapiens
SEQUENCE: 94
agcggggagg aagtgggcgc tgctt                                         25

SEQ ID NO: 95          moltype = RNA  length = 22
FEATURE                Location/Qualifiers
source                 1..22
                       mol_type = transcribed RNA
                       organism = Homo sapiens
SEQUENCE: 95
gggacccagg gagagacgta ag                                            22

SEQ ID NO: 96          moltype = RNA  length = 18
FEATURE                Location/Qualifiers
source                 1..18
                       mol_type = transcribed RNA
```

-continued

```
                         organism = Homo sapiens
SEQUENCE: 96
atcccacctc tgccacca                                                    18

SEQ ID NO: 97            moltype = RNA  length = 22
FEATURE                  Location/Qualifiers
source                   1..22
                         mol_type = transcribed RNA
                         organism = Homo sapiens
SEQUENCE: 97
ccgggagaag gaggtggcct gg                                               22

SEQ ID NO: 98            moltype = RNA  length = 24
FEATURE                  Location/Qualifiers
source                   1..24
                         mol_type = transcribed RNA
                         organism = Homo sapiens
SEQUENCE: 98
ggaggccggg gtggggcggg gcgg                                             24

SEQ ID NO: 99            moltype = RNA  length = 23
FEATURE                  Location/Qualifiers
source                   1..23
                         mol_type = transcribed RNA
                         organism = Homo sapiens
SEQUENCE: 99
gtgcgtggtg gctcgaggcg ggg                                              23

SEQ ID NO: 100           moltype = RNA  length = 22
FEATURE                  Location/Qualifiers
source                   1..22
                         mol_type = transcribed RNA
                         organism = Homo sapiens
SEQUENCE: 100
actggggagc agaaggagaa cc                                               22

SEQ ID NO: 101           moltype = RNA  length = 23
FEATURE                  Location/Qualifiers
source                   1..23
                         mol_type = transcribed RNA
                         organism = Homo sapiens
SEQUENCE: 101
ggatggttgg gggcggtcgg cgt                                              23

SEQ ID NO: 102           moltype = RNA  length = 23
FEATURE                  Location/Qualifiers
source                   1..23
                         mol_type = transcribed RNA
                         organism = Homo sapiens
SEQUENCE: 102
agggccagag gagcctggag tgg                                              23

SEQ ID NO: 103           moltype = RNA  length = 20
FEATURE                  Location/Qualifiers
source                   1..20
                         mol_type = transcribed RNA
                         organism = Homo sapiens
SEQUENCE: 103
gggaaaagga agggggagga                                                  20

SEQ ID NO: 104           moltype = RNA  length = 17
FEATURE                  Location/Qualifiers
source                   1..17
                         mol_type = transcribed RNA
                         organism = Homo sapiens
SEQUENCE: 104
ccccggggag cccggcg                                                     17

SEQ ID NO: 105           moltype = RNA  length = 17
FEATURE                  Location/Qualifiers
source                   1..17
                         mol_type = transcribed RNA
                         organism = Homo sapiens
SEQUENCE: 105
gctgggcgag gctggca                                                     17

SEQ ID NO: 106           moltype = RNA  length = 23
FEATURE                  Location/Qualifiers
source                   1..23
```

```
                        mol_type = transcribed RNA
                        organism = Homo sapiens
SEQUENCE: 106
tgggagggga gaggcagcaa gca                                               23

SEQ ID NO: 107          moltype = RNA  length = 17
FEATURE                 Location/Qualifiers
source                  1..17
                        mol_type = transcribed RNA
                        organism = Homo sapiens
SEQUENCE: 107
gcggggctgg gcgcgcg                                                      17

SEQ ID NO: 108          moltype = RNA  length = 23
FEATURE                 Location/Qualifiers
source                  1..23
                        mol_type = transcribed RNA
                        organism = Homo sapiens
SEQUENCE: 108
cggggccgta gcactgtctg aga                                               23

SEQ ID NO: 109          moltype = RNA  length = 22
FEATURE                 Location/Qualifiers
source                  1..22
                        mol_type = transcribed RNA
                        organism = Homo sapiens
SEQUENCE: 109
agactgacgg ctggaggccc at                                                22

SEQ ID NO: 110          moltype = RNA  length = 24
FEATURE                 Location/Qualifiers
source                  1..24
                        mol_type = transcribed RNA
                        organism = Homo sapiens
SEQUENCE: 110
tggggggaca ggatgagagg ctgt                                              24

SEQ ID NO: 111          moltype = RNA  length = 22
FEATURE                 Location/Qualifiers
source                  1..22
                        mol_type = transcribed RNA
                        organism = Homo sapiens
SEQUENCE: 111
ttgaggagac atggtggggg cc                                                22

SEQ ID NO: 112          moltype = RNA  length = 19
FEATURE                 Location/Qualifiers
source                  1..19
                        mol_type = transcribed RNA
                        organism = Homo sapiens
SEQUENCE: 112
ctggggagtg gctggggag                                                    19

SEQ ID NO: 113          moltype = RNA  length = 20
FEATURE                 Location/Qualifiers
source                  1..20
                        mol_type = transcribed RNA
                        organism = Homo sapiens
SEQUENCE: 113
ggcggcgggg aggtaggcag                                                   20

SEQ ID NO: 114          moltype = RNA  length = 25
FEATURE                 Location/Qualifiers
source                  1..25
                        mol_type = transcribed RNA
                        organism = Homo sapiens
SEQUENCE: 114
gtgaggcggg gccaggaggg tgtgt                                             25

SEQ ID NO: 115          moltype = RNA  length = 18
FEATURE                 Location/Qualifiers
source                  1..18
                        mol_type = transcribed RNA
                        organism = Homo sapiens
SEQUENCE: 115
gaggctgaag gaagatgg                                                     18

SEQ ID NO: 116          moltype = RNA  length = 19
FEATURE                 Location/Qualifiers
```

-continued

```
source                 1..19
                       mol_type = transcribed RNA
                       organism = Homo sapiens
SEQUENCE: 116
ttgatctcgg aagctaagc                                        19

SEQ ID NO: 117         moltype = RNA  length = 22
FEATURE                Location/Qualifiers
source                 1..22
                       mol_type = transcribed RNA
                       organism = Homo sapiens
SEQUENCE: 117
ggaggaacct tggagcttcg gc                                    22

SEQ ID NO: 118         moltype = RNA  length = 17
FEATURE                Location/Qualifiers
source                 1..17
                       mol_type = transcribed RNA
                       organism = Homo sapiens
SEQUENCE: 118
gtggggccag gcggtgg                                          17

SEQ ID NO: 119         moltype = RNA  length = 17
FEATURE                Location/Qualifiers
source                 1..17
                       mol_type = transcribed RNA
                       organism = Homo sapiens
SEQUENCE: 119
ggggctgggc gcgcgcc                                          17

SEQ ID NO: 120         moltype = RNA  length = 22
FEATURE                Location/Qualifiers
source                 1..22
                       mol_type = transcribed RNA
                       organism = Homo sapiens
SEQUENCE: 120
gagggttggg tggaggctct cc                                    22

SEQ ID NO: 121         moltype = RNA  length = 21
FEATURE                Location/Qualifiers
source                 1..21
                       mol_type = transcribed RNA
                       organism = Homo sapiens
SEQUENCE: 121
aggtgggtat ggaggagccc t                                     21

SEQ ID NO: 122         moltype = RNA  length = 23
FEATURE                Location/Qualifiers
source                 1..23
                       mol_type = transcribed RNA
                       organism = Homo sapiens
SEQUENCE: 122
tcggggagtc tggggtccgg aat                                   23

SEQ ID NO: 123         moltype = RNA  length = 23
FEATURE                Location/Qualifiers
source                 1..23
                       mol_type = transcribed RNA
                       organism = Homo sapiens
SEQUENCE: 123
gagggcagcg tgggtgtggc gga                                   23

SEQ ID NO: 124         moltype = RNA  length = 18
FEATURE                Location/Qualifiers
source                 1..18
                       mol_type = transcribed RNA
                       organism = Homo sapiens
SEQUENCE: 124
aggctgggct gggacgga                                         18

SEQ ID NO: 125         moltype = RNA  length = 22
FEATURE                Location/Qualifiers
source                 1..22
                       mol_type = transcribed RNA
                       organism = Homo sapiens
SEQUENCE: 125
cagaagggga gttgggagca ga                                    22

SEQ ID NO: 126         moltype = RNA  length = 21
```

```
FEATURE                Location/Qualifiers
source                 1..21
                       mol_type = transcribed RNA
                       organism = Homo sapiens
SEQUENCE: 126
agccgcgggg atcgccgagg g                                        21

SEQ ID NO: 127         moltype = RNA  length = 17
FEATURE                Location/Qualifiers
source                 1..17
                       mol_type = transcribed RNA
                       organism = Homo sapiens
SEQUENCE: 127
gccggacaag agggagg                                             17

SEQ ID NO: 128         moltype = RNA  length = 19
FEATURE                Location/Qualifiers
source                 1..19
                       mol_type = transcribed RNA
                       organism = Homo sapiens
SEQUENCE: 128
gagggcgggt ggaggagga                                           19

SEQ ID NO: 129         moltype = RNA  length = 23
FEATURE                Location/Qualifiers
source                 1..23
                       mol_type = transcribed RNA
                       organism = Homo sapiens
SEQUENCE: 129
cctccctgcc cgcctctctg cag                                      23

SEQ ID NO: 130         moltype = RNA  length = 22
FEATURE                Location/Qualifiers
source                 1..22
                       mol_type = transcribed RNA
                       organism = Homo sapiens
SEQUENCE: 130
ttggggtgga gggccaagga gc                                       22

SEQ ID NO: 131         moltype = RNA  length = 17
FEATURE                Location/Qualifiers
source                 1..17
                       mol_type = transcribed RNA
                       organism = Homo sapiens
SEQUENCE: 131
cgcgccgggc ccgggtt                                             17

SEQ ID NO: 132         moltype = RNA  length = 20
FEATURE                Location/Qualifiers
source                 1..20
                       mol_type = transcribed RNA
                       organism = Homo sapiens
SEQUENCE: 132
cctgagcccg ggccgcgcag                                          20

SEQ ID NO: 133         moltype = RNA  length = 23
FEATURE                Location/Qualifiers
source                 1..23
                       mol_type = transcribed RNA
                       organism = Homo sapiens
SEQUENCE: 133
cgaggggtag aagagcacag ggg                                      23

SEQ ID NO: 134         moltype = RNA  length = 23
FEATURE                Location/Qualifiers
source                 1..23
                       mol_type = transcribed RNA
                       organism = Homo sapiens
SEQUENCE: 134
tgggctgagg gcaggaggcc tgt                                      23

SEQ ID NO: 135         moltype = RNA  length = 19
FEATURE                Location/Qualifiers
source                 1..19
                       mol_type = transcribed RNA
                       organism = Homo sapiens
SEQUENCE: 135
tgcggcagag ctggggtca                                           19
```

-continued

```
SEQ ID NO: 136         moltype = RNA  length = 22
FEATURE                Location/Qualifiers
source                 1..22
                       mol_type = transcribed RNA
                       organism = Homo sapiens
SEQUENCE: 136
gggggtcccc ggtgctcgga tc                                              22

SEQ ID NO: 137         moltype = RNA  length = 21
FEATURE                Location/Qualifiers
source                 1..21
                       mol_type = transcribed RNA
                       organism = Homo sapiens
SEQUENCE: 137
cggggcagct cagtacagga t                                               21

SEQ ID NO: 138         moltype = RNA  length = 22
FEATURE                Location/Qualifiers
source                 1..22
                       mol_type = transcribed RNA
                       organism = Homo sapiens
SEQUENCE: 138
tgagcccctg tgccgccccc ag                                              22

SEQ ID NO: 139         moltype = RNA  length = 20
FEATURE                Location/Qualifiers
source                 1..20
                       mol_type = transcribed RNA
                       organism = Homo sapiens
SEQUENCE: 139
cggctctggg tctgtgggga                                                 20

SEQ ID NO: 140         moltype = RNA  length = 22
FEATURE                Location/Qualifiers
source                 1..22
                       mol_type = transcribed RNA
                       organism = Homo sapiens
SEQUENCE: 140
ggctacaaca caggacccgg gc                                              22

SEQ ID NO: 141         moltype = RNA  length = 21
FEATURE                Location/Qualifiers
source                 1..21
                       mol_type = transcribed RNA
                       organism = Homo sapiens
SEQUENCE: 141
cccggagcca ggatgcagct c                                               21

SEQ ID NO: 142         moltype = RNA  length = 21
FEATURE                Location/Qualifiers
source                 1..21
                       mol_type = transcribed RNA
                       organism = Homo sapiens
SEQUENCE: 142
tgggggtgtg gggagagaga g                                               21

SEQ ID NO: 143         moltype = RNA  length = 20
FEATURE                Location/Qualifiers
source                 1..20
                       mol_type = transcribed RNA
                       organism = Homo sapiens
SEQUENCE: 143
actcaaactg tgggggcact                                                 20

SEQ ID NO: 144         moltype = RNA  length = 24
FEATURE                Location/Qualifiers
source                 1..24
                       mol_type = transcribed RNA
                       organism = Homo sapiens
SEQUENCE: 144
tggggagctg aggctctggg ggtg                                            24

SEQ ID NO: 145         moltype = RNA  length = 19
FEATURE                Location/Qualifiers
source                 1..19
                       mol_type = transcribed RNA
                       organism = Homo sapiens
SEQUENCE: 145
gagccagttg gacaggagc                                                  19
```

```
SEQ ID NO: 146          moltype = RNA   length = 22
FEATURE                 Location/Qualifiers
source                  1..22
                        mol_type = transcribed RNA
                        organism = Homo sapiens
SEQUENCE: 146
agggacggga cgcggtgcag tg                                                  22

SEQ ID NO: 147          moltype = RNA   length = 22
FEATURE                 Location/Qualifiers
source                  1..22
                        mol_type = transcribed RNA
                        organism = Homo sapiens
SEQUENCE: 147
gtgaacgggc gccatcccga gg                                                  22

SEQ ID NO: 148          moltype = RNA   length = 20
FEATURE                 Location/Qualifiers
source                  1..20
                        mol_type = transcribed RNA
                        organism = Homo sapiens
SEQUENCE: 148
ggggagctgt ggaagcagta                                                     20

SEQ ID NO: 149          moltype = RNA   length = 22
FEATURE                 Location/Qualifiers
source                  1..22
                        mol_type = transcribed RNA
                        organism = Homo sapiens
SEQUENCE: 149
accttgcctt gctgcccggg cc                                                  22

SEQ ID NO: 150          moltype = RNA   length = 20
FEATURE                 Location/Qualifiers
source                  1..20
                        mol_type = transcribed RNA
                        organism = Homo sapiens
SEQUENCE: 150
gtgtctgggc ggacagctgc                                                     20

SEQ ID NO: 151          moltype = RNA   length = 22
FEATURE                 Location/Qualifiers
source                  1..22
                        mol_type = transcribed RNA
                        organism = Homo sapiens
SEQUENCE: 151
ggtggcccgg ccgtgcctga gg                                                  22

SEQ ID NO: 152          moltype = RNA   length = 22
FEATURE                 Location/Qualifiers
source                  1..22
                        mol_type = transcribed RNA
                        organism = Homo sapiens
SEQUENCE: 152
gtgggtacgg cccagtgggg gg                                                  22

SEQ ID NO: 153          moltype = RNA   length = 24
FEATURE                 Location/Qualifiers
source                  1..24
                        mol_type = transcribed RNA
                        organism = Homo sapiens
SEQUENCE: 153
aggcaggggc tggtgctggg cggg                                                24

SEQ ID NO: 154          moltype = RNA   length = 17
FEATURE                 Location/Qualifiers
source                  1..17
                        mol_type = transcribed RNA
                        organism = Homo sapiens
SEQUENCE: 154
ggcgggtgcg ggggtgg                                                        17

SEQ ID NO: 155          moltype = RNA   length = 18
FEATURE                 Location/Qualifiers
source                  1..18
                        mol_type = transcribed RNA
                        organism = Homo sapiens
SEQUENCE: 155
```

-continued

```
agggggcggg ctccggcg                                                  18

SEQ ID NO: 156         moltype = RNA  length = 22
FEATURE                Location/Qualifiers
source                 1..22
                       mol_type = transcribed RNA
                       organism = Homo sapiens
SEQUENCE: 156
acaggtgagg ttcttgggag cc                                             22

SEQ ID NO: 157         moltype = RNA  length = 22
FEATURE                Location/Qualifiers
source                 1..22
                       mol_type = transcribed RNA
                       organism = Homo sapiens
SEQUENCE: 157
ctcggcgcgg ggcgcgggct cc                                             22

SEQ ID NO: 158         moltype = RNA  length = 21
FEATURE                Location/Qualifiers
source                 1..21
                       mol_type = transcribed RNA
                       organism = Homo sapiens
SEQUENCE: 158
gtgggcgggg gcaggtgtgt g                                              21

SEQ ID NO: 159         moltype = RNA  length = 23
FEATURE                Location/Qualifiers
source                 1..23
                       mol_type = transcribed RNA
                       organism = Homo sapiens
SEQUENCE: 159
ccagggggat gggcgagctt ggg                                            23

SEQ ID NO: 160         moltype = RNA  length = 20
FEATURE                Location/Qualifiers
source                 1..20
                       mol_type = transcribed RNA
                       organism = Homo sapiens
SEQUENCE: 160
cgggcgtggt ggtgggggtg                                                20

SEQ ID NO: 161         moltype = RNA  length = 20
FEATURE                Location/Qualifiers
source                 1..20
                       mol_type = transcribed RNA
                       organism = Homo sapiens
SEQUENCE: 161
tagggggtgg caggctggcc                                                20

SEQ ID NO: 162         moltype = RNA  length = 20
FEATURE                Location/Qualifiers
source                 1..20
                       mol_type = transcribed RNA
                       organism = Homo sapiens
SEQUENCE: 162
ccccagggcg acgcggcggg                                                20

SEQ ID NO: 163         moltype = RNA  length = 21
FEATURE                Location/Qualifiers
source                 1..21
                       mol_type = transcribed RNA
                       organism = Homo sapiens
SEQUENCE: 163
caggagtggg gggtgggacg t                                              21

SEQ ID NO: 164         moltype = RNA  length = 21
FEATURE                Location/Qualifiers
source                 1..21
                       mol_type = transcribed RNA
                       organism = Homo sapiens
SEQUENCE: 164
tggcagggag gctgggaggg g                                              21

SEQ ID NO: 165         moltype = RNA  length = 21
FEATURE                Location/Qualifiers
source                 1..21
                       mol_type = transcribed RNA
                       organism = Homo sapiens
```

```
SEQUENCE: 165
acaggagtgg gggtgggaca t                                            21

SEQ ID NO: 166          moltype = RNA  length = 22
FEATURE                 Location/Qualifiers
source                  1..22
                        mol_type = transcribed RNA
                        organism = Homo sapiens
SEQUENCE: 166
cagggcaggg aaggtgggag ag                                           22

SEQ ID NO: 167          moltype = RNA  length = 18
FEATURE                 Location/Qualifiers
source                  1..18
                        mol_type = transcribed RNA
                        organism = Homo sapiens
SEQUENCE: 167
ggtgggcttc ccggaggg                                                18

SEQ ID NO: 168          moltype = RNA  length = 22
FEATURE                 Location/Qualifiers
source                  1..22
                        mol_type = transcribed RNA
                        organism = Homo sapiens
SEQUENCE: 168
ctgggagagg gttgtttact cc                                           22

SEQ ID NO: 169          moltype = RNA  length = 21
FEATURE                 Location/Qualifiers
source                  1..21
                        mol_type = transcribed RNA
                        organism = Homo sapiens
SEQUENCE: 169
actcggctgc ggtggacaag t                                            21

SEQ ID NO: 170          moltype = RNA  length = 20
FEATURE                 Location/Qualifiers
source                  1..20
                        mol_type = transcribed RNA
                        organism = Homo sapiens
SEQUENCE: 170
agagatgaag cggggggggcg                                             20

SEQ ID NO: 171          moltype = RNA  length = 20
FEATURE                 Location/Qualifiers
source                  1..20
                        mol_type = transcribed RNA
                        organism = Homo sapiens
SEQUENCE: 171
tcagggagtc aggggagggc                                              20

SEQ ID NO: 172          moltype = RNA  length = 25
FEATURE                 Location/Qualifiers
source                  1..25
                        mol_type = transcribed RNA
                        organism = Homo sapiens
SEQUENCE: 172
taggggtggg ggaattcagg ggtgt                                        25

SEQ ID NO: 173          moltype = RNA  length = 20
FEATURE                 Location/Qualifiers
source                  1..20
                        mol_type = transcribed RNA
                        organism = Homo sapiens
SEQUENCE: 173
accaggaggc tgaggcccct                                              20

SEQ ID NO: 174          moltype = RNA  length = 22
FEATURE                 Location/Qualifiers
source                  1..22
                        mol_type = transcribed RNA
                        organism = Homo sapiens
SEQUENCE: 174
tcctgtactg agctgccccg ag                                           22

SEQ ID NO: 175          moltype = RNA  length = 22
FEATURE                 Location/Qualifiers
source                  1..22
                        mol_type = transcribed RNA
```

```
                        organism = Homo sapiens
SEQUENCE: 175
caccggggat ggcagagggt cg                                              22

SEQ ID NO: 176          moltype = RNA  length = 17
FEATURE                 Location/Qualifiers
source                  1..17
                        mol_type = transcribed RNA
                        organism = Homo sapiens
SEQUENCE: 176
gtgggggaga ggctgtc                                                    17

SEQ ID NO: 177          moltype = RNA  length = 24
FEATURE                 Location/Qualifiers
source                  1..24
                        mol_type = transcribed RNA
                        organism = Homo sapiens
SEQUENCE: 177
tgtaggcatg aggcagggcc cagg                                            24

SEQ ID NO: 178          moltype = RNA  length = 23
FEATURE                 Location/Qualifiers
source                  1..23
                        mol_type = transcribed RNA
                        organism = Homo sapiens
SEQUENCE: 178
gaacgcctgt tcttgccagg tgg                                             23

SEQ ID NO: 179          moltype = RNA  length = 23
FEATURE                 Location/Qualifiers
source                  1..23
                        mol_type = transcribed RNA
                        organism = Homo sapiens
SEQUENCE: 179
acaggcggct gtagcaatgg ggg                                             23

SEQ ID NO: 180          moltype = RNA  length = 22
FEATURE                 Location/Qualifiers
source                  1..22
                        mol_type = transcribed RNA
                        organism = Homo sapiens
SEQUENCE: 180
ggggggtgtg gagccagggg gc                                              22

SEQ ID NO: 181          moltype = RNA  length = 22
FEATURE                 Location/Qualifiers
source                  1..22
                        mol_type = transcribed RNA
                        organism = Homo sapiens
SEQUENCE: 181
ctcgggaggg catgggccag gc                                              22

SEQ ID NO: 182          moltype = RNA  length = 22
FEATURE                 Location/Qualifiers
source                  1..22
                        mol_type = transcribed RNA
                        organism = Homo sapiens
SEQUENCE: 182
tggggatttg gagaagtggt ga                                              22

SEQ ID NO: 183          moltype = RNA  length = 21
FEATURE                 Location/Qualifiers
source                  1..21
                        mol_type = transcribed RNA
                        organism = Homo sapiens
SEQUENCE: 183
gcagggacag caaaggggtg c                                               21

SEQ ID NO: 184          moltype = RNA  length = 22
FEATURE                 Location/Qualifiers
source                  1..22
                        mol_type = transcribed RNA
                        organism = Homo sapiens
SEQUENCE: 184
aggcggggcg ccgcgggacc gc                                              22

SEQ ID NO: 185          moltype = RNA  length = 22
FEATURE                 Location/Qualifiers
source                  1..22
```

```
                        mol_type = transcribed RNA
                        organism = Homo sapiens
SEQUENCE: 185
tgggggtggt ctctagccaa gg                                              22

SEQ ID NO: 186          moltype = RNA  length = 21
FEATURE                 Location/Qualifiers
source                  1..21
                        mol_type = transcribed RNA
                        organism = Homo sapiens
SEQUENCE: 186
tctgtggagt ggggtgcctg t                                               21

SEQ ID NO: 187          moltype = RNA  length = 21
FEATURE                 Location/Qualifiers
source                  1..21
                        mol_type = transcribed RNA
                        organism = Homo sapiens
SEQUENCE: 187
ctgggagggg ctgggtttgg c                                               21

SEQ ID NO: 188          moltype = RNA  length = 53
FEATURE                 Location/Qualifiers
source                  1..53
                        mol_type = transcribed RNA
                        organism = Homo sapiens
SEQUENCE: 188
ggtgggggtt ggaggcgtgg gttttagaac ctatcccttt ctagccctga gca           53

SEQ ID NO: 189          moltype = RNA  length = 80
FEATURE                 Location/Qualifiers
source                  1..80
                        mol_type = transcribed RNA
                        organism = Homo sapiens
SEQUENCE: 189
cgggaatgcc gcggcgggga cggcgattgg tccgtatgtg tggtgccacc ggccgccggc  60
tccgccccgg cccccgcccc                                                 80

SEQ ID NO: 190          moltype = RNA  length = 86
FEATURE                 Location/Qualifiers
source                  1..86
                        mol_type = transcribed RNA
                        organism = Homo sapiens
SEQUENCE: 190
ggcttagaaa cagtccctag gtaggatttg gggaggagct aagaagcccc tacagggccc  60
agaggtgggg actgagcctt agttgg                                          86

SEQ ID NO: 191          moltype = RNA  length = 73
FEATURE                 Location/Qualifiers
source                  1..73
                        mol_type = transcribed RNA
                        organism = Homo sapiens
SEQUENCE: 191
ggcgagggga ggcgcaggct cggaaaggcg cgcgaggctc caggctcctt cccgatccac  60
cgctctcctc gct                                                        73

SEQ ID NO: 192          moltype = RNA  length = 85
FEATURE                 Location/Qualifiers
source                  1..85
                        mol_type = transcribed RNA
                        organism = Homo sapiens
SEQUENCE: 192
ggcgcctcct gctctgctgt gccgccaggg cctcccctag cgcgccttct ggagaggctt  60
tgtgcggata cggggctgga ggcct                                           85

SEQ ID NO: 193          moltype = RNA  length = 64
FEATURE                 Location/Qualifiers
source                  1..64
                        mol_type = transcribed RNA
                        organism = Homo sapiens
SEQUENCE: 193
tctgggcgag ggtgggctc tcagaggggc tggcagtact gctctgaggc ctgcctctcc  60
ccag                                                                  64

SEQ ID NO: 194          moltype = RNA  length = 84
FEATURE                 Location/Qualifiers
source                  1..84
                        mol_type = transcribed RNA
                        organism = Homo sapiens
```

```
SEQUENCE: 194
gctggcgtcg gtgctgggga gcggcccccg ggtgggcctc tgctctggcc cctcctgggg  60
cccgcactct cgctctgggc ccgc                                          84

SEQ ID NO: 195          moltype = RNA  length = 64
FEATURE                 Location/Qualifiers
source                  1..64
                        mol_type = transcribed RNA
                        organism = Homo sapiens
SEQUENCE: 195
gaggcactgg gtaggtgggg ctccagggct cctgacacct ggacctctcc tccccaggcc  60
caca                                                                64

SEQ ID NO: 196          moltype = RNA  length = 77
FEATURE                 Location/Qualifiers
source                  1..77
                        mol_type = transcribed RNA
                        organism = Homo sapiens
SEQUENCE: 196
gagttgggag gttccctctc caaatgtgtc ttgatccccc accccaagac acatttggag  60
agggaccctc ccaactc                                                  77

SEQ ID NO: 197          moltype = RNA  length = 63
FEATURE                 Location/Qualifiers
source                  1..63
                        mol_type = transcribed RNA
                        organism = Homo sapiens
SEQUENCE: 197
aatgggtggg tgctggtggg agccgtgccc tggccactca ttcggctctc tccctcaccc  60
tag                                                                 63

SEQ ID NO: 198          moltype = RNA  length = 62
FEATURE                 Location/Qualifiers
source                  1..62
                        mol_type = transcribed RNA
                        organism = Homo sapiens
SEQUENCE: 198
gtgagtgggg ctcccgggac ggcgcccgcc ctggccctgg cccggcgacg tctcacggtc  60
cc                                                                  62

SEQ ID NO: 199          moltype = RNA  length = 98
FEATURE                 Location/Qualifiers
source                  1..98
                        mol_type = transcribed RNA
                        organism = Homo sapiens
SEQUENCE: 199
cttggtcaat aggaaagagg tgggacctcc tggcttttcc tctgcagcat ggctcggacc  60
tagtgcaatg tttaagctcc cctctctttc ctgttcag                          98

SEQ ID NO: 200          moltype = RNA  length = 97
FEATURE                 Location/Qualifiers
source                  1..97
                        mol_type = transcribed RNA
                        organism = Homo sapiens
SEQUENCE: 200
cccgggacct tggtccaggc gctggtctgc gtggtgctcg ggtggataag tctgatctga  60
gcaccacaca ggccgggcgc cgggaccaag ggggctc                           97

SEQ ID NO: 201          moltype = RNA  length = 63
FEATURE                 Location/Qualifiers
source                  1..63
                        mol_type = transcribed RNA
                        organism = Homo sapiens
SEQUENCE: 201
gagtcgagga ctggtggaag ggcctttccc ctcagaccaa ggccctggcc ccagcttctt  60
ctc                                                                 63

SEQ ID NO: 202          moltype = RNA  length = 75
FEATURE                 Location/Qualifiers
source                  1..75
                        mol_type = transcribed RNA
                        organism = Homo sapiens
SEQUENCE: 202
tcatccctgg gtggggattt gttgcattac ttgtgttcta tataaagtat tgcacttgtc  60
ccggcctgtg gaaga                                                    75

SEQ ID NO: 203          moltype = RNA  length = 91
FEATURE                 Location/Qualifiers
source                  1..91
```

```
                        mol_type = transcribed RNA
                        organism = Homo sapiens
SEQUENCE: 203
acgccccccg ccccgccacc gccttggagg ctgacctctt actttcggtc ggtcttcttc  60
cctgggcttg gtttgggggc gggggagtgt c                                 91

SEQ ID NO: 204          moltype = RNA  length = 86
FEATURE                 Location/Qualifiers
source                  1..86
                        mol_type = transcribed RNA
                        organism = Homo sapiens
SEQUENCE: 204
aggagtgacc aaaagacaag agtgcgagcc ttctattatg cccagacagg gccaccagag  60
ggctccttgg tctaggggta atgcca                                       86

SEQ ID NO: 205          moltype = RNA  length = 96
FEATURE                 Location/Qualifiers
source                  1..96
                        mol_type = transcribed RNA
                        organism = Homo sapiens
SEQUENCE: 205
gctctggggc gtgccgccgc cgtcgctgcc acctccccta ccgctagtgg aagaagatgg  60
cggaaggcgg agcggcggat ctggacaccc agcggt                            96

SEQ ID NO: 206          moltype = RNA  length = 62
FEATURE                 Location/Qualifiers
source                  1..62
                        mol_type = transcribed RNA
                        organism = Homo sapiens
SEQUENCE: 206
gagggtggtg gaggaagagg gcagctccca tgactgcctg accgccttct ctcctccccc  60
ag                                                                 62

SEQ ID NO: 207          moltype = RNA  length = 109
FEATURE                 Location/Qualifiers
source                  1..109
                        mol_type = transcribed RNA
                        organism = Homo sapiens
SEQUENCE: 207
tgctattgtc ttactgctac agcagggctg gggattgcag tatccgctgt tgctgctgct  60
cccagtcctg cccctgctgc tacctagtcc agcctcaccg catcccaga              109

SEQ ID NO: 208          moltype = RNA  length = 63
FEATURE                 Location/Qualifiers
source                  1..63
                        mol_type = transcribed RNA
                        organism = Homo sapiens
SEQUENCE: 208
tggtggcggc ggtagttatg ggcttctctt tctcaccagc agcccctggg ccgccgcctc  60
cct                                                                63

SEQ ID NO: 209          moltype = RNA  length = 69
FEATURE                 Location/Qualifiers
source                  1..69
                        mol_type = transcribed RNA
                        organism = Homo sapiens
SEQUENCE: 209
ggccctcggg cctggggttg gggagctct gtcctgtctc actcattgct cctcccctgc  60
ctggcccag                                                          69

SEQ ID NO: 210          moltype = RNA  length = 84
FEATURE                 Location/Qualifiers
source                  1..84
                        mol_type = transcribed RNA
                        organism = Homo sapiens
SEQUENCE: 210
atggtccctc ccaatccagc cattcctcag accaggtggc tcccgagcca ccccaggctg  60
taggatgggg gtgagaggtg ctag                                         84

SEQ ID NO: 211          moltype = RNA  length = 100
FEATURE                 Location/Qualifiers
source                  1..100
                        mol_type = transcribed RNA
                        organism = Homo sapiens
SEQUENCE: 211
gaggtgggag gattgcttga gtcagggtgg ttgaggctgc agtaagttgt gatcatacca  60
ctgcactcca gcctgagtga cagagcaaga ccttgtctca                        100

SEQ ID NO: 212          moltype = RNA  length = 71
```

-continued

```
FEATURE                 Location/Qualifiers
source                  1..71
                        mol_type = transcribed RNA
                        organism = Homo sapiens
SEQUENCE: 212
gtgtctgtgc cggtcccagg agaacctgca gaggcatcgg gtcagcggtg ctcctgcggg    60
ccgacactca c                                                         71

SEQ ID NO: 213          moltype = RNA  length = 80
FEATURE                 Location/Qualifiers
source                  1..80
                        mol_type = transcribed RNA
                        organism = Homo sapiens
SEQUENCE: 213
cgtgtgagcc cgccctgtgc ccggcccact tctgcttcct cttagcgcag gaggggtccc    60
gcactgggag gggccctcac                                                80

SEQ ID NO: 214          moltype = RNA  length = 99
FEATURE                 Location/Qualifiers
source                  1..99
                        mol_type = transcribed RNA
                        organism = Homo sapiens
SEQUENCE: 214
gcaagggaca gggagggtcg tggcgacact cgcgccagct cccgggacgg ctgggctcgg    60
gctggtcgcc gacctccgac cctccactag atgcctggc                           99

SEQ ID NO: 215          moltype = RNA  length = 61
FEATURE                 Location/Qualifiers
source                  1..61
                        mol_type = transcribed RNA
                        organism = Homo sapiens
SEQUENCE: 215
gggggcggga gctggggtct gcaggttcgc actgatgcct gctcgccctg tctcccgcta    60
g                                                                    61

SEQ ID NO: 216          moltype = RNA  length = 84
FEATURE                 Location/Qualifiers
source                  1..84
                        mol_type = transcribed RNA
                        organism = Homo sapiens
SEQUENCE: 216
tgtgcagtgg aagggggc cgatacactg tacgagagtg agtagcaggt ctcacagtga      60
accggtctct ttccctactg tgtc                                           84

SEQ ID NO: 217          moltype = RNA  length = 73
FEATURE                 Location/Qualifiers
source                  1..73
                        mol_type = transcribed RNA
                        organism = Homo sapiens
SEQUENCE: 217
cggcgacggc ggggtgggtg aggtcgggcc ccaagactcg gggtttgccg ggcgcctcag    60
ttcaccgcgg ccg                                                       73

SEQ ID NO: 218          moltype = RNA  length = 87
FEATURE                 Location/Qualifiers
source                  1..87
                        mol_type = transcribed RNA
                        organism = Homo sapiens
SEQUENCE: 218
gtgaggcggg gccaggaggg tgtgtggcgt gggtgctgcg gggccgtcag ggtgcctgcg    60
ggacgctcac ctggctggcc cgcccag                                        87

SEQ ID NO: 219          moltype = RNA  length = 68
FEATURE                 Location/Qualifiers
source                  1..68
                        mol_type = transcribed RNA
                        organism = Homo sapiens
SEQUENCE: 219
gaatggaaga agaaggcggt cggtctgcgg gagccaggcc gcagagccat ccgccttctg    60
tccatgtc                                                             68

SEQ ID NO: 220          moltype = RNA  length = 74
FEATURE                 Location/Qualifiers
source                  1..74
                        mol_type = transcribed RNA
                        organism = Homo sapiens
SEQUENCE: 220
gcagcccggt gagcgctcgc tggcctggca gtgcgtcgga agaacagggc gggtggggcc    60
gcgcacatct ctgc                                                      74
```

-continued

```
SEQ ID NO: 221          moltype = RNA  length = 65
FEATURE                 Location/Qualifiers
source                  1..65
                        mol_type = transcribed RNA
                        organism = Homo sapiens
SEQUENCE: 221
gagaatgggg ggacagatgg agaggacaca ggctggcact gaggtcccct ccactttcct  60
cctag                                                              65

SEQ ID NO: 222          moltype = RNA  length = 137
FEATURE                 Location/Qualifiers
source                  1..137
                        mol_type = transcribed RNA
                        organism = Homo sapiens
SEQUENCE: 222
agccagacaa gagggtcatg gggagtcact gtcaacccag agcaggcact gcccctgcga  60
ccagcctggg gcatcggttg gggtgcaggg gtctgctggt gatgctttcc atctctttgc  120
tttgtcctga ttgtagc                                                 137

SEQ ID NO: 223          moltype = RNA  length = 83
FEATURE                 Location/Qualifiers
source                  1..83
                        mol_type = transcribed RNA
                        organism = Homo sapiens
SEQUENCE: 223
acggcatctt tgcactcagc aggcaggctg gtgcagcccg tggtggggga ccatcctgcc  60
tgctgtgggg taaggacggc tgt                                          83

SEQ ID NO: 224          moltype = RNA  length = 79
FEATURE                 Location/Qualifiers
source                  1..79
                        mol_type = transcribed RNA
                        organism = Homo sapiens
SEQUENCE: 224
cagcctgggg aaggcttggc agggaagaca catgagcagt gcctccactt cacgcctctc  60
ccttgtctcc tttccctag                                               79

SEQ ID NO: 225          moltype = RNA  length = 80
FEATURE                 Location/Qualifiers
source                  1..80
                        mol_type = transcribed RNA
                        organism = Homo sapiens
SEQUENCE: 225
ggttccggag ccccggcgcg ggcgggttct ggggtgtaga cgctgctggc cagcccgccc  60
cagccgaggt tctcggcacc                                              80

SEQ ID NO: 226          moltype = RNA  length = 81
FEATURE                 Location/Qualifiers
source                  1..81
                        mol_type = transcribed RNA
                        organism = Homo sapiens
SEQUENCE: 226
tagaggcagt ttcaacagat gtgtagactt ttgatatgag aaattggttt caaaatcagg  60
agtcggggct ttactgcttt t                                            81

SEQ ID NO: 227          moltype = RNA  length = 55
FEATURE                 Location/Qualifiers
source                  1..55
                        mol_type = transcribed RNA
                        organism = Homo sapiens
SEQUENCE: 227
ccggatccga gtcacggcac caaatttcat gcgtgtccgt gtgaagagac cacca       55

SEQ ID NO: 228          moltype = RNA  length = 75
FEATURE                 Location/Qualifiers
source                  1..75
                        mol_type = transcribed RNA
                        organism = Homo sapiens
SEQUENCE: 228
gtcagagggg ggatgtgcat gctggttggg gtgggctgcc tgtggaccaa tcagcgtgca  60
cttccccacc ctgaa                                                   75

SEQ ID NO: 229          moltype = RNA  length = 68
FEATURE                 Location/Qualifiers
source                  1..68
                        mol_type = transcribed RNA
                        organism = Homo sapiens
SEQUENCE: 229
```

```
gtgcaaagag caggaggaca ggggatttat ctcccaaggg aggtcccctg atcctagtca  60
cggcacca                                                           68

SEQ ID NO: 230         moltype = RNA  length = 98
FEATURE                Location/Qualifiers
source                 1..98
                       mol_type = transcribed RNA
                       organism = Homo sapiens
SEQUENCE: 230
ttgggcaagg tgcggggcta gggctaacag cagtcttact gaaggtttcc tggaaaccac  60
gcacatgctg ttgccactaa cctcaacctt actcggtc                          98

SEQ ID NO: 231         moltype = RNA  length = 68
FEATURE                Location/Qualifiers
source                 1..68
                       mol_type = transcribed RNA
                       organism = Homo sapiens
SEQUENCE: 231
tgcccaggct ggagcgagtg cagtggtgca gtcagtccta gctcactgca gcctcgaact  60
cctgggct                                                           68

SEQ ID NO: 232         moltype = RNA  length = 72
FEATURE                Location/Qualifiers
source                 1..72
                       mol_type = transcribed RNA
                       organism = Homo sapiens
SEQUENCE: 232
tgtgggactg caaatgggag ctcagcacct gcctgccacc cacgcagacc agcccctgct  60
ctgttcccac ag                                                      72

SEQ ID NO: 233         moltype = RNA  length = 66
FEATURE                Location/Qualifiers
source                 1..66
                       mol_type = transcribed RNA
                       organism = Homo sapiens
SEQUENCE: 233
ccgagtgggg cggggcaggt ccctgcaggg actgtgacac tgaaggacct gcaccttcgc  60
ccacag                                                             66

SEQ ID NO: 234         moltype = RNA  length = 90
FEATURE                Location/Qualifiers
source                 1..90
                       mol_type = transcribed RNA
                       organism = Homo sapiens
SEQUENCE: 234
cgggcggggc gggtccggcc gcctccgagc ccggccggca gccccggcc ttaaagcgcg  60
ggctgtccgg aggggtcggc tttcccaccg                                   90

SEQ ID NO: 235         moltype = RNA  length = 94
FEATURE                Location/Qualifiers
source                 1..94
                       mol_type = transcribed RNA
                       organism = Homo sapiens
SEQUENCE: 235
cacggtgtcc cctggtggaa cctggcaggg ggagaggtaa ggtctttcag cctctccaaa  60
gcccatggtc aggtactcag gtgggggagc cctg                              94

SEQ ID NO: 236         moltype = RNA  length = 67
FEATURE                Location/Qualifiers
source                 1..67
                       mol_type = transcribed RNA
                       organism = Homo sapiens
SEQUENCE: 236
ccagacccct ggggctgggc aggcggaaag aggtctgaac tgcctctgcc tccttggtct  60
ccggcag                                                            67

SEQ ID NO: 237         moltype = RNA  length = 136
FEATURE                Location/Qualifiers
source                 1..136
                       mol_type = transcribed RNA
                       organism = Homo sapiens
SEQUENCE: 237
ccgcttgcct cgcccagcgc agccccggcc gctgggcgca cccgtcccgt tcgtccccgg  60
acgttgctct ctaccccggg aacgtcgaga ctggagcgcc cgaactgagc caccttcgcg  120
gaccccgaga gcggcg                                                  136

SEQ ID NO: 238         moltype = RNA  length = 49
FEATURE                Location/Qualifiers
source                 1..49
```

```
                         mol_type = transcribed RNA
                         organism = Homo sapiens
SEQUENCE: 238
ttcccagcca acgcaccaaa aatgatatgg gtctgttgtc tggagaaac              49

SEQ ID NO: 239           moltype = RNA  length = 89
FEATURE                  Location/Qualifiers
source                   1..89
                         mol_type = transcribed RNA
                         organism = Homo sapiens
SEQUENCE: 239
acctccggga cggctgggcg ccggcggccg ggagatccgc gcttcctgaa tcccggccgg  60
cccgcccggc gcccgtccgc ccgcgggtc                                    89

SEQ ID NO: 240           moltype = RNA  length = 60
FEATURE                  Location/Qualifiers
source                   1..60
                         mol_type = transcribed RNA
                         organism = Homo sapiens
SEQUENCE: 240
cgctgggtcc gcgcgccctg ggccgggcga tgtccgcttg ggggagcgag gggcggggcg  60

SEQ ID NO: 241           moltype = RNA  length = 64
FEATURE                  Location/Qualifiers
source                   1..64
                         mol_type = transcribed RNA
                         organism = Homo sapiens
SEQUENCE: 241
aaccccgggc cggaggtcaa gggcgtcgct tctccctaat gttgcctctt ttccacggcc  60
tcag                                                               64

SEQ ID NO: 242           moltype = RNA  length = 60
FEATURE                  Location/Qualifiers
source                   1..60
                         mol_type = transcribed RNA
                         organism = Homo sapiens
SEQUENCE: 242
caaggtgggg gagatggggg ttgaacttca tttctcatgc tcatccccat ctcctttcag  60

SEQ ID NO: 243           moltype = RNA  length = 65
FEATURE                  Location/Qualifiers
source                   1..65
                         mol_type = transcribed RNA
                         organism = Homo sapiens
SEQUENCE: 243
gagggtgggc gagggcggct gagcggctcc atcccccggc ctgctcatcc ccctcgccct  60
ctcag                                                              65

SEQ ID NO: 244           moltype = RNA  length = 56
FEATURE                  Location/Qualifiers
source                   1..56
                         mol_type = transcribed RNA
                         organism = Homo sapiens
SEQUENCE: 244
cgaccgcacc cgcccgaagc tgggtcaagg agcccagcag gacgggagcg cggcgc      56

SEQ ID NO: 245           moltype = RNA  length = 103
FEATURE                  Location/Qualifiers
source                   1..103
                         mol_type = transcribed RNA
                         organism = Homo sapiens
SEQUENCE: 245
gtgtcggctg tggcgtgact gtccctctgt gtcccccact aggcccactg ctcagtggag  60
cgtggaggac gaggaggagg ccgtccacga gcaatgccag cat                    103

SEQ ID NO: 246           moltype = RNA  length = 66
FEATURE                  Location/Qualifiers
source                   1..66
                         mol_type = transcribed RNA
                         organism = Homo sapiens
SEQUENCE: 246
gggcatgggg aggtgtggag tcagcatggg gctaggaggc cccgcgctga cccgccttct  60
ccgcag                                                             66

SEQ ID NO: 247           moltype = RNA  length = 87
FEATURE                  Location/Qualifiers
source                   1..87
                         mol_type = transcribed RNA
                         organism = Homo sapiens
```

```
SEQUENCE: 247
cccaggcgcc cgctcccgac ccacgccgcg ccgccgggtc cctcctcccc ggagaggctg  60
ggctcgggac gcgcggctca gctcggg                                      87

SEQ ID NO: 248         moltype = RNA  length = 93
FEATURE                Location/Qualifiers
source                 1..93
                       mol_type = transcribed RNA
                       organism = Homo sapiens
SEQUENCE: 248
ggcgcttttg tgcgcgcccg ggtctgttgg tgctcagagt gtggtcaggc ggctcggact  60
gagcaggtgg gtgcggggct cggaggaggc ggc                               93

SEQ ID NO: 249         moltype = RNA  length = 66
FEATURE                Location/Qualifiers
source                 1..66
                       mol_type = transcribed RNA
                       organism = Homo sapiens
SEQUENCE: 249
cctggagggg ggcactgcgc aagcaaagcc agggaccctg agaggctttg cttcctgctc  60
ccctag                                                             66

SEQ ID NO: 250         moltype = RNA  length = 78
FEATURE                Location/Qualifiers
source                 1..78
                       mol_type = transcribed RNA
                       organism = Homo sapiens
SEQUENCE: 250
ggcctcaggc aggcgcaccc gaccacatgc atggctggtg gcggcgtgca ggggtcgggt  60
gggccaggct gtggggcg                                                78

SEQ ID NO: 251         moltype = RNA  length = 86
FEATURE                Location/Qualifiers
source                 1..86
                       mol_type = transcribed RNA
                       organism = Homo sapiens
SEQUENCE: 251
agggagaagg gtcggggcag ggagggcagg gcaggctctg ggtgggggg tctgtgagtc  60
agccacggct ctgcccacgt ctcccc                                       86

SEQ ID NO: 252         moltype = RNA  length = 69
FEATURE                Location/Qualifiers
source                 1..69
                       mol_type = transcribed RNA
                       organism = Homo sapiens
SEQUENCE: 252
gggcttaggg atgggaggcc aggatgaaga ttaatcccta atccccaaca ctggccttgc  60
tatccccag                                                          69

SEQ ID NO: 253         moltype = RNA  length = 71
FEATURE                Location/Qualifiers
source                 1..71
                       mol_type = transcribed RNA
                       organism = Homo sapiens
SEQUENCE: 253
tgaccacccc cgggcaaaga cctgcagatc ccctgttaga gacgggccca ggactttgtg  60
cggggtgccc a                                                       71

SEQ ID NO: 254         moltype = RNA  length = 115
FEATURE                Location/Qualifiers
source                 1..115
                       mol_type = transcribed RNA
                       organism = Homo sapiens
SEQUENCE: 254
gagcaaaaac cagagaacaa catgggagcg ttcctaaccc ctaaggcaac tggatgggag  60
acctgaccca tccagttctc tgagggggct cttgtgtgtt ctacaaggtt gttca       115

SEQ ID NO: 255         moltype = RNA  length = 63
FEATURE                Location/Qualifiers
source                 1..63
                       mol_type = transcribed RNA
                       organism = Homo sapiens
SEQUENCE: 255
accctagggt ggggctggag gtggggctga ggctgagtct tcctcccctt cctccctgcc  60
cag                                                                63

SEQ ID NO: 256         moltype = RNA  length = 82
FEATURE                Location/Qualifiers
source                 1..82
```

```
                       mol_type = transcribed RNA
                       organism = Homo sapiens
SEQUENCE: 256
acctgtaggt gacagtcagg ggcggggtgt ggtggggctg gggctggccc cctcctcaca  60
cctctcctgg catcgccccc ag                                            82

SEQ ID NO: 257         moltype = RNA  length = 65
FEATURE                Location/Qualifiers
source                 1..65
                       mol_type = transcribed RNA
                       organism = Homo sapiens
SEQUENCE: 257
gggtgctcgg ggcaggcggc tgggagcggc cctcacattg atggctcctg ccacctcctc  60
cgcag                                                               65

SEQ ID NO: 258         moltype = RNA  length = 89
FEATURE                Location/Qualifiers
source                 1..89
                       mol_type = transcribed RNA
                       organism = Homo sapiens
SEQUENCE: 258
agcctgtggg aaagagaaga gcagggcagg gtgaaggccc ggcggagaca ctctgcccac  60
cccacaccct gcctatgggc cacacagct                                     89

SEQ ID NO: 259         moltype = RNA  length = 62
FEATURE                Location/Qualifiers
source                 1..62
                       mol_type = transcribed RNA
                       organism = Homo sapiens
SEQUENCE: 259
gtgggtctcg catcaggagg caaggccagg acccgctgac ccatgcctcc tgccgcggtc  60
ag                                                                  62

SEQ ID NO: 260         moltype = RNA  length = 67
FEATURE                Location/Qualifiers
source                 1..67
                       mol_type = transcribed RNA
                       organism = Homo sapiens
SEQUENCE: 260
ctggtccatt tccctgccat tcccttggct tcaatttact cccagggctg gcagtgacat  60
gggtcaa                                                             67

SEQ ID NO: 261         moltype = RNA  length = 52
FEATURE                Location/Qualifiers
source                 1..52
                       mol_type = transcribed RNA
                       organism = Homo sapiens
SEQUENCE: 261
tagccgggcg tggtggtggg ggcctgtggt cccagctact ttggaggctg ag           52

SEQ ID NO: 262         moltype = RNA  length = 68
FEATURE                Location/Qualifiers
source                 1..68
                       mol_type = transcribed RNA
                       organism = Homo sapiens
SEQUENCE: 262
cgtggtgagg atatggcagg gaaggggagt ttccctctat tcccttcccc ccagtaatct  60
tcatcatg                                                            68

SEQ ID NO: 263         moltype = RNA  length = 60
FEATURE                Location/Qualifiers
source                 1..60
                       mol_type = transcribed RNA
                       organism = Homo sapiens
SEQUENCE: 263
tgtgaatgac ccccttccag agccaaaatc accagggatg gaggaggggt cttgggtact  60

SEQ ID NO: 264         moltype = RNA  length = 77
FEATURE                Location/Qualifiers
source                 1..77
                       mol_type = transcribed RNA
                       organism = Homo sapiens
SEQUENCE: 264
catgagaaat cctgctggtc aaccatagcc ctggtcagac tctccggggc tgtgattgac  60
cagcaggact tctcatg                                                  77

SEQ ID NO: 265         moltype = RNA  length = 87
FEATURE                Location/Qualifiers
source                 1..87
```

```
                        mol_type = transcribed RNA
                        organism = Homo sapiens
SEQUENCE: 265
gtgtggccgg caggcgggtg ggcgggggcg gccggtggga accccgcccc gccccgcgcc  60
cgcactcacc cgcccgtctc cccacag                                      87

SEQ ID NO: 266          moltype = RNA  length = 69
FEATURE                 Location/Qualifiers
source                  1..69
                        mol_type = transcribed RNA
                        organism = Homo sapiens
SEQUENCE: 266
gaggagggga ggtgtgcagg gctggggtca ctgactctgc ttcccctgcc ctgcatggtg  60
tccccacag                                                          69

SEQ ID NO: 267          moltype = RNA  length = 74
FEATURE                 Location/Qualifiers
source                  1..74
                        mol_type = transcribed RNA
                        organism = Homo sapiens
SEQUENCE: 267
cctgcaggag gcagtgggcg agcaggcggg gcagcccaat gccatgggcc tgatctcacc  60
gctgcctcct tccc                                                    74

SEQ ID NO: 268          moltype = RNA  length = 84
FEATURE                 Location/Qualifiers
source                  1..84
                        mol_type = transcribed RNA
                        organism = Homo sapiens
SEQUENCE: 268
gaggctgggc ggggcgcggc cggatcggtc gagagcgtcc tggctgatga cggtctcccg  60
tgcccacgcc ccaaacgcag tctc                                         84

SEQ ID NO: 269          moltype = RNA  length = 85
FEATURE                 Location/Qualifiers
source                  1..85
                        mol_type = transcribed RNA
                        organism = Homo sapiens
SEQUENCE: 269
tctgaggtac ccggggcaga ttggtgtagg gtgcaaagcc tgcccgcccc ctaagccttc  60
tgccccccaac tccagcctgt cagga                                       85

SEQ ID NO: 270          moltype = RNA  length = 153
FEATURE                 Location/Qualifiers
source                  1..153
                        mol_type = transcribed RNA
                        organism = Homo sapiens
SEQUENCE: 270
gctccgcccc acgtcgcatg cgccccggga acgcgtgggg cggagcttcc ggaggccccg  60
ctctgctgcc gaccctgtgg agcggagggt gaagcctccg gatgccagtc cctcatcgct  120
ggcctggtcg cgctgtggcg aagggggcgg agc                               153

SEQ ID NO: 271          moltype = RNA  length = 153
FEATURE                 Location/Qualifiers
source                  1..153
                        mol_type = transcribed RNA
                        organism = Homo sapiens
SEQUENCE: 271
gctccgcccc acgtcgcatg cgccccggga acgcgtgggg cggagcttcc ggaggccccg  60
ccctgctgcc gaccctgtgg agcggagggt gaagcctccg gatgccagtc cctcatcgct  120
ggcccggtcg cgctgtggcg aagggggcgg agc                               153

SEQ ID NO: 272          moltype = RNA  length = 102
FEATURE                 Location/Qualifiers
source                  1..102
                        mol_type = transcribed RNA
                        organism = Homo sapiens
SEQUENCE: 272
gtgggagggc ccaggcgcgg gcaggggtgg gggtggcaga gcgctgtccc gggggcgggg  60
ccgaagcgcg gcgaccgtaa ctccttctgc tccgtccccc ag                     102

SEQ ID NO: 273          moltype = RNA  length = 71
FEATURE                 Location/Qualifiers
source                  1..71
                        mol_type = transcribed RNA
                        organism = Homo sapiens
SEQUENCE: 273
ggtgagtggg agccggtggg gctggagtaa gggcacgccc ggggctgccc cacctgctga  60
ccaccctccc c                                                       71
```

```
SEQ ID NO: 274         moltype = RNA  length = 75
FEATURE                Location/Qualifiers
source                 1..75
                       mol_type = transcribed RNA
                       organism = Homo sapiens
SEQUENCE: 274
aagcaagact gaggggcctc agaccgagct tttggaaaat agaaaagtct cgctctctgc  60
ccctcagcct aactt                                                   75

SEQ ID NO: 275         moltype = RNA  length = 93
FEATURE                Location/Qualifiers
source                 1..93
                       mol_type = transcribed RNA
                       organism = Homo sapiens
SEQUENCE: 275
tacttatggc accccactcc tggtaccata gtcataagtt aggagatgtt agagctgtga  60
gtaccatgac ttaagtgtgg tggcttaaac atg                               93

SEQ ID NO: 276         moltype = RNA  length = 67
FEATURE                Location/Qualifiers
source                 1..67
                       mol_type = transcribed RNA
                       organism = Homo sapiens
SEQUENCE: 276
tacaggccgg ggctttgggt gagggacccc cggagtctgt cacggtctca ccccaactct  60
gccccag                                                            67

SEQ ID NO: 277         moltype = RNA  length = 72
FEATURE                Location/Qualifiers
source                 1..72
                       mol_type = transcribed RNA
                       organism = Homo sapiens
SEQUENCE: 277
ccaggcacac aggaaaagcg gggccctggg ttcggctgct accccaaagg ccacattctc  60
ctgtgcacac ag                                                      72

SEQ ID NO: 278         moltype = RNA  length = 81
FEATURE                Location/Qualifiers
source                 1..81
                       mol_type = transcribed RNA
                       organism = Homo sapiens
SEQUENCE: 278
ctccctggga gggcgtggat gatggtggga gaggagcccc actgtggaag tctgaccccc  60
acatcgcccc accttcccca g                                            81

SEQ ID NO: 279         moltype = RNA  length = 82
FEATURE                Location/Qualifiers
source                 1..82
                       mol_type = transcribed RNA
                       organism = Homo sapiens
SEQUENCE: 279
gctacgggga gcggggagga agtgggcgct gcttctgcgt tatctggaag gagcagccca  60
ctcctgtcct gggctctgtg gt                                           82

SEQ ID NO: 280         moltype = RNA  length = 76
FEATURE                Location/Qualifiers
source                 1..76
                       mol_type = transcribed RNA
                       organism = Homo sapiens
SEQUENCE: 280
actgactttg agtctctcct cagggtgctg caggcaaagc tggggaccca gggagagacg  60
taagtgaggg gagatg                                                  76

SEQ ID NO: 281         moltype = RNA  length = 73
FEATURE                Location/Qualifiers
source                 1..73
                       mol_type = transcribed RNA
                       organism = Homo sapiens
SEQUENCE: 281
acctttccag ctcatcccac ctctgccacc aaaacactca tcgcggggtc agagggagtg  60
ccaaaaaagg taa                                                     73

SEQ ID NO: 282         moltype = RNA  length = 63
FEATURE                Location/Qualifiers
source                 1..63
                       mol_type = transcribed RNA
                       organism = Homo sapiens
SEQUENCE: 282
```

```
cttgcccggg agaaggaggt ggcctggaga gctgctgtct ccagccgccg cctgtctcca  60
cag                                                                63

SEQ ID NO: 283          moltype = RNA  length = 64
FEATURE                 Location/Qualifiers
source                  1..64
                        mol_type = transcribed RNA
                        organism = Homo sapiens
SEQUENCE: 283
ccccgggccc ggcgttccct ccccttccgt gcgccagtgg aggccggggt ggggcggggc  60
gggg                                                               64

SEQ ID NO: 284          moltype = RNA  length = 64
FEATURE                 Location/Qualifiers
source                  1..64
                        mol_type = transcribed RNA
                        organism = Homo sapiens
SEQUENCE: 284
ccccgggccc ggcgttccct ccccttccgt gcgccagtgg aggccggggt ggggcggggc  60
gggg                                                               64

SEQ ID NO: 285          moltype = RNA  length = 74
FEATURE                 Location/Qualifiers
source                  1..74
                        mol_type = transcribed RNA
                        organism = Homo sapiens
SEQUENCE: 285
gtgcgtggtg gctcgaggcg gggtggggg cctcgccctg cttgggccct ccctgacctc  60
tccgctccgc acag                                                    74

SEQ ID NO: 286          moltype = RNA  length = 66
FEATURE                 Location/Qualifiers
source                  1..66
                        mol_type = transcribed RNA
                        organism = Homo sapiens
SEQUENCE: 286
tgactgggga gcagaaggag aacccaagaa aagctgactt ggaggtccct ccttctgtcc  60
ccacag                                                             66

SEQ ID NO: 287          moltype = RNA  length = 86
FEATURE                 Location/Qualifiers
source                  1..86
                        mol_type = transcribed RNA
                        organism = Homo sapiens
SEQUENCE: 287
cgcctgagcg tgcagcagga catcttcctg acctggtaat aattaggtga gaaggatggt  60
tgggggcggt cggcgtaact caggga                                       86

SEQ ID NO: 288          moltype = RNA  length = 58
FEATURE                 Location/Qualifiers
source                  1..58
                        mol_type = transcribed RNA
                        organism = Homo sapiens
SEQUENCE: 288
agggccagag gagcctggag tggtcgggtc gactgaaccc aggttccctc tggccgca    58

SEQ ID NO: 289          moltype = RNA  length = 85
FEATURE                 Location/Qualifiers
source                  1..85
                        mol_type = transcribed RNA
                        organism = Homo sapiens
SEQUENCE: 289
ggggaggtag ggaaaaggaa gggggaggag aaggtgagac caatgtcctg ggtgccactc  60
ctgcccagtg cctcccttcc tcgtt                                        85

SEQ ID NO: 290          moltype = RNA  length = 51
FEATURE                 Location/Qualifiers
source                  1..51
                        mol_type = transcribed RNA
                        organism = Homo sapiens
SEQUENCE: 290
acagaccccg gggagcccgg cggtgaagct cctggtatcc tgggtgtctg a           51

SEQ ID NO: 291          moltype = RNA  length = 63
FEATURE                 Location/Qualifiers
source                  1..63
                        mol_type = transcribed RNA
                        organism = Homo sapiens
SEQUENCE: 291
```

```
gcatgctggg cgaggctggc atctagcaca ggcggtagat gcttgctctt gccattgcaa  60
tga                                                                63

SEQ ID NO: 292         moltype = RNA  length = 67
FEATURE                Location/Qualifiers
source                 1..67
                       mol_type = transcribed RNA
                       organism = Homo sapiens
SEQUENCE: 292
gtgggagggg agaggcagca agcacacagg gcctgggact agcatgctga cctccctcct  60
gccccag                                                            67

SEQ ID NO: 293         moltype = RNA  length = 70
FEATURE                Location/Qualifiers
source                 1..70
                       mol_type = transcribed RNA
                       organism = Homo sapiens
SEQUENCE: 293
aggacccagc ggggctgggc gcgcggagca gcgctgggtg cagcgcctgc gccggcagct  60
gcaagggccg                                                         70

SEQ ID NO: 294         moltype = RNA  length = 82
FEATURE                Location/Qualifiers
source                 1..82
                       mol_type = transcribed RNA
                       organism = Homo sapiens
SEQUENCE: 294
tgagctgttg gattcggggc cgtagcactg tctgagaggt ttacatttct cacagtgaac  60
cggtctcttt ttcagctgct tc                                           82

SEQ ID NO: 295         moltype = RNA  length = 86
FEATURE                Location/Qualifiers
source                 1..86
                       mol_type = transcribed RNA
                       organism = Homo sapiens
SEQUENCE: 295
attctaggtg gggagactga cggctggagg cccataagct gtctaaaact tcggccccca  60
gatttctggt ctccccactt cagaac                                       86

SEQ ID NO: 296         moltype = RNA  length = 68
FEATURE                Location/Qualifiers
source                 1..68
                       mol_type = transcribed RNA
                       organism = Homo sapiens
SEQUENCE: 296
agggttgggg ggacaggatg agaggctgtc ttcattccct cttgaccacc cctcgtttct  60
tcccccag                                                           68

SEQ ID NO: 297         moltype = RNA  length = 70
FEATURE                Location/Qualifiers
source                 1..70
                       mol_type = transcribed RNA
                       organism = Homo sapiens
SEQUENCE: 297
ggtttctcct tgaggagaca tggtgggggc cggtcaggca gcccatgcca tgtgtcctca  60
tggagaggcc                                                         70

SEQ ID NO: 298         moltype = RNA  length = 65
FEATURE                Location/Qualifiers
source                 1..65
                       mol_type = transcribed RNA
                       organism = Homo sapiens
SEQUENCE: 298
ttctcctggg gagtggctgg ggagcagaca gacccaacct catgctcccc ggcctctgcc  60
cccag                                                              65

SEQ ID NO: 299         moltype = RNA  length = 80
FEATURE                Location/Qualifiers
source                 1..80
                       mol_type = transcribed RNA
                       organism = Homo sapiens
SEQUENCE: 299
gcgtcaagat ggcggcgggg aggtaggcag agcaggacgc cgctgctgcc gccgccaccg  60
ccgcctccgc tccagtcgcc                                              80

SEQ ID NO: 300         moltype = RNA  length = 68
FEATURE                Location/Qualifiers
source                 1..68
                       mol_type = transcribed RNA
```

```
                         organism = Homo sapiens
SEQUENCE: 300
ctcaggctca gtggtgcatg cttatagtcc cagccactct ggaggctgaa ggaagatggc  60
ttgagcct                                                           68

SEQ ID NO: 301           moltype = RNA  length = 61
FEATURE                  Location/Qualifiers
source                   1..61
                         mol_type = transcribed RNA
                         organism = Homo sapiens
SEQUENCE: 301
tctcgtttga tctcggaagc taagcagggt tgggcctggt tagtacttgg atgggaaact  60
t                                                                  61

SEQ ID NO: 302           moltype = RNA  length = 53
FEATURE                  Location/Qualifiers
source                   1..53
                         mol_type = transcribed RNA
                         organism = Homo sapiens
SEQUENCE: 302
gtttgatctc ggaagctaag cagggtcggg cctggttagt acttggatgg gag         53

SEQ ID NO: 303           moltype = RNA  length = 58
FEATURE                  Location/Qualifiers
source                   1..58
                         mol_type = transcribed RNA
                         organism = Homo sapiens
SEQUENCE: 303
gctgaagctc taaggttccg cctgcgggca ggaagcggag gaaccttgga gcttcggc    58

SEQ ID NO: 304           moltype = RNA  length = 88
FEATURE                  Location/Qualifiers
source                   1..88
                         mol_type = transcribed RNA
                         organism = Homo sapiens
SEQUENCE: 304
gtggggccag gcggtggtgg gcactgctgg ggtgggcaca gcagccatgc agagcgggca  60
tttgaccccg tgccaccctt ttccccag                                     88

SEQ ID NO: 305           moltype = RNA  length = 80
FEATURE                  Location/Qualifiers
source                   1..80
                         mol_type = transcribed RNA
                         organism = Homo sapiens
SEQUENCE: 305
ctgcagcgtg cttctccagg ccccgcgcgc ggacagacac acggacaagt cccgccaggg  60
gctgggcgcg cgccagccgg                                              80

SEQ ID NO: 306           moltype = RNA  length = 80
FEATURE                  Location/Qualifiers
source                   1..80
                         mol_type = transcribed RNA
                         organism = Homo sapiens
SEQUENCE: 306
aggacccttc cagagggccc cccctcaatc ctgttgtgcc taattcagag ggttgggtgg  60
aggctctcct gaagggctct                                              80

SEQ ID NO: 307           moltype = RNA  length = 73
FEATURE                  Location/Qualifiers
source                   1..73
                         mol_type = transcribed RNA
                         organism = Homo sapiens
SEQUENCE: 307
aggccaggtg ggtatggagg agccctcata tggcagttgg cgagggccca gtgagcccct  60
ctctgctctc cag                                                     73

SEQ ID NO: 308           moltype = RNA  length = 59
FEATURE                  Location/Qualifiers
source                   1..59
                         mol_type = transcribed RNA
                         organism = Homo sapiens
SEQUENCE: 308
ctgtgtcggg gagtctgggg tccggaattc tccagagcct ctgtgcccct acttcccag   59

SEQ ID NO: 309           moltype = RNA  length = 61
FEATURE                  Location/Qualifiers
source                   1..61
                         mol_type = transcribed RNA
                         organism = Homo sapiens
```

```
SEQUENCE: 309
gagggcagcg tgggtgtggc ggaggcaggc gtgaccgttt gccgccctct cgctgctcta  60
g                                                                   61

SEQ ID NO: 310         moltype = RNA  length = 73
FEATURE                Location/Qualifiers
source                 1..73
                       mol_type = transcribed RNA
                       organism = Homo sapiens
SEQUENCE: 310
ggaggctggg ctgggacgga cacccggcct ccactttctg tggcaggtac ctcctccatg  60
tcggcccgcc ttg                                                      73

SEQ ID NO: 311         moltype = RNA  length = 84
FEATURE                Location/Qualifiers
source                 1..84
                       mol_type = transcribed RNA
                       organism = Homo sapiens
SEQUENCE: 311
ggcccctcct tctcagcccc agctcccgct cacccctgcc acgtcaaagg aggcagaagg  60
ggagttggga gcagagaggg gacc                                          84

SEQ ID NO: 312         moltype = RNA  length = 180
FEATURE                Location/Qualifiers
source                 1..180
                       mol_type = transcribed RNA
                       organism = Homo sapiens
SEQUENCE: 312
cgcgactgcg gcggcggtgg tggggggagc cgcggggatc gccgagggcc ggtcggccgc  60
cccgggtgcc gcgcggtgcc gccggcggcg gtgaggcccc gcgcgtgtgt cccggctgcg  120
gtcggccgcg ctcgaggggt ccccgtggcg tccccttccc cgccggccgc ctttctcgcg  180

SEQ ID NO: 313         moltype = RNA  length = 67
FEATURE                Location/Qualifiers
source                 1..67
                       mol_type = transcribed RNA
                       organism = Homo sapiens
SEQUENCE: 313
gcgccctccc tctctccccg gtgtgcaaat gtgtgtgtgc ggtgttatgc cggacaagag  60
ggaggtg                                                             67

SEQ ID NO: 314         moltype = RNA  length = 61
FEATURE                Location/Qualifiers
source                 1..61
                       mol_type = transcribed RNA
                       organism = Homo sapiens
SEQUENCE: 314
tcacccggtg agggcgggtg gaggaggagg gtccccacca tcagccttca ctgggacggg  60
a                                                                   61

SEQ ID NO: 315         moltype = RNA  length = 59
FEATURE                Location/Qualifiers
source                 1..59
                       mol_type = transcribed RNA
                       organism = Homo sapiens
SEQUENCE: 315
ctccagggag acagtgtgtg aggcctcttg ccatggcctc cctgcccgcc tctctgcag   59

SEQ ID NO: 316         moltype = RNA  length = 61
FEATURE                Location/Qualifiers
source                 1..61
                       mol_type = transcribed RNA
                       organism = Homo sapiens
SEQUENCE: 316
gagggttggg gtggagggcc aaggagctgg gtggggtgcc aagcctctgt ccccacccca  60
g                                                                   61

SEQ ID NO: 317         moltype = RNA  length = 84
FEATURE                Location/Qualifiers
source                 1..84
                       mol_type = transcribed RNA
                       organism = Homo sapiens
SEQUENCE: 317
ccgcagccgc cgcgccgggc ccgggttggc cgctgacccc cgcggggccc ccggcggccg  60
gggcgggggc gggggctgcc ccgg                                          84

SEQ ID NO: 318         moltype = RNA  length = 119
FEATURE                Location/Qualifiers
source                 1..119
```

-continued

```
                        mol_type = transcribed RNA
                        organism = Homo sapiens
SEQUENCE: 318
agcctgcgcc ggagccgggg cctgagcccg ggccgcgcag gccgtgaact cgtcgagctg  60
cgcgtgcggc cggtgctcaa cctgccgggt cctggccccg cgctcccgcg cgccctgga   119

SEQ ID NO: 319          moltype = RNA  length = 64
FEATURE                 Location/Qualifiers
source                  1..64
                        mol_type = transcribed RNA
                        organism = Homo sapiens
SEQUENCE: 319
gaaggcgagg ggtagaagag cacaggggtt ctgataaacc cttctgcctg cattctactc  60
ccag                                                               64

SEQ ID NO: 320          moltype = RNA  length = 75
FEATURE                 Location/Qualifiers
source                  1..75
                        mol_type = transcribed RNA
                        organism = Homo sapiens
SEQUENCE: 320
aggctggcgt gggctgaggg caggaggcct gtggccggtc ccaggcctcc tgcttcctgg  60
gctcaggctc ggttt                                                   75

SEQ ID NO: 321          moltype = RNA  length = 62
FEATURE                 Location/Qualifiers
source                  1..62
                        mol_type = transcribed RNA
                        organism = Homo sapiens
SEQUENCE: 321
ccttctgcgg cagagctggg gtcaccagcc ctcatgtact tgtgacttct cccctgccac  60
ag                                                                 62

SEQ ID NO: 322          moltype = RNA  length = 96
FEATURE                 Location/Qualifiers
source                  1..96
                        mol_type = transcribed RNA
                        organism = Homo sapiens
SEQUENCE: 322
ctcgggaggg gcgggagggg ggtccccggt gctcggatct cgagggtgct tattgttcgg  60
tccgagcctg ggtctccctc ttccccccaa cccccc                            96

SEQ ID NO: 323          moltype = RNA  length = 68
FEATURE                 Location/Qualifiers
source                  1..68
                        mol_type = transcribed RNA
                        organism = Homo sapiens
SEQUENCE: 323
gcatcctgta ctgagctgcc ccgaggccct tcatgctgcc cagctcgggg cagctcagta  60
caggatac                                                           68

SEQ ID NO: 324          moltype = RNA  length = 64
FEATURE                 Location/Qualifiers
source                  1..64
                        mol_type = transcribed RNA
                        organism = Homo sapiens
SEQUENCE: 324
tcctgtactg agctgccccg agctgggcag catgaagggc ctcggggcag ctcagtacag  60
gatg                                                               64

SEQ ID NO: 325          moltype = RNA  length = 90
FEATURE                 Location/Qualifiers
source                  1..90
                        mol_type = transcribed RNA
                        organism = Homo sapiens
SEQUENCE: 325
gtgggtacgg cccagtgggg gggagaggga cacgccctgg gctctgccca gggtgcagcc  60
ggactgactg agcccctgtg ccgcccccag                                   90

SEQ ID NO: 326          moltype = RNA  length = 80
FEATURE                 Location/Qualifiers
source                  1..80
                        mol_type = transcribed RNA
                        organism = Homo sapiens
SEQUENCE: 326
ggcgcgtcgc ccccctcagt ccaccagagc ccggatacct cagaaattcg gctctgggtc  60
tgtggggagc gaaatgcaac                                              80

SEQ ID NO: 327          moltype = RNA  length = 109
```

```
FEATURE                Location/Qualifiers
source                 1..109
                       mol_type = transcribed RNA
                       organism = Homo sapiens
SEQUENCE: 327
ggtcgggctc accatgacac agtgtgagac ctcgggctac aacacaggac ccgggcgctg  60
ctctgacccc tcgtgtcttg tgttgcagcc ggagggacgc aggtccgca             109

SEQ ID NO: 328         moltype = RNA  length = 85
FEATURE                Location/Qualifiers
source                 1..85
                       mol_type = transcribed RNA
                       organism = Homo sapiens
SEQUENCE: 328
tcctccccgg agccaggatg cagctcaagc cacagcaggg tgtttagcgc tcttcagtgg  60
ctccagattg tggcgctggt gcagg                                        85

SEQ ID NO: 329         moltype = RNA  length = 86
FEATURE                Location/Qualifiers
source                 1..86
                       mol_type = transcribed RNA
                       organism = Homo sapiens
SEQUENCE: 329
ggggctgggg gtgtggggag agagagtgca cagccagctc agggattaaa gctctttctc  60
tctctctctc tcccacttcc ctgcag                                       86

SEQ ID NO: 330         moltype = RNA  length = 67
FEATURE                Location/Qualifiers
source                 1..67
                       mol_type = transcribed RNA
                       organism = Homo sapiens
SEQUENCE: 330
gtggcactca aactgtgggg gcactttctg ctctctggtg aaagtgccgc catcttttga  60
gtgttac                                                            67

SEQ ID NO: 331         moltype = RNA  length = 82
FEATURE                Location/Qualifiers
source                 1..82
                       mol_type = transcribed RNA
                       organism = Homo sapiens
SEQUENCE: 331
tgtgggcagg gccctgggga gctgaggctc tgggggtggc cggggctgac cctgggcctc  60
tgctccccag tgtctgaccg cg                                           82

SEQ ID NO: 332         moltype = RNA  length = 94
FEATURE                Location/Qualifiers
source                 1..94
                       mol_type = transcribed RNA
                       organism = Homo sapiens
SEQUENCE: 332
aattcagccc tgccactggc ttatgtcatg accttgggct actcaggctg tctgcacaat  60
gagccagttg gacaggagca gtgccactca actc                              94

SEQ ID NO: 333         moltype = RNA  length = 96
FEATURE                Location/Qualifiers
source                 1..96
                       mol_type = transcribed RNA
                       organism = Homo sapiens
SEQUENCE: 333
cgggccccgg gcgggcggga gggacgggac gcggtgcagt gttgtttttt cccccgccaa  60
tattgcactc gtcccggcct ccggcccccc cggccc                            96

SEQ ID NO: 334         moltype = RNA  length = 79
FEATURE                Location/Qualifiers
source                 1..79
                       mol_type = transcribed RNA
                       organism = Homo sapiens
SEQUENCE: 334
gtgcagatcc ttgggagccc tgttagactc tggattttac acttggagtg aacgggcgcc  60
atcccgaggc tttgcacag                                               79

SEQ ID NO: 335         moltype = RNA  length = 75
FEATURE                Location/Qualifiers
source                 1..75
                       mol_type = transcribed RNA
                       organism = Homo sapiens
SEQUENCE: 335
gtagttgttc tacagaagac ctggatgtgt aggagctaag acacactcca ggggagctgt  60
ggaagcagta acacg                                                   75
```

```
SEQ ID NO: 336          moltype = RNA  length = 80
FEATURE                 Location/Qualifiers
source                  1..80
                        mol_type = transcribed RNA
                        organism = Homo sapiens
SEQUENCE: 336
tgagaggccg caccttgcct tgctgcccgg gccgtgcacc cgtgggcccc agggcgacgc  60
ggcgggggcg gccctagcga                                               80

SEQ ID NO: 337          moltype = RNA  length = 92
FEATURE                 Location/Qualifiers
source                  1..92
                        mol_type = transcribed RNA
                        organism = Homo sapiens
SEQUENCE: 337
gtcagtgtct gggcggacag ctgcaggaaa gggaagacca aggcttgctg tctgtccagt  60
ctgccaccct accctgtctg ttcttgccac ag                                 92

SEQ ID NO: 338          moltype = RNA  length = 115
FEATURE                 Location/Qualifiers
source                  1..115
                        mol_type = transcribed RNA
                        organism = Homo sapiens
SEQUENCE: 338
ggtgccgagg gccgtccggc atcctaggcg ggtcgctgcg gtacctccct cctgtctgtg  60
gcggtgggat cccgtggccg tgttttcctg gtggcccggc cgtgcctgag gtttc       115

SEQ ID NO: 339          moltype = RNA  length = 92
FEATURE                 Location/Qualifiers
source                  1..92
                        mol_type = transcribed RNA
                        organism = Homo sapiens
SEQUENCE: 339
cctgtccctc ctgccctgcg cctgcccagc cctcctgctc tggtgactga ggaccgccag  60
gcaggggctg gtgctgggcg gggggcggcg gg                                 92

SEQ ID NO: 340          moltype = RNA  length = 69
FEATURE                 Location/Qualifiers
source                  1..69
                        mol_type = transcribed RNA
                        organism = Homo sapiens
SEQUENCE: 340
ctttcggcca gcgggacggc atccgaggtg ggctaggctc gggcccgtgg cgggtgcggg  60
ggtgggagg                                                           69

SEQ ID NO: 341          moltype = RNA  length = 62
FEATURE                 Location/Qualifiers
source                  1..62
                        mol_type = transcribed RNA
                        organism = Homo sapiens
SEQUENCE: 341
ggtagggggc gggctccggc gctgggaccc cactagggtg gcgccttggc cccgccccgc  60
cc                                                                  62

SEQ ID NO: 342          moltype = RNA  length = 86
FEATURE                 Location/Qualifiers
source                  1..86
                        mol_type = transcribed RNA
                        organism = Homo sapiens
SEQUENCE: 342
tgccagtctc taggtccctg agacccttta acctgtgagg acatccaggg tcacaggtga  60
ggttcttggg agcctggcgt ctggcc                                        86

SEQ ID NO: 343          moltype = RNA  length = 47
FEATURE                 Location/Qualifiers
source                  1..47
                        mol_type = transcribed RNA
                        organism = Homo sapiens
SEQUENCE: 343
ctcggcgcgg ggcgcgggct ccgggttggg gcgagccaac gccgggg                 47

SEQ ID NO: 344          moltype = RNA  length = 73
FEATURE                 Location/Qualifiers
source                  1..73
                        mol_type = transcribed RNA
                        organism = Homo sapiens
SEQUENCE: 344
gtgggcgggg gcaggtgtgt ggtgggtggt ggcctgcggt gagcagggcc ctcacacctg  60
```

```
cctcgccccc cag                                                       73

SEQ ID NO: 345          moltype = RNA  length = 67
FEATURE                 Location/Qualifiers
source                  1..67
                        mol_type = transcribed RNA
                        organism = Homo sapiens
SEQUENCE: 345
ggcagccagg gggatgggcg agcttgggcc cattcctttc cttaccctac cccccatccc  60
cctgtag                                                              67

SEQ ID NO: 346          moltype = RNA  length = 50
FEATURE                 Location/Qualifiers
source                  1..50
                        mol_type = transcribed RNA
                        organism = Homo sapiens
SEQUENCE: 346
acccgggcgt ggtggtgggg gtgggtgcct gtaattccag ctagttggga             50

SEQ ID NO: 347          moltype = RNA  length = 60
FEATURE                 Location/Qualifiers
source                  1..60
                        mol_type = transcribed RNA
                        organism = Homo sapiens
SEQUENCE: 347
aggcctaggg ggtggcaggc tggccatcag tgtgggctaa ccctgtcctc tccctcccag  60

SEQ ID NO: 348          moltype = RNA  length = 102
FEATURE                 Location/Qualifiers
source                  1..102
                        mol_type = transcribed RNA
                        organism = Homo sapiens
SEQUENCE: 348
tgtgttccct atcctcctta tgtcccaccc ccactcctgt ttgaatattt caccagaaac  60
aggagtgggg ggtgggacgt aaggaggatg ggggaaagaa ca                     102

SEQ ID NO: 349          moltype = RNA  length = 87
FEATURE                 Location/Qualifiers
source                  1..87
                        mol_type = transcribed RNA
                        organism = Homo sapiens
SEQUENCE: 349
gcagggctgg cagggaggct gggaggggct ggctgggtct ggtagtgggc atcagctggc  60
cctcatttct taagacagca cttctgt                                        87

SEQ ID NO: 350          moltype = RNA  length = 81
FEATURE                 Location/Qualifiers
source                  1..81
                        mol_type = transcribed RNA
                        organism = Homo sapiens
SEQUENCE: 350
catcctcctt acgtcccacc ccccactcct gtttctggtg aaatattcaa acaggagtgg  60
gggtgggaca taaggaggat a                                              81

SEQ ID NO: 351          moltype = RNA  length = 66
FEATURE                 Location/Qualifiers
source                  1..66
                        mol_type = transcribed RNA
                        organism = Homo sapiens
SEQUENCE: 351
cagagcaggg cagggaaggt gggagagggg cccagctgac cctcctgtca cccgctcctt  60
gcccag                                                               66

SEQ ID NO: 352          moltype = RNA  length = 73
FEATURE                 Location/Qualifiers
source                  1..73
                        mol_type = transcribed RNA
                        organism = Homo sapiens
SEQUENCE: 352
gaaaacaacc aggtgggctt cccggagggc ggaacaccca gccccagcat ccagggctca  60
cctaccacgt ttg                                                       73

SEQ ID NO: 353          moltype = RNA  length = 89
FEATURE                 Location/Qualifiers
source                  1..89
                        mol_type = transcribed RNA
                        organism = Homo sapiens
SEQUENCE: 353
accatgctgt agtgtgtgta aacatcctac actctcagct gtgagctcaa ggtggctggg  60
```

-continued

```
agagggttgt ttactccttc tgccatgga                                89

SEQ ID NO: 354         moltype = RNA  length = 68
FEATURE                Location/Qualifiers
source                 1..68
                       mol_type = transcribed RNA
                       organism = Homo sapiens
SEQUENCE: 354
gactcggctg cggtggacaa gtccggctcc agaacctgga caccgctcag ccggccgcgg  60
caggggtc                                                       68

SEQ ID NO: 355         moltype = RNA  length = 51
FEATURE                Location/Qualifiers
source                 1..51
                       mol_type = transcribed RNA
                       organism = Homo sapiens
SEQUENCE: 355
agagatgaag cggggggcg gggtcttgct ctattgccta cgctgatctc a           51

SEQ ID NO: 356         moltype = RNA  length = 70
FEATURE                Location/Qualifiers
source                 1..70
                       mol_type = transcribed RNA
                       organism = Homo sapiens
SEQUENCE: 356
acaaatagct tcagggagtc aggggagggc agaaatagat ggccttcccc tgctgggaag  60
aaagtgggtc                                                     70

SEQ ID NO: 357         moltype = RNA  length = 69
FEATURE                Location/Qualifiers
source                 1..69
                       mol_type = transcribed RNA
                       organism = Homo sapiens
SEQUENCE: 357
tggggtaggg gtgggggaat tcaggggtgt cgaactcatg gctgccacct ttgtgtcccc  60
atcctgcag                                                      69

SEQ ID NO: 358         moltype = RNA  length = 72
FEATURE                Location/Qualifiers
source                 1..72
                       mol_type = transcribed RNA
                       organism = Homo sapiens
SEQUENCE: 358
tctcctcgag ggtctctgc ctctacccag gactctttca tgaccaggag gctgaggccc  60
ctcacaggcg gc                                                  72

SEQ ID NO: 359         moltype = RNA  length = 74
FEATURE                Location/Qualifiers
source                 1..74
                       mol_type = transcribed RNA
                       organism = Homo sapiens
SEQUENCE: 359
ccaagggcac accggggatg gcagagggtc gtgggaaagt gttgaccctc gtcaggtccc  60
cggggagccc ctgg                                                74

SEQ ID NO: 360         moltype = RNA  length = 80
FEATURE                Location/Qualifiers
source                 1..80
                       mol_type = transcribed RNA
                       organism = Homo sapiens
SEQUENCE: 360
cctctgtgag aaagggtgtg ggggagaggc tgtcttgtgt ctgtaagtat gccaaactta  60
ttttccccaa ggcagaggga                                          80

SEQ ID NO: 361         moltype = RNA  length = 64
FEATURE                Location/Qualifiers
source                 1..64
                       mol_type = transcribed RNA
                       organism = Homo sapiens
SEQUENCE: 361
tgctctgtag gcatgaggca gggcccaggt tccatgtgat gctgaagctc tgacattcct  60
gcag                                                           64

SEQ ID NO: 362         moltype = RNA  length = 90
FEATURE                Location/Qualifiers
source                 1..90
                       mol_type = transcribed RNA
                       organism = Homo sapiens
SEQUENCE: 362
```

-continued

```
tctaagaaac gcagtggtct ctgaagcctg caggggcagg ccagccctgc actgaacgcc  60
tgttcttgcc aggtggcaga aggttgctgc                                   90

SEQ ID NO: 363          moltype = RNA  length = 106
FEATURE                 Location/Qualifiers
source                  1..106
                        mol_type = transcribed RNA
                        organism = Homo sapiens
SEQUENCE: 363
agaagaatgc ccaaccagcc ctcagttgct acagttccct gttgtttcag ctcgacaaca  60
acaggcggct gtagcaatgg ggggctggat gggcatctca atgtgc                 106

SEQ ID NO: 364          moltype = RNA  length = 71
FEATURE                 Location/Qualifiers
source                  1..71
                        mol_type = transcribed RNA
                        organism = Homo sapiens
SEQUENCE: 364
atggaggggg gtgtggagcc agggggccca ggtctacagc ttctccccgc tccctgcccc  60
catactccca g                                                       71

SEQ ID NO: 365          moltype = RNA  length = 60
FEATURE                 Location/Qualifiers
source                  1..60
                        mol_type = transcribed RNA
                        organism = Homo sapiens
SEQUENCE: 365
ggtgcctcgg gagggcatgg gccaggccac ataatgagcc aaacccctgt ctacccgcag  60

SEQ ID NO: 366          moltype = RNA  length = 65
FEATURE                 Location/Qualifiers
source                  1..65
                        mol_type = transcribed RNA
                        organism = Homo sapiens
SEQUENCE: 366
tgtctgggga tttggagaag tggtgagcgc aggtctttgg caccatctcc cctggtccct  60
tggct                                                              65

SEQ ID NO: 367          moltype = RNA  length = 110
FEATURE                 Location/Qualifiers
source                  1..110
                        mol_type = transcribed RNA
                        organism = Homo sapiens
SEQUENCE: 367
tcacctggcc atgtgacttg tgggcttccc tttgtcatcc ttcgcctagg gctctgagca  60
gggcagggac agcaaagggg tgctcagttg tcacttccca cagcacggag             110

SEQ ID NO: 368          moltype = RNA  length = 93
FEATURE                 Location/Qualifiers
source                  1..93
                        mol_type = transcribed RNA
                        organism = Homo sapiens
SEQUENCE: 368
ccttccggcg tcccaggcgg ggcgccgcgg gaccgccctc gtgtctgtgg cggtgggatc  60
ccgcggccgt gttttcctgg tggcccggcc atg                               93

SEQ ID NO: 369          moltype = RNA  length = 65
FEATURE                 Location/Qualifiers
source                  1..65
                        mol_type = transcribed RNA
                        organism = Homo sapiens
SEQUENCE: 369
agccctgggg gtggtctcta gccaaggctc tggggtctca cccttggctg gtctctgctc  60
cgcag                                                              65

SEQ ID NO: 370          moltype = RNA  length = 61
FEATURE                 Location/Qualifiers
source                  1..61
                        mol_type = transcribed RNA
                        organism = Homo sapiens
SEQUENCE: 370
tccgctctgt ggagtggggt gcctgtcccc tgccactggg tgacccaccc ctctccacca  60
g                                                                  61

SEQ ID NO: 371          moltype = RNA  length = 64
FEATURE                 Location/Qualifiers
source                  1..64
                        mol_type = transcribed RNA
                        organism = Homo sapiens
```

```
SEQUENCE: 371
gagctctggg aggggctggg tttggcagga cagtttccaa gccctgtctc ctcccatctt  60
ccag                                                                64

SEQ ID NO: 372          moltype = RNA  length = 21
FEATURE                 Location/Qualifiers
source                  1..21
                        mol_type = transcribed RNA
                        organism = Homo sapiens
SEQUENCE: 372
gttggaggcg tgggttttag a                                             21

SEQ ID NO: 373          moltype = RNA  length = 15
FEATURE                 Location/Qualifiers
source                  1..15
                        mol_type = transcribed RNA
                        organism = Homo sapiens
SEQUENCE: 373
gttggaggcg tgggt                                                    15

SEQ ID NO: 374          moltype = RNA  length = 22
FEATURE                 Location/Qualifiers
source                  1..22
                        mol_type = transcribed RNA
                        organism = Homo sapiens
SEQUENCE: 374
cgcggcgggg acggcgattg gt                                            22

SEQ ID NO: 375          moltype = RNA  length = 17
FEATURE                 Location/Qualifiers
source                  1..17
                        mol_type = transcribed RNA
                        organism = Homo sapiens
SEQUENCE: 375
cggcggggac ggcgatt                                                  17

SEQ ID NO: 376          moltype = RNA  length = 23
FEATURE                 Location/Qualifiers
source                  1..23
                        mol_type = transcribed RNA
                        organism = Homo sapiens
SEQUENCE: 376
ggaggcgcag gctcggaaag gcg                                           23

SEQ ID NO: 377          moltype = RNA  length = 15
FEATURE                 Location/Qualifiers
source                  1..15
                        mol_type = transcribed RNA
                        organism = Homo sapiens
SEQUENCE: 377
gcaggctcgg aaagg                                                    15

SEQ ID NO: 378          moltype = RNA  length = 26
FEATURE                 Location/Qualifiers
source                  1..26
                        mol_type = transcribed RNA
                        organism = Homo sapiens
SEQUENCE: 378
ccttctggag aggctttgtg cggata                                        26

SEQ ID NO: 379          moltype = RNA  length = 15
FEATURE                 Location/Qualifiers
source                  1..15
                        mol_type = transcribed RNA
                        organism = Homo sapiens
SEQUENCE: 379
ccttctggag aggct                                                    15

SEQ ID NO: 380          moltype = RNA  length = 15
FEATURE                 Location/Qualifiers
source                  1..15
                        mol_type = transcribed RNA
                        organism = Homo sapiens
SEQUENCE: 380
tctgggcgag gggtg                                                    15

SEQ ID NO: 381          moltype = RNA  length = 15
FEATURE                 Location/Qualifiers
source                  1..15
```

```
                         mol_type = transcribed RNA
                         organism = Homo sapiens
SEQUENCE: 381
tctgggcgag gggtg                                                   15

SEQ ID NO: 382           moltype = RNA  length = 23
FEATURE                  Location/Qualifiers
source                   1..23
                         mol_type = transcribed RNA
                         organism = Homo sapiens
SEQUENCE: 382
ctcctggggc ccgcactctc gct                                          23

SEQ ID NO: 383           moltype = RNA  length = 18
FEATURE                  Location/Qualifiers
source                   1..18
                         mol_type = transcribed RNA
                         organism = Homo sapiens
SEQUENCE: 383
ctcctggggc ccgcactc                                                18

SEQ ID NO: 384           moltype = RNA  length = 20
FEATURE                  Location/Qualifiers
source                   1..20
                         mol_type = transcribed RNA
                         organism = Homo sapiens
SEQUENCE: 384
aagacacatt tggagaggga                                              20

SEQ ID NO: 385           moltype = RNA  length = 16
FEATURE                  Location/Qualifiers
source                   1..16
                         mol_type = transcribed RNA
                         organism = Homo sapiens
SEQUENCE: 385
agacacattt ggagag                                                  16

SEQ ID NO: 386           moltype = RNA  length = 20
FEATURE                  Location/Qualifiers
source                   1..20
                         mol_type = transcribed RNA
                         organism = Homo sapiens
SEQUENCE: 386
tgagtggggc tcccgggacg                                              20

SEQ ID NO: 387           moltype = RNA  length = 20
FEATURE                  Location/Qualifiers
source                   1..20
                         mol_type = transcribed RNA
                         organism = Homo sapiens
SEQUENCE: 387
tgagtggggc tcccgggacg                                              20

SEQ ID NO: 388           moltype = RNA  length = 24
FEATURE                  Location/Qualifiers
source                   1..24
                         mol_type = transcribed RNA
                         organism = Homo sapiens
SEQUENCE: 388
tcgaggactg gtggaagggc cttt                                         24

SEQ ID NO: 389           moltype = RNA  length = 16
FEATURE                  Location/Qualifiers
source                   1..16
                         mol_type = transcribed RNA
                         organism = Homo sapiens
SEQUENCE: 389
tcgaggactg gtggaa                                                  16

SEQ ID NO: 390           moltype = RNA  length = 25
FEATURE                  Location/Qualifiers
source                   1..25
                         mol_type = transcribed RNA
                         organism = Homo sapiens
SEQUENCE: 390
gggtggggat ttgttgcatt acttg                                        25

SEQ ID NO: 391           moltype = RNA  length = 20
FEATURE                  Location/Qualifiers
```

```
source                  1..20
                        mol_type = transcribed RNA
                        organism = Homo sapiens
SEQUENCE: 391
gggtggggat ttgttgcatt                                                20

SEQ ID NO: 392          moltype = RNA  length = 20
FEATURE                 Location/Qualifiers
source                  1..20
                        mol_type = transcribed RNA
                        organism = Homo sapiens
SEQUENCE: 392
ggctccttgg tctaggggta                                                20

SEQ ID NO: 393          moltype = RNA  length = 15
FEATURE                 Location/Qualifiers
source                  1..15
                        mol_type = transcribed RNA
                        organism = Homo sapiens
SEQUENCE: 393
cttggtctag gggta                                                     15

SEQ ID NO: 394          moltype = RNA  length = 23
FEATURE                 Location/Qualifiers
source                  1..23
                        mol_type = transcribed RNA
                        organism = Homo sapiens
SEQUENCE: 394
ctagtggaag aagatggcgg aag                                            23

SEQ ID NO: 395          moltype = RNA  length = 15
FEATURE                 Location/Qualifiers
source                  1..15
                        mol_type = transcribed RNA
                        organism = Homo sapiens
SEQUENCE: 395
tagtggaaga agatg                                                     15

SEQ ID NO: 396          moltype = RNA  length = 23
FEATURE                 Location/Qualifiers
source                  1..23
                        mol_type = transcribed RNA
                        organism = Homo sapiens
SEQUENCE: 396
acagcagggc tggggattgc agt                                            23

SEQ ID NO: 397          moltype = RNA  length = 19
FEATURE                 Location/Qualifiers
source                  1..19
                        mol_type = transcribed RNA
                        organism = Homo sapiens
SEQUENCE: 397
tgctgctccc agtcctgcc                                                 19

SEQ ID NO: 398          moltype = RNA  length = 25
FEATURE                 Location/Qualifiers
source                  1..25
                        mol_type = transcribed RNA
                        organism = Homo sapiens
SEQUENCE: 398
tggcggcggt agttatgggc ttctc                                          25

SEQ ID NO: 399          moltype = RNA  length = 25
FEATURE                 Location/Qualifiers
source                  1..25
                        mol_type = transcribed RNA
                        organism = Homo sapiens
SEQUENCE: 399
tggcggcggt agttatgggc ttctc                                          25

SEQ ID NO: 400          moltype = RNA  length = 20
FEATURE                 Location/Qualifiers
source                  1..20
                        mol_type = transcribed RNA
                        organism = Homo sapiens
SEQUENCE: 400
taggatgggg gtgagaggtg                                                20

SEQ ID NO: 401          moltype = RNA  length = 18
```

```
FEATURE                Location/Qualifiers
source                 1..18
                       mol_type = transcribed RNA
                       organism = Homo sapiens
SEQUENCE: 401
taggatgggg gtgagagg                                                18

SEQ ID NO: 402         moltype = RNA  length = 21
FEATURE                Location/Qualifiers
source                 1..21
                       mol_type = transcribed RNA
                       organism = Homo sapiens
SEQUENCE: 402
cagcctgagt gacagagcaa g                                            21

SEQ ID NO: 403         moltype = RNA  length = 15
FEATURE                Location/Qualifiers
source                 1..15
                       mol_type = transcribed RNA
                       organism = Homo sapiens
SEQUENCE: 403
actgcactcc agcct                                                   15

SEQ ID NO: 404         moltype = RNA  length = 23
FEATURE                Location/Qualifiers
source                 1..23
                       mol_type = transcribed RNA
                       organism = Homo sapiens
SEQUENCE: 404
aggaggggtc ccgcactggg agg                                          23

SEQ ID NO: 405         moltype = RNA  length = 15
FEATURE                Location/Qualifiers
source                 1..15
                       mol_type = transcribed RNA
                       organism = Homo sapiens
SEQUENCE: 405
tgggaggggc cctca                                                   15

SEQ ID NO: 406         moltype = RNA  length = 23
FEATURE                Location/Qualifiers
source                 1..23
                       mol_type = transcribed RNA
                       organism = Homo sapiens
SEQUENCE: 406
gggggccgat acactgtacg aga                                          23

SEQ ID NO: 407         moltype = RNA  length = 20
FEATURE                Location/Qualifiers
source                 1..20
                       mol_type = transcribed RNA
                       organism = Homo sapiens
SEQUENCE: 407
gggggccgat acactgtacg                                              20

SEQ ID NO: 408         moltype = RNA  length = 23
FEATURE                Location/Qualifiers
source                 1..23
                       mol_type = transcribed RNA
                       organism = Homo sapiens
SEQUENCE: 408
ggtgggtgag gtcgggcccc aag                                          23

SEQ ID NO: 409         moltype = RNA  length = 20
FEATURE                Location/Qualifiers
source                 1..20
                       mol_type = transcribed RNA
                       organism = Homo sapiens
SEQUENCE: 409
cggggtgggt gaggtcgggc                                              20

SEQ ID NO: 410         moltype = RNA  length = 23
FEATURE                Location/Qualifiers
source                 1..23
                       mol_type = transcribed RNA
                       organism = Homo sapiens
SEQUENCE: 410
agaagaaggc ggtcggtctg cgg                                          23
```

```
SEQ ID NO: 411          moltype = RNA  length = 21
FEATURE                 Location/Qualifiers
source                  1..21
                        mol_type = transcribed RNA
                        organism = Homo sapiens
SEQUENCE: 411
aagaaggcgg tcggtctgcg g                                              21

SEQ ID NO: 412          moltype = RNA  length = 17
FEATURE                 Location/Qualifiers
source                  1..17
                        mol_type = transcribed RNA
                        organism = Homo sapiens
SEQUENCE: 412
ggtgagcgct cgctggc                                                   17

SEQ ID NO: 413          moltype = RNA  length = 15
FEATURE                 Location/Qualifiers
source                  1..15
                        mol_type = transcribed RNA
                        organism = Homo sapiens
SEQUENCE: 413
cggtgagcgc tcgct                                                     15

SEQ ID NO: 414          moltype = RNA  length = 16
FEATURE                 Location/Qualifiers
source                  1..16
                        mol_type = transcribed RNA
                        organism = Homo sapiens
SEQUENCE: 414
tgctggtgat gctttc                                                    16

SEQ ID NO: 415          moltype = RNA  length = 16
FEATURE                 Location/Qualifiers
source                  1..16
                        mol_type = transcribed RNA
                        organism = Homo sapiens
SEQUENCE: 415
tgctggtgat gctttc                                                    16

SEQ ID NO: 416          moltype = RNA  length = 23
FEATURE                 Location/Qualifiers
source                  1..23
                        mol_type = transcribed RNA
                        organism = Homo sapiens
SEQUENCE: 416
gccccggcgc gggcgggttc tgg                                            23

SEQ ID NO: 417          moltype = RNA  length = 16
FEATURE                 Location/Qualifiers
source                  1..16
                        mol_type = transcribed RNA
                        organism = Homo sapiens
SEQUENCE: 417
ggagccccgg cgcggg                                                    16

SEQ ID NO: 418          moltype = RNA  length = 21
FEATURE                 Location/Qualifiers
source                  1..21
                        mol_type = transcribed RNA
                        organism = Homo sapiens
SEQUENCE: 418
cggatccgag tcacggcacc a                                              21

SEQ ID NO: 419          moltype = RNA  length = 15
FEATURE                 Location/Qualifiers
source                  1..15
                        mol_type = transcribed RNA
                        organism = Homo sapiens
SEQUENCE: 419
ggatccgagt cacgg                                                     15

SEQ ID NO: 420          moltype = RNA  length = 23
FEATURE                 Location/Qualifiers
source                  1..23
                        mol_type = transcribed RNA
                        organism = Homo sapiens
SEQUENCE: 420
ggggggatgt gcatgctggt tgg                                            23
```

```
SEQ ID NO: 421         moltype = RNA  length = 15
FEATURE                Location/Qualifiers
source                 1..15
                       mol_type = transcribed RNA
                       organism = Homo sapiens
SEQUENCE: 421
atcagcgtgc acttc                                                   15

SEQ ID NO: 422         moltype = RNA  length = 17
FEATURE                Location/Qualifiers
source                 1..17
                       mol_type = transcribed RNA
                       organism = Homo sapiens
SEQUENCE: 422
tcctagtcac ggcacca                                                 17

SEQ ID NO: 423         moltype = RNA  length = 17
FEATURE                Location/Qualifiers
source                 1..17
                       mol_type = transcribed RNA
                       organism = Homo sapiens
SEQUENCE: 423
tcctagtcac ggcacca                                                 17

SEQ ID NO: 424         moltype = RNA  length = 25
FEATURE                Location/Qualifiers
source                 1..25
                       mol_type = transcribed RNA
                       organism = Homo sapiens
SEQUENCE: 424
tgcggggcta gggctaacag cagtc                                        25

SEQ ID NO: 425         moltype = RNA  length = 15
FEATURE                Location/Qualifiers
source                 1..15
                       mol_type = transcribed RNA
                       organism = Homo sapiens
SEQUENCE: 425
tgcggggcta gggct                                                   15

SEQ ID NO: 426         moltype = RNA  length = 21
FEATURE                Location/Qualifiers
source                 1..21
                       mol_type = transcribed RNA
                       organism = Homo sapiens
SEQUENCE: 426
cccaggctgg agcgagtgca g                                            21

SEQ ID NO: 427         moltype = RNA  length = 15
FEATURE                Location/Qualifiers
source                 1..15
                       mol_type = transcribed RNA
                       organism = Homo sapiens
SEQUENCE: 427
agctcactgc agcct                                                   15

SEQ ID NO: 428         moltype = RNA  length = 22
FEATURE                Location/Qualifiers
source                 1..22
                       mol_type = transcribed RNA
                       organism = Homo sapiens
SEQUENCE: 428
tgtgggactg caaatgggag ct                                           22

SEQ ID NO: 429         moltype = RNA  length = 22
FEATURE                Location/Qualifiers
source                 1..22
                       mol_type = transcribed RNA
                       organism = Homo sapiens
SEQUENCE: 429
tgtgggactg caaatgggag ct                                           22

SEQ ID NO: 430         moltype = RNA  length = 26
FEATURE                Location/Qualifiers
source                 1..26
                       mol_type = transcribed RNA
                       organism = Homo sapiens
SEQUENCE: 430
```

```
gcgggctgtc cggaggggtc ggcttt                                          26

SEQ ID NO: 431         moltype = RNA  length = 16
FEATURE                Location/Qualifiers
source                 1..16
                       mol_type = transcribed RNA
                       organism = Homo sapiens
SEQUENCE: 431
gctgtccgga ggggtc                                                     16

SEQ ID NO: 432         moltype = RNA  length = 22
FEATURE                Location/Qualifiers
source                 1..22
                       mol_type = transcribed RNA
                       organism = Homo sapiens
SEQUENCE: 432
ccgggaacgt cgagactgga gc                                              22

SEQ ID NO: 433         moltype = RNA  length = 15
FEATURE                Location/Qualifiers
source                 1..15
                       mol_type = transcribed RNA
                       organism = Homo sapiens
SEQUENCE: 433
cgggaacgtc gagac                                                      15

SEQ ID NO: 434         moltype = RNA  length = 17
FEATURE                Location/Qualifiers
source                 1..17
                       mol_type = transcribed RNA
                       organism = Homo sapiens
SEQUENCE: 434
cctccgggac ggctggg                                                    17

SEQ ID NO: 435         moltype = RNA  length = 15
FEATURE                Location/Qualifiers
source                 1..15
                       mol_type = transcribed RNA
                       organism = Homo sapiens
SEQUENCE: 435
ctccgggacg gctgg                                                      15

SEQ ID NO: 436         moltype = RNA  length = 21
FEATURE                Location/Qualifiers
source                 1..21
                       mol_type = transcribed RNA
                       organism = Homo sapiens
SEQUENCE: 436
cccagcagga cgggagcgcg g                                               21

SEQ ID NO: 437         moltype = RNA  length = 16
FEATURE                Location/Qualifiers
source                 1..16
                       mol_type = transcribed RNA
                       organism = Homo sapiens
SEQUENCE: 437
aagctgggtc aaggag                                                     16

SEQ ID NO: 438         moltype = RNA  length = 22
FEATURE                Location/Qualifiers
source                 1..22
                       mol_type = transcribed RNA
                       organism = Homo sapiens
SEQUENCE: 438
ctgggctcgg gacgcgcggc tc                                              22

SEQ ID NO: 439         moltype = RNA  length = 19
FEATURE                Location/Qualifiers
source                 1..19
                       mol_type = transcribed RNA
                       organism = Homo sapiens
SEQUENCE: 439
ctgggctcgg gacgcgcgg                                                  19

SEQ ID NO: 440         moltype = RNA  length = 29
FEATURE                Location/Qualifiers
source                 1..29
                       mol_type = transcribed RNA
                       organism = Homo sapiens
```

```
SEQUENCE: 440
ggtcaggcgg ctcggactga gcaggtggg                                   29

SEQ ID NO: 441          moltype = RNA  length = 15
FEATURE                 Location/Qualifiers
source                  1..15
                        mol_type = transcribed RNA
                        organism = Homo sapiens
SEQUENCE: 441
agagtgtggt caggc                                                  15

SEQ ID NO: 442          moltype = RNA  length = 23
FEATURE                 Location/Qualifiers
source                  1..23
                        mol_type = transcribed RNA
                        organism = Homo sapiens
SEQUENCE: 442
cagcccgccc cagccgaggt tct                                         23

SEQ ID NO: 443          moltype = RNA  length = 17
FEATURE                 Location/Qualifiers
source                  1..17
                        mol_type = transcribed RNA
                        organism = Homo sapiens
SEQUENCE: 443
agcccgcccc agccgag                                                17

SEQ ID NO: 444          moltype = RNA  length = 23
FEATURE                 Location/Qualifiers
source                  1..23
                        mol_type = transcribed RNA
                        organism = Homo sapiens
SEQUENCE: 444
agggtcgggg cagggagggc agg                                         23

SEQ ID NO: 445          moltype = RNA  length = 15
FEATURE                 Location/Qualifiers
source                  1..15
                        mol_type = transcribed RNA
                        organism = Homo sapiens
SEQUENCE: 445
gggagaaggg tcggg                                                  15

SEQ ID NO: 446          moltype = RNA  length = 21
FEATURE                 Location/Qualifiers
source                  1..21
                        mol_type = transcribed RNA
                        organism = Homo sapiens
SEQUENCE: 446
atccagttct ctgagggggc t                                           21

SEQ ID NO: 447          moltype = RNA  length = 21
FEATURE                 Location/Qualifiers
source                  1..21
                        mol_type = transcribed RNA
                        organism = Homo sapiens
SEQUENCE: 447
atccagttct ctgagggggc t                                           21

SEQ ID NO: 448          moltype = RNA  length = 16
FEATURE                 Location/Qualifiers
source                  1..16
                        mol_type = transcribed RNA
                        organism = Homo sapiens
SEQUENCE: 448
gtgaaggccc ggcgga                                                 16

SEQ ID NO: 449          moltype = RNA  length = 15
FEATURE                 Location/Qualifiers
source                  1..15
                        mol_type = transcribed RNA
                        organism = Homo sapiens
SEQUENCE: 449
gtgaaggccc ggcgg                                                  15

SEQ ID NO: 450          moltype = RNA  length = 23
FEATURE                 Location/Qualifiers
source                  1..23
                        mol_type = transcribed RNA
```

```
                         organism = Homo sapiens
SEQUENCE: 450
ccagggctgg cagtgacatg ggt                                              23

SEQ ID NO: 451           moltype = RNA  length = 19
FEATURE                  Location/Qualifiers
source                   1..19
                         mol_type = transcribed RNA
                         organism = Homo sapiens
SEQUENCE: 451
cagggctggc agtgacatg                                                   19

SEQ ID NO: 452           moltype = RNA  length = 21
FEATURE                  Location/Qualifiers
source                   1..21
                         mol_type = transcribed RNA
                         organism = Homo sapiens
SEQUENCE: 452
gccgggcgtg gtggtggggg c                                                21

SEQ ID NO: 453           moltype = RNA  length = 15
FEATURE                  Location/Qualifiers
source                   1..15
                         mol_type = transcribed RNA
                         organism = Homo sapiens
SEQUENCE: 453
tagccgggcg tggtg                                                       15

SEQ ID NO: 454           moltype = RNA  length = 21
FEATURE                  Location/Qualifiers
source                   1..21
                         mol_type = transcribed RNA
                         organism = Homo sapiens
SEQUENCE: 454
ccggccgccg gctccgcccc g                                                21

SEQ ID NO: 455           moltype = RNA  length = 17
FEATURE                  Location/Qualifiers
source                   1..17
                         mol_type = transcribed RNA
                         organism = Homo sapiens
SEQUENCE: 455
ccggccgccg gctccgc                                                     17

SEQ ID NO: 456           moltype = RNA  length = 23
FEATURE                  Location/Qualifiers
source                   1..23
                         mol_type = transcribed RNA
                         organism = Homo sapiens
SEQUENCE: 456
tgaggatatg gcagggaagg gga                                              23

SEQ ID NO: 457           moltype = RNA  length = 19
FEATURE                  Location/Qualifiers
source                   1..19
                         mol_type = transcribed RNA
                         organism = Homo sapiens
SEQUENCE: 457
tgaggatatg gcagggaag                                                   19

SEQ ID NO: 458           moltype = RNA  length = 21
FEATURE                  Location/Qualifiers
source                   1..21
                         mol_type = transcribed RNA
                         organism = Homo sapiens
SEQUENCE: 458
aggaggcagt gggcgagcag g                                                21

SEQ ID NO: 459           moltype = RNA  length = 21
FEATURE                  Location/Qualifiers
source                   1..21
                         mol_type = transcribed RNA
                         organism = Homo sapiens
SEQUENCE: 459
aggaggcagt gggcgagcag g                                                21

SEQ ID NO: 460           moltype = RNA  length = 24
FEATURE                  Location/Qualifiers
source                   1..24
```

```
                      mol_type = transcribed RNA
                      organism = Homo sapiens
SEQUENCE: 460
gatcggtcga gagcgtcctg gctg                                          24

SEQ ID NO: 461        moltype = RNA  length = 15
FEATURE               Location/Qualifiers
source                1..15
                      mol_type = transcribed RNA
                      organism = Homo sapiens
SEQUENCE: 461
gctgggcggg gcgcg                                                    15

SEQ ID NO: 462        moltype = RNA  length = 24
FEATURE               Location/Qualifiers
source                1..24
                      mol_type = transcribed RNA
                      organism = Homo sapiens
SEQUENCE: 462
cccggggcag attggtgtag ggtg                                          24

SEQ ID NO: 463        moltype = RNA  length = 17
FEATURE               Location/Qualifiers
source                1..17
                      mol_type = transcribed RNA
                      organism = Homo sapiens
SEQUENCE: 463
cggggcagat tggtgta                                                  17

SEQ ID NO: 464        moltype = RNA  length = 23
FEATURE               Location/Qualifiers
source                1..23
                      mol_type = transcribed RNA
                      organism = Homo sapiens
SEQUENCE: 464
tggggcggag cttccggagg ccc                                           23

SEQ ID NO: 465        moltype = RNA  length = 16
FEATURE               Location/Qualifiers
source                1..16
                      mol_type = transcribed RNA
                      organism = Homo sapiens
SEQUENCE: 465
atcgctggcc tggtcg                                                   16

SEQ ID NO: 466        moltype = RNA  length = 15
FEATURE               Location/Qualifiers
source                1..15
                      mol_type = transcribed RNA
                      organism = Homo sapiens
SEQUENCE: 466
tggcagagcg ctgtc                                                    15

SEQ ID NO: 467        moltype = RNA  length = 15
FEATURE               Location/Qualifiers
source                1..15
                      mol_type = transcribed RNA
                      organism = Homo sapiens
SEQUENCE: 467
tggcagagcg ctgtc                                                    15

SEQ ID NO: 468        moltype = RNA  length = 24
FEATURE               Location/Qualifiers
source                1..24
                      mol_type = transcribed RNA
                      organism = Homo sapiens
SEQUENCE: 468
gtgagtggga gccggtgggg ctgg                                          24

SEQ ID NO: 469        moltype = RNA  length = 15
FEATURE               Location/Qualifiers
source                1..15
                      mol_type = transcribed RNA
                      organism = Homo sapiens
SEQUENCE: 469
ggggctggag taagg                                                    15

SEQ ID NO: 470        moltype = RNA  length = 22
FEATURE               Location/Qualifiers
```

```
source                 1..22
                       mol_type = transcribed RNA
                       organism = Homo sapiens
SEQUENCE: 470
accccactcc tggtaccata gt                                                    22

SEQ ID NO: 471         moltype = RNA  length = 15
FEATURE                Location/Qualifiers
source                 1..15
                       mol_type = transcribed RNA
                       organism = Homo sapiens
SEQUENCE: 471
accccactcc tggta                                                            15

SEQ ID NO: 472         moltype = RNA  length = 25
FEATURE                Location/Qualifiers
source                 1..25
                       mol_type = transcribed RNA
                       organism = Homo sapiens
SEQUENCE: 472
agcggggagg aagtgggcgc tgctt                                                 25

SEQ ID NO: 473         moltype = RNA  length = 21
FEATURE                Location/Qualifiers
source                 1..21
                       mol_type = transcribed RNA
                       organism = Homo sapiens
SEQUENCE: 473
agcggggagg aagtgggcgc t                                                     21

SEQ ID NO: 474         moltype = RNA  length = 16
FEATURE                Location/Qualifiers
source                 1..16
                       mol_type = transcribed RNA
                       organism = Homo sapiens
SEQUENCE: 474
ggacccaggg agagac                                                           16

SEQ ID NO: 475         moltype = RNA  length = 16
FEATURE                Location/Qualifiers
source                 1..16
                       mol_type = transcribed RNA
                       organism = Homo sapiens
SEQUENCE: 475
ggacccaggg agagac                                                           16

SEQ ID NO: 476         moltype = RNA  length = 20
FEATURE                Location/Qualifiers
source                 1..20
                       mol_type = transcribed RNA
                       organism = Homo sapiens
SEQUENCE: 476
atcccacctc tgccaccaaa                                                       20

SEQ ID NO: 477         moltype = RNA  length = 15
FEATURE                Location/Qualifiers
source                 1..15
                       mol_type = transcribed RNA
                       organism = Homo sapiens
SEQUENCE: 477
atcccacctc tgcca                                                            15

SEQ ID NO: 478         moltype = RNA  length = 16
FEATURE                Location/Qualifiers
source                 1..16
                       mol_type = transcribed RNA
                       organism = Homo sapiens
SEQUENCE: 478
cgggcccggc gttccc                                                           16

SEQ ID NO: 479         moltype = RNA  length = 15
FEATURE                Location/Qualifiers
source                 1..15
                       mol_type = transcribed RNA
                       organism = Homo sapiens
SEQUENCE: 479
ccgggcccgg cgttc                                                            15

SEQ ID NO: 480         moltype = RNA  length = 24
```

```
FEATURE                Location/Qualifiers
source                 1..24
                       mol_type = transcribed RNA
                       organism = Homo sapiens
SEQUENCE: 480
tgactgggga gcagaaggag aacc                                          24

SEQ ID NO: 481         moltype = RNA  length = 15
FEATURE                Location/Qualifiers
source                 1..15
                       mol_type = transcribed RNA
                       organism = Homo sapiens
SEQUENCE: 481
gactggggag cagaa                                                    15

SEQ ID NO: 482         moltype = RNA  length = 27
FEATURE                Location/Qualifiers
source                 1..27
                       mol_type = transcribed RNA
                       organism = Homo sapiens
SEQUENCE: 482
agggccagag gagcctggag tggtcgg                                       27

SEQ ID NO: 483         moltype = RNA  length = 23
FEATURE                Location/Qualifiers
source                 1..23
                       mol_type = transcribed RNA
                       organism = Homo sapiens
SEQUENCE: 483
agggccagag gagcctggag tgg                                           23

SEQ ID NO: 484         moltype = RNA  length = 18
FEATURE                Location/Qualifiers
source                 1..18
                       mol_type = transcribed RNA
                       organism = Homo sapiens
SEQUENCE: 484
aaaaggaagg gggaggag                                                 18

SEQ ID NO: 485         moltype = RNA  length = 16
FEATURE                Location/Qualifiers
source                 1..16
                       mol_type = transcribed RNA
                       organism = Homo sapiens
SEQUENCE: 485
aaggaagggg gaggag                                                   16

SEQ ID NO: 486         moltype = RNA  length = 20
FEATURE                Location/Qualifiers
source                 1..20
                       mol_type = transcribed RNA
                       organism = Homo sapiens
SEQUENCE: 486
ccccggggag cccggcggtg                                               20

SEQ ID NO: 487         moltype = RNA  length = 15
FEATURE                Location/Qualifiers
source                 1..15
                       mol_type = transcribed RNA
                       organism = Homo sapiens
SEQUENCE: 487
accccgggga gcccg                                                    15

SEQ ID NO: 488         moltype = RNA  length = 19
FEATURE                Location/Qualifiers
source                 1..19
                       mol_type = transcribed RNA
                       organism = Homo sapiens
SEQUENCE: 488
gctgggcgag gctggcatc                                                19

SEQ ID NO: 489         moltype = RNA  length = 17
FEATURE                Location/Qualifiers
source                 1..17
                       mol_type = transcribed RNA
                       organism = Homo sapiens
SEQUENCE: 489
gctgggcgag gctggca                                                  17
```

-continued

```
SEQ ID NO: 490          moltype = RNA  length = 22
FEATURE                 Location/Qualifiers
source                  1..22
                        mol_type = transcribed RNA
                        organism = Homo sapiens
SEQUENCE: 490
tgggagggga gaggcagcaa gc                                            22

SEQ ID NO: 491          moltype = RNA  length = 22
FEATURE                 Location/Qualifiers
source                  1..22
                        mol_type = transcribed RNA
                        organism = Homo sapiens
SEQUENCE: 491
tgggagggga gaggcagcaa gc                                            22

SEQ ID NO: 492          moltype = RNA  length = 18
FEATURE                 Location/Qualifiers
source                  1..18
                        mol_type = transcribed RNA
                        organism = Homo sapiens
SEQUENCE: 492
cagcggggct gggcgcgc                                                 18

SEQ ID NO: 493          moltype = RNA  length = 15
FEATURE                 Location/Qualifiers
source                  1..15
                        mol_type = transcribed RNA
                        organism = Homo sapiens
SEQUENCE: 493
cagcggggct gggcg                                                    15

SEQ ID NO: 494          moltype = RNA  length = 23
FEATURE                 Location/Qualifiers
source                  1..23
                        mol_type = transcribed RNA
                        organism = Homo sapiens
SEQUENCE: 494
cggggccgta gcactgtctg aga                                           23

SEQ ID NO: 495          moltype = RNA  length = 20
FEATURE                 Location/Qualifiers
source                  1..20
                        mol_type = transcribed RNA
                        organism = Homo sapiens
SEQUENCE: 495
cggggccgta gcactgtctg                                               20

SEQ ID NO: 496          moltype = RNA  length = 18
FEATURE                 Location/Qualifiers
source                  1..18
                        mol_type = transcribed RNA
                        organism = Homo sapiens
SEQUENCE: 496
tctaggtggg gagactga                                                 18

SEQ ID NO: 497          moltype = RNA  length = 16
FEATURE                 Location/Qualifiers
source                  1..16
                        mol_type = transcribed RNA
                        organism = Homo sapiens
SEQUENCE: 497
gtggggagac tgacgg                                                   16

SEQ ID NO: 498          moltype = RNA  length = 21
FEATURE                 Location/Qualifiers
source                  1..21
                        mol_type = transcribed RNA
                        organism = Homo sapiens
SEQUENCE: 498
ttgaggagac atggtggggg c                                             21

SEQ ID NO: 499          moltype = RNA  length = 15
FEATURE                 Location/Qualifiers
source                  1..15
                        mol_type = transcribed RNA
                        organism = Homo sapiens
SEQUENCE: 499
ttgaggagac atggt                                                    15
```

SEQ ID NO: 500 moltype = RNA length = 18
FEATURE Location/Qualifiers
source 1..18
mol_type = transcribed RNA
organism = Homo sapiens
SEQUENCE: 500
gaggctgaag gaagatgg 18

SEQ ID NO: 501 moltype = RNA length = 15
FEATURE Location/Qualifiers
source 1..15
mol_type = transcribed RNA
organism = Homo sapiens
SEQUENCE: 501
gaggctgaag gaaga 15

SEQ ID NO: 502 moltype = RNA length = 22
FEATURE Location/Qualifiers
source 1..22
mol_type = transcribed RNA
organism = Homo sapiens
SEQUENCE: 502
ggcaggaagc ggaggaacct tg 22

SEQ ID NO: 503 moltype = RNA length = 17
FEATURE Location/Qualifiers
source 1..17
mol_type = transcribed RNA
organism = Homo sapiens
SEQUENCE: 503
ggaggaacct tggagct 17

SEQ ID NO: 504 moltype = RNA length = 17
FEATURE Location/Qualifiers
source 1..17
mol_type = transcribed RNA
organism = Homo sapiens
SEQUENCE: 504
aggggctggg cgcgcgc 17

SEQ ID NO: 505 moltype = RNA length = 15
FEATURE Location/Qualifiers
source 1..15
mol_type = transcribed RNA
organism = Homo sapiens
SEQUENCE: 505
caggggctgg gcgcg 15

SEQ ID NO: 506 moltype = RNA length = 22
FEATURE Location/Qualifiers
source 1..22
mol_type = transcribed RNA
organism = Homo sapiens
SEQUENCE: 506
gagggttggg tggaggctct cc 22

SEQ ID NO: 507 moltype = RNA length = 15
FEATURE Location/Qualifiers
source 1..15
mol_type = transcribed RNA
organism = Homo sapiens
SEQUENCE: 507
gagggttggg tggag 15

SEQ ID NO: 508 moltype = RNA length = 21
FEATURE Location/Qualifiers
source 1..21
mol_type = transcribed RNA
organism = Homo sapiens
SEQUENCE: 508
gagggcagcg tgggtgtggc g 21

SEQ ID NO: 509 moltype = RNA length = 21
FEATURE Location/Qualifiers
source 1..21
mol_type = transcribed RNA
organism = Homo sapiens
SEQUENCE: 509

```
gagggcagcg tgggtgtggc g                                              21

SEQ ID NO: 510          moltype = RNA  length = 30
FEATURE                 Location/Qualifiers
source                  1..30
                        mol_type = transcribed RNA
                        organism = Homo sapiens
SEQUENCE: 510
gctgggctgg gacggacacc cggcctccac                                     30

SEQ ID NO: 511          moltype = RNA  length = 19
FEATURE                 Location/Qualifiers
source                  1..19
                        mol_type = transcribed RNA
                        organism = Homo sapiens
SEQUENCE: 511
gaggctgggc tgggacgga                                                 19

SEQ ID NO: 512          moltype = RNA  length = 22
FEATURE                 Location/Qualifiers
source                  1..22
                        mol_type = transcribed RNA
                        organism = Homo sapiens
SEQUENCE: 512
cagaagggga gttgggagca ga                                             22

SEQ ID NO: 513          moltype = RNA  length = 16
FEATURE                 Location/Qualifiers
source                  1..16
                        mol_type = transcribed RNA
                        organism = Homo sapiens
SEQUENCE: 513
gaaggggagt tgggag                                                    16

SEQ ID NO: 514          moltype = RNA  length = 29
FEATURE                 Location/Qualifiers
source                  1..29
                        mol_type = transcribed RNA
                        organism = Homo sapiens
SEQUENCE: 514
gggagccgcg gggatcgccg agggccggt                                      29

SEQ ID NO: 515          moltype = RNA  length = 15
FEATURE                 Location/Qualifiers
source                  1..15
                        mol_type = transcribed RNA
                        organism = Homo sapiens
SEQUENCE: 515
ggcggcggtg gtggg                                                     15

SEQ ID NO: 516          moltype = RNA  length = 20
FEATURE                 Location/Qualifiers
source                  1..20
                        mol_type = transcribed RNA
                        organism = Homo sapiens
SEQUENCE: 516
ctccccggtg tgcaaatgtg                                                20

SEQ ID NO: 517          moltype = RNA  length = 15
FEATURE                 Location/Qualifiers
source                  1..15
                        mol_type = transcribed RNA
                        organism = Homo sapiens
SEQUENCE: 517
gtgtgcggtg ttatg                                                     15

SEQ ID NO: 518          moltype = RNA  length = 19
FEATURE                 Location/Qualifiers
source                  1..19
                        mol_type = transcribed RNA
                        organism = Homo sapiens
SEQUENCE: 518
gagggcgggt ggaggagga                                                 19

SEQ ID NO: 519          moltype = RNA  length = 15
FEATURE                 Location/Qualifiers
source                  1..15
                        mol_type = transcribed RNA
                        organism = Homo sapiens
```

```
SEQUENCE: 519
gcgggtggag gagga                                                    15

SEQ ID NO: 520          moltype = RNA  length = 17
FEATURE                 Location/Qualifiers
source                  1..17
                        mol_type = transcribed RNA
                        organism = Homo sapiens
SEQUENCE: 520
ggggcggggg cgggggc                                                  17

SEQ ID NO: 521          moltype = RNA  length = 15
FEATURE                 Location/Qualifiers
source                  1..15
                        mol_type = transcribed RNA
                        organism = Homo sapiens
SEQUENCE: 521
cgcgccgggc ccggg                                                    15

SEQ ID NO: 522          moltype = RNA  length = 23
FEATURE                 Location/Qualifiers
source                  1..23
                        mol_type = transcribed RNA
                        organism = Homo sapiens
SEQUENCE: 522
gggggtcccc ggtgctcgga tct                                           23

SEQ ID NO: 523          moltype = RNA  length = 16
FEATURE                 Location/Qualifiers
source                  1..16
                        mol_type = transcribed RNA
                        organism = Homo sapiens
SEQUENCE: 523
tcgggagggg cgggag                                                   16

SEQ ID NO: 524          moltype = RNA  length = 23
FEATURE                 Location/Qualifiers
source                  1..23
                        mol_type = transcribed RNA
                        organism = Homo sapiens
SEQUENCE: 524
cggggcagct cagtacagga tac                                           23

SEQ ID NO: 525          moltype = RNA  length = 15
FEATURE                 Location/Qualifiers
source                  1..15
                        mol_type = transcribed RNA
                        organism = Homo sapiens
SEQUENCE: 525
agctcagtac aggat                                                    15

SEQ ID NO: 526          moltype = RNA  length = 23
FEATURE                 Location/Qualifiers
source                  1..23
                        mol_type = transcribed RNA
                        organism = Homo sapiens
SEQUENCE: 526
tcggctctgg gtctgtgggg agc                                           23

SEQ ID NO: 527          moltype = RNA  length = 15
FEATURE                 Location/Qualifiers
source                  1..15
                        mol_type = transcribed RNA
                        organism = Homo sapiens
SEQUENCE: 527
gcccggatac ctcag                                                    15

SEQ ID NO: 528          moltype = RNA  length = 23
FEATURE                 Location/Qualifiers
source                  1..23
                        mol_type = transcribed RNA
                        organism = Homo sapiens
SEQUENCE: 528
ggctacaaca caggacccgg gcg                                           23

SEQ ID NO: 529          moltype = RNA  length = 21
FEATURE                 Location/Qualifiers
source                  1..21
                        mol_type = transcribed RNA
```

```
                         organism = Homo sapiens
SEQUENCE: 529
ggctacaaca caggacccgg g                                              21

SEQ ID NO: 530           moltype = RNA  length = 22
FEATURE                  Location/Qualifiers
source                   1..22
                         mol_type = transcribed RNA
                         organism = Homo sapiens
SEQUENCE: 530
actcaaactg tgggggcact tt                                             22

SEQ ID NO: 531           moltype = RNA  length = 19
FEATURE                  Location/Qualifiers
source                   1..19
                         mol_type = transcribed RNA
                         organism = Homo sapiens
SEQUENCE: 531
actcaaactg tgggggcac                                                 19

SEQ ID NO: 532           moltype = RNA  length = 24
FEATURE                  Location/Qualifiers
source                   1..24
                         mol_type = transcribed RNA
                         organism = Homo sapiens
SEQUENCE: 532
tggggagctg aggctctggg ggtg                                           24

SEQ ID NO: 533           moltype = RNA  length = 15
FEATURE                  Location/Qualifiers
source                   1..15
                         mol_type = transcribed RNA
                         organism = Homo sapiens
SEQUENCE: 533
ggccctgggg agctg                                                     15

SEQ ID NO: 534           moltype = RNA  length = 27
FEATURE                  Location/Qualifiers
source                   1..27
                         mol_type = transcribed RNA
                         organism = Homo sapiens
SEQUENCE: 534
gtgaacgggc gccatcccga ggctttg                                        27

SEQ ID NO: 535           moltype = RNA  length = 16
FEATURE                  Location/Qualifiers
source                   1..16
                         mol_type = transcribed RNA
                         organism = Homo sapiens
SEQUENCE: 535
gtgaacgggc gccatc                                                    16

SEQ ID NO: 536           moltype = RNA  length = 23
FEATURE                  Location/Qualifiers
source                   1..23
                         mol_type = transcribed RNA
                         organism = Homo sapiens
SEQUENCE: 536
caccttgcct tgctgcccgg gcc                                            23

SEQ ID NO: 537           moltype = RNA  length = 22
FEATURE                  Location/Qualifiers
source                   1..22
                         mol_type = transcribed RNA
                         organism = Homo sapiens
SEQUENCE: 537
caccttgcct tgctgcccgg gc                                             22

SEQ ID NO: 538           moltype = RNA  length = 23
FEATURE                  Location/Qualifiers
source                   1..23
                         mol_type = transcribed RNA
                         organism = Homo sapiens
SEQUENCE: 538
ggcccggccg tgcctgaggt ttc                                            23

SEQ ID NO: 539           moltype = RNA  length = 15
FEATURE                  Location/Qualifiers
source                   1..15
```

```
                         mol_type = transcribed RNA
                         organism = Homo sapiens
SEQUENCE: 539
ggcggtggga tcccg                                                    15

SEQ ID NO: 540           moltype = RNA  length = 24
FEATURE                  Location/Qualifiers
source                   1..24
                         mol_type = transcribed RNA
                         organism = Homo sapiens
SEQUENCE: 540
aggcaggggc tggtgctggg cggg                                          24

SEQ ID NO: 541           moltype = RNA  length = 15
FEATURE                  Location/Qualifiers
source                   1..15
                         mol_type = transcribed RNA
                         organism = Homo sapiens
SEQUENCE: 541
gggcgggggg cggcg                                                    15

SEQ ID NO: 542           moltype = RNA  length = 19
FEATURE                  Location/Qualifiers
source                   1..19
                         mol_type = transcribed RNA
                         organism = Homo sapiens
SEQUENCE: 542
tggcgggtgc gggggtggg                                                19

SEQ ID NO: 543           moltype = RNA  length = 15
FEATURE                  Location/Qualifiers
source                   1..15
                         mol_type = transcribed RNA
                         organism = Homo sapiens
SEQUENCE: 543
tggcgggtgc ggggg                                                    15

SEQ ID NO: 544           moltype = RNA  length = 19
FEATURE                  Location/Qualifiers
source                   1..19
                         mol_type = transcribed RNA
                         organism = Homo sapiens
SEQUENCE: 544
agggggcggg ctccggcgc                                                19

SEQ ID NO: 545           moltype = RNA  length = 15
FEATURE                  Location/Qualifiers
source                   1..15
                         mol_type = transcribed RNA
                         organism = Homo sapiens
SEQUENCE: 545
gtagggggcg ggctc                                                    15

SEQ ID NO: 546           moltype = RNA  length = 23
FEATURE                  Location/Qualifiers
source                   1..23
                         mol_type = transcribed RNA
                         organism = Homo sapiens
SEQUENCE: 546
cacaggtgag gttcttggga gcc                                           23

SEQ ID NO: 547           moltype = RNA  length = 15
FEATURE                  Location/Qualifiers
source                   1..15
                         mol_type = transcribed RNA
                         organism = Homo sapiens
SEQUENCE: 547
acaggtgagg ttctt                                                    15

SEQ ID NO: 548           moltype = RNA  length = 22
FEATURE                  Location/Qualifiers
source                   1..22
                         mol_type = transcribed RNA
                         organism = Homo sapiens
SEQUENCE: 548
gtgggcgggg gcaggtgtgt gg                                            22

SEQ ID NO: 549           moltype = RNA  length = 15
FEATURE                  Location/Qualifiers
```

-continued

```
source                  1..15
                        mol_type = transcribed RNA
                        organism = Homo sapiens
SEQUENCE: 549
cgggggcagg tgtgt                                                       15

SEQ ID NO: 550          moltype = RNA  length = 24
FEATURE                 Location/Qualifiers
source                  1..24
                        mol_type = transcribed RNA
                        organism = Homo sapiens
SEQUENCE: 550
cgggcgtggt ggtgggggtg ggtg                                             24

SEQ ID NO: 551          moltype = RNA  length = 15
FEATURE                 Location/Qualifiers
source                  1..15
                        mol_type = transcribed RNA
                        organism = Homo sapiens
SEQUENCE: 551
cgggcgtggt ggtgg                                                       15

SEQ ID NO: 552          moltype = RNA  length = 20
FEATURE                 Location/Qualifiers
source                  1..20
                        mol_type = transcribed RNA
                        organism = Homo sapiens
SEQUENCE: 552
ccccagggcg acgcggcggg                                                  20

SEQ ID NO: 553          moltype = RNA  length = 15
FEATURE                 Location/Qualifiers
source                  1..15
                        mol_type = transcribed RNA
                        organism = Homo sapiens
SEQUENCE: 553
cgcggcgggg gcggc                                                       15

SEQ ID NO: 554          moltype = RNA  length = 23
FEATURE                 Location/Qualifiers
source                  1..23
                        mol_type = transcribed RNA
                        organism = Homo sapiens
SEQUENCE: 554
acaggagtgg gggtgggaca taa                                              23

SEQ ID NO: 555          moltype = RNA  length = 20
FEATURE                 Location/Qualifiers
source                  1..20
                        mol_type = transcribed RNA
                        organism = Homo sapiens
SEQUENCE: 555
acaggagtgg gggtgggaca                                                  20

SEQ ID NO: 556          moltype = RNA  length = 18
FEATURE                 Location/Qualifiers
source                  1..18
                        mol_type = transcribed RNA
                        organism = Homo sapiens
SEQUENCE: 556
ggtgggcttc ccggaggg                                                    18

SEQ ID NO: 557          moltype = RNA  length = 15
FEATURE                 Location/Qualifiers
source                  1..15
                        mol_type = transcribed RNA
                        organism = Homo sapiens
SEQUENCE: 557
ggtgggcttc ccgga                                                       15

SEQ ID NO: 558          moltype = RNA  length = 27
FEATURE                 Location/Qualifiers
source                  1..27
                        mol_type = transcribed RNA
                        organism = Homo sapiens
SEQUENCE: 558
caaggtggct gggagagggt tgtttac                                          27

SEQ ID NO: 559          moltype = RNA  length = 15
```

```
FEATURE                Location/Qualifiers
source                 1..15
                       mol_type = transcribed RNA
                       organism = Homo sapiens
SEQUENCE: 559
gtgagctcaa ggtgg                                                        15

SEQ ID NO: 560         moltype = RNA  length = 22
FEATURE                Location/Qualifiers
source                 1..22
                       mol_type = transcribed RNA
                       organism = Homo sapiens
SEQUENCE: 560
actcggctgc ggtggacaag tc                                                22

SEQ ID NO: 561         moltype = RNA  length = 20
FEATURE                Location/Qualifiers
source                 1..20
                       mol_type = transcribed RNA
                       organism = Homo sapiens
SEQUENCE: 561
actcggctgc ggtggacaag                                                   20

SEQ ID NO: 562         moltype = RNA  length = 15
FEATURE                Location/Qualifiers
source                 1..15
                       mol_type = transcribed RNA
                       organism = Homo sapiens
SEQUENCE: 562
tgaagcgggg gggcg                                                        15

SEQ ID NO: 563         moltype = RNA  length = 15
FEATURE                Location/Qualifiers
source                 1..15
                       mol_type = transcribed RNA
                       organism = Homo sapiens
SEQUENCE: 563
tgaagcgggg gggcg                                                        15

SEQ ID NO: 564         moltype = RNA  length = 22
FEATURE                Location/Qualifiers
source                 1..22
                       mol_type = transcribed RNA
                       organism = Homo sapiens
SEQUENCE: 564
accaggaggc tgaggcccct ca                                                22

SEQ ID NO: 565         moltype = RNA  length = 15
FEATURE                Location/Qualifiers
source                 1..15
                       mol_type = transcribed RNA
                       organism = Homo sapiens
SEQUENCE: 565
accaggaggc tgagg                                                        15

SEQ ID NO: 566         moltype = RNA  length = 25
FEATURE                Location/Qualifiers
source                 1..25
                       mol_type = transcribed RNA
                       organism = Homo sapiens
SEQUENCE: 566
tcctgtactg agctgccccg aggcc                                             25

SEQ ID NO: 567         moltype = RNA  length = 15
FEATURE                Location/Qualifiers
source                 1..15
                       mol_type = transcribed RNA
                       organism = Homo sapiens
SEQUENCE: 567
tcctgtactg agctg                                                        15

SEQ ID NO: 568         moltype = RNA  length = 22
FEATURE                Location/Qualifiers
source                 1..22
                       mol_type = transcribed RNA
                       organism = Homo sapiens
SEQUENCE: 568
acaccgggga tggcagaggg tc                                                22
```

```
SEQ ID NO: 569          moltype = RNA  length = 20
FEATURE                 Location/Qualifiers
source                  1..20
                        mol_type = transcribed RNA
                        organism = Homo sapiens
SEQUENCE: 569
caccggggat ggcagagggt                                              20

SEQ ID NO: 570          moltype = RNA  length = 23
FEATURE                 Location/Qualifiers
source                  1..23
                        mol_type = transcribed RNA
                        organism = Homo sapiens
SEQUENCE: 570
gtgggggaga ggctgtcttg tgt                                          23

SEQ ID NO: 571          moltype = RNA  length = 15
FEATURE                 Location/Qualifiers
source                  1..15
                        mol_type = transcribed RNA
                        organism = Homo sapiens
SEQUENCE: 571
gtgtggggga gaggc                                                   15

SEQ ID NO: 572          moltype = RNA  length = 17
FEATURE                 Location/Qualifiers
source                  1..17
                        mol_type = transcribed RNA
                        organism = Homo sapiens
SEQUENCE: 572
tgcaggggca ggccagc                                                 17

SEQ ID NO: 573          moltype = RNA  length = 17
FEATURE                 Location/Qualifiers
source                  1..17
                        mol_type = transcribed RNA
                        organism = Homo sapiens
SEQUENCE: 573
tgcaggggca ggccagc                                                 17

SEQ ID NO: 574          moltype = RNA  length = 22
FEATURE                 Location/Qualifiers
source                  1..22
                        mol_type = transcribed RNA
                        organism = Homo sapiens
SEQUENCE: 574
tggggatttg gagaagtggt ga                                           22

SEQ ID NO: 575          moltype = RNA  length = 22
FEATURE                 Location/Qualifiers
source                  1..22
                        mol_type = transcribed RNA
                        organism = Homo sapiens
SEQUENCE: 575
tggggatttg gagaagtggt ga                                           22

SEQ ID NO: 576          moltype = RNA  length = 22
FEATURE                 Location/Qualifiers
source                  1..22
                        mol_type = transcribed RNA
                        organism = Homo sapiens
SEQUENCE: 576
ggcagggaca gcaaaggggt gc                                           22

SEQ ID NO: 577          moltype = RNA  length = 18
FEATURE                 Location/Qualifiers
source                  1..18
                        mol_type = transcribed RNA
                        organism = Homo sapiens
SEQUENCE: 577
gcagggacag caaagggg                                                18

SEQ ID NO: 578          moltype = RNA  length = 26
FEATURE                 Location/Qualifiers
source                  1..26
                        mol_type = transcribed RNA
                        organism = Homo sapiens
SEQUENCE: 578
cggtgggatc ccgcggccgt gttttc                                       26
```

```
SEQ ID NO: 579          moltype = RNA  length = 15
FEATURE                 Location/Qualifiers
source                  1..15
                        mol_type = transcribed RNA
                        organism = Homo sapiens
SEQUENCE: 579
ggggcgccgc gggac                                                   15

SEQ ID NO: 580          moltype = RNA  length = 21
FEATURE                 Location/Qualifiers
source                  1..21
                        mol_type = transcribed RNA
                        organism = Homo sapiens
SEQUENCE: 580
gctgggaagg caaagggacg t                                            21

SEQ ID NO: 581          moltype = RNA  length = 22
FEATURE                 Location/Qualifiers
source                  1..22
                        mol_type = transcribed RNA
                        organism = Homo sapiens
SEQUENCE: 581
agacacattt ggagagggaa cc                                           22

SEQ ID NO: 582          moltype = RNA  length = 22
FEATURE                 Location/Qualifiers
source                  1..22
                        mol_type = transcribed RNA
                        organism = Homo sapiens
SEQUENCE: 582
ggggctgggg ccggggccga gc                                           22

SEQ ID NO: 583          moltype = RNA  length = 21
FEATURE                 Location/Qualifiers
source                  1..21
                        mol_type = transcribed RNA
                        organism = Homo sapiens
SEQUENCE: 583
gtgccagctg cagtggggga g                                            21

SEQ ID NO: 584          moltype = RNA  length = 23
FEATURE                 Location/Qualifiers
source                  1..23
                        mol_type = transcribed RNA
                        organism = Homo sapiens
SEQUENCE: 584
ttagggagta gaagggtggg gag                                          23

SEQ ID NO: 585          moltype = RNA  length = 18
FEATURE                 Location/Qualifiers
source                  1..18
                        mol_type = transcribed RNA
                        organism = Homo sapiens
SEQUENCE: 585
cggggcggca ggggcctc                                                18

SEQ ID NO: 586          moltype = RNA  length = 22
FEATURE                 Location/Qualifiers
source                  1..22
                        mol_type = transcribed RNA
                        organism = Homo sapiens
SEQUENCE: 586
caggcacggg agctcaggtg ag                                           22

SEQ ID NO: 587          moltype = RNA  length = 18
FEATURE                 Location/Qualifiers
source                  1..18
                        mol_type = transcribed RNA
                        organism = Homo sapiens
SEQUENCE: 587
agcaggtgcg gggcggcg                                                18

SEQ ID NO: 588          moltype = RNA  length = 20
FEATURE                 Location/Qualifiers
source                  1..20
                        mol_type = transcribed RNA
                        organism = Homo sapiens
SEQUENCE: 588
```

-continued

```
gtgggttggg gcgggctctg                                              20

SEQ ID NO: 589          moltype = RNA  length = 17
FEATURE                 Location/Qualifiers
source                  1..17
                        mol_type = transcribed RNA
                        organism = Homo sapiens
SEQUENCE: 589
gggagtctac agcaggg                                                 17

SEQ ID NO: 590          moltype = RNA  length = 18
FEATURE                 Location/Qualifiers
source                  1..18
                        mol_type = transcribed RNA
                        organism = Homo sapiens
SEQUENCE: 590
gggtgcgggc cggcgggg                                                18

SEQ ID NO: 591          moltype = RNA  length = 22
FEATURE                 Location/Qualifiers
source                  1..22
                        mol_type = transcribed RNA
                        organism = Homo sapiens
SEQUENCE: 591
caggaaggat ttagggacag gc                                           22

SEQ ID NO: 592          moltype = RNA  length = 24
FEATURE                 Location/Qualifiers
source                  1..24
                        mol_type = transcribed RNA
                        organism = Homo sapiens
SEQUENCE: 592
tgggggagcc atgagataag agca                                         24

SEQ ID NO: 593          moltype = RNA  length = 22
FEATURE                 Location/Qualifiers
source                  1..22
                        mol_type = transcribed RNA
                        organism = Homo sapiens
SEQUENCE: 593
tggggaaggc gtcagtgtcg gg                                           22

SEQ ID NO: 594          moltype = RNA  length = 23
FEATURE                 Location/Qualifiers
source                  1..23
                        mol_type = transcribed RNA
                        organism = Homo sapiens
SEQUENCE: 594
ctggcggagc ccattccatg cca                                          23

SEQ ID NO: 595          moltype = RNA  length = 25
FEATURE                 Location/Qualifiers
source                  1..25
                        mol_type = transcribed RNA
                        organism = Homo sapiens
SEQUENCE: 595
aagggaggag gagcggaggg gccct                                        25

SEQ ID NO: 596          moltype = RNA  length = 22
FEATURE                 Location/Qualifiers
source                  1..22
                        mol_type = transcribed RNA
                        organism = Homo sapiens
SEQUENCE: 596
gcgggggtgg cggcggcatc cc                                           22

SEQ ID NO: 597          moltype = RNA  length = 20
FEATURE                 Location/Qualifiers
source                  1..20
                        mol_type = transcribed RNA
                        organism = Homo sapiens
SEQUENCE: 597
gggctggggc gcggggaggt                                              20

SEQ ID NO: 598          moltype = RNA  length = 19
FEATURE                 Location/Qualifiers
source                  1..19
                        mol_type = transcribed RNA
                        organism = Homo sapiens
```

```
SEQUENCE: 598
aaggggctgg gggagcaca                                               19

SEQ ID NO: 599          moltype = RNA  length = 22
FEATURE                 Location/Qualifiers
source                  1..22
                        mol_type = transcribed RNA
                        organism = Homo sapiens
SEQUENCE: 599
aggcgatgtg gggatgtaga ga                                           22

SEQ ID NO: 600          moltype = RNA  length = 23
FEATURE                 Location/Qualifiers
source                  1..23
                        mol_type = transcribed RNA
                        organism = Homo sapiens
SEQUENCE: 600
ctgggcccgc ggcgggcgtg ggg                                          23

SEQ ID NO: 601          moltype = RNA  length = 23
FEATURE                 Location/Qualifiers
source                  1..23
                        mol_type = transcribed RNA
                        organism = Homo sapiens
SEQUENCE: 601
acggggagtc aggcagtggt gga                                          23

SEQ ID NO: 602          moltype = RNA  length = 22
FEATURE                 Location/Qualifiers
source                  1..22
                        mol_type = transcribed RNA
                        organism = Homo sapiens
SEQUENCE: 602
agtgggagga caggaggcag gt                                           22

SEQ ID NO: 603          moltype = RNA  length = 22
FEATURE                 Location/Qualifiers
source                  1..22
                        mol_type = transcribed RNA
                        organism = Homo sapiens
SEQUENCE: 603
tggcgggggt agagctggct gc                                           22

SEQ ID NO: 604          moltype = RNA  length = 24
FEATURE                 Location/Qualifiers
source                  1..24
                        mol_type = transcribed RNA
                        organism = Homo sapiens
SEQUENCE: 604
gtaggggcgt cccgggcgcg cggg                                         24

SEQ ID NO: 605          moltype = RNA  length = 19
FEATURE                 Location/Qualifiers
source                  1..19
                        mol_type = transcribed RNA
                        organism = Homo sapiens
SEQUENCE: 605
cggggccaga gcagagagc                                               19

SEQ ID NO: 606          moltype = RNA  length = 21
FEATURE                 Location/Qualifiers
source                  1..21
                        mol_type = transcribed RNA
                        organism = Homo sapiens
SEQUENCE: 606
caggcaggtg tagggtggag c                                            21

SEQ ID NO: 607          moltype = RNA  length = 22
FEATURE                 Location/Qualifiers
source                  1..22
                        mol_type = transcribed RNA
                        organism = Homo sapiens
SEQUENCE: 607
tagcagcacg taaatattgg cg                                           22

SEQ ID NO: 608          moltype = RNA  length = 23
FEATURE                 Location/Qualifiers
source                  1..23
                        mol_type = transcribed RNA
```

```
                          organism = Homo sapiens
SEQUENCE: 608
tgaggggcag agagcgagac ttt                                      23

SEQ ID NO: 609            moltype = RNA  length = 22
FEATURE                   Location/Qualifiers
source                    1..22
                          mol_type = transcribed RNA
                          organism = Homo sapiens
SEQUENCE: 609
aaaccgttac cattactgag tt                                       22

SEQ ID NO: 610            moltype = RNA  length = 19
FEATURE                   Location/Qualifiers
source                    1..19
                          mol_type = transcribed RNA
                          organism = Homo sapiens
SEQUENCE: 610
aggcacggtg tcagcaggc                                           19

SEQ ID NO: 611            moltype = RNA  length = 23
FEATURE                   Location/Qualifiers
source                    1..23
                          mol_type = transcribed RNA
                          organism = Homo sapiens
SEQUENCE: 611
aggaagccct ggaggggctg gag                                      23

SEQ ID NO: 612            moltype = RNA  length = 110
FEATURE                   Location/Qualifiers
source                    1..110
                          mol_type = transcribed RNA
                          organism = Homo sapiens
SEQUENCE: 612
ggctacagtc tttcttcatg tgactcgtgg acttcccttt gtcatcctat gcctgagaat  60
atatgaagga ggctgggaag gcaaagggac gttcaattgt catcactggc             110

SEQ ID NO: 613            moltype = RNA  length = 97
FEATURE                   Location/Qualifiers
source                    1..97
                          mol_type = transcribed RNA
                          organism = Homo sapiens
SEQUENCE: 613
atctgagttg ggagggtccc tctccaaatg tgtcttgggg tgggggatca agacacattt  60
ggagagggaa cctcccaact cggcctctgc catcatt                       97

SEQ ID NO: 614            moltype = RNA  length = 83
FEATURE                   Location/Qualifiers
source                    1..83
                          mol_type = transcribed RNA
                          organism = Homo sapiens
SEQUENCE: 614
ggcccggctc cgggtctcgg cccgtacagt ccggccggcc atgctggcgg ggctggggcc  60
ggggccgagc ccgcggcggg gcc                                      83

SEQ ID NO: 615            moltype = RNA  length = 83
FEATURE                   Location/Qualifiers
source                    1..83
                          mol_type = transcribed RNA
                          organism = Homo sapiens
SEQUENCE: 615
cctgctgcag aggtgccagc tgcagtgggg gaggcactgc cagggctgcc cactctgctt  60
agccagcagg tgccaagaac agg                                      83

SEQ ID NO: 616            moltype = RNA  length = 82
FEATURE                   Location/Qualifiers
source                    1..82
                          mol_type = transcribed RNA
                          organism = Homo sapiens
SEQUENCE: 616
ctgacttttt tagggagtag aagggtgggg agcatgaaca atgtttctca ctccctaccc  60
ctccactccc caaaaaagtc ag                                       82

SEQ ID NO: 617            moltype = RNA  length = 64
FEATURE                   Location/Qualifiers
source                    1..64
                          mol_type = transcribed RNA
                          organism = Homo sapiens
SEQUENCE: 617
```

```
gggtgggggc ggggcggcag gggcctcccc cagtgccagg ccccattctg cttctctccc  60
agct                                                               64

SEQ ID NO: 618          moltype = RNA  length = 83
FEATURE                 Location/Qualifiers
source                  1..83
                        mol_type = transcribed RNA
                        organism = Homo sapiens
SEQUENCE: 618
aatagagggt gcacaggcac gggagctcag gtgaggcagg gagctgagct cacctgacct  60
cccatgcctg tgcaccctct att                                          83

SEQ ID NO: 619          moltype = RNA  length = 105
FEATURE                 Location/Qualifiers
source                  1..105
                        mol_type = transcribed RNA
                        organism = Homo sapiens
SEQUENCE: 619
gcgggcggcg gcggcggcag cagcagcagg tgcggggcgg cggccgcgct ggccgctcga  60
ctccgcagct gctcgttctg cttctccagc ttgcgcacca gctcc                  105

SEQ ID NO: 620          moltype = RNA  length = 102
FEATURE                 Location/Qualifiers
source                  1..102
                        mol_type = transcribed RNA
                        organism = Homo sapiens
SEQUENCE: 620
gcttatcgag gaaaagatcg aggtgggttg gggcgggctc tggggatttg gtctcacagc  60
ccggatccca gcccacttac cttggttact ctccttcctt ct                     102

SEQ ID NO: 621          moltype = RNA  length = 76
FEATURE                 Location/Qualifiers
source                  1..76
                        mol_type = transcribed RNA
                        organism = Homo sapiens
SEQUENCE: 621
ccgatgcctc gggagtctac agcagggcca tgtctgtgag ggcccaaggg tgcatgtgtc  60
tcccaggttt cggtgc                                                  76

SEQ ID NO: 622          moltype = RNA  length = 54
FEATURE                 Location/Qualifiers
source                  1..54
                        mol_type = transcribed RNA
                        organism = Homo sapiens
SEQUENCE: 622
acgcgggtgc gggccggcgg ggtagaagcc acccggcccg gcccggcccg gcga        54

SEQ ID NO: 623          moltype = RNA  length = 70
FEATURE                 Location/Qualifiers
source                  1..70
                        mol_type = transcribed RNA
                        organism = Homo sapiens
SEQUENCE: 623
aaaagcctgt ccctaagtcc ctcccagcct tccagagttg gtgccaggaa ggatttaggg  60
acaggctttg                                                         70

SEQ ID NO: 624          moltype = RNA  length = 81
FEATURE                 Location/Qualifiers
source                  1..81
                        mol_type = transcribed RNA
                        organism = Homo sapiens
SEQUENCE: 624
agttggtggg ggagccatga gataagagca cctcctagag aatgttgaac taaaggtgcc  60
ctctctggct cctccccaaa g                                            81

SEQ ID NO: 625          moltype = RNA  length = 90
FEATURE                 Location/Qualifiers
source                  1..90
                        mol_type = transcribed RNA
                        organism = Homo sapiens
SEQUENCE: 625
gtgtctctct ggagaccctg cagccttccc acccaccagg gagctttcca tgggctgtgg  60
ggaaggcgtc agtgtcgggt gagggaacac                                   90

SEQ ID NO: 626          moltype = RNA  length = 76
FEATURE                 Location/Qualifiers
source                  1..76
                        mol_type = transcribed RNA
                        organism = Homo sapiens
```

```
SEQUENCE: 626
cgcaggcctc tggcggagcc cattccatgc cagatgctga gcgatggctg gtgtgtgctg  60
ctccacaggc ctggtg                                                  76

SEQ ID NO: 627         moltype = RNA  length = 74
FEATURE                Location/Qualifiers
source                 1..74
                       mol_type = transcribed RNA
                       organism = Homo sapiens
SEQUENCE: 627
gggaggaaga agggaggagg agcggagggg cccttgtctt cccagagcct ctcccttcct  60
cccctccccc tccc                                                    74

SEQ ID NO: 628         moltype = RNA  length = 84
FEATURE                Location/Qualifiers
source                 1..84
                       mol_type = transcribed RNA
                       organism = Homo sapiens
SEQUENCE: 628
cggtccagac gtggcggggg tggcggcggc atcccggacg gcctgtgagg gatgcgccgc  60
ccactgcccc gcgccgcctg accg                                         84

SEQ ID NO: 629         moltype = RNA  length = 55
FEATURE                Location/Qualifiers
source                 1..55
                       mol_type = transcribed RNA
                       organism = Homo sapiens
SEQUENCE: 629
gggggctggg gcgcggggag gtgctaggtc ggcctcggct cccgcgccgc acccc       55

SEQ ID NO: 630         moltype = RNA  length = 110
FEATURE                Location/Qualifiers
source                 1..110
                       mol_type = transcribed RNA
                       organism = Homo sapiens
SEQUENCE: 630
gtctaccagg tgtgggccca gctttacata gttcatgctg aggccgggat ttcatgcaga  60
aaactggttg caaaaggtgc tgaaggggct gggggagcac aagggagaag            110

SEQ ID NO: 631         moltype = RNA  length = 73
FEATURE                Location/Qualifiers
source                 1..73
                       mol_type = transcribed RNA
                       organism = Homo sapiens
SEQUENCE: 631
ctggtgtttg aggcgatgtg gggatgtaga gacaacttcc cagtctcatt tcctcatcct  60
gccaggccac cat                                                     73

SEQ ID NO: 632         moltype = RNA  length = 92
FEATURE                Location/Qualifiers
source                 1..92
                       mol_type = transcribed RNA
                       organism = Homo sapiens
SEQUENCE: 632
cgctgcgctt ctgggcccgc ggcgggcgtg gggctgcccg ggccggtcga ccagcgcgcc  60
gtagctcccg aggcccgagc cgcgacccgc gg                                92

SEQ ID NO: 633         moltype = RNA  length = 66
FEATURE                Location/Qualifiers
source                 1..66
                       mol_type = transcribed RNA
                       organism = Homo sapiens
SEQUENCE: 633
tcaagacggg gagtcaggca gtggtggaga tggagagccc tgagcctcca ctctcctggc  60
ccccag                                                             66

SEQ ID NO: 634         moltype = RNA  length = 73
FEATURE                Location/Qualifiers
source                 1..73
                       mol_type = transcribed RNA
                       organism = Homo sapiens
SEQUENCE: 634
gttcaagtgg gaggacagga ggcaggtgtg gttggaggaa gcagcctgaa cctgcctccc  60
tgacattcca cag                                                     73

SEQ ID NO: 635         moltype = RNA  length = 61
FEATURE                Location/Qualifiers
source                 1..61
                       mol_type = transcribed RNA
```

```
                         organism = Homo sapiens
SEQUENCE: 635
tcggctggcg ggggtagagc tggctgcagg cccggcccct ctcagctgct gccctctcca  60
g                                                                  61

SEQ ID NO: 636           moltype = RNA  length = 98
FEATURE                  Location/Qualifiers
source                   1..98
                         mol_type = transcribed RNA
                         organism = Homo sapiens
SEQUENCE: 636
cgaggtaggg gcgtcccggg cgcgcgggcg ggtcccaggc tgggcccctc ggaggccggg  60
tgctcactgc cccgtcccgg cgcccgtgtc tcctccag                          98

SEQ ID NO: 637           moltype = RNA  length = 61
FEATURE                  Location/Qualifiers
source                   1..61
                         mol_type = transcribed RNA
                         organism = Homo sapiens
SEQUENCE: 637
aactgcgggg ccagagcaga gagcccttgc acaccaccag cctctcctcc ctgtgcccca  60
g                                                                  61

SEQ ID NO: 638           moltype = RNA  length = 69
FEATURE                  Location/Qualifiers
source                   1..69
                         mol_type = transcribed RNA
                         organism = Homo sapiens
SEQUENCE: 638
ccgggcaggc aggtgtaggg tggagcccac tgtggctcct gactcagccc tgctgccttc  60
acctgccag                                                          69

SEQ ID NO: 639           moltype = RNA  length = 89
FEATURE                  Location/Qualifiers
source                   1..89
                         mol_type = transcribed RNA
                         organism = Homo sapiens
SEQUENCE: 639
gtcagcagtg ccttagcagc acgtaaatat tggcgttaag attctaaaat tatctccagt  60
attaactgtg ctgctgaagt aaggttgac                                    89

SEQ ID NO: 640           moltype = RNA  length = 81
FEATURE                  Location/Qualifiers
source                   1..81
                         mol_type = transcribed RNA
                         organism = Homo sapiens
SEQUENCE: 640
gttccactct agcagcacgt aaatattggc gtagtgaaat atatattaaa caccaatatt  60
actgtgctgc tttagtgtga c                                            81

SEQ ID NO: 641           moltype = RNA  length = 94
FEATURE                  Location/Qualifiers
source                   1..94
                         mol_type = transcribed RNA
                         organism = Homo sapiens
SEQUENCE: 641
ataaaggaag ttaggctgag gggcagagag cgagactttt ctattttcca aaagctcggt  60
ctgaggcccc tcagtcttgc ttcctaaccc gcgc                              94

SEQ ID NO: 642           moltype = RNA  length = 72
FEATURE                  Location/Qualifiers
source                   1..72
                         mol_type = transcribed RNA
                         organism = Homo sapiens
SEQUENCE: 642
cttgggaatg gcaaggaaac cgttaccatt actgagttta gtaatggtaa tggttctctt  60
gctataccca ga                                                      72

SEQ ID NO: 643           moltype = RNA  length = 94
FEATURE                  Location/Qualifiers
source                   1..94
                         mol_type = transcribed RNA
                         organism = Homo sapiens
SEQUENCE: 643
cgggcagcgg gtgccaggca cggtgtcagc aggcaacatg gccgagaggc cggggcctcc  60
gggcggcgcc gtgtccgcga ccgcgtaccc tgac                              94

SEQ ID NO: 644           moltype = RNA  length = 118
FEATURE                  Location/Qualifiers
```

```
source                1..118
                      mol_type = transcribed RNA
                      organism = Homo sapiens
SEQUENCE: 644
gcaggtgaac tggcaggcca ggaagaggag gaagccctgg aggggctgga ggtgatggat  60
gttttcctcc ggttctcagg gctccacctc tttcgggccg tagagccagg gctggtgc    118

SEQ ID NO: 645        moltype = RNA  length = 24
FEATURE               Location/Qualifiers
source                1..24
                      mol_type = transcribed RNA
                      organism = Homo sapiens
SEQUENCE: 645
gaggctggga aggcaaaggg acgt                                         24

SEQ ID NO: 646        moltype = RNA  length = 15
FEATURE               Location/Qualifiers
source                1..15
                      mol_type = transcribed RNA
                      organism = Homo sapiens
SEQUENCE: 646
ctgggaaggc aaagg                                                   15

SEQ ID NO: 647        moltype = RNA  length = 24
FEATURE               Location/Qualifiers
source                1..24
                      mol_type = transcribed RNA
                      organism = Homo sapiens
SEQUENCE: 647
agacacattt ggagagggaa cctc                                         24

SEQ ID NO: 648        moltype = RNA  length = 16
FEATURE               Location/Qualifiers
source                1..16
                      mol_type = transcribed RNA
                      organism = Homo sapiens
SEQUENCE: 648
agacacattt ggagag                                                  16

SEQ ID NO: 649        moltype = RNA  length = 15
FEATURE               Location/Qualifiers
source                1..15
                      mol_type = transcribed RNA
                      organism = Homo sapiens
SEQUENCE: 649
gctgcagtgg gggag                                                   15

SEQ ID NO: 650        moltype = RNA  length = 23
FEATURE               Location/Qualifiers
source                1..23
                      mol_type = transcribed RNA
                      organism = Homo sapiens
SEQUENCE: 650
agggagtaga agggtgggga gca                                          23

SEQ ID NO: 651        moltype = RNA  length = 16
FEATURE               Location/Qualifiers
source                1..16
                      mol_type = transcribed RNA
                      organism = Homo sapiens
SEQUENCE: 651
tagggagtag aagggt                                                  16

SEQ ID NO: 652        moltype = RNA  length = 17
FEATURE               Location/Qualifiers
source                1..17
                      mol_type = transcribed RNA
                      organism = Homo sapiens
SEQUENCE: 652
gcggggcggc aggggcc                                                 17

SEQ ID NO: 653        moltype = RNA  length = 15
FEATURE               Location/Qualifiers
source                1..15
                      mol_type = transcribed RNA
                      organism = Homo sapiens
SEQUENCE: 653
gggggcgggg cggca                                                   15
```

```
SEQ ID NO: 654          moltype = RNA  length = 18
FEATURE                 Location/Qualifiers
source                  1..18
                        mol_type = transcribed RNA
                        organism = Homo sapiens
SEQUENCE: 654
gcacgggagc tcaggtga                                                18

SEQ ID NO: 655          moltype = RNA  length = 18
FEATURE                 Location/Qualifiers
source                  1..18
                        mol_type = transcribed RNA
                        organism = Homo sapiens
SEQUENCE: 655
gcggcggcgg cggcagca                                                18

SEQ ID NO: 656          moltype = RNA  length = 15
FEATURE                 Location/Qualifiers
source                  1..15
                        mol_type = transcribed RNA
                        organism = Homo sapiens
SEQUENCE: 656
gcgggcggcg gcggc                                                   15

SEQ ID NO: 657          moltype = RNA  length = 19
FEATURE                 Location/Qualifiers
source                  1..19
                        mol_type = transcribed RNA
                        organism = Homo sapiens
SEQUENCE: 657
gtgggttggg gcgggctct                                               19

SEQ ID NO: 658          moltype = RNA  length = 19
FEATURE                 Location/Qualifiers
source                  1..19
                        mol_type = transcribed RNA
                        organism = Homo sapiens
SEQUENCE: 658
gtgggttggg gcgggctct                                               19

SEQ ID NO: 659          moltype = RNA  length = 19
FEATURE                 Location/Qualifiers
source                  1..19
                        mol_type = transcribed RNA
                        organism = Homo sapiens
SEQUENCE: 659
gggtgcgggc cggcggggt                                               19

SEQ ID NO: 660          moltype = RNA  length = 15
FEATURE                 Location/Qualifiers
source                  1..15
                        mol_type = transcribed RNA
                        organism = Homo sapiens
SEQUENCE: 660
tgcgggccgg cgggg                                                   15

SEQ ID NO: 661          moltype = RNA  length = 22
FEATURE                 Location/Qualifiers
source                  1..22
                        mol_type = transcribed RNA
                        organism = Homo sapiens
SEQUENCE: 661
aaggatttag ggacaggctt tg                                           22

SEQ ID NO: 662          moltype = RNA  length = 19
FEATURE                 Location/Qualifiers
source                  1..19
                        mol_type = transcribed RNA
                        organism = Homo sapiens
SEQUENCE: 662
caggaaggat ttagggaca                                               19

SEQ ID NO: 663          moltype = RNA  length = 22
FEATURE                 Location/Qualifiers
source                  1..22
                        mol_type = transcribed RNA
                        organism = Homo sapiens
SEQUENCE: 663
gttggtgggg gagccatgag at                                           22
```

```
SEQ ID NO: 664          moltype = RNA  length = 22
FEATURE                 Location/Qualifiers
source                  1..22
                        mol_type = transcribed RNA
                        organism = Homo sapiens
SEQUENCE: 664
ggggagccat gagataagag ca                                            22

SEQ ID NO: 665          moltype = RNA  length = 23
FEATURE                 Location/Qualifiers
source                  1..23
                        mol_type = transcribed RNA
                        organism = Homo sapiens
SEQUENCE: 665
tggggaaggc gtcagtgtcg ggt                                           23

SEQ ID NO: 666          moltype = RNA  length = 16
FEATURE                 Location/Qualifiers
source                  1..16
                        mol_type = transcribed RNA
                        organism = Homo sapiens
SEQUENCE: 666
tggggaaggc gtcagt                                                   16

SEQ ID NO: 667          moltype = RNA  length = 22
FEATURE                 Location/Qualifiers
source                  1..22
                        mol_type = transcribed RNA
                        organism = Homo sapiens
SEQUENCE: 667
tggcggagcc cattccatgc ca                                            22

SEQ ID NO: 668          moltype = RNA  length = 21
FEATURE                 Location/Qualifiers
source                  1..21
                        mol_type = transcribed RNA
                        organism = Homo sapiens
SEQUENCE: 668
ctggcggagc ccattccatg c                                             21

SEQ ID NO: 669          moltype = RNA  length = 23
FEATURE                 Location/Qualifiers
source                  1..23
                        mol_type = transcribed RNA
                        organism = Homo sapiens
SEQUENCE: 669
aagggaggag gagcggaggg gcc                                           23

SEQ ID NO: 670          moltype = RNA  length = 15
FEATURE                 Location/Qualifiers
source                  1..15
                        mol_type = transcribed RNA
                        organism = Homo sapiens
SEQUENCE: 670
gggaggagga gcgga                                                    15

SEQ ID NO: 671          moltype = RNA  length = 15
FEATURE                 Location/Qualifiers
source                  1..15
                        mol_type = transcribed RNA
                        organism = Homo sapiens
SEQUENCE: 671
ggcgcgggga ggtgc                                                    15

SEQ ID NO: 672          moltype = RNA  length = 15
FEATURE                 Location/Qualifiers
source                  1..15
                        mol_type = transcribed RNA
                        organism = Homo sapiens
SEQUENCE: 672
ggcgcgggga ggtgc                                                    15

SEQ ID NO: 673          moltype = RNA  length = 21
FEATURE                 Location/Qualifiers
source                  1..21
                        mol_type = transcribed RNA
                        organism = Homo sapiens
SEQUENCE: 673
```

```
gaggcgatgt ggggatgtag a                                     21

SEQ ID NO: 674          moltype = RNA  length = 20
FEATURE                 Location/Qualifiers
source                  1..20
                        mol_type = transcribed RNA
                        organism = Homo sapiens
SEQUENCE: 674
cccagtctca tttcctcatc                                       20

SEQ ID NO: 675          moltype = RNA  length = 25
FEATURE                 Location/Qualifiers
source                  1..25
                        mol_type = transcribed RNA
                        organism = Homo sapiens
SEQUENCE: 675
ttctgggccc gcggcgggcg tgggg                                 25

SEQ ID NO: 676          moltype = RNA  length = 15
FEATURE                 Location/Qualifiers
source                  1..15
                        mol_type = transcribed RNA
                        organism = Homo sapiens
SEQUENCE: 676
cgcggcgggc gtggg                                            15

SEQ ID NO: 677          moltype = RNA  length = 27
FEATURE                 Location/Qualifiers
source                  1..27
                        mol_type = transcribed RNA
                        organism = Homo sapiens
SEQUENCE: 677
tagcagcacg taaatattgg cgttaag                               27

SEQ ID NO: 678          moltype = RNA  length = 15
FEATURE                 Location/Qualifiers
source                  1..15
                        mol_type = transcribed RNA
                        organism = Homo sapiens
SEQUENCE: 678
cacgtaaata ttggc                                            15

SEQ ID NO: 679          moltype = RNA  length = 30
FEATURE                 Location/Qualifiers
source                  1..30
                        mol_type = transcribed RNA
                        organism = Homo sapiens
SEQUENCE: 679
tgaggggcag agagcgagac ttttctattt                            30

SEQ ID NO: 680          moltype = RNA  length = 15
FEATURE                 Location/Qualifiers
source                  1..15
                        mol_type = transcribed RNA
                        organism = Homo sapiens
SEQUENCE: 680
cagagagcga gactt                                            15

SEQ ID NO: 681          moltype = RNA  length = 27
FEATURE                 Location/Qualifiers
source                  1..27
                        mol_type = transcribed RNA
                        organism = Homo sapiens
SEQUENCE: 681
aaaccgttac cattactgag tttagta                               27

SEQ ID NO: 682          moltype = RNA  length = 15
FEATURE                 Location/Qualifiers
source                  1..15
                        mol_type = transcribed RNA
                        organism = Homo sapiens
SEQUENCE: 682
taccattact gagtt                                            15

SEQ ID NO: 683          moltype = RNA  length = 25
FEATURE                 Location/Qualifiers
source                  1..25
                        mol_type = transcribed RNA
                        organism = Homo sapiens
```

-continued

```
SEQUENCE: 683
aggaagccct ggaggggctg gaggt                                 25

SEQ ID NO: 684          moltype = RNA  length = 15
FEATURE                 Location/Qualifiers
source                  1..15
                        mol_type = transcribed RNA
                        organism = Homo sapiens
SEQUENCE: 684
aggaagagga ggaag                                            15
```

PROSTATE CANCER DETECTION KIT OR DEVICE, AND DETECTION METHOD

CROSS-REFERENCE TO RELATED APPLICATIONS

This application is a Divisional of application Ser. No. 16/808,095 filed Mar. 3, 2020, which is a Divisional of application Ser. No. 15/317,882, filed on Dec. 9, 2016 (now U.S. Pat. No. 10,619,213), which was filed as a national phase application of PCT International Application No. PCT/JP2015/066964 on Jun. 12, 2015, which claims the benefit under 35 U.S.C. § 119(a) to Patent Application No. 2014-121377, filed in Japan on Jun. 12, 2014 and Patent Application No. 2015-071756, filed in Japan on Mar. 31, 2015, all of which are hereby expressly incorporated by reference into the present application.

REFERENCE TO ELECTRONIC SEQUENCE LISTING

This application includes an electronically submitted Sequence Listing in .XML format entitled "PH-6233-PCT-US-DIV1-DIV1.xml" created on Oct. 25, 2022, and is 615,824 bytes in size. The sequence listing contained in this .XML file is part of the specification and is hereby incorporated by reference herein in its entirety.

TECHNICAL FIELD

The present invention relates to a kit or a device for the detection of prostate cancer, comprising a nucleic acid capable of specifically binding to a particular miRNA, which is used for examining the presence or absence of prostate cancer in a subject, and a method for detecting prostate cancer, comprising measuring an expression level of the miRNA using the nucleic acid.

BACKGROUND ART

The prostate is an organ that produces a component of the semen in males, and is positioned underneath the urinary bladder and in front of the rectum. Prostate cancer is a disease caused by the disorganized and repeated proliferation of cells of this prostate. According to the 2011 statistics of cancer type specific mortality in Japan disclosed by the Center for Cancer Control and Information Services, National Cancer Center, the number of individuals affected by prostate cancer was 51,534 people. Namely, it is estimated that one out of 14 Japanese males will experience prostate cancer. The number of incidences of this cancer in males takes the 4th place by cancer type. Also, the number of prostate cancer deaths climbed to 10,823 people and takes the 6th place by cancer type in males. It is estimated that one out of 7 American males will experience prostate cancer. Prostate cancer is particularly common in elderly people, and 6 out of 10 men aged 65 or older are diagnosed with prostate cancer (Non-Patent Literature 1). The estimated number of American individuals affected by prostate cancer climbed to 233,000 people in 2014, among which approximately 29,480 people reportedly died (Non-Patent Literature 1).

The progression stages of prostate cancer are specified in Non-Patent Literature 2 and classified into stage I (T1 to T2a/N0/M0), stage II (T2b to T2c/N0/M0), stage III (T3/N0/M0), and stage IV (T4/N0/M0 and N1 and cM1) according to tumor spread (T1a to T1c, T2a to T2c, T3a to T3b, and T4), lymph node metastasis (N0 and N1), distant metastasis (M0 and M1a to M1c), etc.

Since prostate cancer progresses relatively slowly in most cases, its 5-year relative survival rate is almost 100%, indicating one of cancers having the best prognosis (Non-Patent Literature 1). Some of prostate cancer cases, however, progress relatively fast and cause various disorders or symptoms. Prostate cancer found to have distant metastasis at stage 4 exhibits a 5-year relative survival rate as significantly low as 28% (Non-Patent Literature 1).

The treatment of prostate cancer in regular protocols includes surgical treatment, radiotherapy, endocrine therapy (hormone therapy), and palliative treatment which continues follow-up while monitoring a tumor marker PSA without special treatment. Particularly, the treatment of early prostate cancer has some options such as external beam radiotherapy, internal radiotherapy (brachytherapy), radical prostatectomy, and cryosurgery, in addition to palliative treatment (Non-Patent Literature 1).

As described in Non-Patent Literature 1, a test of PSA, a tumor marker in blood, is widely used as a primary test for prostate cancer. Rectal examination or transrectal ultrasonography of the prostate is carried out when the PSA measurement value is high. Biopsy is further carried out as definite diagnosis when a subject is suspected of having prostate cancer. An imaging test such as CT scan, MRI scan, or bone scintigraphy is also conducted when a subject is suspected of having distant metastasis.

The prostate-specific antigen (PSA) is produced by the prostate and contained in the semen, but is also present in blood, albeit slightly. The PSA concentration in blood of ordinary males is usually 4 ng/mL or lower, and a subject is suspected of having prostate cancer when the measurement value exceeds this reference value (Non-Patent Literature 1). The PSA concentration in blood is reportedly useful and widely implemented, for example, because this concentration elevates even in asymptomatic early prostate cancer and correlates with the stages of cancer progression. The American Cancer Society promotes the early detection of prostate cancer and recommends that subjects who desire screening of prostate cancer should undergo the PSA test (Non-Patent Literature 1).

As shown in Patent Literatures 1 to 3, there are reports, albeit at a research stage, on the detection of prostate cancer using the expression levels of microRNAs (miRNAs) or combinations of the expression levels of miRNAs and the expression levels of additional markers in biological samples including blood.

Patent Literature 1 discloses a method for detecting prostate cancer as well as Wilms tumor and COPD using hsa-miR-760, hsa-miR-920, has-miR-887-3p, hsa-miR-486-3p, hsa-miR-663b, hsa-miR-187-5p, hsa-miR-1231, hsa-miR-371a-5p, has-miR-575, hsa-miR-615-5p, hsa-miR-711, hsa-miR-939-5p, hsa-miR-1203, hsa-miR-1225-3p, hsa-miR-1225-5p, hsa-miR-1915-5p and the like in blood.

Patent Literature 2 discloses a method for detecting prostate cancer, etc., comprising isolating a vesicle from blood using EpCam and using a miRNA such as hsa-miR-92b-5p contained in the vesicle, for the detection.

Patent Literature 3 has reported that prostate cancer is determined by combining the expression level of PCA3 gene with the expression level of miR-141.

CITATION LIST

Patent Literature

Patent Literature 1: European Patent Application Publication No. 2341145

Patent Literature 2: International Publication No. WO 2013/022995

Patent Literature 3: International Publication No. WO 2010/062706

Non-Patent Literature

Non-Patent Literature 1: American Cancer Society "Prostate Cancer", 2013, p. 5, 14 to 26, 32 to 54, and 68 to 70

Non-Patent Literature 2: Sobin, L. et al., "TNM Classification of Malignant Tumours, the 7th edition", 2010, p. 230 to 234

Non-Patent Literature 3: Wolf, A M. et al., 2010, A Cancer Journal for Clinicians, Vol. 60 (2), p. 70-98

Non-Patent Literature 4: Mitchell P S. et al., 2008, Proceedings of the National Academy of Sciences of the United States of America, Vol. 105 (30), p. 10513-10518

SUMMARY OF INVENTION

Technical Problem

An object of the present invention is to find a novel tumor marker for prostate cancer and to provide a method that can effectively detect prostate cancer using a nucleic acid capable of specifically binding to the marker. The PSA test is widely used as a tumor marker test for prostate cancer. The PSA test is, however, known that 15% of males having a PSA concentration in blood corresponding to the reference value 4 ng/mL or lower are confirmed to be prostate cancer-positive as a result of biopsy. On the other hand, it is also known that the PSA concentration in blood elevates in males having benign prostatic hyperplasia or prostatitis and in ordinary elderly men, leading to a high probability of false positives even in the absence of cancer (Non-Patent Literature 1). Furthermore, the false detection of a cancer other than prostate cancer also leads to false positives. Such a high probability of false positives in the PSA test leads to overdiagnosis and overtreatment, and various aftereffects ascribable to the unnecessary treatment of prostate cancer has been viewed as problems in recent years (Non-Patent Literature 3). According to the large-scale research using 5000 or more recruited subjects (Non-Patent Literature 3), the specific performance of the PSA test showed the sensitivity as low as 20.5% for the overall prostate cancer cases and the sensitivity of merely 51% even limited for highly malignant prostate cancer cases, suggesting that the tumor marker measurement is less significant as a preoperative test.

As described below, there are reports, albeit at a research stage, on the determination of prostate cancer using the expression levels of microRNAs (miRNAs) in biological samples including blood, none of which, however, have yet been brought into practical use.

Patent Literature 1 discloses a method for detecting prostate cancer as well as Wilms tumor and COPD using hsa-miR-760, hsa-miR-920, has-miR-887-3p, hsa-miR-486-3p, hsa-miR-663b, hsa-miR-187-5p, hsa-miR-1231, hsa-miR-371a-5p, has-miR-575, hsa-miR-615-5p, hsa-miR-711, hsa-miR-939-5p, hsa-miR-1203, hsa-miR-1225-3p, hsa-miR-1225-5p, hsa-miR-1915-5p and the like in blood. Patent Literature 1 describes many miRNAs, whereas this literature lacks a direct statement showing that these miRNA markers are markers for prostate cancer, and includes insufficient evidence for the usefulness of the miRNA markers as prostate cancer markers.

Patent Literature 2 discloses a method for detecting prostate cancer, etc., comprising isolating a vesicle from blood using EpCam and using a miRNA such as hsa-miR-92b-5p contained in the vesicle, for the detection. This literature, however, is less reliable because the miRNA marker was not reproducibly validated in an independent sample group and the literature has no mention about a threshold for detecting prostate cancer.

Patent Literature 3 specifically states that prostate cancer can be determined with 100% sensitivity and specificity by combining the expression levels of miR-141 and PCA3. This literature, however, does not state that prostate cancer can be determined conveniently and highly accurately using a single marker. In fact, Non-Patent Literature 4 is cited in Patent Literature 3. Non-Patent Literature 4 has reported the determination of prostate cancer using miR-141 in serum and states that the accuracy of the determination is 60% sensitivity when the specificity is 100%. In addition, a sample that is subjected to the PCA3 test currently used generally is urine, particularly, urine after digital rectal examination. On the other hand, the sample that is subjected to the determination of prostate cancer using miR-141 is blood (serum) as mentioned above. Thus, for obtaining highly sensitive and specific results by combining them, it is necessary to collect two samples.

Solution to Problem

The present inventors have conducted diligent studies to attain the object and consequently completed the present invention by finding several genes usable as markers for the detection of prostate cancer from blood, which can be collected with limited invasiveness, and finding that prostate cancer can be significantly detected by using nucleic acids capable of specifically binding to any of these markers.

SUMMARY OF INVENTION

Specifically, the present invention has the following features:

(1) A kit for the detection of prostate cancer, comprising a nucleic acid capable of specifically binding to at least one or more polynucleotide(s) selected from the group consisting of prostate cancer markers miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR- 4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

(2) The kit according to (1), wherein miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other prostate cancer markers miR-615-5p, miR-486-3p, miR-1225-3p, miR-760, miR- 187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

(5) The kit according to (4), wherein miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, any variant thereof, any derivative thereof, or any fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other prostate cancer markers miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

(8) The kit according to (7), wherein miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c 3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR 5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two or more nucleic acids capable of specifically binding to at least two or more polynucleotides, respectively, selected from all of the prostate cancer markers according to (1) or (2).

(11) A device for the detection of prostate cancer, comprising a nucleic acid capable of specifically binding to at least one or more polynucleotide(s) selected from the group consisting of prostate cancer markers miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-

5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

(12) The device according to (11), wherein miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

(13) The device according to (11) or (12), wherein the nucleic acid is a polynucleotide selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s) selected from the group consisting of other prostate cancer markers miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564, and miR-671-5p.

(15) The device according to (14), wherein miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other prostate cancer markers miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

(18) The device according to (17), wherein miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c-1-3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR-486-5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the prostate cancer markers according to (11) or (12).

(23) A method for detecting prostate cancer, comprising measuring an expression level of a target nucleic acid in a sample from a subject using a kit according to any one of (1) to (10) or a device according to any one of (11) to (22), and evaluating in vitro whether or not the subject has prostate cancer using the measured expression level and a control expression level in a sample from a healthy subject measured in the same way as above.

(24) The method according to (23), wherein the subject is a human.

(25) The method according to (23) or (24), wherein the sample is blood, serum, or plasma.

Definition of Term

The terms used in the present specification are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

In the present specification, the term "polynucleotide" is used for a nucleic acid including all of RNA, DNA, and RNA/DNA (chimera). The DNA includes all of cDNA, genomic DNA, and synthetic DNA. The RNA includes all of total RNA, mRNA, rRNA, miRNA, siRNA, snoRNA, snRNA, non-coding RNA and synthetic RNA. In the present specification, the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). In the present specification, the "non-natural sequence" is intended to be used in a broad sense and includes, for example, a sequence containing substitution, deletion, insertion, and/or addition of one or more nucleotide(s) (i.e., a variant sequence) and a sequence containing one or more modified nucleotide(s) (i.e., a modified sequence), which are different from the natural sequence. In the present specification, the polynucleotide is used interchangeably with a nucleic acid.

In the present specification, the term "fragment" is a polynucleotide having a nucleotide sequence having a consecutive portion of a polynucleotide and desirably has a length of 15 or more nucleotides, preferably 17 or more nucleotides, more preferably 19 or more nucleotides.

In the present specification, the term "gene" is intended to include not only RNA and double-stranded DNA but also each single-stranded DNA such as a plus strand (or a sense strand) or a complementary strand (or an antisense strand) constituting the duplex. The gene is not particularly limited by its length.

Thus, in the present specification, the "gene" includes all of double-stranded DNA including human genomic DNA, single-stranded DNA (plus strand) including cDNA, single-stranded DNA having a sequence complementary to the plus strand (complementary strand), microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 684 or a nucleotide sequence derived from the nucleotide sequence by the replacement of u with t. The "gene" is not particularly limited by its functional region and can contain, for example, an expression control region, a coding region, an exon, or an intron. The "gene" may be contained in a cell or may exist alone after being released into the outside of a cell. Alternatively, the "gene" may be in a state enclosed in a vesicle called exosome.

In the present specification, the term "exosome" is a vesicle that is capsulated with a lipid bilayer and secreted from a cell. The exosome is derived from a multivesicular endosome and may incorporate a biomaterial such as a "gene" (e.g., RNA or DNA) or a protein when released into an extracellular environment. The exosome is known to be contained in a body fluid such as blood, serum, plasma, serum, or lymph.

In the present specification, the term "transcript" refers to an RNA synthesized with the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a poly A sequence, including an expression regulatory region, a coding region, an exon, or an intron.

In the present specification, the term "microRNA (miRNA)" is intended to mean a 15- to 25-nucleotide non-coding RNA that is transcribed as an RNA precursor having a hairpin-like structure, cleaved by a dsRNA-cleaving enzyme which has RNase III cleavage activity, integrated into a protein complex called RISC, and involved in the suppression of translation of mRNA, unless otherwise specified. The term "miRNA" used in the present specification includes not only a "miRNA" represented by a particular nucleotide sequence (or SEQ ID N0) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 684. The term "miRNA" used in the present specification may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

In the present specification, the term "probe" includes a polynucleotide that is used for specifically detecting an RNA resulting from the expression of a gene or a polynucleotide derived from the RNA, and/or a polynucleotide complementary thereto.

In the present specification, the term "primer" includes a polynucleotide that specifically recognizes and amplifies an RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship based on A:T (U) and G:C base pairs with the full-length sequence of a polynucleotide consisting of a nucleotide sequence defined by any of SEQ ID NOs: 1 to 684 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

In the present specification, the term "stringent conditions" refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

In the present specification, the term "Tm value" means a temperature at which the double-stranded moiety of a polynucleotide is denatured into single strands so that the double strands and the single strands exist at a ratio of 1:1.

In the present specification, the term "variant" means, in the case of a nucleic acid, a natural variant attributed to polymorphism, mutation, or the like; a variant containing the deletion, substitution, addition, or insertion of 1, 2, or 3 or more nucleotides in a nucleotide sequence represented by any of SEQ ID NOs: 1 to 684 or a nucleotide sequence derived from the nucleotide sequence by the replacement of u with t, or a partial sequence thereof; a variant containing the deletion, substitution, addition, or insertion of 1 or 2 or more nucleotides in a nucleotide sequence of a premature miRNA of a sequence represented by any of SEQ ID NOs: 1 to 684 or a nucleotide sequence derived from the nucleotide sequence by the replacement of u with t, or a partial sequence thereof; a variant that exhibits % identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

In the present specification, the term "several" means an integer of approximately 10, 9, 8, 7, 6, 5, 4, 3, or 2.

In the present specification, the variant can be prepared by use of a well-known technique such as site-directed mutagenesis or PCR-based mutagenesis.

In the present specification, the term "percent (%) identity" can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

In the present specification, the term "derivative" is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

In the present specification, the "nucleic acid" capable of specifically binding to a polynucleotide selected from the prostate cancer marker miRNAs described above is a synthesized or prepared nucleic acid and specifically includes a "nucleic acid probe" or a "primer". The "nucleic acid" is utilized directly or indirectly for detecting the presence or absence of prostate cancer in a subject, for diagnosing the severity, the degree of amelioration, or the therapeutic sensitivity of prostate cancer, or for screening for a candidate substance useful in the prevention, amelioration, or treatment of prostate cancer. The "nucleic acid" includes a nucleotide, an oligonucleotide, and a polynucleotide capable of specifically recognizing and binding to a transcript represented by any of SEQ ID NOs: 1 to 684, or a synthetic cDNA nucleic acid thereof in vivo, particularly, in a sample such as a body fluid (e.g., blood or urine), in relation to the development of prostate cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used in the present specification is interchangeable with the term "examination", "measurement", or "detection or decision support". In the present specification, the term "evaluation" is meant to include diagnosis or evaluation support on the basis of examination results or measurement results.

The term "subject" used in the present specification means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used in the present specification refers to a probability at which a more extreme statistic than that actually calculated from data under a null hypothesis is observed in a statistical test. Thus, smaller "P" or "P value" means more significant difference between subjects to be compared.

In the present specification, the term "sensitivity" means a value of (the number of true positives)/(the number of true positives+the number of false negatives). High sensitivity allows prostate cancer to be detected early, leading to the complete resection of cancer sites and reduction in the rate of recurrence.

In the present specification, the term "specificity" means a value of (the number of true negatives)/(the number of true negatives+the number of false positives). High specificity prevents needless extra examination for healthy subjects misjudged as being prostate cancer patients, leading to reduction in burden on patients and reduction in medical expense.

In the present specification, the term "accuracy" means a value of (the number of true positives+the number of true negatives)/(the total number of cases). The accuracy indicates the ratio of samples that were correctly identified to all samples and serves as a primary index to evaluate detection performance.

In the present specification, the "sample" that is subjected to determination, detection, or diagnosis refers to a tissue and a biological material in which the expression of the gene of the present invention varies as prostate cancer develops, prostate cancer progresses, and therapeutic effects on prostate cancer are exerted. Specifically, the "sample" refers to a prostatic tissue, a periprostatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4443 gene" or "hsa-miR-4443" used in the present specification includes the hsa-miR-4443 gene (miRBase Accession No. MIMAT0018961) described in SEQ ID NO: 1, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 188) having a hairpin-like structure is known as a precursor of "hsa-miR-4443".

The term "hsa-miR-1908-5p gene" or "hsa-miR-1908-5p" used in the present specification includes the hsa-miR-1908-5p gene (miRBase Accession No. MIMAT0007881) described in SEQ ID NO: 2, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 189) having a hairpin-like structure is known as a precursor of "hsa-miR-1908-5p".

The term "hsa-miR-4257 gene" or "hsa-miR-4257" used in the present specification includes the hsa-miR-4257 gene (miRBase Accession No. MIMAT0016878) described in SEQ ID NO: 3, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 190) having a hairpin-like structure is known as a precursor of "hsa-miR-4257".

The term "hsa-miR-3197 gene" or "hsa-miR-3197" used in the present specification includes the hsa-miR-3197 gene (miRBase Accession No. MIMAT0015082) described in SEQ ID NO: 4, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 191) having a hairpin-like structure is known as a precursor of "hsa-miR-3197".

The term "hsa-miR-3188 gene" or "hsa-miR-3188" used in the present specification includes the hsa-miR-3188 gene (miRBase Accession No. MIMAT0015070) described in SEQ ID NO: 5, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 192) having a hairpin-like structure is known as a precursor of "hsa-miR-3188".

The term "hsa-miR-4649-5p gene" or "hsa-miR-4649-5p" used in the present specification includes the hsa-miR-4649-5p gene (miRBase Accession No. MIMAT0019711) described in SEQ ID NO: 6, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 193) having a hairpin-like structure is known as a precursor of "hsa-miR-4649-5p".

The term "hsa-miR-1343-3p gene" or "hsa-miR-1343-3p" used in the present specification includes the hsa-miR-1343-3p gene (miRBase Accession No. MIMAT0019776) described in SEQ ID NO: 7, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 194) having a hairpin-like structure is known as a precursor of "hsa-miR-1343-3p".

The term "hsa-miR-6861-5p gene" or "hsa-miR-6861-5p" used in the present specification includes the hsa-miR-6861-5p gene (miRBase Accession No. MIMAT0027623) described in SEQ ID NO: 8, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 195) having a hairpin-like structure is known as a precursor of "hsa-miR-6861-5p".

The term "hsa-miR-1343-5p gene" or "hsa-miR-1343-5p" used in the present specification includes the hsa-miR-1343-5p gene (miRBase Accession No. MIMAT0027038) described in SEQ ID NO: 9, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 194) having a hairpin-like structure is known as a precursor of "hsa-miR-1343-5p".

The term "hsa-miR-642b-3p gene" or "hsa-miR-642b-3p" used in the present specification includes the hsa-miR-642b-3p gene (miRBase Accession No. MIMAT0018444) described in SEQ ID NO: 10, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 196) having a hairpin-like structure is known as a precursor of "hsa-miR-642b-3p".

The term "hsa-miR-6741-5p gene" or "hsa-miR-6741-5p" used in the present specification includes the hsa-miR-6741-5p gene (miRBase Accession No. MIMAT0027383) described in SEQ ID NO: 11, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. M10022586, SEQ ID NO: 197) having a hairpin-like structure is known as a precursor of "hsa-miR-6741-5p".

The term "hsa-miR-4745-5p gene" or "hsa-miR-4745-5p" used in the present specification includes the hsa-miR-4745-5p gene (miRBase Accession No. MIMAT0019878) described in SEQ ID NO: 12, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 198) having a hairpin-like structure is known as a precursor of "hsa-miR-4745-5p".

The term "hsa-miR-6826-5p gene" or "hsa-miR-6826-5p" used in the present specification includes the hsa-miR-6826-5p gene (miRBase Accession No. MIMAT0027552) described in SEQ ID NO: 13, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. M10022671, SEQ ID NO: 199) having a hairpin-like structure is known as a precursor of "hsa-miR-6826-5p".

The term "hsa-miR-3663-3p gene" or "hsa-miR-3663-3p" used in the present specification includes the hsa-miR-3663-3p gene (miRBase Accession No. MIMAT0018085) described in SEQ ID NO: 14, a homolog or an ortholog of a different organism species, and the like. The hsa-miR-3663-3p gene can be obtained by a method described in Liao J Y et al., 2010, PLoS One, Vol. 5, e10563. Also, "hsa-mir- 3663" (miRBase Accession No. MI0016064, SEQ ID NO: 200) having a hairpin-like structure is known as a precursor of "hsa-miR-3663-3p".

The term "hsa-miR-3131 gene" or "hsa-miR-3131" used in the present specification includes the hsa-miR-3131 gene (miRBase Accession No. MIMAT0014996) described in SEQ ID NO: 15, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 201) having a hairpin-like structure is known as a precursor of "hsa-miR-3131".

The term "hsa-miR-92a-2-5p gene" or "hsa-miR-92a-2-5p" used in the present specification includes the hsa-miR-92a-2-5p gene (miRBase Accession No. MIMAT0004508) described in SEQ ID NO: 16, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. M10000094, SEQ ID NO: 202) having a hairpin-like structure is known as a precursor of "hsa-miR-92a-2-5p".

The term "hsa-miR-4258 gene" or "hsa-miR-4258" used in the present specification includes the hsa-miR-4258 gene (miRBase Accession No. MIMAT0016879) described in SEQ ID NO: 17, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 203) having a hairpin-like structure is known as a precursor of "hsa-miR-4258".

The term "hsa-miR-4448 gene" or "hsa-miR-4448" used in the present specification includes the hsa-miR-4448 gene (miRBase Accession No. MIMAT0018967) described in SEQ ID NO: 18, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 204) having a hairpin-like structure is known as a precursor of "hsa-miR-4448".

The term "hsa-miR-6125 gene" or "hsa-miR-6125" used in the present specification includes the hsa-miR-6125 gene (miRBase Accession No. MIMAT0024598) described in SEQ ID NO: 19, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 205) having a hairpin-like structure is known as a precursor of "hsa-miR-6125".

The term "hsa-miR-6880-5p gene" or "hsa-miR-6880-5p" used in the present specification includes the hsa-miR-6880-5p gene (miRBase Accession No. MIMAT0027660) described in SEQ ID NO: 20, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. M10022727, SEQ ID NO: 206) having a hairpin-like structure is known as a precursor of "hsa-miR-6880-5p".

The term "hsa-miR-6132 gene" or "hsa-miR-6132" used in the present specification includes the hsa-miR-6132 gene (miRBase Accession No. MIMAT0024616) described in SEQ ID NO: 21, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 207) having a hairpin-like structure is known as a precursor of "hsa-miR-6132".

The term "hsa-miR-4467 gene" or "hsa-miR-4467" used in the present specification includes the hsa-miR-4467 gene (miRBase Accession No. MIMAT0018994) described in SEQ ID NO: 22, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 208) having a hairpin-like structure is known as a precursor of "hsa-miR-4467".

The term "hsa-miR-6749-5p gene" or "hsa-miR-6749-5p" used in the present specification includes the hsa-miR-6749-5p gene (miRBase Accession No. MIMAT0027398) described in SEQ ID NO: 23, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. M10022594, SEQ ID NO: 209) having a hairpin-like structure is known as a precursor of "hsa-miR-6749-5p".

The term "hsa-miR-2392 gene" or "hsa-miR-2392" used in the present specification includes the hsa-miR-2392 gene (miRBase Accession No. MIMAT0019043) described in SEQ ID NO: 24, a homolog or an ortholog of a different organism species, and the like. The hsa-miR-2392 gene can be obtained by a method described in Jima D D et al., 2010, Blood, Vol. 116, e118-e127. Also, "hsa-mir-2392" (miRBase Accession No. MI0016870, SEQ ID NO: 210) having a hairpin-like structure is known as a precursor of "hsa-miR-2392".

The term "hsa-miR-1273g-3p gene" or "hsa-miR-1273g-3p" used in the present specification includes the hsa-miR-1273g-3p gene (miRBase Accession No. MIMAT0022742) described in SEQ ID NO: 25, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 211) having a hairpin-like structure is known as a precursor of "hsa-miR-1273g-3p".

The term "hsa-miR-4746-3p gene" or "hsa-miR-4746-3p" used in the present specification includes the hsa-miR-4746-3p gene (miRBase Accession No. MIMAT0019881) described in SEQ ID NO: 26, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 212) having a hairpin-like structure is known as a precursor of "hsa-miR-4746-3p".

The term "hsa-miR-1914-3p gene" or "hsa-miR-1914-3p" used in the present specification includes the hsa-miR-1914-3p gene (miRBase Accession No. MIMAT0007890) described in SEQ ID NO: 27, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 213) having a hairpin-like structure is known as a precursor of "hsa-miR-1914-3p".

The term "hsa-miR-7845-5p gene" or "hsa-miR-7845-5p" used in the present specification includes the hsa-miR-7845-5p gene (miRBase Accession No. MIMAT0030420) described in SEQ ID NO: 28, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 214) having a hairpin-like structure is known as a precursor of "hsa-miR-7845-5p".

The term "hsa-miR-6726-5p gene" or "hsa-miR-6726-5p" used in the present specification includes the hsa-miR-6726-5p gene (miRBase Accession No. MIMAT0027353) described in SEQ ID NO: 29, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 215) having a hairpin-like structure is known as a precursor of "hsa-miR-6726-5p".

The term "hsa-miR-128-2-5p gene" or "hsa-miR-128-2-5p" used in the present specification includes the hsa-miR-128-2-5p gene (miRBase Accession No. MIMAT0031095) described in SEQ ID NO: 30, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. M10000727, SEQ ID NO: 216) having a hairpin-like structure is known as a precursor of "hsa-miR-128-2-5p".

The term "hsa-miR-4651 gene" or "hsa-miR-4651" used in the present specification includes the hsa-miR-4651 gene (miRBase Accession No. MIMAT0019715) described in SEQ ID NO: 31, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 217) having a hairpin-like structure is known as a precursor of "hsa-miR-4651".

The term "hsa-miR-6765-3p gene" or "hsa-miR-6765-3p" used in the present specification includes the hsa-miR-6765-3p gene (miRBase Accession No. MIMAT0027431) described in SEQ ID NO: 32, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 218) having a hairpin-like structure is known as a precursor of "hsa-miR-6765-3p".

The term "hsa-miR-3185 gene" or "hsa-miR-3185" used in the present specification includes the hsa-miR-3185 gene (miRBase Accession No. MIMAT0015065) described in SEQ ID NO: 33, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 219) having a hairpin-like structure is known as a precursor of "hsa-miR-3185".

The term "hsa-miR-4792 gene" or "hsa-miR-4792" used in the present specification includes the hsa-miR-4792 gene (miRBase Accession No. MIMAT0019964) described in SEQ ID NO: 34, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 220) having a hairpin-like structure is known as a precursor of "hsa-miR-4792".

The term "hsa-miR-6887-5p gene" or "hsa-miR-6887-5p" used in the present specification includes the hsa-miR-6887-5p gene (miRBase Accession No. MIMAT0027674) described in SEQ ID NO: 35, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. M10022734, SEQ ID NO: 221) having a hairpin-like structure is known as a precursor of "hsa-miR-6887-5p".

The term "hsa-miR-5572 gene" or "hsa-miR-5572" used in the present specification includes the hsa-miR-5572 gene (miRBase Accession No. MIMAT0022260) described in SEQ ID NO: 36, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 222) having a hairpin-like structure is known as a precursor of "hsa-miR-5572".

The term "hsa-miR-3619-3p gene" or "hsa-miR-3619-3p" used in the present specification includes the hsa-miR-3619-3p gene (miRBase Accession No. MIMAT0019219) described in SEQ ID NO: 37, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 223) having a hairpin-like structure is known as a precursor of "hsa-miR-3619-3p".

The term "hsa-miR-6780b-5p gene" or "hsa-miR-6780b-5p" used in the present specification includes the hsa-miR-6780b-5p gene (miRBase Accession No. MIMAT0027572) described in SEQ ID NO: 38, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. M10022681, SEQ ID NO: 224) having a hairpin-like structure is known as a precursor of "hsa-miR-6780b-5p".

The term "hsa-miR-4707-5p gene" or "hsa-miR-4707-5p" used in the present specification includes the hsa-miR-4707-5p gene (miRBase Accession No. MIMAT0019807) described in SEQ ID NO: 39, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 225) having a hairpin-like structure is known as a precursor of "hsa-miR-4707-5p".

The term "hsa-miR-8063 gene" or "hsa-miR-8063" used in the present specification includes the hsa-miR-8063 gene (miRBase Accession No. MIMAT0030990) described in SEQ ID NO: 40, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 226) having a hairpin-like structure is known as a precursor of "hsa-miR-8063".

The term "hsa-miR-4454 gene" or "hsa-miR-4454" used in the present specification includes the hsa-miR-4454 gene (miRBase Accession No. MIMAT0018976) described in SEQ ID NO: 41, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 227) having a hairpin-like structure is known as a precursor of "hsa-miR-4454".

The term "hsa-miR-4525 gene" or "hsa-miR-4525" used in the present specification includes the hsa-miR-4525 gene (miRBase Accession No. MIMAT0019064) described in SEQ ID NO: 42, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 228) having a hairpin-like structure is known as a precursor of "hsa-miR-4525".

The term "hsa-miR-7975 gene" or "hsa-miR-7975" used in the present specification includes the hsa-miR-7975 gene (miRBase Accession No. MIMAT0031178) described in SEQ ID NO: 43, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 229) having a hairpin-like structure is known as a precursor of "hsa-miR-7975".

The term "hsa-miR-744-5p gene" or "hsa-miR-744-5p" used in the present specification includes the hsa-miR-744-5p gene (miRBase Accession No. MIMAT0004945) described in SEQ ID NO: 44, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 230) having a hairpin-like structure is known as a precursor of "hsa-miR-744-5p".

The term "hsa-miR-3135b gene" or "hsa-miR-3135b" used in the present specification includes the hsa-miR-3135b gene (miRBase Accession No. MIMAT0018985) described in SEQ ID NO: 45, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 231) having a hairpin-like structure is known as a precursor of "hsa-miR-3135b".

The term "hsa-miR-4648 gene" or "hsa-miR-4648" used in the present specification includes the hsa-miR-4648 gene (miRBase Accession No. MIMAT0019710) described in SEQ ID NO: 46, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 232) having a hairpin-like structure is known as a precursor of "hsa-miR-4648".

The term "hsa-miR-6816-5p gene" or "hsa-miR-6816-5p" used in the present specification includes the hsa-miR-6816-5p gene (miRBase Accession No. MIMAT0027532) described in SEQ ID NO: 47, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 233) having a hairpin-like structure is known as a precursor of "hsa-miR-6816-5p".

The term "hsa-miR-4741 gene" or "hsa-miR-4741" used in the present specification includes the hsa-miR-4741 gene (miRBase Accession No. MIMAT0019871) described in SEQ ID NO: 48, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 234) having a hairpin-like structure is known as a precursor of "hsa-miR-4741".

The term "hsa-miR-7150 gene" or "hsa-miR-7150" used in the present specification includes the hsa-miR-7150 gene (miRBase Accession No. MIMAT0028211) described in SEQ ID NO: 49, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 235) having a hairpin-like structure is known as a precursor of "hsa-miR-7150".

The term "hsa-miR-6791-5p gene" or "hsa-miR-6791-5p" used in the present specification includes the hsa-miR-6791-5p gene (miRBase Accession No. MIMAT0027482) described in SEQ ID NO: 50, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 236) having a hairpin-like structure is known as a precursor of "hsa-miR-6791-5p".

The term "hsa-miR-1247-3p gene" or "hsa-miR-1247-3p" used in the present specification includes the hsa-miR-1247-3p gene (miRBase Accession No. MIMAT0022721) described in SEQ ID NO: 51, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 237) having a hairpin-like structure is known as a precursor of "hsa-miR-1247-3p".

The term "hsa-miR-7977 gene" or "hsa-miR-7977" used in the present specification includes the hsa-miR-7977 gene (miRBase Accession No. MIMAT0031180) described in SEQ ID NO: 52, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 238) having a hairpin-like structure is known as a precursor of "hsa-miR-7977".

The term "hsa-miR-4497 gene" or "hsa-miR-4497" used in the present specification includes the hsa-miR-4497 gene (miRBase Accession No. MIMAT0019032) described in SEQ ID NO: 53, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 239) having a hairpin-like structure is known as a precursor of "hsa-miR-4497".

The term "hsa-miR-6090 gene" or "hsa-miR-6090" used in the present specification includes the hsa-miR-6090 gene (miRBase Accession No. MIMAT0023715) described in SEQ ID NO: 54, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir- 6090" (miRBase Accession No. M10020367, SEQ ID NO: 240) having a hairpin-like structure is known as a precursor of "hsa-miR-6090".

The term "hsa-miR-6781-5p gene" or "hsa-miR-6781-5p" used in the present specification includes the hsa-miR-6781-5p gene (miRBase Accession No. MIMAT0027462) described in SEQ ID NO: 55, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. M10022626, SEQ ID NO: 241) having a hairpin-like structure is known as a precursor of "hsa-miR-6781-5p".

The term "hsa-miR-6870-5p gene" or "hsa-miR-6870-5p" used in the present specification includes the hsa-miR-6870-5p gene (miRBase Accession No. MIMAT0027640) described in SEQ ID NO: 56, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. M10022717, SEQ ID NO: 242) having a hairpin-like structure is known as a precursor of "hsa-miR-6870-5p".

The term "hsa-miR-6729-5p gene" or "hsa-miR-6729-5p" used in the present specification includes the hsa-miR-6729-5p gene (miRBase Accession No. MIMAT0027359) described in SEQ ID NO: 57, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. M10022574, SEQ ID NO: 243) having a hairpin-like structure is known as a precursor of "hsa-miR-6729-5p".

The term "hsa-miR-4530 gene" or "hsa-miR-4530" used in the present specification includes the hsa-miR-4530 gene (miRBase Accession No. MIMAT0019069) described in SEQ ID NO: 58, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 244) having a hairpin-like structure is known as a precursor of "hsa-miR-4530".

The term "hsa-miR-7847-3p gene" or "hsa-miR-7847-3p" used in the present specification includes the hsa-miR-7847-3p gene (miRBase Accession No. MIMAT0030422) described in SEQ ID NO: 59, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 245) having a hairpin-like structure is known as a precursor of "hsa-miR-7847-3p".

The term "hsa-miR-6825-5p gene" or "hsa-miR-6825-5p" used in the present specification includes the hsa-miR-6825-5p gene (miRBase Accession No. MIMAT0027550) described in SEQ ID NO: 60, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. M10022670, SEQ ID NO: 246) having a hairpin-like structure is known as a precursor of "hsa-miR-6825-5p".

The term "hsa-miR-4674 gene" or "hsa-miR-4674" used in the present specification includes the hsa-miR-4674 gene (miRBase Accession No. MIMAT0019756) described in SEQ ID NO: 61, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 247) having a hairpin-like structure is known as a precursor of "hsa-miR-4674".

The term "hsa-miR-3917 gene" or "hsa-miR-3917" used in the present specification includes the hsa-miR-3917 gene (miRBase Accession No. MIMAT0018191) described in SEQ ID NO: 62, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 248) having a hairpin-like structure is known as a precursor of "hsa-miR-3917".

The term "hsa-miR-4707-3p gene" or "hsa-miR-4707-3p" used in the present specification includes the hsa-miR-4707-3p gene (miRBase Accession No. MIMAT0019808) described in SEQ ID NO: 63, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 225) having a hairpin-like structure is known as a precursor of "hsa-miR-4707-3p".

The term "hsa-miR-6885-5p gene" or "hsa-miR-6885-5p" used in the present specification includes the hsa-miR-6885-5p gene (miRBase Accession No. MIMAT0027670) described in SEQ ID NO: 64, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. M10022732, SEQ ID NO: 249) having a hairpin-like structure is known as a precursor of "hsa-miR-6885-5p".

The term "hsa-miR-6722-3p gene" or "hsa-miR-6722-3p" used in the present specification includes the hsa-miR-6722-3p gene (miRBase Accession No. MIMAT0025854) described in SEQ ID NO: 65, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 250) having a hairpin-like structure is known as a precursor of "hsa-miR-6722-3p".

The term "hsa-miR-4516 gene" or "hsa-miR-4516" used in the present specification includes the hsa-miR-4516 gene (miRBase Accession No. MIMAT0019053) described in SEQ ID NO: 66, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 251) having a hairpin-like structure is known as a precursor of "hsa-miR-4516".

The term "hsa-miR-6757-5p gene" or "hsa-miR-6757-5p" used in the present specification includes the hsa-miR-6757-5p gene (miRBase Accession No. MIMAT0027414) described in SEQ ID NO: 67, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. M10022602, SEQ ID NO: 252) having a hairpin-like structure is known as a precursor of "hsa-miR-6757-5p".

The term "hsa-miR-6840-3p gene" or "hsa-miR-6840-3p" used in the present specification includes the hsa-miR-6840-3p gene (miRBase Accession No. MIMAT0027583) described in SEQ ID NO: 68, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 253) having a hairpin-like structure is known as a precursor of "hsa-miR-6840-3p".

The term "hsa-miR-5195-3p gene" or "hsa-miR-5195-3p" used in the present specification includes the hsa-miR-5195-3p gene (miRBase Accession No. MIMAT0021127) described in SEQ ID NO: 69, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 254) having a hairpin-like structure is known as a precursor of "hsa-miR-5195-3p".

The term "hsa-miR-6756-5p gene" or "hsa-miR-6756-5p" used in the present specification includes the hsa-miR-6756-5p gene (miRBase Accession No. MIMAT0027412) described in SEQ ID NO: 70, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 255) having a hairpin-like structure is known as a precursor of "hsa-miR-6756-5p".

The term "hsa-miR-6800-5p gene" or "hsa-miR-6800-5p" used in the present specification includes the hsa-miR-6800-5p gene (miRBase Accession No. MIMAT0027500) described in SEQ ID NO: 71, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 256) having a hairpin-like structure is known as a precursor of "hsa-miR-6800-5p".

The term "hsa-miR-6727-5p gene" or "hsa-miR-6727-5p" used in the present specification includes the hsa-miR-6727-5p gene (miRBase Accession No. MIMAT0027355) described in SEQ ID NO: 72, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. M10022572, SEQ ID NO: 257) having a hairpin-like structure is known as a precursor of "hsa-miR-6727-5p".

The term "hsa-miR-6126 gene" or "hsa-miR-6126" used in the present specification includes the hsa-miR-6126 gene (miRBase Accession No. MIMAT0024599) described in SEQ ID NO: 73, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 258) having a hairpin-like structure is known as a precursor of "hsa-miR-6126".

The term "hsa-miR-6872-3p gene" or "hsa-miR-6872-3p" used in the present specification includes the hsa-miR-6872-3p gene (miRBase Accession No. MIMAT0027645) described in SEQ ID NO: 74, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. M10022719, SEQ ID NO: 259) having a hairpin-like structure is known as a precursor of "hsa-miR-6872-3p".

The term "hsa-miR-4446-3p gene" or "hsa-miR-4446-3p" used in the present specification includes the hsa-miR-4446-3p gene (miRBase Accession No. MIMAT0018965) described in SEQ ID NO: 75, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 260) having a hairpin-like structure is known as a precursor of "hsa-miR-4446-3p".

The term "hsa-miR-1268a gene" or "hsa-miR-1268a" used in the present specification includes the hsa-miR-1268a gene (miRBase Accession No. MIMAT0005922) described in SEQ ID NO: 76, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 261) having a hairpin-like structure is known as a precursor of "hsa-miR-1268a".

The term "hsa-miR-1908-3p gene" or "hsa-miR-1908-3p" used in the present specification includes the hsa-miR-1908-3p gene (miRBase Accession No. MIMAT0026916) described in SEQ ID NO: 77, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 189) having a hairpin-like structure is known as a precursor of "hsa-miR-1908-3p".

The term "hsa-miR-3679-5p gene" or "hsa-miR-3679-5p" used in the present specification includes the hsa-miR-3679-5p gene (miRBase Accession No. MIMAT0018104) described in SEQ ID NO: 78, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 262) having a hairpin-like structure is known as a precursor of "hsa-miR-3679-5p".

The term "hsa-miR-4534 gene" or "hsa-miR-4534" used in the present specification includes the hsa-miR-4534 gene (miRBase Accession No. MIMAT0019073) described in SEQ ID NO: 79, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 263) having a hairpin-like structure is known as a precursor of "hsa-miR-4534".

The term "hsa-miR-4675 gene" or "hsa-miR-4675" used in the present specification includes the hsa-miR-4675 gene (miRBase Accession No. MIMAT0019757) described in SEQ ID NO: 80, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 264) having a hairpin-like structure is known as a precursor of "hsa-miR-4675".

The term "hsa-miR-7108-5p gene" or "hsa-miR-7108-5p" used in the present specification includes the hsa-miR-7108-5p gene (miRBase Accession No. MIMAT0028113) described in SEQ ID NO: 81, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. M10022959, SEQ ID NO: 265) having a hairpin-like structure is known as a precursor of "hsa-miR-7108-5p".

The term "hsa-miR-6799-5p gene" or "hsa-miR-6799-5p" used in the present specification includes the hsa-miR-6799-5p gene (miRBase Accession No. MIMAT0027498) described in SEQ ID NO: 82, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. M10022644, SEQ ID NO: 266) having a hairpin-like structure is known as a precursor of "hsa-miR-6799-5p".

The term "hsa-miR-4695-5p gene" or "hsa-miR-4695-5p" used in the present specification includes the hsa-miR-4695-5p gene (miRBase Accession No. MIMAT0019788) described in SEQ ID NO: 83, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 267) having a hairpin-like structure is known as a precursor of "hsa-miR-4695-5p".

The term "hsa-miR-3178 gene" or "hsa-miR-3178" used in the present specification includes the hsa-miR-3178 gene (miRBase Accession No. MIMAT0015055) described in SEQ ID NO: 84, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 268) having a hairpin-like structure is known as a precursor of "hsa-miR-3178".

The term "hsa-miR-5090 gene" or "hsa-miR-5090" used in the present specification includes the hsa-miR-5090 gene (miRBase Accession No. MIMAT0021082) described in SEQ ID NO: 85, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 269) having a hairpin-like structure is known as a precursor of "hsa-miR-5090".

The term "hsa-miR-3180 gene" or "hsa-miR-3180" used in the present specification includes the hsa-miR-3180 gene (miRBase Accession No. MIMAT0018178) described in SEQ ID NO: 86, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and M10016409, SEQ ID NOs: 270 and 271) having a hairpin-like structure is known as precursors of "hsa-miR-3180".

The term "hsa-miR-1237-5p gene" or "hsa-miR-1237-5p" used in the present specification includes the hsa-miR-1237-5p gene (miRBase Accession No. MIMAT0022946) described in SEQ ID NO: 87, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 272) having a hairpin-like structure is known as a precursor of "hsa-miR-1237-5p".

The term "hsa-miR-4758-5p gene" or "hsa-miR-4758-5p" used in the present specification includes the hsa-miR-4758-5p gene (miRBase Accession No. MIMAT0019903) described in SEQ ID NO: 88, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 273) having a hairpin-like structure is known as a precursor of "hsa-miR-4758-5p".

The term "hsa-miR-3184-5p gene" or "hsa-miR-3184-5p" used in the present specification includes the hsa-miR-3184-5p gene (miRBase Accession No. MIMAT0015064) described in SEQ ID NO: 89, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 274) having a hairpin-like structure is known as a precursor of "hsa-miR-3184-5p".

The term "hsa-miR-4286 gene" or "hsa-miR-4286" used in the present specification includes the hsa-miR-4286 gene (miRBase Accession No. MIMAT0016916) described in SEQ ID NO: 90, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 275) having a hairpin-like structure is known as a precursor of "hsa-miR-4286".

The term "hsa-miR-6784-5p gene" or "hsa-miR-6784-5p" used in the present specification includes the hsa-miR-6784-5p gene (miRBase Accession No. MIMAT0027468) described in SEQ ID NO: 91, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. M10022629, SEQ ID NO: 276) having a hairpin-like structure is known as a precursor of "hsa-miR-6784-5p".

The term "hsa-miR-6768-5p gene" or "hsa-miR-6768-5p" used in the present specification includes the hsa-miR-6768-5p gene (miRBase Accession No. MIMAT0027436) described in SEQ ID NO: 92, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. M10022613, SEQ ID NO: 277) having a hairpin-like structure is known as a precursor of "hsa-miR-6768-5p".

The term "hsa-miR-6785-5p gene" or "hsa-miR-6785-5p" used in the present specification includes the hsa-miR-6785-5p gene (miRBase Accession No. MIMAT0027470) described in SEQ ID NO: 93, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. M10022630, SEQ ID NO: 278) having a hairpin-like structure is known as a precursor of "hsa-miR-6785-5p".

The term "hsa-miR-4706 gene" or "hsa-miR-4706" used in the present specification includes the hsa-miR-4706 gene (miRBase Accession No. MIMAT0019806) described in SEQ ID NO: 94, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miR- Base Accession No. MI0017339, SEQ ID NO: 279) having a hairpin-like structure is known as a precursor of "hsa-miR-4706".

The term "hsa-miR-711 gene" or "hsa-miR-711" used in the present specification includes the hsa-miR-711 gene (miRBase Accession No. MIMAT0012734) described in SEQ ID NO: 95, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 280) having a hairpin-like structure is known as a precursor of "hsa-miR-711".

The term "hsa-miR-1260a gene" or "hsa-miR-1260a" used in the present specification includes the hsa-miR-1260a gene (miRBase Accession No. MIMAT0005911) described in SEQ ID NO: 96, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 281) having a hairpin-like structure is known as a precursor of "hsa-miR-1260a".

The term "hsa-miR-6746-5p gene" or "hsa-miR-6746-5p" used in the present specification includes the hsa-miR-6746-5p gene (miRBase Accession No. MIMAT0027392) described in SEQ ID NO: 97, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. M10022591, SEQ ID NO: 282) having a hairpin-like structure is known as a precursor of "hsa-miR-6746-5p".

The term "hsa-miR-6089 gene" or "hsa-miR-6089" used in the present specification includes the hsa-miR-6089 gene (miRBase Accession No. MIMAT0023714) described in SEQ ID NO: 98, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 283 and 284) having a hairpin-like structure are known as precursors of "hsa-miR-6089".

The term "hsa-miR-6821-5p gene" or "hsa-miR-6821-5p" used in the present specification includes the hsa-miR-6821-5p gene (miRBase Accession No. MIMAT0027542) described in SEQ ID NO: 99, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 285) having a hairpin-like structure is known as a precursor of "hsa-miR-6821-5p".

The term "hsa-miR-4667-5p gene" or "hsa-miR-4667-5p" used in the present specification includes the hsa-miR-4667-5p gene (miRBase Accession No. MIMAT0019743) described in SEQ ID NO: 100, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 286) having a hairpin-like structure is known as a precursor of "hsa-miR-4667-5p".

The term "hsa-miR-8069 gene" or "hsa-miR-8069" used in the present specification includes the hsa-miR-8069 gene (miRBase Accession No. MIMAT0030996) described in SEQ ID NO: 101, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 287) having a hairpin-like structure is known as a precursor of "hsa-miR-8069".

The term "hsa-miR-4726-5p gene" or "hsa-miR-4726-5p" used in the present specification includes the hsa-miR-4726-5p gene (miRBase Accession No. MIMAT0019845) described in SEQ ID NO: 102, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 288) having a hairpin-like structure is known as a precursor of "hsa-miR-4726-5p".

The term "hsa-miR-6124 gene" or "hsa-miR-6124" used in the present specification includes the hsa-miR-6124 gene (miRBase Accession No. MIMAT0024597) described in SEQ ID NO: 103, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 289) having a hairpin-like structure is known as a precursor of "hsa-miR-6124".

The term "hsa-miR-4532 gene" or "hsa-miR-4532" used in the present specification includes the hsa-miR-4532 gene (miRBase Accession No. MIMAT0019071) described in SEQ ID NO: 104, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 290) having a hairpin-like structure is known as a precursor of "hsa-miR-4532".

The term "hsa-miR-4486 gene" or "hsa-miR-4486" used in the present specification includes the hsa-miR-4486 gene (miRBase Accession No. MIMAT0019020) described in SEQ ID NO: 105, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 291) having a hairpin-like structure is known as a precursor of "hsa-miR-4486".

The term "hsa-miR-4728-5p gene" or "hsa-miR-4728-5p" used in the present specification includes the hsa-miR-4728-5p gene (miRBase Accession No. MIMAT0019849) described in SEQ ID NO: 106, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 292) having a hairpin-like structure is known as a precursor of "hsa-miR-4728-5p".

The term "hsa-miR-4508 gene" or "hsa-miR-4508" used in the present specification includes the hsa-miR-4508 gene (miRBase Accession No. MIMAT0019045) described in SEQ ID NO: 107, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 293) having a hairpin-like structure is known as a precursor of "hsa-miR-4508".

The term “hsa-miR-128-1-5p gene” or “hsa-miR-128-1-5p” used in the present specification includes the hsa-miR-128-1-5p gene (miRBase Accession No. MIMAT0026477) described in SEQ ID NO: 108, a homolog or an ortholog of a different organism species, and the like. The hsa-miR-128-1-5p gene can be obtained by a method described in Lagos-Quintana M et al., 2002, Curr Biol, Vol. 12, p. 735-739. Also, “hsa-mir-128-1” (miRBase Accession No. M10000447, SEQ ID NO: 294) having a hairpin-like structure is known as a precursor of “hsa-miR-128-1-5p”.

The term “hsa-miR-4513 gene” or “hsa-miR-4513” used in the present specification includes the hsa-miR-4513 gene (miRBase Accession No. MIMAT0019050) described in SEQ ID NO: 109, a homolog or an ortholog of a different organism species, and the like. The hsa-miR-4513 gene can be obtained by a method described in Jima D D et al., 2010, Blood, Vol. 116, e118-e127. Also, “hsa-mir-4513” (miRBase Accession No. MI0016879, SEQ ID NO: 295) having a hairpin-like structure is known as a precursor of “hsa-miR-4513”.

The term “hsa-miR-6795-5p gene” or “hsa-miR-6795-5p” used in the present specification includes the hsa-miR-6795-5p gene (miRBase Accession No. MIMAT0027490) described in SEQ ID NO: 110, a homolog or an ortholog of a different organism species, and the like. The hsa-miR-6795-5p gene can be obtained by a method described in Ladewig E et al., 2012, Genome Res, Vol. 22, p. 1634-1645. Also, “hsa-mir-6795” (miRBase Accession No. M10022640, SEQ ID NO: 296) having a hairpin-like structure is known as a precursor of “hsa-miR-6795-5p”.

The term “hsa-miR-4689 gene” or “hsa-miR-4689” used in the present specification includes the hsa-miR-4689 gene (miRBase Accession No. MIMAT0019778) described in SEQ ID NO: 111, a homolog or an ortholog of a different organism species, and the like. The hsa-miR-4689 gene can be obtained by a method described in Persson H et al., 2011, Cancer Res, Vol. 71, p. 78-86. Also, “hsa-mir-4689” (miRBase Accession No. MI0017322, SEQ ID NO: 297) having a hairpin-like structure is known as a precursor of “hsa-miR-4689”.

The term “hsa-miR-6763-5p gene” or “hsa-miR-6763-5p” used in the present specification includes the hsa-miR-6763-5p gene (miRBase Accession No. MIMAT0027426) described in SEQ ID NO: 112, a homolog or an ortholog of a different organism species, and the like. The hsa-miR-6763-5p gene can be obtained by a method described in Ladewig E et al., 2012, Genome Res, Vol. 22, p. 1634-1645. Also, “hsa-mir-6763” (miRBase Accession No. MI0022608, SEQ ID NO: 298) having a hairpin-like structure is known as a precursor of “hsa-miR-6763-5p”.

The term “hsa-miR-8072 gene” or “hsa-miR-8072” used in the present specification includes the hsa-miR-8072 gene (miRBase Accession No. MIMAT0030999) described in SEQ ID NO: 113, a homolog or an ortholog of a different organism species, and the like. The hsa-miR-8072 gene can be obtained by a method described in Wang H J et al., 2013, Shock, Vol. 39, p. 480-487. Also, “hsa-mir-8072” (miRBase Accession No. MI0025908, SEQ ID NO: 299) having a hairpin-like structure is known as a precursor of “hsa-miR-8072”.

The term “hsa-miR-6765-5p gene” or “hsa-miR-6765-5p” used in the present specification includes the hsa-miR-6765-5p gene (miRBase Accession No. MIMAT0027430) described in SEQ ID NO: 114, a homolog or an ortholog of a different organism species, and the like. The hsa-miR-6765-5p gene can be obtained by a method described in Ladewig E et al., 2012, Genome Res, Vol. 22, p. 1634-1645. Also, “hsa-mir-6765” (miRBase Accession No. MI0022610, SEQ ID NO: 218) having a hairpin-like structure is known as a precursor of “hsa-miR-6765-5p”.

The term “hsa-miR-4419b gene” or “hsa-miR-4419b” used in the present specification includes the hsa-miR-4419b gene (miRBase Accession No. MIMAT0019034) described in SEQ ID NO: 115, a homolog or an ortholog of a different organism species, and the like. The hsa-miR-4419b gene can be obtained by a method described in Jima D D et al., 2010, Blood, Vol. 116, e118-e127. Also, “hsa-mir-4419b” (miRBase Accession No. MI0016861, SEQ ID NO: 300) having a hairpin-like structure is known as a precursor of “hsa-miR-4419b”.

The term “hsa-miR-7641 gene” or “hsa-miR-7641” used in the present specification includes the hsa-miR-7641 gene (miRBase Accession No. MIMAT0029782) described in SEQ ID NO: 116, a homolog or an ortholog of a different organism species, and the like. The hsa-miR-7641 gene can be obtained by a method described in Yoo J K et al., 2013, Arch Pharm Res, Vol. 36, p. 353-358. Also, “hsa-mir-7641-1 and hsa-mir-7641-2” (miRBase Accession Nos. MI0024975 and MI0024976, SEQ ID NOs: 301 and 302) having a hairpin-like structure are known as precursors of “hsa-miR-7641”.

The term “hsa-miR-3928-3p gene” or “hsa-miR-3928-3p” used in the present specification includes the hsa-miR-3928-3p gene (miRBase Accession No. MIMAT0018205) described in SEQ ID NO: 117, a homolog or an ortholog of a different organism species, and the like. The hsa-miR-3928-3p gene can be obtained by a method described in Creighton C J et al., 2010, PLoS One, Vol. 5, e9637. Also, “hsa-mir-3928” (miRBase Accession No. MI0016438, SEQ ID NO: 303) having a hairpin-like structure is known as a precursor of “hsa-miR-3928-3p”.

The term “hsa-miR-1227-5p gene” or “hsa-miR-1227-5p” used in the present specification includes the hsa-miR-1227-5p gene (miRBase Accession No. MIMAT0022941) described in SEQ ID NO: 118, a homolog or an ortholog of a different organism species, and the like. The hsa-miR-1227-5p gene can be obtained by a method described in Berezikov E et al., 2007, Mol Cell, Vol. 28, p. 328-336. Also, “hsa-mir-1227” (miRBase Accession No. MI0006316, SEQ ID NO: 304) having a hairpin-like structure is known as a precursor of “hsa-miR-1227-5p”.

The term “hsa-miR-4492 gene” or “hsa-miR-4492” used in the present specification includes the hsa-miR-4492 gene (miRBase Accession No. MIMAT0019027) described in SEQ ID NO: 119, a homolog or an ortholog of a different organism species, and the like. The hsa-miR-4492 gene can be obtained by a method described in Jima D D et al., 2010, Blood, Vol. 116, e118-e127. Also, “hsa-mir-4492” (miRBase Accession No. MI0016854, SEQ ID NO: 305) having a hairpin-like structure is known as a precursor of “hsa-miR-4492”.

The term “hsa-miR-296-3p gene” or “hsa-miR-296-3p” used in the present specification includes the hsa-miR-296-3p gene (miRBase Accession No. MIMAT0004679) described in SEQ ID NO: 120, a homolog or an ortholog of a different organism species, and the like. The hsa-miR-296-3p gene can be obtained by a method described in Houbaviy H B et al., 2003, Dev Cell, Vol. 5, p. 351-358. Also, “hsa-mir-296” (miRBase Accession No. MI0000747, SEQ ID NO: 306) having a hairpin-like structure is known as a precursor of “hsa-miR-296-3p”.

The term “hsa-miR-6769a-5p gene” or “hsa-miR-6769a-5p” used in the present specification includes the hsa-miR-6769a-5p gene (miRBase Accession No. MIMAT0027438)

described in SEQ ID NO: 121, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 307) having a hairpin-like structure is known as a precursor of "hsa-miR-6769a-5p".

The term "hsa-miR-6889-5p gene" or "hsa-miR-6889-5p" used in the present specification includes the hsa-miR-6889-5p gene (miRBase Accession No. MIMAT0027678) described in SEQ ID NO: 122, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. M10022736, SEQ ID NO: 308) having a hairpin-like structure is known as a precursor of "hsa-miR-6889-5p".

The term "hsa-miR-4632-5p gene" or "hsa-miR-4632-5p" used in the present specification includes the hsa-miR-4632-5p gene (miRBase Accession No. MIMAT0022977) described in SEQ ID NO: 123, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 309) having a hairpin-like structure is known as a precursor of "hsa-miR-4632-5p".

The term "hsa-miR-4505 gene" or "hsa-miR-4505" used in the present specification includes the hsa-miR-4505 gene (miRBase Accession No. MIMAT0019041) described in SEQ ID NO: 124, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 310) having a hairpin-like structure is known as a precursor of "hsa-miR-4505".

The term "hsa-miR-3154 gene" or "hsa-miR-3154" used in the present specification includes the hsa-miR-3154 gene (miRBase Accession No. MIMAT0015028) described in SEQ ID NO: 125, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 311) having a hairpin-like structure is known as a precursor of "hsa-miR-3154".

The term "hsa-miR-3648 gene" or "hsa-miR-3648" used in the present specification includes the hsa-miR-3648 gene (miRBase Accession No. MIMAT0018068) described in SEQ ID NO: 126, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 312) having a hairpin-like structure is known as a precursor of "hsa-miR-3648".

The term "hsa-miR-4442 gene" or "hsa-miR-4442" used in the present specification includes the hsa-miR-4442 gene (miRBase Accession No. MIMAT0018960) described in SEQ ID NO: 127, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 313) having a hairpin-like structure is known as a precursor of "hsa-miR-4442".

The term "hsa-miR-3141 gene" or "hsa-miR-3141" used in the present specification includes the hsa-miR-3141 gene (miRBase Accession No. MIMAT0015010) described in SEQ ID NO: 128, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 314) having a hairpin-like structure is known as a precursor of "hsa-miR-3141".

The term "hsa-miR-7113-3p gene" or "hsa-miR-7113-3p" used in the present specification includes the hsa-miR-7113-3p gene (miRBase Accession No. MIMAT0028124) described in SEQ ID NO: 129, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 315) having a hairpin-like structure is known as a precursor of "hsa-miR-7113-3p".

The term "hsa-miR-6819-5p gene" or "hsa-miR-6819-5p" used in the present specification includes the hsa-miR-6819-5p gene (miRBase Accession No. MIMAT0027538) described in SEQ ID NO: 130, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 316) having a hairpin-like structure is known as a precursor of "hsa-miR-6819-5p".

The term "hsa-miR-3195 gene" or "hsa-miR-3195" used in the present specification includes the hsa-miR-3195 gene (miRBase Accession No. MIMAT0015079) described in SEQ ID NO: 131, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 317) having a hairpin-like structure is known as a precursor of "hsa-miR-3195".

The term "hsa-miR-1199-5p gene" or "hsa-miR-1199-5p" used in the present specification includes the hsa-miR-1199-5p gene (miRBase Accession No. MIMAT0031119) described in SEQ ID NO: 132, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 318) having a hairpin-like structure is known as a precursor of "hsa-miR-1199-5p".

The term "hsa-miR-6738-5p gene" or "hsa-miR-6738-5p" used in the present specification includes the hsa-miR-6738-5p gene (miRBase Accession No. MIMAT0027377) described in SEQ ID NO: 133, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 319) having a hairpin-like structure is known as a precursor of "hsa-miR-6738-5p".

The term "hsa-miR-4656 gene" or "hsa-miR-4656" used in the present specification includes the hsa-miR-4656 gene (miRBase Accession No. MIMAT0019723) described in SEQ ID NO: 134, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miR- Base Accession No. MI0017284, SEQ ID NO: 320) having a hairpin-like structure is known as a precursor of "hsa-miR-4656".

The term "hsa-miR-6820-5p gene" or "hsa-miR-6820-5p" used in the present specification includes the hsa-miR-6820-5p gene (miRBase Accession No. MIMAT0027540) described in SEQ ID NO: 135, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 321) having a hairpin-like structure is known as a precursor of "hsa-miR-6820-5p".

The term "hsa-miR-615-5p gene" or "hsa-miR-615-5p" used in the present specification includes the hsa-miR-615-5p gene (miRBase Accession No. MIMAT0004804) described in SEQ ID NO: 136, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 322) having a hairpin-like structure is known as a precursor of "hsa-miR-615-5p".

The term "hsa-miR-486-3p gene" or "hsa-miR-486-3p" used in the present specification includes the hsa-miR-486-3p gene (miRBase Accession No. MIMAT0004762) described in SEQ ID NO: 137, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. M10002470 and M10023622, SEQ ID NO: 323 and 324) having a hairpin-like structure are known as precursors of "hsa-miR-486-3p".

The term "hsa-miR-1225-3p gene" or "hsa-miR-1225-3p" used in the present specification includes the hsa-miR-1225-3p gene (miRBase Accession No. MIMAT0005573) described in SEQ ID NO: 138, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 325) having a hairpin-like structure is known as a precursor of "hsa-miR-1225-3p".

The term "hsa-miR-760 gene" or "hsa-miR-760" used in the present specification includes the hsa-miR-760 gene (miRBase Accession No. MIMAT0004957) described in SEQ ID NO: 139, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 326) having a hairpin-like structure is known as a precursor of "hsa-miR-760".

The term "hsa-miR-187-5p gene" or "hsa-miR-187-5p" used in the present specification includes the hsa-miR-187-5p gene (miRBase Accession No. MIMAT0004561) described in SEQ ID NO: 140, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 327) having a hairpin-like structure is known as a precursor of "hsa-miR-187-5p".

The term "hsa-miR-1203 gene" or "hsa-miR-1203" used in the present specification includes the hsa-miR-1203 gene (miRBase Accession No. MIMAT0005866) described in SEQ ID NO: 141, a homolog or an ortholog of a different organism species, and the like. The hsa-miR-1203 gene can be obtained by a method described in Marton S et al., 2008, Leukemia, Vol. 22, p. 330-338. Also, "hsa-mir-1203" (miRBase Accession No. MI0006335, SEQ ID NO: 328) having a hairpin-like structure is known as a precursor of "hsa-miR-1203".

The term "hsa-miR-7110-5p gene" or "hsa-miR-7110-5p" used in the present specification includes the hsa-miR-7110-5p gene (miRBase Accession No. MIMAT0028117) described in SEQ ID NO: 142, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. M10022961, SEQ ID NO: 329) having a hairpin-like structure is known as a precursor of "hsa-miR-7110-5p".

The term "hsa-miR-371a-5p gene" or "hsa-miR-371a-5p" used in the present specification includes the hsa-miR-371a-5p gene (miRBase Accession No. MIMAT0004687) described in SEQ ID NO: 143, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 330) having a hairpin-like structure is known as a precursor of "hsa-miR-371a-5p".

The term "hsa-miR-939-5p gene" or "hsa-miR-939-5p" used in the present specification includes the hsa-miR-939-5p gene (miRBase Accession No. MIMAT0004982) described in SEQ ID NO: 144, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 331) having a hairpin-like structure is known as a precursor of "hsa-miR-939-5p".

The term "hsa-miR-575 gene" or "hsa-miR-575" used in the present specification includes the hsa-miR-575 gene (miRBase Accession No. MIMAT0003240) described in SEQ ID NO: 145, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 332) having a hairpin-like structure is known as a precursor of "hsa-miR-575".

The term "hsa-miR-92b-5p gene" or "hsa-miR-92b-5p" used in the present specification includes the hsa-miR-92b-5p gene (miRBase Accession No. MIMAT0004792) described in SEQ ID NO: 146, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 333) having a hairpin-like structure is known as a precursor of "hsa-miR-92b-5p".

The term "hsa-miR-887-3p gene" or "hsa-miR-887-3p" used in the present specification includes the hsa-miR-887-3p gene (miRBase Accession No. MIMAT0004951) described in SEQ ID NO: 147, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 334) having a hairpin-like structure is known as a precursor of "hsa-miR-887-3p".

The term "hsa-miR-920 gene" or "hsa-miR-920" used in the present specification includes the hsa-miR-920 gene (miRBase Accession No. MIMAT0004970) described in SEQ ID NO: 148, a homolog or an ortholog of a different organism species, and the like. The hsa-miR-920 gene can be obtained by a method described in Novotny G W et al., 2007, Int J Androl, Vol. 30, p. 316-326. Also, "hsa-mir-920" (miRBase Accession No. MI0005712, SEQ ID NO: 335) having a hairpin-like structure is known as a precursor of "hsa-miR-920".

The term "hsa-miR-1915-5p gene" or "hsa-miR-1915-5p" used in the present specification includes the hsa-miR-1915-5p gene (miRBase Accession No. MIMAT0007891) described in SEQ ID NO: 149, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 336) having a hairpin-like structure is known as a precursor of "hsa-miR-1915-5p".

The term "hsa-miR-1231 gene" or "hsa-miR-1231" used in the present specification includes the hsa-miR-1231 gene (miRBase Accession No. MIMAT0005586) described in SEQ ID NO: 150, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 337) having a hairpin-like structure is known as a precursor of "hsa-miR-1231".

The term "hsa-miR-663b gene" or "hsa-miR-663b" used in the present specification includes the hsa-miR-663b gene (miRBase Accession No. MIMAT0005867) described in SEQ ID NO: 151, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 338) having a hairpin-like structure is known as a precursor of "hsa-miR-663b".

The term "hsa-miR-1225-5p gene" or "hsa-miR-1225-5p" used in the present specification includes the hsa-miR-1225-5p gene (miRBase Accession No. MIMAT0005572) described in SEQ ID NO: 152, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 325) having a hairpin-like structure is known as a precursor of "hsa-miR-1225-5p".

The term "hsa-miR-4763-3p gene" or "hsa-miR-4763-3p" used in the present specification includes the hsa-miR-4763-3p gene (miRBase Accession No. MIMAT0019913) described in SEQ ID NO: 153, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 339) having a hairpin-like structure is known as a precursor of "hsa-miR-4763-3p".

The term "hsa-miR-3656 gene" or "hsa-miR-3656" used in the present specification includes the hsa-miR-3656 gene (miRBase Accession No. MIMAT0018076) described in SEQ ID NO: 154, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 340) having a hairpin-like structure is known as a precursor of "hsa-miR-3656".

The term "hsa-miR-4488 gene" or "hsa-miR-4488" used in the present specification includes the hsa-miR-4488 gene (miRBase Accession No. MIMAT0019022) described in SEQ ID NO: 155, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 341) having a hairpin-like structure is known as a precursor of "hsa-miR-4488".

The term "hsa-miR-125a-3p gene" or "hsa-miR-125a-3p" used in the present specification includes the hsa-miR-125a-3p gene (miRBase Accession No. MIMAT0004602) described in SEQ ID NO: 156, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. M10000469, SEQ ID NO: 342) having a hairpin-like structure is known as a precursor of "hsa-miR-125a-3p".

The term "hsa-miR-1469 gene" or "hsa-miR-1469" used in the present specification includes the hsa-miR-1469 gene (miRBase Accession No. MIMAT0007347) described in SEQ ID NO: 157, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 343) having a hairpin-like structure is known as a precursor of "hsa-miR-1469".

The term "hsa-miR-1228-5p gene" or "hsa-miR-1228-5p" used in the present specification includes the hsa-miR-1228-5p gene (miRBase Accession No. MIMAT0005582) described in SEQ ID NO: 158, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 344) having a hairpin-like structure is known as a precursor of "hsa-miR-1228-5p".

The term "hsa-miR-6798-5p gene" or "hsa-miR-6798-5p" used in the present specification includes the hsa-miR-6798-5p gene (miRBase Accession No. MIMAT0027496) described in SEQ ID NO: 159, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 345) having a hairpin-like structure is known as a precursor of "hsa-miR-6798-5p".

The term "hsa-miR-1268b gene" or "hsa-miR-1268b" used in the present specification includes the hsa-miR-1268b gene (miRBase Accession No. MIMAT0018925) described in SEQ ID NO: 160, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 346) having a hairpin-like structure is known as a precursor of "hsa-miR-1268b".

The term "hsa-miR-6732-5p gene" or "hsa-miR-6732-5p" used in the present specification includes the hsa-miR-6732-5p gene (miRBase Accession No. MIMAT0027365) described in SEQ ID NO: 161, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. M10022577, SEQ ID NO: 347) having a hairpin-like structure is known as a precursor of "hsa-miR-6732-5p".

The term "hsa-miR-1915-3p gene" or "hsa-miR-1915-3p" used in the present specification includes the hsa-miR-1915-3p gene (miRBase Accession No. MIMAT0007892) described in SEQ ID NO: 162, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 336) having a hairpin-like structure is known as a precursor of "hsa-miR-1915-3p".

The term "hsa-miR-4433b-3p gene" or "hsa-miR-4433b-3p" used in the present specification includes the hsa-miR-4433b-3p gene (miRBase Accession No. MIMAT0030414) described in SEQ ID NO: 163, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 348) having a hairpin-like structure is known as a precursor of "hsa-miR-4433b-3p".

The term "hsa-miR-1207-5p gene" or "hsa-miR-1207-5p" used in the present specification includes the hsa-miR-1207-5p gene (miRBase Accession No. MIMAT0005871) described in SEQ ID NO: 164, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. M10006340, SEQ ID NO: 349) having a hairpin-like structure is known as a precursor of "hsa-miR-1207-5p".

The term "hsa-miR-4433-3p gene" or "hsa-miR-4433-3p" used in the present specification includes the hsa-miR-4433-3p gene (miRBase Accession No. MIMAT0018949) described in SEQ ID NO: 165, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 350) having a hairpin-like structure is known as a precursor of "hsa-miR-4433-3p".

The term "hsa-miR-6879-5p gene" or "hsa-miR-6879-5p" used in the present specification includes the hsa-miR-6879-5p gene (miRBase Accession No. MIMAT0027658) described in SEQ ID NO: 166, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. M10022726, SEQ ID NO: 351) having a hairpin-like structure is known as a precursor of "hsa-miR-6879-5p".

The term "hsa-miR-4417 gene" or "hsa-miR-4417" used in the present specification includes the hsa-miR-4417 gene (miRBase Accession No. MIMAT0018929) described in SEQ ID NO: 167, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 352) having a hairpin-like structure is known as a precursor of "hsa-miR-4417".

The term "hsa-miR-30c-1-3p gene" or "hsa-miR-30c-1-3p" used in the present specification includes the hsa-miR-30c-1-3p gene (miRBase Accession No. MIMAT0004674) described in SEQ ID NO: 168, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 353) having a hairpin-like structure is known as a precursor of "hsa-miR-30c-1-3p".

The term "hsa-miR-4638-5p gene" or "hsa-miR-4638-5p" used in the present specification includes the hsa-miR-4638-5p gene (miRBase Accession No. MIMAT0019695) described in SEQ ID NO: 169, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 354) having a hairpin-like structure is known as a precursor of "hsa-miR-4638-5p".

The term "hsa-miR-6088 gene" or "hsa-miR-6088" used in the present specification includes the hsa-miR-6088 gene (miRBase Accession No. MIMAT0023713) described in SEQ ID NO: 170, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 355) having a hairpin-like structure is known as a precursor of "hsa-miR-6088".

The term "hsa-miR-4270 gene" or "hsa-miR-4270" used in the present specification includes the hsa-miR-4270 gene (miRBase Accession No. MIMAT0016900) described in SEQ ID NO: 171, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 356) having a hairpin-like structure is known as a precursor of "hsa-miR-4270".

The term "hsa-miR-6782-5p gene" or "hsa-miR-6782-5p" used in the present specification includes the hsa-miR-6782-5p gene (miRBase Accession No. MIMAT0027464) described in SEQ ID NO: 172, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. M10022627, SEQ ID NO: 357) having a hairpin-like structure is known as a precursor of "hsa-miR-6782-5p".

The term "hsa-miR-665 gene" or "hsa-miR-665" used in the present specification includes the hsa-miR-665 gene (miRBase Accession No. MIMAT0004952) described in SEQ ID NO: 173, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 358) having a hairpin-like structure is known as a precursor of "hsa-miR-665".

The term "hsa-miR-486-5p gene" or "hsa-miR-486-5p" used in the present specification includes the hsa-miR-486-5p gene (miRBase Accession No. MIMAT0002177) described in SEQ ID NO: 174, a homolog or an ortholog of a different organism species, and the like. The hsa-miR-486-5p gene can be obtained by a method described in Fu H et al., 2005, FEBS Lett, Vol. 579, p. 3849-3854. Also, "hsamir-486 and hsa-mir-486-2" (miRBase Accession Nos. MI0002470 and MI0023622, SEQ ID NOs: 323 and 324) having a hairpin-like structure are known as precursors of "hsa-miR-486-5p".

The term "hsa-miR-4655-5p gene" or "hsa-miR-4655-5p" used in the present specification includes the hsa-miR-4655-5p gene (miRBase Accession No. MIMAT0019721) described in SEQ ID NO: 175, a homolog or an ortholog of a different organism species, and the like. The hsa-miR-4655-5p gene can be obtained by a method described in Persson H et al., 2011, Cancer Res, Vol. 71, p. 78-86. Also, "hsa-mir-4655" (miRBase Accession No. MI0017283, SEQ ID NO: 359) having a hairpin-like structure is known as a precursor of "hsa-miR-4655-5p".

The term "hsa-miR-1275 gene" or "hsa-miR-1275" used in the present specification includes the hsa-miR-1275 gene (miRBase Accession No. MIMAT0005929) described in SEQ ID NO: 176, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 360) having a hairpin-like structure is known as a precursor of "hsa-miR-1275".

The term "hsa-miR-6806-5p gene" or "hsa-miR-6806-5p" used in the present specification includes the hsa-miR-6806-5p gene (miRBase Accession No. MIMAT0027512) described in SEQ ID NO: 177, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 361) having a hairpin-like structure is known as a precursor of "hsa-miR-6806-5p".

The term "hsa-miR-614 gene" or "hsa-miR-614" used in the present specification includes the hsa-miR-614 gene (miRBase Accession No. MIMAT0003282) described in SEQ ID NO: 178, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 362) having a hairpin-like structure is known as a precursor of "hsa-miR-614".

The term "hsa-miR-3937 gene" or "hsa-miR-3937" used in the present specification includes the hsa-miR-3937 gene (miRBase Accession No. MIMAT0018352) described in SEQ ID NO: 179, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 363) having a hairpin-like structure is known as a precursor of "hsa-miR-3937".

The term "hsa-miR-6752-5p gene" or "hsa-miR-6752-5p" used in the present specification includes the hsa-miR-6752-5p gene (miRBase Accession No. MIMAT0027404) described in SEQ ID NO: 180, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. M10022597, SEQ ID NO: 364) having a hairpin-like structure is known as a precursor of "hsa-miR-6752-5p".

The term "hsa-miR-6771-5p gene" or "hsa-miR-6771-5p" used in the present specification includes the hsa-miR-6771-5p gene (miRBase Accession No. MIMAT0027442) described in SEQ ID NO: 181, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771" (miRBase Accession No. MI0022616, SEQ ID NO: 365) having a hairpin-like structure is known as a precursor of "hsa-miR-6771-5p".

The term "hsa-miR-4450 gene" or "hsa-miR-4450" used in the present specification includes the hsa-miR-4450 gene (miRBase Accession No. MIMAT0018971) described in SEQ ID NO: 182, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795, SEQ ID NO: 366) having a hairpin-like structure is known as a precursor of "hsa-miR-4450".

The term "hsa-miR-211-3p gene" or "hsa-miR-211-3p" used in the present specification includes the hsa-miR-211-3p gene (miRBase Accession No. MIMAT0022694) described in SEQ ID NO: 183, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 367) having a hairpin-like structure is known as a precursor of "hsa-miR-211-3p".

The term "hsa-miR-663a gene" or "hsa-miR-663a" used in the present specification includes the hsa-miR-663a gene (miRBase Accession No. MIMAT0003326) described in SEQ ID NO: 184, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 368) having a hairpin-like structure is known as a precursor of "hsa-miR-663a".

The term "hsa-miR-6842-5p gene" or "hsa-miR-6842-5p" used in the present specification includes the hsa-miR-6842-5p gene (miRBase Accession No. MIMAT0027586) described in SEQ ID NO: 185, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 369) having a hairpin-like structure is known as a precursor of "hsa-miR-6842-5p".

The term "hsa-miR-7114-5p gene" or "hsa-miR-7114-5p" used in the present specification includes the hsa-miR-7114-5p gene (miRBase Accession No. MIMAT0028125) described in SEQ ID NO: 186, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 370) having a hairpin-like structure is known as a precursor of "hsa-miR-7114-5p".

The term "hsa-miR-6779-5p gene" or "hsa-miR-6779-5p" used in the present specification includes the hsa-miR-6779-5p gene (miRBase Accession No. MIMAT0027458) described in SEQ ID NO: 187, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. M10022624, SEQ ID NO: 371) having a hairpin-like structure is known as a precursor of "hsa-miR-6779-5p".

The term “hsa-miR-204-3p gene” or “hsa-miR-204-3p” used in the present specification includes the hsa-miR-204-3p gene (miRBase Accession No. MIMAT0022693) described in SEQ ID NO: 580, a homolog or an ortholog of a different organism species, and the like. The hsa-miR-204-3p gene can be obtained by a method described in Lim L P et al., 2003, Science, Vol. 299, p. 1540. Also, “hsa-mir-204” (miRBase Accession No. MI0000284, SEQ ID NO: 612) having a hairpin-like structure is known as a precursor of “hsa-miR-204-3p”.

The term “hsa-miR-642a-3p gene” or “hsa-miR-642a-3p” used in the present specification includes the hsa-miR-642a-3p gene (miRBase Accession No. MIMAT0020924) described in SEQ ID NO: 581, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, “hsa-mir-642a” (miRBase Accession No. MI0003657, SEQ ID NO: 613) having a hairpin-like structure is known as a precursor of “hsa-miR-642a-3p”.

The term “hsa-miR-762 gene” or “hsa-miR-762” used in the present specification includes the hsa-miR-762 gene (miRBase Accession No. MIMAT0010313) described in SEQ ID NO: 582, a homolog or an ortholog of a different organism species, and the like. The hsa-miR-762 gene can be obtained by a method described in Berezikov E et al., 2006, Genome Res, Vol. 16, p. 1289-1298. Also, “hsa-mir-762” (miRBase Accession No. MI0003892, SEQ ID NO: 614) having a hairpin-like structure is known as a precursor of “hsa-miR-762”.

The term “hsa-miR-1202 gene” or “hsa-miR-1202” used in the present specification includes the hsa-miR-1202 gene (miRBase Accession No. MIMAT0005865) described in SEQ ID NO: 583, a homolog or an ortholog of a different organism species, and the like. The hsa-miR-1202 gene can be obtained by a method described in Marton S et al., 2008, Leukemia, Vol. 22, p. 330-338. Also, “hsa-mir-1202” (miRBase Accession No. MI0006334, SEQ ID NO: 615) having a hairpin-like structure is known as a precursor of “hsa-miR-1202”.

The term “hsa-miR-3162-5p gene” or “hsa-miR-3162-5p” used in the present specification includes the hsa-miR-3162-5p gene (miRBase Accession No. MIMAT0015036) described in SEQ ID NO: 584, a homolog or an ortholog of a different organism species, and the like. The hsa-miR-3162-5p gene can be obtained by a method described in Stark M S et al., 2010, PLoS One, Vol. 5, e9685. Also, “hsa-mir-3162” (miRBase Accession No. MI0014192, SEQ ID NO: 616) having a hairpin-like structure is known as a precursor of “hsa-miR-3162-5p”.

The term “hsa-miR-3196 gene” or “hsa-miR-3196” used in the present specification includes the hsa-miR-3196 gene (miRBase Accession No. MIMAT0015080) described in SEQ ID NO: 585, a homolog or an ortholog of a different organism species, and the like. The hsa-miR-3196 gene can be obtained by a method described in Stark M S et al., 2010, PLoS One, Vol. 5, e9685. Also, “hsa-mir-3196” (miRBase Accession No. MI0014241, SEQ ID NO: 617) having a hairpin-like structure is known as a precursor of “hsa-miR-3196”.

The term “hsa-miR-3622a-5p gene” or “hsa-miR-3622a-5p” used in the present specification includes the hsa-miR-3622a-5p gene (miRBase Accession No. MIMAT0018003) described in SEQ ID NO: 586, a homolog or an ortholog of a different organism species, and the like. The hsa-miR-3622a-5p gene can be obtained by a method described in Witten D et al., 2010, BMC Biol., Vol. 8, p. 58. Also, “hsa-mir-3622a” (miRBase Accession No. MI0016013, SEQ ID NO: 618) having a hairpin-like structure is known as a precursor of “hsa-miR-3622a-5p”.

The term “hsa-miR-3665 gene” or “hsa-miR-3665” used in the present specification includes the hsa-miR-3665 gene (miRBase Accession No. MIMAT0018087) described in SEQ ID NO: 587, a homolog or an ortholog of a different organism species, and the like. The hsa-miR-3665 gene can be obtained by a method described in Xie X et al., 2005, Nature, Vol. 434, p. 338-345. Also, “hsa-mir-3665” (miRBase Accession No. MI0016066, SEQ ID NO: 619) having a hairpin-like structure is known as a precursor of “hsa-miR-3665”.

The term “hsa-miR-3940-5p gene” or “hsa-miR-3940-5p” used in the present specification includes the hsa-miR-3940-5p gene (miRBase Accession No. MIMAT0019229) described in SEQ ID NO: 588, a homolog or an ortholog of a different organism species, and the like. The hsa-miR-3940-5p gene can be obtained by a method described in Liao J Y et al., 2010, PLoS One, Vol. 5, e10563. Also, “hsa-mir-3940” (miRBase Accession No. MI0016597, SEQ ID NO: 620) having a hairpin-like structure is known as a precursor of “hsa-miR-3940-5p”.

The term “hsa-miR-4294 gene” or “hsa-miR-4294” used in the present specification includes the hsa-miR-4294 gene (miRBase Accession No. MIMAT0016849) described in SEQ ID NO: 589, a homolog or an ortholog of a different organism species, and the like. The hsa-miR-4294 gene can be obtained by a method described in Goff L A et al., 2009, PLoS One, Vol. 4, e7192. Also, “hsa-mir-4294” (miRBase Accession No. MI0015827, SEQ ID NO: 621) having a hairpin-like structure is known as a precursor of “hsa-miR-4294”.

The term “hsa-miR-4466 gene” or “hsa-miR-4466” used in the present specification includes the hsa-miR-4466 gene (miRBase Accession No. MIMAT0018993) described in SEQ ID NO: 590, a homolog or an ortholog of a different organism species, and the like. The hsa-miR-4466 gene can be obtained by a method described in Jima D D et al., 2010, Blood, Vol. 116, e118-e127. Also, “hsa-mir-4466” (miRBase Accession No. MI0016817, SEQ ID NO: 622) having a hairpin-like structure is known as a precursor of “hsa-miR-4466”.

The term “hsa-miR-4476 gene” or “hsa-miR-4476” used in the present specification includes the hsa-miR-4476 gene (miRBase Accession No. MIMAT0019003) described in SEQ ID NO: 591, a homolog or an ortholog of a different organism species, and the like. The hsa-miR-4476 gene can be obtained by a method described in Jima D D et al., 2010, Blood, Vol. 116, e118-e127. Also, “hsa-mir-4476” (miRBase Accession No. MI0016828, SEQ ID NO: 623) having a hairpin-like structure is known as a precursor of “hsa-miR-4476”.

The term “hsa-miR-4723-5p gene” or “hsa-miR-4723-5p” used in the present specification includes the hsa-miR-4723-5p gene (miRBase Accession No. MIMAT0019838) described in SEQ ID NO: 592, a homolog or an ortholog of a different organism species, and the like. The hsa-miR-4723-5p gene can be obtained by a method described in Persson H et al., 2011, Cancer Res., Vol. 71, p. 78-86. Also, “hsa-mir-4723” (miRBase Accession No. MI0017359, SEQ ID NO: 624) having a hairpin-like structure is known as a precursor of “hsa-miR-4723-5p”.

The term “hsa-miR-4725-3p gene” or “hsa-miR-4725-3p” used in the present specification includes the hsa-miR-4725-3p gene (miRBase Accession No. MIMAT0019844) described in SEQ ID NO: 593, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 625) having a hairpin-like structure is known as a precursor of "hsa-miR-4725-3p".

The term "hsa-miR-4730 gene" or "hsa-miR-4730" used in the present specification includes the hsa-miR-4730 gene (miRBase Accession No. MIMAT0019852) described in SEQ ID NO: 594, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 626) having a hairpin-like structure is known as a precursor of "hsa-miR-4730".

The term "hsa-miR-4739 gene" or "hsa-miR-4739" used in the present specification includes the hsa-miR-4739 gene (miRBase Accession No. MIMAT0019868) described in SEQ ID NO: 595, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 627) having a hairpin-like structure is known as a precursor of "hsa-miR-4739".

The term "hsa-miR-4787-5p gene" or "hsa-miR-4787-5p" used in the present specification includes the hsa-miR-4787-5p gene (miRBase Accession No. MIMAT0019956) described in SEQ ID NO: 596, a homolog or an ortholog of a different organism species, and the like. The hsa-miR-4787-5p gene can be obtained by a method described in Persson H et al., 2011, Cancer Res, Vol. 71, p. 78-86. Also, "hsa-mir-4787" (miRBase Accession No. MI0017434, SEQ ID NO: 628) having a hairpin-like structure is known as a precursor of "hsa-miR-4787-5p".

The term "hsa-miR-5787 gene" or "hsa-miR-5787" used in the present specification includes the hsa-miR-5787 gene (miRBase Accession No. MIMAT0023252) described in SEQ ID NO: 597, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. M10019797, SEQ ID NO: 629) having a hairpin-like structure is known as a precursor of "hsa-miR-5787".

The term "hsa-miR-6085 gene" or "hsa-miR-6085" used in the present specification includes the hsa-miR-6085 gene (miRBase Accession No. MIMAT0023710) described in SEQ ID NO: 598, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 630) having a hairpin-like structure is known as a precursor of "hsa-miR-6085".

The term "hsa-miR-6717-5p gene" or "hsa-miR-6717-5p" used in the present specification includes the hsa-miR-6717-5p gene (miRBase Accession No. MIMAT0025846) described in SEQ ID NO: 599, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 631) having a hairpin-like structure is known as a precursor of "hsa-miR-6717-5p".

The term "hsa-miR-6724-5p gene" or "hsa-miR-6724-5p" used in the present specification includes the hsa-miR-6724-5p gene (miRBase Accession No. MIMAT0025856) described in SEQ ID NO: 600, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 632) having a hairpin-like structure is known as a precursor of "hsa-miR-6724-5p".

The term "hsa-miR-6777-5p gene" or "hsa-miR-6777-5p" used in the present specification includes the hsa-miR-6777-5p gene (miRBase Accession No. MIMAT0027454) described in SEQ ID NO: 601, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. M10022622, SEQ ID NO: 633) having a hairpin-like structure is known as a precursor of "hsa-miR-6777-5p".

The term "hsa-miR-6778-5p gene" or "hsa-miR-6778-5p" used in the present specification includes the hsa-miR-6778-5p gene (miRBase Accession No. MIMAT0027456) described in SEQ ID NO: 602, a homolog or an ortholog of a different organism species, and the like. The hsa-miR-6778-5p gene can be obtained by a method described in Ladewig E et al., 2012, Genome Res., Vol. 22, p. 1634-1645. Also, "hsa-mir-6778" (miRBase Accession No. M10022623, SEQ ID NO: 634) having a hairpin-like structure is known as a precursor of "hsa-miR-6778-5p".

The term "hsa-miR-6787-5p gene" or "hsa-miR-6787-5p" used in the present specification includes the hsa-miR-6787-5p gene (miRBase Accession No. MIMAT0027474) described in SEQ ID NO: 603, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 635) having a hairpin-like structure is known as a precursor of "hsa-miR-6787-5p".

The term "hsa-miR-6789-5p gene" or "hsa-miR-6789-5p" used in the present specification includes the hsa-miR-6789-5p gene (miRBase Accession No. MIMAT0027478) described in SEQ ID NO: 604, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 636) having a hairpin-like structure is known as a precursor of "hsa-miR-6789-5p".

The term "hsa-miR-6845-5p gene" or "hsa-miR-6845-5p" used in the present specification includes the hsa-miR-6845-5p gene (miRBase Accession No. MIMAT0027590) described in SEQ ID NO: 605, a homolog or an ortholog of a different organism species, and the like. The hsa-miR-6845-5p gene can be obtained by a method described in Ladewig E et al., 2012, Genome Res., Vol. 22, p. 1634-1645. Also, "hsa-mir-6845" (miRBase Accession No. MI0022691, SEQ ID NO: 637) having a hairpin-like structure is known as a precursor of "hsa-miR-6845-5p".

The term "hsa-miR-6893-5p gene" or "hsa-miR-6893-5p" used in the present specification includes the hsa-miR-6893-5p gene (miRBase Accession No. MIMAT0027686) described in SEQ ID NO: 606, a homolog or an ortholog of a different organism species, and the like. The hsa-miR-6893-5p gene can be obtained by a method described in Ladewig E et al., 2012, Genome Res., Vol. 22, p. 1634-1645.

Also, "hsa-mir-6893" (miRBase Accession No. M10022740, SEQ ID NO: 638) having a hairpin-like structure is known as a precursor of "hsa-miR-6893-5p".

The term "hsa-miR-16-5p gene" or "hsa-miR-16-5p" used in the present specification includes the hsa-miR-16-5p gene (miRBase Accession No. MIMAT0000069) described in SEQ ID NO: 607, a homolog or an ortholog of a different organism species, and the like. The hsa-miR-16-5p gene can be obtained by a method described in Lagos-Quintana M et al., 2002, Curr Biol., Vol. 12, p. 735-739. Also, "hsa-mir-16-1 and hsa-mir-16-2" (miRBase Accession Nos. MI0000070 and MI0000115, SEQ ID NOs: 639 and 640) having a hairpin-like structure are known as precursors of "hsa-miR-16-5p".

The term "hsa-miR-423-5p gene" or "hsa-miR-423-5p" used in the present specification includes the hsa-miR-423-5p gene (miRBase Accession No. MIMAT0004748) described in SEQ ID NO: 608, a homolog or an ortholog of a different organism species, and the like. The hsa-miR-423-5p gene can be obtained by a method described in Kasashima K et al., 2004, Biochem Biophys Res Commun., Vol. 322, p. 403-410. Also, "hsa-mir-423" (miRBase Accession No. MI0001445, SEQ ID NO: 641) having a hairpin-like structure is known as a precursor of "hsa-miR-423-5p".

The term "hsa-miR-451a gene" or "hsa-miR-451a" used in the present specification includes the hsa-miR-451a gene (miRBase Accession No. MIMAT0001631) described in SEQ ID NO: 609, a homolog or an ortholog of a different organism species, and the like. The hsa-miR-451a gene can be obtained by a method described in Altuvia Y et al., 2005, Nucleic Acids Res., Vol. 33, p. 2697-2706. Also, "hsa-mir-451a" (miRBase Accession No. MI0001729, SEQ ID NO: 642) having a hairpin-like structure is known as a precursor of "hsa-miR-451a".

The term "hsa-miR-564 gene" or "hsa-miR-564" used in the present specification includes the hsa-miR-564 gene (miRBase Accession No. MIMAT0003228) described in SEQ ID NO: 610, a homolog or an ortholog of a different organism species, and the like. The hsa-miR-564 gene can be obtained by a method described in Cummins J M, 2006, Proc Natl. Acad Sci, Vol. 103, p. 3687-3692. Also, "hsa-mir-564" (miRBase Accession No. MI0003570, SEQ ID NO: 643) having a hairpin-like structure is known as a precursor of "hsa-miR-564".

The term "hsa-miR-671-5p gene" or "hsa-miR-671-5p" used in the present specification includes the hsa-miR-671-5p gene (miRBase Accession No. MIMAT0003880) described in SEQ ID NO: 611, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. M10003760, SEQ ID NO: 644) having a hairpin-like structure is known as a precursor of "hsa-miR-671-5p".

A mature miRNA may become a variant due to the sequence cleaved shorter or longer by one to several upstream or downstream bases or base substitution when cleaved as the mature miRNA from its RNA precursor that has a hairpin-like structure. This variant is called isomiR (Morin R D. et al., 2008, Genome Res., Vol. 18, p. 610-621). miRBase Release 20 shows the nucleotide sequences represented by SEQ ID NOs: 1 to 187 and 580 to 611 as well as a large number of the nucleotide sequence variants and fragments represented by SEQ ID NOs: 137 to 579 and 645 to 684, called isomiRs. These variants can also be obtained as miRNAs having a nucleotide sequence represented by any of SEQ ID NOs: 1 to 187 and 580 to 611. Specifically, among the variants of polynucleotides consisting of a nucleotide sequence represented by any of SEQ ID NOs: 1, 2, 4, 5, 6, 7, 10, 12, 15, 16, 18, 19, 21, 22, 24, 25, 27, 30, 31, 33, 34, 36, 39, 41, 42, 43, 44, 45, 46, 48, 51, 53, 58, 61, 62, 63, 66, 69, 73, 75, 76, 77, 78, 83, 84, 85, 86, 87, 88, 90, 94, 95, 96, 98, 100, 102, 103, 104, 105, 106, 107, 108, 109, 111, 115, 117, 119, 120, 123, 124, 125, 126, 127, 128, 131, 136, 137, 139, 140, 143, 144, 147, 149, 151, 153, 154, 155, 156, 158, 160, 162, 165, 167, 168, 169, 170, 173, 174, 175, 176, 178, 182, 183, 184, 580, 581, 584, 585, 587, 588, 590, 591, 592, 593, 594, 595, 597, 599, 600, 607, 608, 609 and 611 or a nucleotide sequence derived from the nucleotide sequence by the replacement of u with t according to the present invention, examples of the longest variants registered in miRBase Release 20 include polynucleotides represented by SEQ ID NOs: 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 645, 647, 650, 652, 655, 657, 659, 661, 663, 665, 667, 669, 671, 673, 675, 677, 679, 681 and 683, respectively. Also, among the variants of polynucleotides consisting of a nucleotide sequence represented by any of SEQ ID NOs: 1, 2, 4, 5, 6, 7, 10, 12, 15, 16, 18, 19, 21, 22, 24, 25, 27, 30, 31, 33, 34, 36, 39, 41, 42, 43, 44, 45, 46, 48, 51, 53, 58, 61, 62, 63, 66, 69, 73, 75, 76, 77, 78, 83, 84, 85, 86, 87, 88, 90, 94, 95, 96, 98, 100, 102, 103, 104, 105, 106, 107, 108, 109, 111, 115, 117, 119, 120, 123, 124, 125, 126, 127, 128, 131, 136, 137, 139, 140, 143, 144, 147, 149, 151, 153, 154, 155, 156, 158, 160, 162, 165, 167, 168, 169, 170, 173, 174, 175, 176, 178, 182, 183, 184, 580, 581, 583, 584, 585, 586, 587, 588, 590, 591, 592, 593, 594, 595, 597, 599, 600, 607, 608, 609 and 611 or a nucleotide sequence derived from the nucleotide sequence by the replacement of u with t according to the present invention, examples of the shortest variants registered in miRBase Release 20 include polynucleotides having sequences represented by SEQ ID NOs: 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 646, 648, 649, 651, 653, 654, 656, 658, 660, 662, 664, 666, 668, 670, 672, 674, 676, 678, 680, 682 and 684, respectively. In addition to these variants and fragments, examples thereof include a large number of isomiR polynucleotides of SEQ ID NOs: 1 to 187 and 580 to 611 registered in miRBase. Examples of the polynucleotide comprising a nucleotide sequence represented by any of SEQ ID NOs: 1 to 187 and 580 to 611 include a polynucleotide represented by any of SEQ ID NOs: 188 to 371, and 612 to 644, which are their respective precursors.

The names and miRBase Accession Nos. (registration numbers) of the genes represented by SEQ ID NOs: 1 to 684 are shown in Table 1.

In the present specification, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miR Base registration No. |
|---|---|---|
| 1 | hsa-miR-4443 | MIMAT0018961 |
| 2 | hsa-miR-1908-5p | MIMAT0007881 |
| 3 | hsa-miR-4257 | MIMAT0016878 |
| 4 | hsa-miR-3197 | MIMAT0015082 |
| 5 | hsa-miR-3188 | MIMAT0015070 |
| 6 | hsa-miR-4649-5p | MIMAT0019711 |
| 7 | hsa-miR-1343-3p | MIMAT0019776 |
| 8 | hsa-miR-6861-5p | MIMAT0027623 |
| 9 | hsa-miR-1343-5p | MIMAT0027038 |
| 10 | hsa-miR-642b-3p | MIMAT0018444 |
| 11 | hsa-miR-6741-5p | MIMAT0027383 |
| 12 | hsa-miR-4745-5p | MIMAT0019878 |
| 13 | hsa-miR-6826-5p | MIMAT0027552 |
| 14 | hsa-miR-3663-3p | MIMAT0018085 |
| 15 | hsa-miR-3131 | MIMAT0014996 |
| 16 | hsa-miR-92a-2-5p | MIMAT0004508 |
| 17 | hsa-miR-4258 | MIMAT0016879 |
| 18 | hsa-miR-4448 | MIMAT0018967 |
| 19 | hsa-miR-6125 | MIMAT0024598 |
| 20 | hsa-miR-6880-5p | MIMAT0027660 |
| 21 | hsa-miR-6132 | MIMAT0024616 |
| 22 | hsa-miR-4467 | MIMAT0018994 |
| 23 | hsa-miR-6749-5p | MIMAT0027398 |
| 24 | hsa-miR-2392 | MIMAT0019043 |
| 25 | hsa-miR-1273g-3p | MIMAT0022742 |
| 26 | hsa-miR-4746-3p | MIMAT0019881 |
| 27 | hsa-miR-1914-3p | MIMAT0007890 |
| 28 | hsa-miR-7845-5p | MIMAT0030420 |
| 29 | hsa-miR-6726-5p | MIMAT0027353 |
| 30 | hsa-miR-128-2-5p | MIMAT0031095 |
| 31 | hsa-miR-4651 | MIMAT0019715 |
| 32 | hsa-miR-6765-3p | MIMAT0027431 |
| 33 | hsa-miR-3185 | MIMAT0015065 |
| 34 | hsa-miR-4792 | MIMAT0019964 |
| 35 | hsa-miR-6887-5p | MIMAT0027674 |
| 36 | hsa-miR-5572 | MIMAT0022260 |
| 37 | hsa-miR-3619-3p | MIMAT0019219 |
| 38 | hsa-miR-6780b-5p | MIMAT0027572 |
| 39 | hsa-miR-4707-5p | MIMAT0019807 |
| 40 | hsa-miR-8063 | MIMAT0030990 |
| 41 | hsa-miR-4454 | MIMAT0018976 |
| 42 | hsa-miR-4525 | MIMAT0019064 |
| 43 | hsa-miR-7975 | MIMAT0031178 |
| 44 | hsa-miR-744-5p | MIMAT0004945 |
| 45 | hsa-miR-3135b | MIMAT0018985 |
| 46 | hsa-miR-4648 | MIMAT0019710 |
| 47 | hsa-miR-6816-5p | MIMAT0027532 |
| 48 | hsa-miR-4741 | MIMAT0019871 |
| 49 | hsa-miR-7150 | MIMAT0028211 |
| 50 | hsa-miR-6791-5p | MIMAT0027482 |
| 51 | hsa-miR-1247-3p | MIMAT0022721 |
| 52 | hsa-miR-7977 | MIMAT0031180 |
| 53 | hsa-miR-4497 | MIMAT0019032 |
| 54 | hsa-miR-6090 | MIMAT0023715 |
| 55 | hsa-miR-6781-5p | MIMAT0027462 |
| 56 | hsa-miR-6870-5p | MIMAT0027640 |
| 57 | hsa-miR-6729-5p | MIMAT0027359 |
| 58 | hsa-miR-4530 | MIMAT0019069 |
| 59 | hsa-miR-7847-3p | MIMAT0030422 |
| 60 | hsa-miR-6825-5p | MIMAT0027550 |
| 61 | hsa-miR-4674 | MIMAT0019756 |
| 62 | hsa-miR-3917 | MIMAT0018191 |
| 63 | hsa-miR-4707-3p | MIMAT0019808 |
| 64 | hsa-miR-6885-5p | MIMAT0027670 |
| 65 | hsa-miR-6722-3p | MIMAT0025854 |
| 66 | hsa-miR-4516 | MIMAT0019053 |
| 67 | hsa-miR-6757-5p | MIMAT0027414 |
| 68 | hsa-miR-6840-3p | MIMAT0027583 |
| 69 | hsa-miR-5195-3p | MIMAT0021127 |
| 70 | hsa-miR-6756-5p | MIMAT0027412 |
| 71 | hsa-miR-6800-5p | MIMAT0027500 |

TABLE 1-continued

| SEQ ID NO: | Gene name | miR Base registration No. |
|---|---|---|
| 72 | hsa-miR-6727-5p | MIMAT0027355 |
| 73 | hsa-miR-6126 | MIMAT0024599 |
| 74 | hsa-miR-6872-3p | MIMAT0027645 |
| 75 | hsa-miR-4446-3p | MIMAT0018965 |
| 76 | hsa-miR-1268a | MIMAT0005922 |
| 77 | hsa-miR-1908-3p | MIMAT0026916 |
| 78 | hsa-miR-3679-5p | MIMAT0018104 |
| 79 | hsa-miR-4534 | MIMAT0019073 |
| 80 | hsa-miR-4675 | MIMAT0019757 |
| 81 | hsa-miR-7108-5p | MIMAT0028113 |
| 82 | hsa-miR-6799-5p | MIMAT0027498 |
| 83 | hsa-miR-4695-5p | MIMAT0019788 |
| 84 | hsa-miR-3178 | MIMAT0015055 |
| 85 | hsa-miR-5090 | MIMAT0021082 |
| 86 | hsa-miR-3180 | MIMAT0018178 |
| 87 | hsa-miR-1237-5p | MIMAT0022946 |
| 88 | hsa-miR-4758-5p | MIMAT0019903 |
| 89 | hsa-miR-3184-5p | MIMAT0015064 |
| 90 | hsa-miR-4286 | MIMAT0016916 |
| 91 | hsa-miR-6784-5p | MIMAT0027468 |
| 92 | hsa-miR-6768-5p | MIMAT0027436 |
| 93 | hsa-miR-6785-5p | MIMAT0027470 |
| 94 | hsa-miR-4706 | MIMAT0019806 |
| 95 | hsa-miR-711 | MIMAT0012734 |
| 96 | hsa-miR-1260a | MIMAT0005911 |
| 97 | hsa-miR-6746-5p | MIMAT0027392 |
| 98 | hsa-miR-6089 | MIMAT0023714 |
| 99 | hsa-miR-6821-5p | MIMAT0027542 |
| 100 | hsa-miR-4667-5p | MIMAT0019743 |
| 101 | hsa-miR-8069 | MIMAT0030996 |
| 102 | hsa-miR-4726-5p | MIMAT0019845 |
| 103 | hsa-miR-6124 | MIMAT0024597 |
| 104 | hsa-miR-4532 | MIMAT0019071 |
| 105 | hsa-miR-4486 | MIMAT0019020 |
| 106 | hsa-miR-4728-5p | MIMAT0019849 |
| 107 | hsa-miR-4508 | MIMAT0019045 |
| 108 | hsa-miR-128-1-5p | MIMAT0026477 |
| 109 | hsa-miR-4513 | MIMAT0019050 |
| 110 | hsa-miR-6795-5p | MIMAT0027490 |
| 111 | hsa-miR-4689 | MIMAT0019778 |
| 112 | hsa-miR-6763-5p | MIMAT0027426 |
| 113 | hsa-miR-8072 | MIMAT0030999 |
| 114 | hsa-miR-6765-5p | MIMAT0027430 |
| 115 | hsa-miR-4419b | MIMAT0019034 |
| 116 | hsa-miR-7641 | MIMAT0029782 |
| 117 | hsa-miR-3928-3p | MIMAT0018205 |
| 118 | hsa-miR-1227-5p | MIMAT0022941 |
| 119 | hsa-miR-4492 | MIMAT0019027 |
| 120 | hsa-miR-296-3p | MIMAT0004679 |
| 121 | hsa-miR-6769a-5p | MIMAT0027438 |
| 122 | hsa-miR-6889-5p | MIMAT0027678 |
| 123 | hsa-miR-4632-5p | MIMAT0022977 |
| 124 | hsa-miR-4505 | MIMAT0019041 |
| 125 | hsa-miR-3154 | MIMAT0015028 |
| 126 | hsa-miR-3648 | MIMAT0018068 |
| 127 | hsa-miR-4442 | MIMAT0018960 |
| 128 | hsa-miR-3141 | MIMAT0015010 |
| 129 | hsa-miR-7113-3p | MIMAT0028124 |
| 130 | hsa-miR-6819-5p | MIMAT0027538 |
| 131 | hsa-miR-3195 | MIMAT0015079 |
| 132 | hsa-miR-1199-5p | MIMAT0031119 |
| 133 | hsa-miR-6738-5p | MIMAT0027377 |
| 134 | hsa-miR-4656 | MIMAT0019723 |
| 135 | hsa-miR-6820-5p | MIMAT0027540 |
| 136 | hsa-miR-615-5p | MIMAT0004804 |
| 137 | hsa-miR-486-3p | MIMAT0004762 |
| 138 | hsa-miR-1225-3p | MIMAT0005573 |
| 139 | hsa-miR-760 | MIMAT0004957 |
| 140 | hsa-miR-187-5p | MIMAT0004561 |
| 141 | hsa-miR-1203 | MIMAT0005866 |
| 142 | hsa-miR-7110-5p | MIMAT0028117 |
| 143 | hsa-miR-371a-5p | MIMAT0004687 |
| 144 | hsa-miR-939-5p | MIMAT0004982 |
| 145 | hsa-miR-575 | MIMAT0003240 |
| 146 | hsa-miR-92b-5p | MIMAT0004792 |
| 147 | hsa-miR-887-3p | MIMAT0004951 |

TABLE 1-continued

| SEQ ID NO: | Gene name | miR Base registration No. |
|---|---|---|
| 148 | hsa-miR-920 | MIMAT0004970 |
| 149 | hsa-miR-1915-5p | MIMAT0007891 |
| 150 | hsa-miR-1231 | MIMAT0005586 |
| 151 | hsa-miR-663b | MIMAT0005867 |
| 152 | hsa-miR-1225-5p | MIMAT0005572 |
| 153 | hsa-miR-4763-3p | MIMAT0019913 |
| 154 | hsa-miR-3656 | MIMAT0018076 |
| 155 | hsa-miR-4488 | MIMAT0019022 |
| 156 | hsa-miR-125a-3p | MIMAT0004602 |
| 157 | hsa-miR-1469 | MIMAT0007347 |
| 158 | hsa-miR-1228-5p | MIMAT0005582 |
| 159 | hsa-miR-6798-5p | MIMAT0027496 |
| 160 | hsa-miR-1268b | MIMAT0018925 |
| 161 | hsa-miR-6732-5p | MIMAT0027365 |
| 162 | hsa-miR-1915-3p | MIMAT0007892 |
| 163 | hsa-miR-4433b-3p | MIMAT0030414 |
| 164 | hsa-miR-1207-5p | MIMAT0005871 |
| 165 | hsa-miR-4433-3p | MIMAT0018949 |
| 166 | hsa-miR-6879-5p | MIMAT0027658 |
| 167 | hsa-miR-4417 | MIMAT0018929 |
| 168 | hsa-miR-30c-1-3p | MIMAT0004674 |
| 169 | hsa-miR-4638-5p | MIMAT0019695 |
| 170 | hsa-miR-6088 | MIMAT0023713 |
| 171 | hsa-miR-4270 | MIMAT0016900 |
| 172 | hsa-miR-6782-5p | MIMAT0027464 |
| 173 | hsa-miR-665 | MIMAT0004952 |
| 174 | hsa-miR-486-5p | MIMAT0002177 |
| 175 | hsa-miR-4655-5p | MIMAT0019721 |
| 176 | hsa-miR-1275 | MIMAT0005929 |
| 177 | hsa-miR-6806-5p | MIMAT0027512 |
| 178 | hsa-miR-614 | MIMAT0003282 |
| 179 | hsa-miR-3937 | MIMAT0018352 |
| 180 | hsa-miR-6752-5p | MIMAT0027404 |
| 181 | hsa-miR-6771-5p | MIMAT0027442 |
| 182 | hsa-miR-4450 | MIMAT0018971 |
| 183 | hsa-miR-211-3p | MIMAT0022694 |
| 184 | hsa-miR-663a | MIMAT0003326 |
| 185 | hsa-miR-6842-5p | MIMAT0027586 |
| 186 | hsa-miR-7114-5p | MIMAT0028125 |
| 187 | hsa-miR-6779-5p | MIMAT0027458 |
| 188 | hsa-mir-4443 | MI0016786 |
| 189 | hsa-mir-1908 | MI0008329 |
| 190 | hsa-mir-4257 | MI0015856 |
| 191 | hsa-mir-3197 | MI0014245 |
| 192 | hsa-mir-3188 | MI0014232 |
| 193 | hsa-mir-4649 | MI0017276 |
| 194 | hsa-mir-1343 | MI0017320 |
| 195 | hsa-mir-6861 | MI0022708 |
| 196 | hsa-mir-642b | MI0016685 |
| 197 | hsa-mir-6741 | MI0022586 |
| 198 | hsa-mir-4745 | MI0017384 |
| 199 | hsa-mir-6826 | MI0022671 |
| 200 | hsa-mir-3663 | MI0016064 |
| 201 | hsa-mir-3131 | MI0014151 |
| 202 | hsa-mir-92a-2 | MI0000094 |
| 203 | hsa-mir-4258 | MI0015857 |
| 204 | hsa-mir-4448 | MI0016791 |
| 205 | hsa-mir-6125 | MI0021259 |
| 206 | hsa-mir-6880 | MI0022727 |
| 207 | hsa-mir-6132 | MI0021277 |
| 208 | hsa-mir-4467 | MI0016818 |
| 209 | hsa-mir-6749 | MI0022594 |
| 210 | hsa-mir-2392 | MI0016870 |
| 211 | hsa-mir-1273g | MI0018003 |
| 212 | hsa-mir-4746 | MI0017385 |
| 213 | hsa-mir-1914 | MI0008335 |
| 214 | hsa-mir-7845 | MI0025515 |
| 215 | hsa-mir-6726 | MI0022571 |
| 216 | hsa-mir-128-2 | MI0000727 |
| 217 | hsa-mir-4651 | MI0017279 |
| 218 | hsa-mir-6765 | MI0022610 |
| 219 | hsa-mir-3185 | MI0014227 |
| 220 | hsa-mir-4792 | MI0017439 |
| 221 | hsa-mir-6887 | MI0022734 |
| 222 | hsa-mir-5572 | MI0019117 |
| 223 | hsa-mir-3619 | MI0016009 |

TABLE 1-continued

| SEQ ID NO: | Gene name | miR Base registration No. |
|---|---|---|
| 224 | hsa-mir-6780b | MI0022681 |
| 225 | hsa-mir-4707 | MI0017340 |
| 226 | hsa-mir-8063 | MI0025899 |
| 227 | hsa-mir-4454 | MI0016800 |
| 228 | hsa-mir-4525 | MI0016892 |
| 229 | hsa-mir-7975 | MI0025751 |
| 230 | hsa-mir-744 | MI0005559 |
| 231 | hsa-mir-3135b | MI0016809 |
| 232 | hsa-mir-4648 | MI0017275 |
| 233 | hsa-mir-6816 | MI0022661 |
| 234 | hsa-mir-4741 | MI0017379 |
| 235 | hsa-mir-7150 | MI0023610 |
| 236 | hsa-mir-6791 | MI0022636 |
| 237 | hsa-mir-1247 | MI0006382 |
| 238 | hsa-mir-7977 | MI0025753 |
| 239 | hsa-mir-4497 | MI0016859 |
| 240 | hsa-mir-6090 | MI0020367 |
| 241 | hsa-mir-6781 | MI0022626 |
| 242 | hsa-mir-6870 | MI0022717 |
| 243 | hsa-mir-6729 | MI0022574 |
| 244 | hsa-mir-4530 | MI0016897 |
| 245 | hsa-mir-7847 | MI0025517 |
| 246 | hsa-mir-6825 | MI0022670 |
| 247 | hsa-mir-4674 | MI0017305 |
| 248 | hsa-mir-3917 | MI0016423 |
| 249 | hsa-mir-6885 | MI0022732 |
| 250 | hsa-mir-6722 | MI0022557 |
| 251 | hsa-mir-4516 | MI0016882 |
| 252 | hsa-mir-6757 | MI0022602 |
| 253 | hsa-mir-6840 | MI0022686 |
| 254 | hsa-mir-5195 | MI0018174 |
| 255 | hsa-mir-6756 | MI0022601 |
| 256 | hsa-mir-6800 | MI0022645 |
| 257 | hsa-mir-6727 | MI0022572 |
| 258 | hsa-mir-6126 | MI0021260 |
| 259 | hsa-mir-6872 | MI0022719 |
| 260 | hsa-mir-4446 | MI0016789 |
| 261 | hsa-mir-1268a | MI0006405 |
| 262 | hsa-mir-3679 | MI0016080 |
| 263 | hsa-mir-4534 | MI0016901 |
| 264 | hsa-mir-4675 | MI0017306 |
| 265 | hsa-mir-7108 | MI0022959 |
| 266 | hsa-mir-6799 | MI0022644 |
| 267 | hsa-mir-4695 | MI0017328 |
| 268 | hsa-mir-3178 | MI0014212 |
| 269 | hsa-mir-5090 | MI0017979 |
| 270 | hsa-mir-3180-4 | MI0016408 |
| 271 | hsa-mir-3180-5 | MI0016409 |
| 272 | hsa-mir-1237 | MI0006327 |
| 273 | hsa-mir-4758 | MI0017399 |
| 274 | hsa-mir-3184 | MI0014226 |
| 275 | hsa-mir-4286 | MI0015894 |
| 276 | hsa-mir-6784 | MI0022629 |
| 277 | hsa-mir-6768 | MI0022613 |
| 278 | hsa-mir-6785 | MI0022630 |
| 279 | hsa-mir-4706 | MI0017339 |
| 280 | hsa-mir-711 | MI0012488 |
| 281 | hsa-mir-1260a | MI0006394 |
| 282 | hsa-mir-6746 | MI0022591 |
| 283 | hsa-mir-6089-1 | MI0020366 |
| 284 | hsa-mir-6089-2 | MI0023563 |
| 285 | hsa-mir-6821 | MI0022666 |
| 286 | hsa-mir-4667 | MI0017297 |
| 287 | hsa-mir-8069 | MI0025905 |
| 288 | hsa-mir-4726 | MI0017363 |
| 289 | hsa-mir-6124 | MI0021258 |
| 290 | hsa-mir-4532 | MI0016899 |
| 291 | hsa-mir-4486 | MI0016847 |
| 292 | hsa-mir-4728 | MI0017365 |
| 293 | hsa-mir-4508 | MI0016872 |
| 294 | hsa-mir-128-1 | MI0000447 |
| 295 | hsa-mir-4513 | MI0016879 |
| 296 | hsa-mir-6795 | MI0022640 |
| 297 | hsa-mir-4689 | MI0017322 |
| 298 | hsa-mir-6763 | MI0022608 |
| 299 | hsa-mir-8072 | MI0025908 |

TABLE 1-continued

| SEQ ID NO: | Gene name | miR Base registration No. |
|---|---|---|
| 300 | hsa-mir-4419b | MI0016861 |
| 301 | hsa-mir-7641-1 | MI0024975 |
| 302 | hsa-mir-7641-2 | MI0024976 |
| 303 | hsa-mir-3928 | MI0016438 |
| 304 | hsa-mir-1227 | MI0006316 |
| 305 | hsa-mir-4492 | MI0016854 |
| 306 | hsa-mir-296 | MI0000747 |
| 307 | hsa-mir-6769a | MI0022614 |
| 308 | hsa-mir-6889 | MI0022736 |
| 309 | hsa-mir-4632 | MI0017259 |
| 310 | hsa-mir-4505 | MI0016868 |
| 311 | hsa-mir-3154 | MI0014182 |
| 312 | hsa-mir-3648 | MI0016048 |
| 313 | hsa-mir-4442 | MI0016785 |
| 314 | hsa-mir-3141 | MI0014165 |
| 315 | hsa-mir-7113 | MI0022964 |
| 316 | hsa-mir-6819 | MI0022664 |
| 317 | hsa-mir-3195 | MI0014240 |
| 318 | hsa-mir-1199 | MI0020340 |
| 319 | hsa-mir-6738 | MI0022583 |
| 320 | hsa-mir-4656 | MI0017284 |
| 321 | hsa-mir-6820 | MI0022665 |
| 322 | hsa-mir-615 | MI0003628 |
| 323 | hsa-mir-486 | MI0002470 |
| 324 | hsa-mir-486-2 | MI0023622 |
| 325 | hsa-mir-1225 | MI0006311 |
| 326 | hsa-mir-760 | MI0005567 |
| 327 | hsa-mir-187 | MI0000274 |
| 328 | hsa-mir-1203 | MI0006335 |
| 329 | hsa-mir-7110 | MI0022961 |
| 330 | hsa-mir-371a | MI0000779 |
| 331 | hsa-mir-939 | MI0005761 |
| 332 | hsa-mir-575 | MI0003582 |
| 333 | hsa-mir-92b | MI0003560 |
| 334 | hsa-mir-887 | MI0005562 |
| 335 | hsa-mir-920 | MI0005712 |
| 336 | hsa-mir-1915 | MI0008336 |
| 337 | hsa-mir-1231 | MI0006321 |
| 338 | hsa-mir-663b | MI0006336 |
| 339 | hsa-mir-4763 | MI0017404 |
| 340 | hsa-mir-3656 | MI0016056 |
| 341 | hsa-mir-4488 | MI0016849 |
| 342 | hsa-mir-125a | MI0000469 |
| 343 | hsa-mir-1469 | MI0007074 |
| 344 | hsa-mir-1228 | MI0006318 |
| 345 | hsa-mir-6798 | MI0022643 |
| 346 | hsa-mir-1268b | MI0016748 |
| 347 | hsa-mir-6732 | MI0022577 |
| 348 | hsa-mir-4433b | MI0025511 |
| 349 | hsa-mir-1207 | MI0006340 |
| 350 | hsa-mir-4433 | MI0016773 |
| 351 | hsa-mir-6879 | MI0022726 |
| 352 | hsa-mir-4417 | MI0016753 |
| 353 | hsa-mir-30c-1 | MI0000736 |
| 354 | hsa-mir-4638 | MI0017265 |
| 355 | hsa-mir-6088 | MI0020365 |
| 356 | hsa-mir-4270 | MI0015878 |
| 357 | hsa-mir-6782 | MI0022627 |
| 358 | hsa-mir-665 | MI0005563 |
| 359 | hsa-mir-4655 | MI0017283 |
| 360 | hsa-mir-1275 | MI0006415 |
| 361 | hsa-mir-6806 | MI0022651 |
| 362 | hsa-mir-614 | MI0003627 |
| 363 | hsa-mir-3937 | MI0016593 |
| 364 | hsa-mir-6752 | MI0022597 |
| 365 | hsa-mir-6771 | MI0022616 |
| 366 | hsa-mir-4450 | MI0016795 |
| 367 | hsa-mir-211 | MI0000287 |
| 368 | hsa-mir-663a | MI0003672 |
| 369 | hsa-mir-6842 | MI0022688 |
| 370 | hsa-mir-7114 | MI0022965 |
| 371 | hsa-mir-6779 | MI0022624 |
| 372 | isomiR example 1 of SEQ ID NO: 1 | — |
| 373 | isomiR example 2 of SEQ ID NO: 1 | — |
| 374 | isomiR example 1 of SEQ ID NO: 2 | — |
| 375 | isomiR example 2 of SEQ ID NO: 2 | — |

TABLE 1-continued

| SEQ ID NO: | Gene name | miR Base registration No. |
|---|---|---|
| 376 | isomiR example 1 of SEQ ID NO: 4 | — |
| 377 | isomiR example 2 of SEQ ID NO: 4 | — |
| 378 | isomiR example 1 of SEQ ID NO: 5 | — |
| 379 | isomiR example 2 of SEQ ID NO: 5 | — |
| 380 | isomiR example 1 of SEQ ID NO: 6 | — |
| 381 | isomiR example 2 of SEQ ID NO: 6 | — |
| 382 | isomiR example 1 of SEQ ID NO: 7 | — |
| 383 | isomiR example 2 of SEQ ID NO: 7 | — |
| 384 | isomiR example 1 of SEQ ID NO: 10 | — |
| 385 | isomiR example 2 of SEQ ID NO: 10 | — |
| 386 | isomiR example 1 of SEQ ID NO: 12 | — |
| 387 | isomiR example 2 of SEQ ID NO: 12 | — |
| 388 | isomiR example 1 of SEQ ID NO: 15 | — |
| 389 | isomiR example 2 of SEQ ID NO: 15 | — |
| 390 | isomiR example 1 of SEQ ID NO: 16 | — |
| 391 | isomiR example 2 of SEQ ID NO: 16 | — |
| 392 | isomiR example 1 of SEQ ID NO: 18 | — |
| 393 | isomiR example 2 of SEQ ID NO: 18 | — |
| 394 | isomiR example 1 of SEQ ID NO: 19 | — |
| 395 | isomiR example 2 of SEQ ID NO: 19 | — |
| 396 | isomiR example 1 of SEQ ID NO: 21 | — |
| 397 | isomiR example 2 of SEQ ID NO: 21 | — |
| 398 | isomiR example 1 of SEQ ID NO: 22 | — |
| 399 | isomiR example 2 of SEQ ID NO: 22 | — |
| 400 | isomiR example 1 of SEQ ID NO: 24 | — |
| 401 | isomiR example 2 of SEQ ID NO: 24 | — |
| 402 | isomiR example 1 of SEQ ID NO: 25 | — |
| 403 | isomiR example 2 of SEQ ID NO: 25 | — |
| 404 | isomiR example 1 of SEQ ID NO: 27 | — |
| 405 | isomiR example 2 of SEQ ID NO: 27 | — |
| 406 | isomiR example 1 of SEQ ID NO: 30 | — |
| 407 | isomiR example 2 of SEQ ID NO: 30 | — |
| 408 | isomiR example 1 of SEQ ID NO: 31 | — |
| 409 | isomiR example 2 of SEQ ID NO: 31 | — |
| 410 | isomiR example 1 of SEQ ID NO: 33 | — |
| 411 | isomiR example 2 of SEQ ID NO: 33 | — |
| 412 | isomiR example 1 of SEQ ID NO: 34 | — |
| 413 | isomiR example 2 of SEQ ID NO: 34 | — |
| 414 | isomiR example 1 of SEQ ID NO: 36 | — |
| 415 | isomiR example 2 of SEQ ID NO: 36 | — |
| 416 | isomiR example 1 of SEQ ID NO: 39 | — |
| 417 | isomiR example 2 of SEQ ID NO: 39 | — |
| 418 | isomiR example 1 of SEQ ID NO: 41 | — |
| 419 | isomiR example 2 of SEQ ID NO: 41 | — |
| 420 | isomiR example 1 of SEQ ID NO: 42 | — |
| 421 | isomiR example 2 of SEQ ID NO: 42 | — |
| 422 | isomiR example 1 of SEQ ID NO: 43 | — |
| 423 | isomiR example 2 of SEQ ID NO: 43 | — |
| 424 | isomiR example 1 of SEQ ID NO: 44 | — |
| 425 | isomiR example 2 of SEQ ID NO: 44 | — |
| 426 | isomiR example 1 of SEQ ID NO: 45 | — |
| 427 | isomiR example 2 of SEQ ID NO: 45 | — |
| 428 | isomiR example 1 of SEQ ID NO: 46 | — |
| 429 | isomiR example 2 of SEQ ID NO: 46 | — |
| 430 | isomiR example 1 of SEQ ID NO: 48 | — |
| 431 | isomiR example 2 of SEQ ID NO: 48 | — |
| 432 | isomiR example 1 of SEQ ID NO: 51 | — |
| 433 | isomiR example 2 of SEQ ID NO: 51 | — |
| 434 | isomiR example 1 of SEQ ID NO: 53 | — |
| 435 | isomiR example 2 of SEQ ID NO: 53 | — |
| 436 | isomiR example 1 of SEQ ID NO: 58 | — |
| 437 | isomiR example 2 of SEQ ID NO: 58 | — |
| 438 | isomiR example 1 of SEQ ID NO: 61 | — |
| 439 | isomiR example 2 of SEQ ID NO: 61 | — |
| 440 | isomiR example 1 of SEQ ID NO: 62 | — |
| 441 | isomiR example 2 of SEQ ID NO: 62 | — |
| 442 | isomiR example 1 of SEQ ID NO: 63 | — |
| 443 | isomiR example 2 of SEQ ID NO: 63 | — |
| 444 | isomiR example 1 of SEQ ID NO: 66 | — |
| 445 | isomiR example 2 of SEQ ID NO: 66 | — |
| 446 | isomiR example 1 of SEQ ID NO: 69 | — |
| 447 | isomiR example 2 of SEQ ID NO: 69 | — |
| 448 | isomiR example 1 of SEQ ID NO: 73 | — |
| 449 | isomiR example 2 of SEQ ID NO: 73 | — |
| 450 | isomiR example 1 of SEQ ID NO: 75 | — |
| 451 | isomiR example 2 of SEQ ID NO: 75 | — |

TABLE 1-continued

| SEQ ID NO: | Gene name | miR Base registration No. |
|---|---|---|
| 452 | isomiR example 1 of SEQ ID NO: 76 | — |
| 453 | isomiR example 2 of SEQ ID NO: 76 | — |
| 454 | isomiR example 1 of SEQ ID NO: 77 | — |
| 455 | isomiR example 2 of SEQ ID NO: 77 | — |
| 456 | isomiR example 1 of SEQ ID NO: 78 | — |
| 457 | isomiR example 2 of SEQ ID NO: 78 | — |
| 458 | isomiR example 1 of SEQ ID NO: 83 | — |
| 459 | isomiR example 2 of SEQ ID NO: 83 | — |
| 460 | isomiR example 1 of SEQ ID NO: 84 | — |
| 461 | isomiR example 2 of SEQ ID NO: 84 | — |
| 462 | isomiR example 1 of SEQ ID NO: 85 | — |
| 463 | isomiR example 2 of SEQ ID NO: 85 | — |
| 464 | isomiR example 1 of SEQ ID NO: 86 | — |
| 465 | isomiR example 2 of SEQ ID NO: 86 | — |
| 466 | isomiR example 1 of SEQ ID NO: 87 | — |
| 467 | isomiR example 2 of SEQ ID NO: 87 | — |
| 468 | isomiR example 1 of SEQ ID NO: 88 | — |
| 469 | isomiR example 2 of SEQ ID NO: 88 | — |
| 470 | isomiR example 1 of SEQ ID NO: 90 | — |
| 471 | isomiR example 2 of SEQ ID NO: 90 | — |
| 472 | isomiR example 1 of SEQ ID NO: 94 | — |
| 473 | isomiR example 2 of SEQ ID NO: 94 | — |
| 474 | isomiR example 1 of SEQ ID NO: 95 | — |
| 475 | isomiR example 2 of SEQ ID NO: 95 | — |
| 476 | isomiR example 1 of SEQ ID NO: 96 | — |
| 477 | isomiR example 2 of SEQ ID NO: 96 | — |
| 478 | isomiR example 1 of SEQ ID NO: 98 | — |
| 479 | isomiR example 2 of SEQ ID NO: 98 | — |
| 480 | isomiR example 1 of SEQ ID NO: 100 | — |
| 481 | isomiR example 2 of SEQ ID NO: 100 | — |
| 482 | isomiR example 1 of SEQ ID NO: 102 | — |
| 483 | isomiR example 2 of SEQ ID NO: 102 | — |
| 484 | isomiR example 1 of SEQ ID NO: 103 | — |
| 485 | isomiR example 2 of SEQ ID NO: 103 | — |
| 486 | isomiR example 1 of SEQ ID NO: 104 | — |
| 487 | isomiR example 2 of SEQ ID NO: 104 | — |
| 488 | isomiR example 1 of SEQ ID NO: 105 | — |
| 489 | isomiR example 2 of SEQ ID NO: 105 | — |
| 490 | isomiR example 1 of SEQ ID NO: 106 | — |
| 491 | isomiR example 2 of SEQ ID NO: 106 | — |
| 492 | isomiR example 1 of SEQ ID NO: 107 | — |
| 493 | isomiR example 2 of SEQ ID NO: 107 | — |
| 494 | isomiR example 1 of SEQ ID NO: 108 | — |
| 495 | isomiR example 2 of SEQ ID NO: 108 | — |
| 496 | isomiR example 1 of SEQ ID NO: 109 | — |
| 497 | isomiR example 2 of SEQ ID NO: 109 | — |
| 498 | isomiR example 1 of SEQ ID NO: 111 | — |
| 499 | isomiR example 2 of SEQ ID NO: 111 | — |
| 500 | isomiR example 1 of SEQ ID NO: 115 | — |
| 501 | isomiR example 2 of SEQ ID NO: 115 | — |
| 502 | isomiR example 1 of SEQ ID NO: 117 | — |
| 503 | isomiR example 2 of SEQ ID NO: 117 | — |
| 504 | isomiR example 1 of SEQ ID NO: 119 | — |
| 505 | isomiR example 2 of SEQ ID NO: 119 | — |
| 506 | isomiR example 1 of SEQ ID NO: 120 | — |
| 507 | isomiR example 2 of SEQ ID NO: 120 | — |
| 508 | isomiR example 1 of SEQ ID NO: 123 | — |
| 509 | isomiR example 2 of SEQ ID NO: 123 | — |
| 510 | isomiR example 1 of SEQ ID NO: 124 | — |
| 511 | isomiR example 2 of SEQ ID NO: 124 | — |
| 512 | isomiR example 1 of SEQ ID NO: 125 | — |
| 513 | isomiR example 2 of SEQ ID NO: 125 | — |
| 514 | isomiR example 1 of SEQ ID NO: 126 | — |
| 515 | isomiR example 2 of SEQ ID NO: 126 | — |
| 516 | isomiR example 1 of SEQ ID NO: 127 | — |
| 517 | isomiR example 2 of SEQ ID NO: 127 | — |
| 518 | isomiR example 1 of SEQ ID NO: 128 | — |
| 519 | isomiR example 2 of SEQ ID NO: 128 | — |
| 520 | isomiR example 1 of SEQ ID NO: 131 | — |
| 521 | isomiR example 2 of SEQ ID NO: 131 | — |
| 522 | isomiR example 1 of SEQ ID NO: 136 | — |
| 523 | isomiR example 2 of SEQ ID NO: 136 | — |
| 524 | isomiR example 1 of SEQ ID NO: 137 | — |
| 525 | isomiR example 2 of SEQ ID NO: 137 | — |
| 526 | isomiR example 1 of SEQ ID NO: 139 | — |
| 527 | isomiR example 2 of SEQ ID NO: 139 | — |

TABLE 1-continued

| SEQ ID NO: | Gene name | miR Base registration No. |
|---|---|---|
| 528 | isomiR example 1 of SEQ ID NO: 140 | — |
| 529 | isomiR example 2 of SEQ ID NO: 140 | — |
| 530 | isomiR example 1 of SEQ ID NO: 143 | — |
| 531 | isomiR example 2 of SEQ ID NO: 143 | — |
| 532 | isomiR example 1 of SEQ ID NO: 144 | — |
| 533 | isomiR example 2 of SEQ ID NO: 144 | — |
| 534 | isomiR example 1 of SEQ ID NO: 147 | — |
| 535 | isomiR example 2 of SEQ ID NO: 147 | — |
| 536 | isomiR example 1 of SEQ ID NO: 149 | — |
| 537 | isomiR example 2 of SEQ ID NO: 149 | — |
| 538 | isomiR example 1 of SEQ ID NO: 151 | — |
| 539 | isomiR example 2 of SEQ ID NO: 151 | — |
| 540 | isomiR example 1 of SEQ ID NO: 153 | — |
| 541 | isomiR example 2 of SEQ ID NO: 153 | — |
| 542 | isomiR example 1 of SEQ ID NO: 154 | — |
| 543 | isomiR example 2 of SEQ ID NO: 154 | — |
| 544 | isomiR example 1 of SEQ ID NO: 155 | — |
| 545 | isomiR example 2 of SEQ ID NO: 155 | — |
| 546 | isomiR example 1 of SEQ ID NO: 156 | — |
| 547 | isomiR example 2 of SEQ ID NO: 156 | — |
| 548 | isomiR example 1 of SEQ ID NO: 158 | — |
| 549 | isomiR example 2 of SEQ ID NO: 158 | — |
| 550 | isomiR example 1 of SEQ ID NO: 160 | — |
| 551 | isomiR example 2 of SEQ ID NO: 160 | — |
| 552 | isomiR example 1 of SEQ ID NO: 162 | — |
| 553 | isomiR example 2 of SEQ ID NO: 162 | — |
| 554 | isomiR example 1 of SEQ ID NO: 165 | — |
| 555 | isomiR example 2 of SEQ ID NO: 165 | — |
| 556 | isomiR example 1 of SEQ ID NO: 167 | — |
| 557 | isomiR example 2 of SEQ ID NO: 167 | — |
| 558 | isomiR example 1 of SEQ ID NO: 168 | — |
| 559 | isomiR example 2 of SEQ ID NO: 168 | — |
| 560 | isomiR example 1 of SEQ ID NO: 169 | — |
| 561 | isomiR example 2 of SEQ ID NO: 169 | — |
| 562 | isomiR example 1 of SEQ ID NO: 170 | — |
| 563 | isomiR example 2 of SEQ ID NO: 170 | — |
| 564 | isomiR example 1 of SEQ ID NO: 173 | — |
| 565 | isomiR example 2 of SEQ ID NO: 173 | — |
| 566 | isomiR example 1 of SEQ ID NO: 174 | — |
| 567 | isomiR example 2 of SEQ ID NO: 174 | — |
| 568 | isomiR example 1 of SEQ ID NO: 175 | — |
| 569 | isomiR example 2 of SEQ ID NO: 175 | — |
| 570 | isomiR example 1 of SEQ ID NO: 176 | — |
| 571 | isomiR example 2 of SEQ ID NO: 176 | — |
| 572 | isomiR example 1 of SEQ ID NO: 178 | — |
| 573 | isomiR example 2 of SEQ ID NO: 178 | — |
| 574 | isomiR example 1 of SEQ ID NO: 182 | — |
| 575 | isomiR example 2 of SEQ ID NO: 182 | — |
| 576 | isomiR example 1 of SEQ ID NO: 183 | — |
| 577 | isomiR example 2 of SEQ ID NO: 183 | — |
| 578 | isomiR example 1 of SEQ ID NO: 184 | — |
| 579 | isomiR example 1 of SEQ ID NO: 184 | — |
| 580 | hsa-miR-204-3p | MIMAT0022693 |
| 581 | hsa-miR-642a-3p | MIMAT0020924 |
| 582 | hsa-miR-762 | MIMAT0010313 |
| 583 | hsa-miR-1202 | MIMAT0005865 |
| 584 | hsa-miR-3162-5p | MIMAT0015036 |
| 585 | hsa-miR-3196 | MIMAT0015080 |
| 586 | hsa-miR-3622a-5p | MIMAT0018003 |
| 587 | hsa-miR-3665 | MIMAT0018087 |
| 588 | hsa-miR-3940-5p | MIMAT0019229 |
| 589 | hsa-miR-4294 | MIMAT0016849 |
| 590 | hsa-miR-4466 | MIMAT0018993 |
| 591 | hsa-miR-4476 | MIMAT0019003 |
| 592 | hsa-miR-4723-5p | MIMAT0019838 |
| 593 | hsa-miR-4725-3p | MIMAT0019844 |
| 594 | hsa-miR-4730 | MIMAT0019852 |
| 595 | hsa-miR-4739 | MIMAT0019868 |
| 596 | hsa-miR-4787-5p | MIMAT0019956 |
| 597 | hsa-miR-5787 | MIMAT0023252 |
| 598 | hsa-miR-6085 | MIMAT0023710 |
| 599 | hsa-miR-6717-5p | MIMAT0025846 |
| 600 | hsa-miR-6724-5p | MIMAT0025856 |
| 601 | hsa-miR-6777-5p | MIMAT0027454 |
| 602 | hsa-miR-6778-5p | MIMAT0027456 |
| 603 | hsa-miR-6787-5p | MIMAT0027474 |

TABLE 1-continued

| SEQ ID NO: | Gene name | miR Base registration No. |
|---|---|---|
| 604 | hsa-miR-6789-5p | MIMAT0027478 |
| 605 | hsa-miR-6845-5p | MIMAT0027590 |
| 606 | hsa-miR-6893-5p | MIMAT0027686 |
| 607 | hsa-miR-16-5p | MIMAT0000069 |
| 608 | hsa-miR-423-5p | MIMAT0004748 |
| 609 | hsa-miR-451a | MIMAT0001631 |
| 610 | hsa-miR-564 | MIMAT0003228 |
| 611 | hsa-miR-671-5p | MIMAT0003880 |
| 612 | hsa-mir-204 | MI0000284 |
| 613 | hsa-mir-642a | MI0003657 |
| 614 | hsa-mir-762 | MI0003892 |
| 615 | hsa-mir-1202 | MI0006334 |
| 616 | hsa-mir-3162 | MI0014192 |
| 617 | hsa-mir-3196 | MI0014241 |
| 618 | hsa-mir-3622a | MI0016013 |
| 619 | hsa-mir-3665 | MI0016066 |
| 620 | hsa-mir-3940 | MI0016597 |
| 621 | hsa-mir-4294 | MI0015827 |
| 622 | hsa-mir-4466 | MI0016817 |
| 623 | hsa-mir-4476 | MI0016828 |
| 624 | hsa-mir-4723 | MI0017359 |
| 625 | hsa-mir-4725 | MI0017362 |
| 626 | hsa-mir-4730 | MI0017367 |
| 627 | hsa-mir-4739 | MI0017377 |
| 628 | hsa-mir-4787 | MI0017434 |
| 629 | hsa-mir-5787 | MI0019797 |
| 630 | hsa-mir-6085 | MI0020362 |
| 631 | hsa-mir-6717 | MI0022551 |
| 632 | hsa-mir-6724 | MI0022559 |
| 633 | hsa-mir-6777 | MI0022622 |
| 634 | hsa-mir-6778 | MI0022623 |
| 635 | hsa-mir-6787 | MI0022632 |
| 636 | hsa-mir-6789 | MI0022634 |
| 637 | hsa-mir-6845 | MI0022691 |
| 638 | hsa-mir-6893 | MI0022740 |
| 639 | hsa-mir-16-1 | MI0000070 |
| 640 | hsa-mir-16-2 | MI0000115 |
| 641 | hsa-mir-423 | MI0001445 |
| 642 | hsa-mir-451a | MI0001729 |
| 643 | hsa-mir-564 | MI0003570 |
| 644 | hsa-mir-671 | MI0003760 |
| 645 | isomiR example 1 of SEQ ID NO: 580 | — |
| 646 | isomiR example 2 of SEQ ID NO: 580 | — |
| 647 | isomiR example 1 of SEQ ID NO: 581 | — |
| 648 | isomiR example 2 of SEQ ID NO: 581 | — |
| 649 | isomiR example 1 of SEQ ID NO: 583 | — |
| 650 | isomiR example 1 of SEQ ID NO: 584 | — |
| 651 | isomiR example 2 of SEQ ID NO: 584 | — |
| 652 | isomiR example 1 of SEQ ID NO: 585 | — |
| 653 | isomiR example 2 of SEQ ID NO: 585 | — |
| 654 | isomiR example 1 of SEQ ID NO: 586 | — |
| 655 | isomiR example 1 of SEQ ID NO: 587 | — |
| 656 | isomiR example 2 of SEQ ID NO: 587 | — |
| 657 | isomiR example 1 of SEQ ID NO: 588 | — |
| 658 | isomiR example 2 of SEQ ID NO: 588 | — |
| 659 | isomiR example 1 of SEQ ID NO: 590 | — |
| 660 | isomiR example 2 of SEQ ID NO: 590 | — |
| 661 | isomiR example 1 of SEQ ID NO: 591 | — |
| 662 | isomiR example 2 of SEQ ID NO: 591 | — |
| 663 | isomiR example 1 of SEQ ID NO: 592 | — |
| 664 | isomiR example 2 of SEQ ID NO: 592 | — |
| 665 | isomiR example 1 of SEQ ID NO: 593 | — |
| 666 | isomiR example 2 of SEQ ID NO: 593 | — |
| 667 | isomiR example 1 of SEQ ID NO: 594 | — |
| 668 | isomiR example 2 of SEQ ID NO: 594 | — |
| 669 | isomiR example 1 of SEQ ID NO: 595 | — |
| 670 | isomiR example 2 of SEQ ID NO: 595 | — |
| 671 | isomiR example 1 of SEQ ID NO: 597 | — |
| 672 | isomiR example 2 of SEQ ID NO: 597 | — |
| 673 | isomiR example 1 of SEQ ID NO: 599 | — |
| 674 | isomiR example 2 of SEQ ID NO: 599 | — |
| 675 | isomiR example 1 of SEQ ID NO: 600 | — |
| 676 | isomiR example 2 of SEQ ID NO: 600 | — |
| 677 | isomiR example 1 of SEQ ID NO: 607 | — |
| 678 | isomiR example 2 of SEQ ID NO: 607 | — |
| 679 | isomiR example 1 of SEQ ID NO: 608 | — |
| 680 | isomiR example 2 of SEQ ID NO: 608 | — |
| 681 | isomiR example 1 of SEQ ID NO: 609 | — |
| 682 | isomiR example 2 of SEQ ID NO: 609 | — |
| 683 | isomiR example 1 of SEQ ID NO: 611 | — |
| 684 | isomiR example 2 of SEQ ID NO: 611 | — |

The present application claims the priority of Japanese Patent Application No. 2014-121377 filed on Jun. 12, 2014 and Japanese Patent Application No. 2015-71756 filed on Mar. 31, 2015, and encompasses the contents described in the specifications of these patent applications.

Advantageous Effects of Invention

According to the present invention, prostate cancer can be detected easily and highly accurately. For example, the presence or absence of prostate cancer in a patient can be easily detected by using, as an index, the measurement values of several miRNAs in blood, serum, and/or plasma of the patient, which can be collected with limited invasiveness.

DESCRIPTION OF EMBODIMENTS

Figure 1:
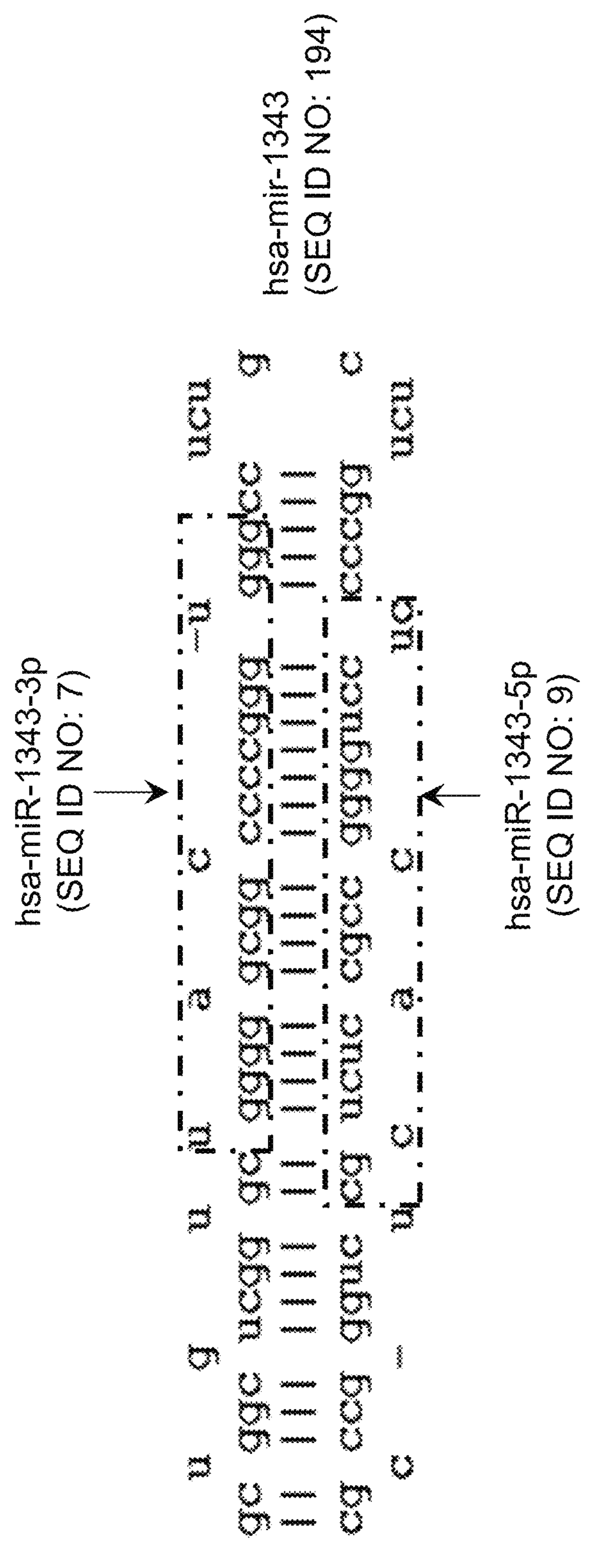
FIG. 1 This figure shows the relationship between the nucleotide sequences of hsa-miR-1343-3p represented by SEQ ID NO: 7 and hsa-miR-1343-5p represented by SEQ ID NO: 9, which are formed from a precursor hsa-mir-1343 represented by SEQ ID NO: 194.

Hereinafter, the present invention will be described further specifically.

1. Target Nucleic Acid for Prostate Cancer

A primary target nucleic acid as a prostate cancer marker for detecting the presence and/or absence of prostate cancer or prostate cancer cells using the nucleic acid probe or the primer for the detection of prostate cancer defined above according to the present invention comprises at least one or more miRNA(s) selected from the group consisting of hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p and hsa-miR-6893-5p. Furthermore, at least one or more miRNA(s) selected from the group consisting of other prostate cancer markers that can be combined with these miRNAs, i.e., hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564 and hsa-miR-671-5p can also be preferably used as a target nucleic acid(s). Moreover, at least one or more miRNA(s) selected from the group consisting of other prostate cancer markers that can be combined with these miRNAs, i.e., hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p can also be preferably used as a target nucleic acid(s).

These miRNAs include, for example, a human gene comprising a nucleotide sequence represented by any of SEQ ID NOs: 1 to 187 and 580 to 611 (i.e., hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p and hsa-miR-6893-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564 and hsa-miR-671-5p, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p, respectively), any congener thereof, any transcript thereof, and any variant or any derivative thereof. In this context, the gene, the congener, the transcript, the variant, and the derivative are as defined above.

The target nucleic acid is preferably a human gene comprising a nucleotide sequence represented by any of SEQ ID NOs: 1 to 684 or a transcript thereof, more preferably the transcript, i.e., a miRNA or its precursor RNA (pri-miRNA or pre-miRNA).

The first target gene is the hsa-miR-4443 gene, a congener thereof, a transcript thereof, or a variant or a derivative thereof. None of the previously known reports show that change in the expression of the gene or the transcript thereof can serve as a marker for prostate cancer.

The second target gene is the hsa-miR-1908-5p gene, a congener thereof, a transcript thereof, or a variant or a derivative thereof. None of the previously known reports show that change in the expression of the gene or the transcript thereof can serve as a marker for prostate cancer.

The third target gene is the hsa-miR-4257 gene, a congener thereof, a transcript thereof, or a variant or a derivative thereof. None of the previously known reports show that change in the expression of the gene or the transcript thereof can serve as a marker for prostate cancer.

The fourth target gene is the hsa-miR-3197 gene, a congener thereof, a transcript thereof, or a variant or a derivative thereof. None of the previously known reports show that change in the expression of the gene or the transcript thereof can serve as a marker for prostate cancer.

The fifth target gene is the hsa-miR-3188 gene, a congener thereof, a transcript thereof, or a variant or a derivative thereof. None of the previously known reports show that change in the expression of the gene or the transcript thereof can serve as a marker for prostate cancer.

The sixth target gene is the hsa-miR-4649-5p gene, a congener thereof, a transcript thereof, or a variant or a derivative thereof. None of the previously known reports show that change in the expression of the gene or the transcript thereof can serve as a marker for prostate cancer.

The seventh target gene is the hsa-miR-1343-3p gene, a congener thereof, a transcript thereof, or a variant or a derivative thereof. None of the previously known reports show that change in the expression of the gene or the transcript thereof can serve as a marker for prostate cancer.

The eighth target gene is the hsa-miR-6861-5p gene, a congener thereof, a transcript thereof, or a variant or a derivative thereof. None of the previously known reports show that change in the expression of the gene or the transcript thereof can serve as a marker for prostate cancer.

The ninth target gene is the hsa-miR-1343-5p gene, a congener thereof, a transcript thereof, or a variant or a derivative thereof. None of the previously known reports show that change in the expression of the gene or the transcript thereof can serve as a marker for prostate cancer.

The 10th target gene is the hsa-miR-642b-3p gene, a congener thereof, a transcript thereof, or a variant or a derivative thereof. None of the previously known reports show that change in the expression of the gene or the transcript thereof can serve as a marker for prostate cancer.

The 11th target gene is the hsa-miR-6741-5p gene, a congener thereof, a transcript thereof, or a variant or a derivative thereof. None of the previously known reports show that change in the expression of the gene or the transcript thereof can serve as a marker for prostate cancer.

The 12th target gene is the hsa-miR-4745-5p gene, a congener thereof, a transcript thereof, or a variant or a derivative thereof. None of the previously known reports show that change in the expression of the gene or the transcript thereof can serve as a marker for prostate cancer.

The 13th target gene is the hsa-miR-6826-5p gene, a congener thereof, a transcript thereof, or a variant or a derivative thereof. None of the previously known reports show that change in the expression of the gene or the transcript thereof can serve as a marker for prostate cancer.

The 14th target gene is the hsa-miR-3663-3p gene, a congener thereof, a transcript thereof, or a variant or a derivative thereof. None of the previously known reports show that change in the expression of the gene or the transcript thereof can serve as a marker for prostate cancer.

The 15th target gene is the hsa-miR-3131 gene, a congener thereof, a transcript thereof, or a variant or a derivative thereof. None of the previously known reports show that change in the expression of the gene or the transcript thereof can serve as a marker for prostate cancer.

The 16th target gene is the hsa-miR-92a-2-5p gene, a congener thereof, a transcript thereof, or a variant or a derivative thereof. None of the previously known reports show that change in the expression of the gene or the transcript thereof can serve as a marker for prostate cancer.

The 17th target gene is the hsa-miR-4258 gene, a congener thereof, a transcript thereof, or a variant or a derivative thereof. None of the previously known reports show that change in the expression of the gene or the transcript thereof can serve as a marker for prostate cancer.

The 18th target gene is the hsa-miR-4448 gene, a congener thereof, a transcript thereof, or a variant or a derivative thereof. None of the previously known reports show that change in the expression of the gene or the transcript thereof can serve as a marker for prostate cancer.

The 19th target gene is the hsa-miR-6125 gene, a congener thereof, a transcript thereof, or a variant or a derivative thereof. None of the previously known reports show that change in the expression of the gene or the transcript thereof can serve as a marker for prostate cancer.

The 20th target gene is the hsa-miR-6880-5p gene, a congener thereof, a transcript thereof, or a variant or a derivative thereof. None of the previously known reports show that change in the expression of the gene or the transcript thereof can serve as a marker for prostate cancer.

The 21st target gene is the hsa-miR-6132 gene, a congener thereof, a transcript thereof, or a variant or a derivative thereof. None of the previously known reports show that change in the expression of the gene or the transcript thereof can serve as a marker for prostate cancer.

The 22nd target gene is the hsa-miR-4467 gene, a congener thereof, a transcript thereof, or a variant or a derivative thereof. None of the previously known reports show that change in the expression of the gene or the transcript thereof can serve as a marker for prostate cancer.

The 23rd target gene is the hsa-miR-6749-5p gene, a congener thereof, a transcript thereof, or a variant or a derivative thereof. None of the previously known reports show that change in the expression of the gene or the transcript thereof can serve as a marker for prostate cancer.

The 24th target gene is the hsa-miR-2392 gene, a congener thereof, a transcript thereof, or a variant or a derivative thereof. None of the previously known reports show that change in the expression of the gene or the transcript thereof can serve as a marker for prostate cancer.

The 25th target gene is the hsa-miR-1273g-3p gene, a congener thereof, a transcript thereof, or a variant or a derivative thereof. None of the previously known reports show that change in the expression of the gene or the transcript thereof can serve as a marker for prostate cancer.

The 26th target gene is the hsa-miR-4746-3p gene, a congener thereof, a transcript thereof, or a variant or a derivative thereof. None of the previously known reports show that change in the expression of the gene or the transcript thereof can serve as a marker for prostate cancer.

The 27th target gene is the hsa-miR-1914-3p gene, a congener thereof, a transcript thereof, or a variant or a derivative thereof. None of the previously known reports show that change in the expression of the gene or the transcript thereof can serve as a marker for prostate cancer.

The 28th target gene is the hsa-miR-7845-5p gene, a congener thereof, a transcript thereof, or a variant or a derivative thereof. None of the previously known reports show that change in the expression of the gene or the transcript thereof can serve as a marker for prostate cancer.

The 29th target gene is the hsa-miR-6726-5p gene, a congener thereof, a transcript thereof, or a variant or a derivative thereof. None of the previously known reports show that change in the expression of the gene or the transcript thereof can serve as a marker for prostate cancer.

The 30th target gene is the hsa-miR-128-2-5p gene, a congener thereof, a transcript thereof, or a variant or a derivative thereof. None of the previously known reports show that change in the expression of the gene or the transcript thereof can serve as a marker for prostate cancer.

The 31st target gene is the hsa-miR-4651 gene, a congener thereof, a transcript thereof, or a variant or a derivative thereof. None of the previously known reports show that change in the expression of the gene or the transcript thereof can serve as a marker for prostate cancer.

The 32nd target gene is the hsa-miR-6765-3p gene, a congener thereof, a transcript thereof, or a variant or a derivative thereof. None of the previously known reports show that change in the expression of the gene or the transcript thereof can serve as a marker for prostate cancer.

The 33rd target gene is the hsa-miR-3185 gene, a congener thereof, a transcript thereof, or a variant or a derivative thereof. None of the previously known reports show that change in the expression of the gene or the transcript thereof can serve as a marker for prostate cancer.

The 34th target gene is the hsa-miR-4792 gene, a congener thereof, a transcript thereof, or a variant or a derivative thereof. None of the previously known reports show that change in the expression of the gene or the transcript thereof can serve as a marker for prostate cancer.

The 35th target gene is the hsa-miR-6887-5p gene, a congener thereof, a transcript thereof, or a variant or a derivative thereof. None of the previously known reports show that change in the expression of the gene or the transcript thereof can serve as a marker for prostate cancer.

The 36th target gene is the hsa-miR-5572 gene, a congener thereof, a transcript thereof, or a variant or a derivative thereof. None of the previously known reports show that change in the expression of the gene or the transcript thereof can serve as a marker for prostate cancer.

The 37th target gene is the hsa-miR-3619-3p gene, a congener thereof, a transcript thereof, or a variant or a derivative thereof. None of the previously known reports show that change in the expression of the gene or the transcript thereof can serve as a marker for prostate cancer.

The 38th target gene is the hsa-miR-6780b-5p gene, a congener thereof, a transcript thereof, or a variant or a derivative thereof. None of the previously known reports show that change in the expression of the gene or the transcript thereof can serve as a marker for prostate cancer.

The 39th target gene is the hsa-miR-4707-5p gene, a congener thereof, a transcript thereof, or a variant or a derivative thereof. None of the previously known reports show that change in the expression of the gene or the transcript thereof can serve as a marker for prostate cancer.

The 40th target gene is the hsa-miR-8063 gene, a congener thereof, a transcript thereof, or a variant or a derivative thereof. None of the previously known reports show that change in the expression of the gene or the transcript thereof can serve as a marker for prostate cancer.

The 41st target gene is the hsa-miR-4454 gene, a congener thereof, a transcript thereof, or a variant or a derivative thereof. None of the previously known reports show that change in the expression of the gene or the transcript thereof can serve as a marker for prostate cancer.

The 42nd target gene is the hsa-miR-4525 gene, a congener thereof, a transcript thereof, or a variant or a derivative thereof. None of the previously known reports show that change in the expression of the gene or the transcript thereof can serve as a marker for prostate cancer.

The 43rd target gene is the hsa-miR-7975 gene, a congener thereof, a transcript thereof, or a variant or a derivative thereof. None of the previously known reports show that change in the expression of the gene or the transcript thereof can serve as a marker for prostate cancer.

The 44th target gene is the hsa-miR-744-5p gene, a congener thereof, a transcript thereof, or a variant or a derivative thereof. None of the previously known reports show that change in the expression of the gene or the transcript thereof can serve as a marker for prostate cancer.

The 45th target gene is the hsa-miR-3135b gene, a congener thereof, a transcript thereof, or a variant or a derivative thereof. None of the previously known reports show that change in the expression of the gene or the transcript thereof can serve as a marker for prostate cancer.

The 46th target gene is the hsa-miR-4648 gene, a congener thereof, a transcript thereof, or a variant or a derivative thereof. None of the previously known reports show that change in the expression of the gene or the transcript thereof can serve as a marker for prostate cancer.

The 47th target gene is the hsa-miR-6816-5p gene, a congener thereof, a transcript thereof, or a variant or a derivative thereof. None of the previously known reports show that change in the expression of the gene or the transcript thereof can serve as a marker for prostate cancer.

The 48th target gene is the hsa-miR-4741 gene, a congener thereof, a transcript thereof, or a variant or a derivative thereof. None of the previously known reports show that change in the expression of the gene or the transcript thereof can serve as a marker for prostate cancer.

The 49th target gene is the hsa-miR-7150 gene, a congener thereof, a transcript thereof, or a variant or a derivative thereof. None of the previously known reports show that change in the expression of the gene or the transcript thereof can serve as a marker for prostate cancer.

The 50th target gene is the hsa-miR-6791-5p gene, a congener thereof, a transcript thereof, or a variant or a derivative thereof. None of the previously known reports show that change in the expression of the gene or the transcript thereof can serve as a marker for prostate cancer.

The 51st target gene is the hsa-miR-1247-3p gene, a congener thereof, a transcript thereof, or a variant or a derivative thereof. None of the previously known reports show that change in the expression of the gene or the transcript thereof can serve as a marker for prostate cancer.

The 52nd target gene is the hsa-miR-7977 gene, a congener thereof, a transcript thereof, or a variant or a derivative thereof. None of the previously known reports show that change in the expression of the gene or the transcript thereof can serve as a marker for prostate cancer.

The 53rd target gene is the hsa-miR-4497 gene, a congener thereof, a transcript thereof, or a variant or a derivative thereof. None of the previously known reports show that change in the expression of the gene or the transcript thereof can serve as a marker for prostate cancer.

The 54th target gene is the hsa-miR-6090 gene, a congener thereof, a transcript thereof, or a variant or a derivative thereof. None of the previously known reports show that change in the expression of the gene or the transcript thereof can serve as a marker for prostate cancer.

The 55th target gene is the hsa-miR-6781-5p gene, a congener thereof, a transcript thereof, or a variant or a derivative thereof. None of the previously known reports show that change in the expression of the gene or the transcript thereof can serve as a marker for prostate cancer.

The 56th target gene is the hsa-miR-6870-5p gene, a congener thereof, a transcript thereof, or a variant or a derivative thereof. None of the previously known reports show that change in the expression of the gene or the transcript thereof can serve as a marker for prostate cancer.

The 57th target gene is the hsa-miR-6729-5p gene, a congener thereof, a transcript thereof, or a variant or a derivative thereof. None of the previously known reports show that change in the expression of the gene or the transcript thereof can serve as a marker for prostate cancer.

The 58th target gene is the hsa-miR-4530 gene, a congener thereof, a transcript thereof, or a variant or a derivative thereof. None of the previously known reports show that change in the expression of the gene or the transcript thereof can serve as a marker for prostate cancer.

The 59th target gene is the hsa-miR-7847-3p gene, a congener thereof, a transcript thereof, or a variant or a derivative thereof. None of the previously known reports show that change in the expression of the gene or the transcript thereof can serve as a marker for prostate cancer.

The 60th target gene is the hsa-miR-6825-5p gene, a congener thereof, a transcript thereof, or a variant or a derivative thereof. None of the previously known reports show that change in the expression of the gene or the transcript thereof can serve as a marker for prostate cancer.

The 61st target gene is the hsa-miR-4674 gene, a congener thereof, a transcript thereof, or a variant or a derivative thereof. None of the previously known reports show that change in the expression of the gene or the transcript thereof can serve as a marker for prostate cancer.

The 62nd target gene is the hsa-miR-3917 gene, a congener thereof, a transcript thereof, or a variant or a derivative thereof. None of the previously known reports show that change in the expression of the gene or the transcript thereof can serve as a marker for prostate cancer.

The 63rd target gene is the hsa-miR-4707-3p gene, a congener thereof, a transcript thereof, or a variant or a derivative thereof. None of the previously known reports show that change in the expression of the gene or the transcript thereof can serve as a marker for prostate cancer.

The 64th target gene is the hsa-miR-6885-5p gene, a congener thereof, a transcript thereof, or a variant or a derivative thereof. None of the previously known reports show that change in the expression of the gene or the transcript thereof can serve as a marker for prostate cancer.

The 65th target gene is the hsa-miR-6722-3p gene, a congener thereof, a transcript thereof, or a variant or a derivative thereof. None of the previously known reports show that change in the expression of the gene or the transcript thereof can serve as a marker for prostate cancer.

The 66th target gene is the hsa-miR-4516 gene, a congener thereof, a transcript thereof, or a variant or a derivative thereof. None of the previously known reports show that change in the expression of the gene or the transcript thereof can serve as a marker for prostate cancer.

The 67th target gene is the hsa-miR-6757-5p gene, a congener thereof, a transcript thereof, or a variant or a derivative thereof. None of the previously known reports show that change in the expression of the gene or the transcript thereof can serve as a marker for prostate cancer.

The 68th target gene is the hsa-miR-6840-3p gene, a congener thereof, a transcript thereof, or a variant or a derivative thereof. None of the previously known reports show that change in the expression of the gene or the transcript thereof can serve as a marker for prostate cancer.

The 69th target gene is the hsa-miR-5195-3p gene, a congener thereof, a transcript thereof, or a variant or a derivative thereof. None of the previously known reports show that change in the expression of the gene or the transcript thereof can serve as a marker for prostate cancer.

The 70th target gene is the hsa-miR-6756-5p gene, a congener thereof, a transcript thereof, or a variant or a derivative thereof. None of the previously known reports show that change in the expression of the gene or the transcript thereof can serve as a marker for prostate cancer.

The 71st target gene is the hsa-miR-6800-5p gene, a congener thereof, a transcript thereof, or a variant or a derivative thereof. None of the previously known reports show that change in the expression of the gene or the transcript thereof can serve as a marker for prostate cancer.

The 72nd target gene is the hsa-miR-6727-5p gene, a congener thereof, a transcript thereof, or a variant or a derivative thereof. None of the previously known reports show that change in the expression of the gene or the transcript thereof can serve as a marker for prostate cancer.

The 73rd target gene is the hsa-miR-6126 gene, a congener thereof, a transcript thereof, or a variant or a derivative thereof. None of the previously known reports show that change in the expression of the gene or the transcript thereof can serve as a marker for prostate cancer.

The 74th target gene is the hsa-miR-6872-3p gene, a congener thereof, a transcript thereof, or a variant or a derivative thereof. None of the previously known reports show that change in the expression of the gene or the transcript thereof can serve as a marker for prostate cancer.

The 75th target gene is the hsa-miR-4446-3p gene, a congener thereof, a transcript thereof, or a variant or a derivative thereof. None of the previously known reports show that change in the expression of the gene or the transcript thereof can serve as a marker for prostate cancer.

The 76th target gene is the hsa-miR-1268a gene, a congener thereof, a transcript thereof, or a variant or a derivative thereof. None of the previously known reports show that change in the expression of the gene or the transcript thereof can serve as a marker for prostate cancer.

The 77th target gene is the hsa-miR-1908-3p gene, a congener thereof, a transcript thereof, or a variant or a derivative thereof. None of the previously known reports show that change in the expression of the gene or the transcript thereof can serve as a marker for prostate cancer.

The 78th target gene is the hsa-miR-3679-5p gene, a congener thereof, a transcript thereof, or a variant or a derivative thereof. None of the previously known reports show that change in the expression of the gene or the transcript thereof can serve as a marker for prostate cancer.

The 79th target gene is the hsa-miR-4534 gene, a congener thereof, a transcript thereof, or a variant or a derivative thereof. None of the previously known reports show that change in the expression of the gene or the transcript thereof can serve as a marker for prostate cancer.

The 80th target gene is the hsa-miR-4675 gene, a congener thereof, a transcript thereof, or a variant or a derivative thereof. None of the previously known reports show that change in the expression of the gene or the transcript thereof can serve as a marker for prostate cancer.

The 81st target gene is the hsa-miR-7108-5p gene, a congener thereof, a transcript thereof, or a variant or a derivative thereof. None of the previously known reports show that change in the expression of the gene or the transcript thereof can serve as a marker for prostate cancer.

The 82nd target gene is the hsa-miR-6799-5p gene, a congener thereof, a transcript thereof, or a variant or a derivative thereof. None of the previously known reports show that change in the expression of the gene or the transcript thereof can serve as a marker for prostate cancer.

The 83rd target gene is the hsa-miR-4695-5p gene, a congener thereof, a transcript thereof, or a variant or a derivative thereof. None of the previously known reports show that change in the expression of the gene or the transcript thereof can serve as a marker for prostate cancer.

The 84th target gene is the hsa-miR-3178 gene, a congener thereof, a transcript thereof, or a variant or a derivative thereof. None of the previously known reports show that change in the expression of the gene or the transcript thereof can serve as a marker for prostate cancer.

The 85th target gene is the hsa-miR-5090 gene, a congener thereof, a transcript thereof, or a variant or a derivative thereof. None of the previously known reports show that change in the expression of the gene or the transcript thereof can serve as a marker for prostate cancer.

The 86th target gene is the hsa-miR-3180 gene, a congener thereof, a transcript thereof, or a variant or a derivative thereof. None of the previously known reports show that change in the expression of the gene or the transcript thereof can serve as a marker for prostate cancer.

The 87th target gene is the hsa-miR-1237-5p gene, a congener thereof, a transcript thereof, or a variant or a derivative thereof. None of the previously known reports show that change in the expression of the gene or the transcript thereof can serve as a marker for prostate cancer.

The 88th target gene is the hsa-miR-4758-5p gene, a congener thereof, a transcript thereof, or a variant or a derivative thereof. None of the previously known reports show that change in the expression of the gene or the transcript thereof can serve as a marker for prostate cancer.

The 89th target gene is the hsa-miR-3184-5p gene, a congener thereof, a transcript thereof, or a variant or a derivative thereof. None of the previously known reports show that change in the expression of the gene or the transcript thereof can serve as a marker for prostate cancer.

The 90th target gene is the hsa-miR-4286 gene, a congener thereof, a transcript thereof, or a variant or a derivative thereof. None of the previously known reports show that change in the expression of the gene or the transcript thereof can serve as a marker for prostate cancer.

The 91st target gene is the hsa-miR-6784-5p gene, a congener thereof, a transcript thereof, or a variant or a derivative thereof. None of the previously known reports show that change in the expression of the gene or the transcript thereof can serve as a marker for prostate cancer.

The 92nd target gene is the hsa-miR-6768-5p gene, a congener thereof, a transcript thereof, or a variant or a derivative thereof. None of the previously known reports show that change in the expression of the gene or the transcript thereof can serve as a marker for prostate cancer.

The 93rd target gene is the hsa-miR-6785-5p gene, a congener thereof, a transcript thereof, or a variant or a derivative thereof. None of the previously known reports show that change in the expression of the gene or the transcript thereof can serve as a marker for prostate cancer.

The 94th target gene is the hsa-miR-4706 gene, a congener thereof, a transcript thereof, or a variant or a derivative thereof. None of the previously known reports show that change in the expression of the gene or the transcript thereof can serve as a marker for prostate cancer.

The 95th target gene is the hsa-miR-711 gene, a congener thereof, a transcript thereof, or a variant or a derivative thereof. None of the previously known reports show that change in the expression of the gene or the transcript thereof can serve as a marker for prostate cancer.

The 96th target gene is the hsa-miR-1260a gene, a congener thereof, a transcript thereof, or a variant or a derivative thereof. None of the previously known reports show that change in the expression of the gene or the transcript thereof can serve as a marker for prostate cancer.

The 97th target gene is the hsa-miR-6746-5p gene, a congener thereof, a transcript thereof, or a variant or a derivative thereof. None of the previously known reports show that change in the expression of the gene or the transcript thereof can serve as a marker for prostate cancer.

The 98th target gene is the hsa-miR-6089 gene, a congener thereof, a transcript thereof, or a variant or a derivative thereof. None of the previously known reports show that change in the expression of the gene or the transcript thereof can serve as a marker for prostate cancer.

The 99th target gene is the hsa-miR-6821-5p gene, a congener thereof, a transcript thereof, or a variant or a derivative thereof. None of the previously known reports show that change in the expression of the gene or the transcript thereof can serve as a marker for prostate cancer.

The 100th target gene is the hsa-miR-4667-5p gene, a congener thereof, a transcript thereof, or a variant or a derivative thereof. None of the previously known reports show that change in the expression of the gene or the transcript thereof can serve as a marker for prostate cancer.

The 101st target gene is the hsa-miR-8069 gene, a congener thereof, a transcript thereof, or a variant or a derivative thereof. None of the previously known reports show that change in the expression of the gene or the transcript thereof can serve as a marker for prostate cancer.

The 102nd target gene is the hsa-miR-4726-5p gene, a congener thereof, a transcript thereof, or a variant or a derivative thereof. None of the previously known reports show that change in the expression of the gene or the transcript thereof can serve as a marker for prostate cancer.

The 103rd target gene is the hsa-miR-6124 gene, a congener thereof, a transcript thereof, or a variant or a derivative thereof. None of the previously known reports show that change in the expression of the gene or the transcript thereof can serve as a marker for prostate cancer.

The 104th target gene is the hsa-miR-4532 gene, a congener thereof, a transcript thereof, or a variant or a derivative thereof. None of the previously known reports show that change in the expression of the gene or the transcript thereof can serve as a marker for prostate cancer.

The 105th target gene is the hsa-miR-4486 gene, a congener thereof, a transcript thereof, or a variant or a derivative thereof. None of the previously known reports show that change in the expression of the gene or the transcript thereof can serve as a marker for prostate cancer.

The 106th target gene is the hsa-miR-4728-5p gene, a congener thereof, a transcript thereof, or a variant or a derivative thereof. None of the previously known reports show that change in the expression of the gene or the transcript thereof can serve as a marker for prostate cancer.

The 107th target gene is the hsa-miR-4508 gene, a congener thereof, a transcript thereof, or a variant or a derivative thereof. None of the previously known reports show that change in the expression of the gene or the transcript thereof can serve as a marker for prostate cancer.

The 108th target gene is the hsa-miR-128-1-5p gene, a congener thereof, a transcript thereof, or a variant or a derivative thereof. None of the previously known reports show that change in the expression of the gene or the transcript thereof can serve as a marker for prostate cancer.

The 109th target gene is the hsa-miR-4513 gene, a congener thereof, a transcript thereof, or a variant or a derivative thereof. None of the previously known reports show that change in the expression of the gene or the transcript thereof can serve as a marker for prostate cancer.

The 110th target gene is the hsa-miR-6795-5p gene, a congener thereof, a transcript thereof, or a variant or a derivative thereof. None of the previously known reports show that change in the expression of the gene or the transcript thereof can serve as a marker for prostate cancer.

The 111th target gene is the hsa-miR-4689 gene, a congener thereof, a transcript thereof, or a variant or a derivative thereof. None of the previously known reports show that change in the expression of the gene or the transcript thereof can serve as a marker for prostate cancer.

The 112th target gene is the hsa-miR-6763-5p gene, a congener thereof, a transcript thereof, or a variant or a derivative thereof. None of the previously known reports show that change in the expression of the gene or the transcript thereof can serve as a marker for prostate cancer.

The 113th target gene is the hsa-miR-8072 gene, a congener thereof, a transcript thereof, or a variant or a derivative thereof. None of the previously known reports show that change in the expression of the gene or the transcript thereof can serve as a marker for prostate cancer.

The 114th target gene is the hsa-miR-6765-5p gene, a congener thereof, a transcript thereof, or a variant or a derivative thereof. None of the previously known reports show that change in the expression of the gene or the transcript thereof can serve as a marker for prostate cancer.

The 115th target gene is the hsa-miR-4419b gene, a congener thereof, a transcript thereof, or a variant or a derivative thereof. None of the previously known reports show that change in the expression of the gene or the transcript thereof can serve as a marker for prostate cancer.

The 116th target gene is the hsa-miR-7641 gene, a congener thereof, a transcript thereof, or a variant or a derivative thereof. None of the previously known reports show that change in the expression of the gene or the transcript thereof can serve as a marker for prostate cancer.

The 117th target gene is the hsa-miR-3928-3p gene, a congener thereof, a transcript thereof, or a variant or a derivative thereof. None of the previously known reports show that change in the expression of the gene or the transcript thereof can serve as a marker for prostate cancer.

The 118th target gene is the hsa-miR-1227-5p gene, a congener thereof, a transcript thereof, or a variant or a derivative thereof. None of the previously known reports show that change in the expression of the gene or the transcript thereof can serve as a marker for prostate cancer.

The 119th target gene is the hsa-miR-4492 gene, a congener thereof, a transcript thereof, or a variant or a derivative thereof. None of the previously known reports show that change in the expression of the gene or the transcript thereof can serve as a marker for prostate cancer.

The 120th target gene is the hsa-miR-296-3p gene, a congener thereof, a transcript thereof, or a variant or a derivative thereof. None of the previously known reports show that change in the expression of the gene or the transcript thereof can serve as a marker for prostate cancer.

The 121st target gene is the hsa-miR-6769a-5p gene, a congener thereof, a transcript thereof, or a variant or a derivative thereof. None of the previously known reports show that change in the expression of the gene or the transcript thereof can serve as a marker for prostate cancer.

The 122nd target gene is the hsa-miR-6889-5p gene, a congener thereof, a transcript thereof, or a variant or a derivative thereof. None of the previously known reports show that change in the expression of the gene or the transcript thereof can serve as a marker for prostate cancer.

The 123rd target gene is the hsa-miR-4632-5p gene, a congener thereof, a transcript thereof, or a variant or a derivative thereof. None of the previously known reports show that change in the expression of the gene or the transcript thereof can serve as a marker for prostate cancer.

The 124th target gene is the hsa-miR-4505 gene, a congener thereof, a transcript thereof, or a variant or a derivative thereof. None of the previously known reports show that change in the expression of the gene or the transcript thereof can serve as a marker for prostate cancer.

The 125th target gene is the hsa-miR-3154 gene, a congener thereof, a transcript thereof, or a variant or a derivative thereof. None of the previously known reports show that change in the expression of the gene or the transcript thereof can serve as a marker for prostate cancer.

The 126th target gene is the hsa-miR-3648 gene, a congener thereof, a transcript thereof, or a variant or a derivative thereof. None of the previously known reports show that change in the expression of the gene or the transcript thereof can serve as a marker for prostate cancer.

The 127th target gene is the hsa-miR-4442 gene, a congener thereof, a transcript thereof, or a variant or a derivative thereof. None of the previously known reports show that change in the expression of the gene or the transcript thereof can serve as a marker for prostate cancer.

The 128th target gene is the hsa-miR-3141 gene, a congener thereof, a transcript thereof, or a variant or a derivative thereof. None of the previously known reports show that change in the expression of the gene or the transcript thereof can serve as a marker for prostate cancer.

The 129th target gene is the hsa-miR-7113-3p gene, a congener thereof, a transcript thereof, or a variant or a derivative thereof. None of the previously known reports show that change in the expression of the gene or the transcript thereof can serve as a marker for prostate cancer.

The 130th target gene is the hsa-miR-6819-5p gene, a congener thereof, a transcript thereof, or a variant or a derivative thereof. None of the previously known reports show that change in the expression of the gene or the transcript thereof can serve as a marker for prostate cancer.

The 131st target gene is the hsa-miR-3195 gene, a congener thereof, a transcript thereof, or a variant or a derivative thereof. None of the previously known reports show that change in the expression of the gene or the transcript thereof can serve as a marker for prostate cancer.

The 132nd target gene is the hsa-miR-1199-5p gene, a congener thereof, a transcript thereof, or a variant or a derivative thereof. None of the previously known reports show that change in the expression of the gene or the transcript thereof can serve as a marker for prostate cancer.

The 133rd target gene is the hsa-miR-6738-5p gene, a congener thereof, a transcript thereof, or a variant or a derivative thereof. None of the previously known reports show that change in the expression of the gene or the transcript thereof can serve as a marker for prostate cancer.

The 134th target gene is the hsa-miR-4656 gene, a congener thereof, a transcript thereof, or a variant or a derivative thereof. None of the previously known reports show that change in the expression of the gene or the transcript thereof can serve as a marker for prostate cancer.

The 135th target gene is the hsa-miR-6820-5p gene, a congener thereof, a transcript thereof, or a variant or a derivative thereof. None of the previously known reports show that change in the expression of the gene or the transcript thereof can serve as a marker for prostate cancer.

The 136th target gene is the hsa-miR-615-5p gene, a congener thereof, a transcript thereof, or a variant or a derivative thereof. The previously known report shows that change in the expression of the gene or the transcript thereof can serve as a marker for prostate cancer (Patent Literature 1).

The 137th target gene is the hsa-miR-486-3p gene, a congener thereof, a transcript thereof, or a variant or a derivative thereof. The previously known report shows that change in the expression of the gene or the transcript thereof can serve as a marker for prostate cancer (Patent Literature 1).

The 138th target gene is the hsa-miR-1225-3p gene, a congener thereof, a transcript thereof, or a variant or a derivative thereof. The previously known report shows that change in the expression of the gene or the transcript thereof can serve as a marker for prostate cancer (Patent Literature 1).

The 139th target gene is the hsa-miR-760 gene, a congener thereof, a transcript thereof, or a variant or a derivative thereof. The previously known report shows that change in the expression of the gene or the transcript thereof can serve as a marker for prostate cancer (Patent Literature 1).

The 140th target gene is the hsa-miR-187-5p gene, a congener thereof, a transcript thereof, or a variant or a derivative thereof. The previously known report shows that change in the expression of the gene or the transcript thereof can serve as a marker for prostate cancer (Patent Literature 1).

The 141st target gene is the hsa-miR-1203 gene, a congener thereof, a transcript thereof, or a variant or a derivative thereof. The previously known report shows that change in the expression of the gene or the transcript thereof can serve as a marker for prostate cancer (Patent Literature 1).

The 142nd target gene is the hsa-miR-7110-5p gene, a congener thereof, a transcript thereof, or a variant or a derivative thereof. The previously known report shows that change in the expression of the gene or the transcript thereof can serve as a marker for prostate cancer (Patent Literature 1).

The 143rd target gene is the hsa-miR-371a-5p gene, a congener thereof, a transcript thereof, or a variant or a derivative thereof. The previously known report shows that change in the expression of the gene or the transcript thereof can serve as a marker for prostate cancer (Patent Literature 1).

The 144th target gene is the hsa-miR-939-5p gene, a congener thereof, a transcript thereof, or a variant or a derivative thereof. The previously known report shows that change in the expression of the gene or the transcript thereof can serve as a marker for prostate cancer (Patent Literature 1).

The 145th target gene is the hsa-miR-575 gene, a congener thereof, a transcript thereof, or a variant or a derivative thereof. The previously known report shows that change in the expression of the gene or the transcript thereof can serve as a marker for prostate cancer (Patent Literature 1).

The 146th target gene is the hsa-miR-92b-5p gene, a congener thereof, a transcript thereof, or a variant or a derivative thereof. The previously known report shows that change in the expression of the gene or the transcript thereof can serve as a marker for prostate cancer (Patent Literature 2).

The 147th target gene is the hsa-miR-887-3p gene, a congener thereof, a transcript thereof, or a variant or a derivative thereof. The previously known report shows that change in the expression of the gene or the transcript thereof can serve as a marker for prostate cancer (Patent Literature 1).

The 148th target gene is the hsa-miR-920 gene, a congener thereof, a transcript thereof, or a variant or a derivative thereof. The previously known report shows that change in the expression of the gene or the transcript thereof can serve as a marker for prostate cancer (Patent Literature 1).

The 149th target gene is the hsa-miR-1915-5p gene, a congener thereof, a transcript thereof, or a variant or a derivative thereof. The previously known report shows that change in the expression of the gene or the transcript thereof can serve as a marker for prostate cancer (Patent Literature 1).

The 150th target gene is the hsa-miR-1231 gene, a congener thereof, a transcript thereof, or a variant or a derivative thereof. The previously known report shows that change in the expression of the gene or the transcript thereof can serve as a marker for prostate cancer (Patent Literature 1).

The 151st target gene is the hsa-miR-663b gene, a congener thereof, a transcript thereof, or a variant or a derivative thereof. The previously known report shows that change in the expression of the gene or the transcript thereof can serve as a marker for prostate cancer (Patent Literature 1).

The 152nd target gene is the hsa-miR-1225-5p gene, a congener thereof, a transcript thereof, or a variant or a derivative thereof. The previously known report shows that change in the expression of the gene or the transcript thereof can serve as a marker for prostate cancer (Patent Literature 1).

The 153rd target gene is the hsa-miR-4763-3p gene, a congener thereof, a transcript thereof, or a variant or a derivative thereof. None of the previously known reports show that change in the expression of the gene or the transcript thereof can serve as a marker for prostate cancer.

The 154th target gene is the hsa-miR-3656 gene, a congener thereof, a transcript thereof, or a variant or a derivative thereof. None of the previously known reports show that change in the expression of the gene or the transcript thereof can serve as a marker for prostate cancer.

The 155th target gene is the hsa-miR-4488 gene, a congener thereof, a transcript thereof, or a variant or a derivative thereof. None of the previously known reports show that change in the expression of the gene or the transcript thereof can serve as a marker for prostate cancer.

The 156th target gene is the hsa-miR-125a-3p gene, a congener thereof, a transcript thereof, or a variant or a derivative thereof. The previously known report shows that change in the expression of the gene or the transcript thereof can serve as a marker for prostate cancer (Patent Literature 1).

The 157th target gene is the hsa-miR-1469 gene, a congener thereof, a transcript thereof, or a variant or a derivative thereof. None of the previously known reports show that change in the expression of the gene or the transcript thereof can serve as a marker for prostate cancer.

The 158th target gene is the hsa-miR-1228-5p gene, a congener thereof, a transcript thereof, or a variant or a derivative thereof. The previously known report shows that change in the expression of the gene or the transcript thereof can serve as a marker for prostate cancer (Patent Literature 1).

The 159th target gene is the hsa-miR-6798-5p gene, a congener thereof, a transcript thereof, or a variant or a derivative thereof. None of the previously known reports show that change in the expression of the gene or the transcript thereof can serve as a marker for prostate cancer.

The 160th target gene is the hsa-miR-1268b gene, a congener thereof, a transcript thereof, or a variant or a derivative thereof. The previously known report shows that change in the expression of the gene or the transcript thereof can serve as a marker for prostate cancer (Patent Literature 1).

The 161st target gene is the hsa-miR-6732-5p gene, a congener thereof, a transcript thereof, or a variant or a derivative thereof. None of the previously known reports show that change in the expression of the gene or the transcript thereof can serve as a marker for prostate cancer.

The 162nd target gene is the hsa-miR-1915-3p gene, a congener thereof, a transcript thereof, or a variant or a derivative thereof. The previously known report shows that change in the expression of the gene or the transcript thereof can serve as a marker for prostate cancer (Patent Literature 1).

The 163rd target gene is the hsa-miR-4433b-3p gene, a congener thereof, a transcript thereof, or a variant or a derivative thereof. None of the previously known reports show that change in the expression of the gene or the transcript thereof can serve as a marker for prostate cancer.

The 164th target gene is the hsa-miR-1207-5p gene, a congener thereof, a transcript thereof, or a variant or a derivative thereof. The previously known report shows that change in the expression of the gene or the transcript thereof can serve as a marker for prostate cancer (Patent Literature 1).

The 165th target gene is the hsa-miR-4433-3p gene, a congener thereof, a transcript thereof, or a variant or a derivative thereof. None of the previously known reports show that change in the expression of the gene or the transcript thereof can serve as a marker for prostate cancer.

The 166th target gene is the hsa-miR-6879-5p gene, a congener thereof, a transcript thereof, or a variant or a derivative thereof. None of the previously known reports show that change in the expression of the gene or the transcript thereof can serve as a marker for prostate cancer.

The 167th target gene is the hsa-miR-4417 gene, a congener thereof, a transcript thereof, or a variant or a derivative thereof. None of the previously known reports show that change in the expression of the gene or the transcript thereof can serve as a marker for prostate cancer.

The 168th target gene is the hsa-miR-30c-1-3p gene, a congener thereof, a transcript thereof, or a variant or a derivative thereof. The previously known report shows that change in the expression of the gene or the transcript thereof can serve as a marker for prostate cancer (Patent Literature 1).

The 169th target gene is the hsa-miR-4638-5p gene, a congener thereof, a transcript thereof, or a variant or a derivative thereof. None of the previously known reports show that change in the expression of the gene or the transcript thereof can serve as a marker for prostate cancer.

The 170th target gene is the hsa-miR-6088 gene, a congener thereof, a transcript thereof, or a variant or a derivative thereof. None of the previously known reports show that change in the expression of the gene or the transcript thereof can serve as a marker for prostate cancer.

The 171st target gene is the hsa-miR-4270 gene, a congener thereof, a transcript thereof, or a variant or a derivative thereof. None of the previously known reports show that change in the expression of the gene or the transcript thereof can serve as a marker for prostate cancer.

The 172nd target gene is the hsa-miR-6782-5p gene, a congener thereof, a transcript thereof, or a variant or a derivative thereof. None of the previously known reports show that change in the expression of the gene or the transcript thereof can serve as a marker for prostate cancer.

The 173rd target gene is the hsa-miR-665 gene, a congener thereof, a transcript thereof, or a variant or a derivative thereof. The previously known report shows that change in the expression of the gene or the transcript thereof can serve as a marker for prostate cancer (Patent Literature 1).

The 174th target gene is the hsa-miR-486-5p gene, a congener thereof, a transcript thereof, or a variant or a derivative thereof. The previously known report shows that change in the expression of the gene or the transcript thereof can serve as a marker for prostate cancer (Patent Literature 1).

The 175th target gene is the hsa-miR-4655-5p gene, a congener thereof, a transcript thereof, or a variant or a derivative thereof. None of the previously known reports show that change in the expression of the gene or the transcript thereof can serve as a marker for prostate cancer.

The 176th target gene is the hsa-miR-1275 gene, a congener thereof, a transcript thereof, or a variant or a derivative thereof. The previously known report shows that change in the expression of the gene or the transcript thereof can serve as a marker for prostate cancer (Patent Literature 1).

The 177th target gene is the hsa-miR-6806-5p gene, a congener thereof, a transcript thereof, or a variant or a derivative thereof. None of the previously known reports show that change in the expression of the gene or the transcript thereof can serve as a marker for prostate cancer.

The 178th target gene is the hsa-miR-614 gene, a congener thereof, a transcript thereof, or a variant or a derivative thereof. The previously known report shows that change in the expression of the gene or the transcript thereof can serve as a marker for prostate cancer (Patent Literature 1).

The 179th target gene is the hsa-miR-3937 gene, a congener thereof, a transcript thereof, or a variant or a derivative thereof. None of the previously known reports show that change in the expression of the gene or the transcript thereof can serve as a marker for prostate cancer.

The 180th target gene is the hsa-miR-6752-5p gene, a congener thereof, a transcript thereof, or a variant or a derivative thereof. None of the previously known reports show that change in the expression of the gene or the transcript thereof can serve as a marker for prostate cancer.

The 181st target gene is the hsa-miR-6771-5p gene, a congener thereof, a transcript thereof, or a variant or a derivative thereof. None of the previously known reports show that change in the expression of the gene or the transcript thereof can serve as a marker for prostate cancer.

The 182nd target gene is the hsa-miR-4450 gene, a congener thereof, a transcript thereof, or a variant or a derivative thereof. None of the previously known reports show that change in the expression of the gene or the transcript thereof can serve as a marker for prostate cancer.

The 183rd target gene is the hsa-miR-211-3p gene, a congener thereof, a transcript thereof, or a variant or a derivative thereof. The previously known report shows that change in the expression of the gene or the transcript thereof can serve as a marker for prostate cancer (Patent Literature 1).

The 184th target gene is the hsa-miR-663a gene, a congener thereof, a transcript thereof, or a variant or a derivative thereof. The previously known report shows that change in the expression of the gene or the transcript thereof can serve as a marker for prostate cancer (Patent Literature 1).

The 185th target gene is the hsa-miR-6842-5p gene, a congener thereof, a transcript thereof, or a variant or a derivative thereof. None of the previously known reports show that change in the expression of the gene or the transcript thereof can serve as a marker for prostate cancer.

The 186th target gene is the hsa-miR-7114-5p gene, a congener thereof, a transcript thereof, or a variant or a derivative thereof. None of the previously known reports show that change in the expression of the gene or the transcript thereof can serve as a marker for prostate cancer.

The 187th target gene is the hsa-miR-6779-5p gene, a congener thereof, a transcript thereof, or a variant or a derivative thereof. None of the previously known reports show that change in the expression of the gene or the transcript thereof can serve as a marker for prostate cancer.

The 580th target gene is the hsa-miR-204-3p gene, a congener thereof, a transcript thereof, or a variant or a derivative thereof. None of the previously known reports show that change in the expression of the gene or the transcript thereof can serve as a marker for prostate cancer.

The 581st target gene is the hsa-miR-642a-3p gene, a congener thereof, a transcript thereof, or a variant or a derivative thereof. None of the previously known reports show that change in the expression of the gene or the transcript thereof can serve as a marker for prostate cancer.

The 582nd target gene is the hsa-miR-762 gene, a congener thereof, a transcript thereof, or a variant or a derivative thereof. None of the previously known reports show that change in the expression of the gene or the transcript thereof can serve as a marker for prostate cancer.

The 583rd target gene is the hsa-miR-1202 gene, a congener thereof, a transcript thereof, or a variant or a derivative thereof. None of the previously known reports show that change in the expression of the gene or the transcript thereof can serve as a marker for prostate cancer.

The 584th target gene is the hsa-miR-3162-5p gene, a congener thereof, a transcript thereof, or a variant or a derivative thereof. None of the previously known reports show that change in the expression of the gene or the transcript thereof can serve as a marker for prostate cancer.

The 585th target gene is the hsa-miR-3196 gene, a congener thereof, a transcript thereof, or a variant or a derivative thereof. None of the previously known reports show that change in the expression of the gene or the transcript thereof can serve as a marker for prostate cancer.

The 586th target gene is the hsa-miR-3622a-5p gene, a congener thereof, a transcript thereof, or a variant or a derivative thereof. None of the previously known reports show that change in the expression of the gene or the transcript thereof can serve as a marker for prostate cancer.

The 587th target gene is the hsa-miR-3665 gene, a congener thereof, a transcript thereof, or a variant or a derivative thereof. None of the previously known reports show that change in the expression of the gene or the transcript thereof can serve as a marker for prostate cancer.

The 588th target gene is the hsa-miR-3940-5p gene, a congener thereof, a transcript thereof, or a variant or a derivative thereof. None of the previously known reports show that change in the expression of the gene or the transcript thereof can serve as a marker for prostate cancer.

The 589th target gene is the hsa-miR-4294 gene, a congener thereof, a transcript thereof, or a variant or a derivative thereof. None of the previously known reports show that change in the expression of the gene or the transcript thereof can serve as a marker for prostate cancer.

The 590th target gene is the hsa-miR-4466 gene, a congener thereof, a transcript thereof, or a variant or a derivative thereof. None of the previously known reports show that change in the expression of the gene or the transcript thereof can serve as a marker for prostate cancer.

The 591st target gene is the hsa-miR-4476 gene, a congener thereof, a transcript thereof, or a variant or a derivative thereof. None of the previously known reports show that change in the expression of the gene or the transcript thereof can serve as a marker for prostate cancer.

The 592nd target gene is the hsa-miR-4723-5p gene, a congener thereof, a transcript thereof, or a variant or a derivative thereof. None of the previously known reports show that change in the expression of the gene or the transcript thereof can serve as a marker for prostate cancer.

The 593rd target gene is the hsa-miR-4725-3p gene, a congener thereof, a transcript thereof, or a variant or a derivative thereof. None of the previously known reports show that change in the expression of the gene or the transcript thereof can serve as a marker for prostate cancer.

The 594th target gene is the hsa-miR-4730 gene, a congener thereof, a transcript thereof, or a variant or a derivative thereof. None of the previously known reports show that change in the expression of the gene or the transcript thereof can serve as a marker for prostate cancer.

The 595th target gene is the hsa-miR-4739 gene, a congener thereof, a transcript thereof, or a variant or a derivative thereof. None of the previously known reports show that change in the expression of the gene or the transcript thereof can serve as a marker for prostate cancer.

The 596th target gene is the hsa-miR-4787-5p gene, a congener thereof, a transcript thereof, or a variant or a derivative thereof. None of the previously known reports show that change in the expression of the gene or the transcript thereof can serve as a marker for prostate cancer.

The 597th target gene is the hsa-miR-5787 gene, a congener thereof, a transcript thereof, or a variant or a derivative thereof. None of the previously known reports show that change in the expression of the gene or the transcript thereof can serve as a marker for prostate cancer.

The 598th target gene is the hsa-miR-6085 gene, a congener thereof, a transcript thereof, or a variant or a derivative thereof. None of the previously known reports show that change in the expression of the gene or the transcript thereof can serve as a marker for prostate cancer.

The 599th target gene is the hsa-miR-6717-5p gene, a congener thereof, a transcript thereof, or a variant or a derivative thereof. None of the previously known reports show that change in the expression of the gene or the transcript thereof can serve as a marker for prostate cancer.

The 600th target gene is the hsa-miR-6724-5p gene, a congener thereof, a transcript thereof, or a variant or a derivative thereof. None of the previously known reports show that change in the expression of the gene or the transcript thereof can serve as a marker for prostate cancer.

The 601st target gene is the hsa-miR-6777-5p gene, a congener thereof, a transcript thereof, or a variant or a derivative thereof. None of the previously known reports show that change in the expression of the gene or the transcript thereof can serve as a marker for prostate cancer.

The 602nd target gene is the hsa-miR-6778-5p gene, a congener thereof, a transcript thereof, or a variant or a derivative thereof. None of the previously known reports show that change in the expression of the gene or the transcript thereof can serve as a marker for prostate cancer.

The 603rd target gene is the hsa-miR-6787-5p gene, a congener thereof, a transcript thereof, or a variant or a derivative thereof. None of the previously known reports show that change in the expression of the gene or the transcript thereof can serve as a marker for prostate cancer.

The 604th target gene is the hsa-miR-6789-5p gene, a congener thereof, a transcript thereof, or a variant or a derivative thereof. None of the previously known reports show that change in the expression of the gene or the transcript thereof can serve as a marker for prostate cancer.

The 605th target gene is the hsa-miR-6845-5p gene, a congener thereof, a transcript thereof, or a variant or a derivative thereof. None of the previously known reports show that change in the expression of the gene or the transcript thereof can serve as a marker for prostate cancer.

The 606th target gene is the hsa-miR-6893-5p gene, a congener thereof, a transcript thereof, or a variant or a derivative thereof. None of the previously known reports show that change in the expression of the gene or the transcript thereof can serve as a marker for prostate cancer.

The 607th target gene is the hsa-miR-16-5p gene, a congener thereof, a transcript thereof, or a variant or a derivative thereof. The previously known report shows that change in the expression of the gene or the transcript thereof can serve as a marker for prostate cancer (Patent Literature 2).

The 608th target gene is the hsa-miR-423-5p gene, a congener thereof, a transcript thereof, or a variant or a derivative thereof. The previously known report shows that change in the expression of the gene or the transcript thereof can serve as a marker for prostate cancer (Patent Literature 2).

The 609th target gene is the hsa-miR-451a gene, a congener thereof, a transcript thereof, or a variant or a derivative thereof. The previously known report shows that change in the expression of the gene or the transcript thereof can serve as a marker for prostate cancer (Patent Literature 2).

The 610th target gene is the hsa-miR-564 gene, a congener thereof, a transcript thereof, or a variant or a derivative thereof. The previously known report shows that change in the expression of the gene or the transcript thereof can serve as a marker for prostate cancer (Patent Literature 2).

The 611th target gene is the hsa-miR-671-5p gene, a congener thereof, a transcript thereof, or a variant or a derivative thereof. The previously known report shows that change in the expression of the gene or the transcript thereof can serve as a marker for prostate cancer (Patent Literature 2).

2. Nucleic Acid Probe or Primer for Detection of Prostate Cancer

In the present invention, a nucleic acid capable of specifically binding to any of the target nucleic acids as the prostate cancer markers described above can be used as a nucleic acid, for example, a nucleic acid probe or a primer, for the detection or diagnosis of prostate cancer.

In the present invention, the nucleic acid probe or the primer that can be used for detecting prostate cancer or for diagnosing prostate cancer permits qualitative and/or quantitative measurement of the presence, expression level, or abundance of any of the target nucleic acids as the prostate cancer markers described above, for example, human-derived hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p, or hsa-miR-6893-5p, or combinations thereof, congeners thereof, transcripts thereof, or variants or derivatives thereof.

The expression level of each target nucleic acid described above is increased or decreased (hereinafter, referred to as “increased/decreased”) according to the type of the target nucleic acid(s) in a subject having prostate cancer as compared with a healthy subject. Hence, the nucleic acid of the present invention can be effectively used for measuring the expression level of the target nucleic acid(s) in a body fluid derived from a subject (e.g., a human) suspected of having prostate cancer and a body fluid derived from a healthy subject and detecting prostate cancer by the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 135 and 580 to 606, or a primer for amplifying a polynucleotide consisting of a nucleotide sequence represented by at least one of SEQ ID NOs: 1 to 135 and 580 to 606.

The nucleic acid probe or the primer that can be further used in the present invention can comprise a nucleic acid probe capable of specifically binding to a polynucleotide consisting of a nucleotide sequence represented by at least one of SEQ ID NOs: 136 to 152 and 607 to 611, or a primer for amplifying a polynucleotide consisting of a nucleotide sequence represented by at least one of SEQ ID NOs: 136 to 152 and 607 to 611.

The nucleic acid probe or the primer that can be further used in the present invention can comprise a nucleic acid probe capable of specifically binding to a polynucleotide consisting of a nucleotide sequence represented by at least one of SEQ ID NOs: 153 to 187, or a primer for amplifying a polynucleotide consisting of a nucleotide sequence represented by at least one of SEQ ID NOs: 153 to 187.

Specifically, these nucleic acid probes or primers comprise a combination of one or more polynucleotides selected from a polynucleotide group comprising nucleotide sequences represented by any of SEQ ID NOs: 1 to 684 or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the prostate cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 135, 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135, 580 to 606, (c) a polynucleotide consisting of a nucleotide sequence complementary to a nucleotide sequence represented by any of SEQ ID NOs: 1 to 135, 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135, 580 to 606 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise any of the following polynucleotides (f) to (j):

(f) a polynucleotide consisting of a nucleotide sequence represented by any of SEQ ID NOs: 136 to 152, 607 to 611 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 136 to 152, 607 to 611, (h) a polynucleotide consisting of a nucleotide sequence complementary to a nucleotide sequence represented by any of SEQ ID NOs: 136 to 152, 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152, 607 to 611 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise any of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

For these polynucleotides, the "fragment thereof comprising 15 or more consecutive nucleotides" can contain the number of nucleotides in the range of, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-204-3p, hsa-miR-642a-3p, hsa-miR-762, hsa-miR-1202, hsa-miR-3162-5p, hsa-miR-3196, hsa-miR-3622a-5p, hsa-miR-3665, hsa-miR-3940-5p, hsa-miR-4294, hsa-miR-4466, hsa-miR-4476, hsa-miR-4723-5p, hsa-miR-4725-3p, hsa-miR-4730, hsa-miR-4739, hsa-miR-4787-5p, hsa-miR-5787, hsa-miR-6085, hsa-miR-6717-5p, hsa-miR-6724-5p, hsa-miR-6777-5p, hsa-miR-6778-5p, hsa-miR-6787-5p, hsa-miR-6789-5p, hsa-miR-6845-5p, hsa-miR-6893-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663b, hsa-miR-1225-5p, hsa-miR-16-5p, hsa-miR-423-5p, hsa-miR-451a, hsa-miR-564, hsa-miR-671-5p, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p represented by SEQ ID NOs: 1 to 187, and 580 to 611 are known in the art, and their obtainment methods are also known as mentioned above. Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 bases can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probes and the primers for detecting the polynucleotides consisting of a nucleotide sequence represented by any of SEQ ID NOs: 1 to 187, and 580 to 611 do not exist as miRNAs or precursors thereof in vivo. For example, the nucleotide sequences represented by SEQ ID NO: 7 and SEQ ID NO: 9 are formed from the precursor represented by SEQ ID NO: 194. This precursor has a hairpin-like structure as shown in FIG. 1, and the nucleotide sequences represented by SEQ ID NO: 7 and SEQ ID NO: 9 have mismatch sequences with each other. Therefore, a nucleotide sequence completely complementary to the nucleotide sequence represented by SEQ ID NO: 7 or SEQ ID NO: 9 does not naturally occur in vivo. Likewise, the nucleic acid probe and the primer for detecting the nucleotide sequence represented by any of SEQ ID NOs: 1 to 187, and 580 to 611 each have an artificial nucleotide sequence that does not exist in vivo.

3. Kit or Device for Detection of Prostate Cancer

The present invention also provides a kit or a device for the detection of prostate cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a prostate cancer marker.

The target nucleic acid as a prostate cancer marker according to the present invention is selected from the following group 1:

miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p.

An additional target nucleic acid that can be optionally used in the measurement is selected from the following group 2: miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

An additional target nucleic acid that can be optionally further used in the measurement is selected from the following group 3: miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

The kit or the device of the present invention comprises nucleic acid(s) capable of specifically binding to any of the target nucleic acids as the prostate cancer markers described above, preferably one or more polynucleotide(s) selected from the nucleic acid probes or the primers described in the preceding Section 2, specifically, the polynucleotides described in the preceding Section 2, or variant(s) thereof, etc.

Specifically, the kit or the device of the present invention can comprise at least one or more polynucleotide(s) comprising (or consisting of) a nucleotide sequence represented by any of SEQ ID NOs: 1 to 135, 580 to 606 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 136 to 152, 607 to 611 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 153 to 187 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):

(1) a polynucleotide comprising 15 or more consecutive nucleotides in a nucleotide sequence derived from a nucleotide sequence represented by any of SEQ ID NOs: 1 to 135, 580 to 606 by the replacement of u with t, or a complementary sequence thereof;

(2) a polynucleotide comprising 15 or more consecutive nucleotides in a nucleotide sequence derived from a nucleotide sequence represented by any of SEQ ID NOs: 136 to 152, 607 to 611 by the replacement of u with t, or a complementary sequence thereof; and (3) a polynucleotide comprising 15 or more consecutive nucleotides in a nucleotide sequence derived from a nucleotide sequence represented by any of SEQ ID NOs: 153 to 187 by the replacement of u with t, or a complementary sequence thereof.

In a preferred embodiment, the polynucleotide is a polynucleotide consisting of a nucleotide sequence represented by any of SEQ ID NOs: 1 to 135, 580 to 606 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 136 to 152, 607 to 611 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 153 to 187 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range of, for example, 15 consecutive nucleotides to less than the total number of bases of the sequence, 17 consecutive nucleotides to less than the total number of bases of the sequence, or 19 consecutive nucleotides to less than the total number of bases of the sequence, in the nucleotide sequence of each polynucleotide.

Specific examples of the aforementioned polynucleotide combination constituting the kit or the device of the present invention can include combinations of 1, 2, 3, 4, 5, 6, 7, 8, 9, 10 or more of the polynucleotides consisting of nucleotide sequences represented by SEQ ID NOs as shown in Table 1 (SEQ ID NOs: 1 to 187 and 580 to 611 corresponding to the miRNA markers in the table). However, these are given merely for illustrative purposes, and various other possible combinations are included in the present invention.

The aforementioned combination constituting the kit or the device for discriminating a prostate cancer patient from a healthy subject according to the present invention is desirably, for example, a combination of two or more of the polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a prostate cancer patient from a healthy subject is preferably a combination comprising at least one or more of newly found polynucleotides consisting of the nucleotide sequences represented by SEQ ID NOs: 1 to 135, among the combinations constituted by two of the polynucleotides consisting of the nucleotide sequences represented by SEQ ID NOs: 1 to 187, and 580 to 611.

The combination of polynucleotides with cancer type specificity capable of discriminating a prostate cancer patient not only from a healthy subject but also from other cancer patients is preferably, for example, a combination of multiple polynucleotides comprising at least one polynucleotide selected from the group consisting of polynucleotides of SEQ ID NOs: 1, 3, 4, 5, 6, 7, 9, 10, 12, 14, 15, 16, 17, 18, 20, 24, 29, 35, 37, 42, 51, 55, 58, 61, 63, 64, 67, 70, 72, 79, 82, 89, 91, 97, 98, 101, 103, 104, 112, 113, 114, 116, 119, 126, 135, 136, 139, 140, 141, 145, 147, 154, 155, 156, 158, 169, 173, 175, 178, 182, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610 and 611 (hereinafter, this group is referred to as "cancer type-specific polynucleotide group 1"), with any of the polynucleotides of the other SEQ ID NOs.

The combination of polynucleotides with cancer type specificity capable of discriminating a prostate cancer patient not only from a healthy subject but also from other cancer patients is more preferably a combination of multiple polynucleotides selected from the cancer type-specific polynucleotide group 1.

The combination of polynucleotides with cancer type specificity capable of discriminating a prostate cancer patient not only from a healthy subject but also from other cancer patients is more preferably a combination comprising at least one or more polynucleotide(s) selected from the group consisting of polynucleotides of SEQ ID NOs: 1, 12, 16, 37, 42, 63, 119, 126, 139 173, 178, 599. 609, and 611 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the aforementioned polynucleotides with cancer type specificity used in the combination can be 1, 2, 3, 4, 5, 6, 7, 8, 9, 10 or more for the combination and is more preferably 4 or more for the combination. Usually, the combination of 4 of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of three polynucleotides selected from the cancer type-specific polynucleotide group 1 or complementary sequences thereof will be listed below.

(1) a combination of SEQ ID NOs: 1, 63, 139, and 600 (markers: hsa-miR-4443, hsa-miR-4707-3p, hsa-miR-760, and hsa-miR-6724-5p);

(2) a combination of SEQ ID NOs: 1, 12, 63, and 599 (markers: hsa-miR-4443, hsa-miR-4745-5p, hsa-miR-4707-3p, and hsa-miR-6717-5p);

(3) a combination of SEQ ID NOs: 1, 141, 173, and 599 (markers: hsa-miR-4443, hsa-miR-1203, hsa-miR-665, and hsa-miR-6717-5p);

(4) a combination of SEQ ID NOs: 1, 16, 139, and 178 (markers: hsa-miR-4443, hsa-miR-92a-2-5p, hsa-miR-760, and hsa-miR-614); and (5) a combination of SEQ ID NOs: 1, 63, 173, and 599 (markers: hsa-miR-4443, hsa-miR-4707-3p, hsa-miR-665, and hsa-miR-6717-5p).

Non-limiting examples of the combination of the polynucleotide consisting of the nucleotide sequence represented by SEQ ID NO: 12 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 42, 63, and 609 (markers: hsa-miR-4745-5p, hsa-miR-4525, hsa-miR-4707-3p, and hsa-miR-451a);

(2) a combination of SEQ ID NOs: 12, 16, 135, and 156 (markers: hsa-miR-4745-5p, hsa-miR-92a-2-5p, hsa-miR-6820-5p, and hsa-miR-125a-3p);

(3) a combination of SEQ ID NOs: 12, 16, 169, and 178 (markers: hsa-miR-4745-5p, hsa-miR-92a-2-5p, hsa-miR-4638-5p, and hsa-miR-614);

(4) a combination of SEQ ID NOs: 12, 16, 139, and 601 (markers: hsa-miR-4745-5p, hsa-miR-92a-2-5p, hsa-miR-760, and hsa-miR-6777-5p); and (5) a combination of SEQ ID NOs: 12, 16, 42, and 607 (markers: hsa-miR-4745-5p, hsa-miR-92a-2-5p, hsa-miR-4525, and hsa-miR-16-5p).

Non-limiting examples of the combination of the polynucleotide consisting of the nucleotide sequence represented by SEQ ID NO: 16 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 18, 139, and 178 (markers: hsa-miR-92a-2-5p, hsa-miR-4448, hsa-miR-760, and hsa-miR-614);

(2) a combination of SEQ ID NOs: 12, 16, 37, and 178 (markers: hsa-miR-4745-5p, hsa-miR-92a-2-5p, hsa-miR-3619-3p, and hsa-miR-614);

(3) a combination of SEQ ID NOs: 12, 16, 37, and 599 (markers: hsa-miR-4745-5p, hsa-miR-92a-2-5p, hsa-miR-3619-3p, and hsa-miR-6717-5p);

(4) a combination of SEQ ID NOs: 12, 16, 37, and 97 (markers: hsa-miR-4745-5p, hsa-miR-92a-2-5p, hsa-miR-3619-3p, and hsa-miR-6746-5p); and (5) a combination of SEQ ID NOs: 12, 14, 16, and 599 (markers: hsa-miR-4745-5p, hsa-miR-3663-3p, hsa-miR-92a-2-5p, and hsa-miR-6717-5p).

Non-limiting examples of the combination of the polynucleotide consisting of the nucleotide sequence represented by SEQ ID NO: 37 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 37, 63, 139, and 611 (markers: hsa-miR-3619-3p, hsa-miR-4707-3p, hsa-miR-760, and hsa-miR-671-5p);

(2) a combination of SEQ ID NOs: 37, 42, 63, and 178 (markers: hsa-miR-3619-3p, hsa-miR-4525, hsa-miR-4707-3p, and hsa-miR-614);

(3) a combination of SEQ ID NOs: 37, 42, 63, and 599 (markers: hsa-miR-3619-3p, hsa-miR-4525, hsa-miR-4707-3p, and hsa-miR-6717-5p);

(4) a combination of SEQ ID NOs: 37, 42, 63, and 139 (markers: hsa-miR-3619-3p, hsa-miR-4525, hsa-miR-4707-3p, and hsa-miR-760); and (5) a combination of SEQ ID NOs: 12, 16, 37, and 603 (markers: hsa-miR-4745-5p, hsa-miR-92a-2-5p, hsa-miR-3619-3p, and hsa-miR-6787-5p).

Non-limiting examples of the combination of the polynucleotide consisting of the nucleotide sequence represented by SEQ ID NO: 42 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 42, 63, 607, and 611 (markers: hsa-miR-4525, hsa-miR-4707-3p, hsa-miR-16-5p, and hsa-miR-671-5p);

(2) a combination of SEQ ID NOs: 42, 63, 609, and 611 (markers: hsa-miR-4525, hsa-miR-4707-3p, hsa-miR-451a, and hsa-miR-671-5p);

(3) a combination of SEQ ID NOs: 42, 63, 173, and 599 (markers: hsa-miR-4525, hsa-miR-4707-3p, hsa-miR-665, and hsa-miR-6717-5p);

(4) a combination of SEQ ID NOs: 12, 16, 42, and 609 (markers: hsa-miR-4745-5p, hsa-miR-92a-2-5p, hsa-miR-4525, and hsa-miR-451a); and (5) a combination of SEQ ID NOs: 42, 63, 91, and 609 (markers: hsa-miR-4525, hsa-miR-4707-3p, hsa-miR-6784-5p, and hsa-miR-451a).

Non-limiting examples of the combination of the polynucleotide consisting of the nucleotide sequence represented by SEQ ID NO: 63 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 10, 42, 63, and 599 (markers: hsa-miR-642b-3p, hsa-miR-4525, hsa-miR-4707-3p, and hsa-miR-6717-5p);

(2) a combination of SEQ ID NOs: 42, 63, 599, and 609 (markers: hsa-miR-4525, hsa-miR-4707-3p, hsa-miR-6717-5p, and hsa-miR-451a);

(3) a combination of SEQ ID NOs: 42, 63, 583, and 609 (markers: hsa-miR-4525, hsa-miR-4707-3p, hsa-miR-1202, and hsa-miR-451a);

(4) a combination of SEQ ID NOs: 37, 42, 63, and 611 (markers: hsa-miR-3619-3p, hsa-miR-4525, hsa-miR-4707-3p, and hsa-miR-671-5p); and (5) a combination of SEQ ID NOs: 12, 63, 70, and 599 (markers: hsa-miR-4745-5p, hsa-miR-4707-3p, hsa-miR-6756-5p, and hsa-miR-6717-5p).

Non-limiting examples of the combination of the polynucleotide consisting of the nucleotide sequence represented by SEQ ID NO: 119 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 16, 37, and 119 (markers: hsa-miR-4745-5p, hsa-miR-92a-2-5p, hsa-miR-3619-3p, and hsa-miR-4492);

(2) a combination of SEQ ID NOs: 37, 63, 119, and 584 (markers: hsa-miR-3619-3p, hsa-miR-4707-3p, hsa-miR-4492, and hsa-miR-3162-5p);

(3) a combination of SEQ ID NOs: 63, 119, 173, and 178 (markers: hsa-miR-4707-3p, hsa-miR-4492, hsa-miR-665, and hsa-miR-614);

(4) a combination of SEQ ID NOs: 63, 119, 158, and 173 (markers: hsa-miR-4707-3p, hsa-miR-4492, hsa-miR-1228-5p, and hsa-miR-665); and (5) a combination of SEQ ID NOs: 63, 119, 173, and 605 (markers: hsa-miR-4707-3p, hsa-miR-4492, hsa-miR-665, and hsa-miR-6845-5p).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 126, 597, and 599 (markers: hsa-miR-92a-2-5p, hsa-miR-3648, hsa-miR-5787, and hsa-miR-6717-5p);

(2) a combination of SEQ ID NOs: 16, 42, 126, and 599 (markers: hsa-miR-92a-2-5p, hsa-miR-4525, hsa-miR-3648, and hsa-miR-6717-5p);

(3) a combination of SEQ ID NOs: 16, 126, 139, and 601 (markers: hsa-miR-92a-2-5p, hsa-miR-3648, hsa-miR-760, and hsa-miR-6777-5p);

(4) a combination of SEQ ID NOs: 16, 126, 593, and 599 (markers: hsa-miR-92a-2-5p, hsa-miR-3648, hsa-miR-4725-3p, and hsa-miR-6717-5p); and (5) a combination of SEQ ID NOs: 15, 16, 126, and 599 (markers: hsa-miR-3131, hsa-miR-92a-2-5p, hsa-miR-3648, and hsa-miR-6717-5p).

Non-limiting examples of the combination of the polynucleotide consisting of the nucleotide sequence represented by SEQ ID NO: 139 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 37, 63, 139, and 584 (markers: hsa-miR-3619-3p, hsa-miR-4707-3p, hsa-miR-760, and hsa-miR-3162-5p);

(2) a combination of SEQ ID NOs: 63, 139, 173, and 178 (markers: hsa-miR-4707-3p, hsa-miR-760, hsa-miR-665, and hsa-miR-614);

(3) a combination of SEQ ID NOs: 16, 63, 139, and 601 (markers: hsa-miR-92a-2-5p, hsa-miR-4707-3p, hsa-miR-760, and hsa-miR-6777-5p);

(4) a combination of SEQ ID NOs: 37, 63, 139, and 600 (markers: hsa-miR-3619-3p, hsa-miR-4707-3p, hsa-miR-760, and hsa-miR-6724-5p); and (5) a combination of SEQ ID NOs: 16, 139, 178, and 586 (markers: hsa-miR-92a-2-5p, hsa-miR-760, hsa-miR-614, and hsa-miR-3622a-5p).

Non-limiting examples of the combination of the polynucleotide consisting of the nucleotide sequence represented by SEQ ID NO: 173 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 63, 139, 173, and 599 (markers: hsa-miR-4707-3p, hsa-miR-760, hsa-miR-665, and hsa-miR-6717-5p);

(2) a combination of SEQ ID NOs: 63, 119, 173, and 581 (markers: hsa-miR-4707-3p, hsa-miR-4492, hsa-miR-665, and hsa-miR-642a-3p);

(3) a combination of SEQ ID NOs: 63, 173, 582, and 599 (markers: hsa-miR-4707-3p, hsa-miR-665, hsa-miR-762, and hsa-miR-6717-5p);

(4) a combination of SEQ ID NOs: 63, 136, 173, and 599 (markers: hsa-miR-4707-3p, hsa-miR-615-5p, hsa-miR-665, and hsa-miR-6717-5p); and (5) a combination of SEQ ID NOs: 29, 63, 173, and 178 (markers: hsa-miR-6726-5p, hsa-miR-4707-3p, hsa-miR-665, and hsa-miR-614).

Non-limiting examples of the combination of the polynucleotide consisting of the nucleotide sequence represented by SEQ ID NO: 178 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 16, 139, 178, and 601 (markers: hsa-miR-92a-2-5p, hsa-miR-760, hsa-miR-614, and hsa-miR-6777-5p);

(2) a combination of SEQ ID NOs: 16, 37, 139, and 178 (markers: hsa-miR-92a-2-5p, hsa-miR-3619-3p, hsa-miR-760, and hsa-miR-614);

(3) a combination of SEQ ID NOs: 1, 12, 16, and 178 (markers: hsa-miR-4443, hsa-miR-4745-5p, hsa-miR-92a-2-5p, and hsa-miR-614);

(4) a combination of SEQ ID NOs: 1, 63, 173, and 178 (markers: hsa-miR-4443, hsa-miR-4707-3p, hsa-miR-665, and hsa-miR-614); and (5) a combination of SEQ ID NOs: 16, 139, 178, and 597 (markers: hsa-miR-92a-2-5p, hsa-miR-760, hsa-miR-614, and hsa-miR-5787).

Non-limiting examples of the combination of the polynucleotide consisting of the nucleotide sequence represented by SEQ ID NO: 599 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 37, 63, and 599 (markers: hsa-miR-4745-5p, hsa-miR-3619-3p, hsa-miR-4707-3p, and hsa-miR-6717-5p);

(2) a combination of SEQ ID NOs: 42, 58, 63, and 599 (markers: hsa-miR-4525, hsa-miR-4530, hsa-miR-4707-3p, and hsa-miR-6717-5p);

(3) a combination of SEQ ID NOs: 1, 12, 16, and 599 (markers: hsa-miR-4443, hsa-miR-4745-5p, hsa-miR-92a-2-5p, and hsa-miR-6717-5p);

(4) a combination of SEQ ID NOs: 63, 119, 173, and 599 (markers: hsa-miR-4707-3p, hsa-miR-4492, hsa-miR-665, and hsa-miR-6717-5p); and (5) a combination of SEQ ID NOs: 16, 18, 139, and 599 (markers: hsa-miR-92a-2-5p, hsa-miR-4448, hsa-miR-760, and hsa-miR-6717-5p).

Non-limiting examples of the combination of the polynucleotide consisting of the nucleotide sequence represented by SEQ ID NO: 609 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 42, 63, 585, and 609 (markers: hsa-miR-4525, hsa-miR-4707-3p, hsa-miR-3196, and hsa-miR-451a);

(2) a combination of SEQ ID NOs: 42, 63, 592, and 609 (markers: hsa-miR-4525, hsa-miR-4707-3p, hsa-miR-4723-5p, and hsa-miR-451a);

(3) a combination of SEQ ID NOs: 18, 42, 581, and 609 (markers: hsa-miR-4448, hsa-miR-4525, hsa-miR-642a-3p, and hsa-miR-451a);

(4) a combination of SEQ ID NOs: 12, 16, 599, and 609 (markers: hsa-miR-4745-5p, hsa-miR-92a-2-5p, hsa-miR-6717-5p, and hsa-miR-451a); and (5) a combination of SEQ ID NOs: 16, 126, 599, and 609 (markers: hsa-miR-92a-2-5p, hsa-miR-3648, hsa-miR-6717-5p, and hsa-miR-451a).

Non-limiting examples of the combination of the polynucleotide consisting of the nucleotide sequence represented by SEQ ID NO: 611 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 12, 16, 37, and 611 (markers: hsa-miR-4745-5p, hsa-miR-92a-2-5p, hsa-miR-3619-3p, and hsa-miR-671-5p);

(2) a combination of SEQ ID NOs: 1, 63, 139, and 611 (markers: hsa-miR-4443, hsa-miR-4707-3p, hsa-miR-760, and hsa-miR-671-5p);

(3) a combination of SEQ ID NOs: 63, 158, 173, and 611 (markers: hsa-miR-4707-3p, hsa-miR-1228-5p, hsa-miR-665, and hsa-miR-671-5p);

(4) a combination of SEQ ID NOs: 16, 37, 139, and 611 (markers: hsa-miR-92a-2-5p, hsa-miR-3619-3p, hsa-miR-760, and hsa-miR-671-5p); and (5) a combination of SEQ ID NOs: 16, 37, 595, and 611 (markers: hsa-miR-92a-2-5p, hsa-miR-3619-3p, hsa-miR-4739, and hsa-miR-671-5p).

The kit or the device of the present invention can also contain a polynucleotide that is already known or that will be found in future, to enable detection of prostate cancer, in addition to the polynucleotide(s) (which can include a variant, a fragment, and a derivative) according to the present invention described above.

The kit of the present invention can also contain an antibody for measuring a marker for prostate cancer examination known in the art, such as PSA, in addition to the polynucleotide(s) according to the present invention described above, and a variant thereof or a fragment thereof.

These polynucleotides and the variants thereof or the fragments thereof contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid(s) through the use of hybridization using this array.

The kit or the device of the present invention comprises nucleic acids capable of specifically binding to the polynucleotides of at least one or more, preferably at least two or more, more preferably at least three or more, most preferably at least five or more to all of the prostate cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the prostate cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the prostate cancer marker miRNAs, respectively, of the group 3 described above.

The kit or the device of the present invention can be used for detecting prostate cancer as described in the Section 4 below.

4. Method for Detecting Prostate Cancer

The present invention further provides a method for detecting prostate cancer, comprising using the kit or the device of the present invention (including the nucleic acid(s) that can be used in the present invention) described in the preceding Section 3 to measure an expression level(s) of one or more prostate cancer-derived gene(s) represented by an expression level(s) of prostate cancer-derived gene(s) selected from the following group: miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR- 4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p, optionally an expression level of prostate cancer-derived gene(s) selected from the following group: miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p, and optionally an expression level of prostate cancer-derived gene(s) selected from the following group: miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p in a sample in vitro, further comparing, for example, the expression level(s) of the gene(s) in the sample (e.g., blood, serum, or plasma) collected from a subject suspected of having prostate cancer with a control expression level in the sample collected from a healthy subject (including a non-prostate cancer patient), and evaluating the subject as having prostate cancer when the expression level of the target nucleic acid is statistically significantly different between the samples.

This method of the present invention permits limitedly invasive early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the prostate cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol® (Life Technologies Corp.) may be used. The prostate cancer-derived genes may be prepared by the addition of a reagent for RNA extraction containing acidic phenol, such as Trizol (Life Technologies Corp.) or Isogen (Nippon Gene Co., Ltd). Alternatively, a kit such as miRNeasy® Mini Kit (Qiagen N.V.) can be used, though the method is not limited thereto.

The present invention also provides use of the kit or the device of the present invention for detecting in vitro an expression product of a prostate cancer-derived miRNA gene(s) in a sample derived from a subject.

In the method of the present invention, a kit or a device comprising, each alone or in every possible composition, the polynucleotides that can be used in the present invention as described above is used as the kit or the device.

In the detection or (genetic) diagnosis of prostate cancer according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine of the subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of prostate cancer or the detection of the presence or absence of prostate cancer. Specifically, the detection of prostate cancer using the kit or the device can be performed by detecting in vitro an expression level(s) of a gene(s) using the nucleic acid probe(s) or the primer(s) contained in the kit or the device in a sample such as blood, serum, plasma, or urine from a subject suspected of having prostate cancer. The subject suspected of having prostate cancer can be evaluated as having prostate cancer when the expression level(s) of a target miRNA marker(s) measured using polynucleotide(s) (including any variant, any fragment, and any derivative thereof) consisting of a nucleotide sequence(s) represented by at least one or more of SEQ ID NOs: 1 to 135, 580 to 606, or a complementary sequence(s) thereof, optionally a nucleotide sequence(s) represented by one or more of SEQ ID NOs: 136 to 152, 607 to 611 or a complementary sequence(s) thereof, and optionally a nucleotide sequence(s) represented by one or more of SEQ ID NOs: 153 to 187 or a complementary sequence(s) thereof in the sample such as blood, serum, plasma, or urine of the subject is statistically significantly different from the expression level(s) thereof in the sample such as blood, serum, or plasma, or urine of a healthy subject.

The method of the present invention can be combined with rectal examination, transrectal ultrasonography of the prostate, or a diagnostic imaging method such as CT scan, MRI scan, or bone scintigraphy. The method of the present invention is capable of specifically detecting prostate cancer and can substantially discriminate prostate cancer from the other cancers.

The method for detecting the absence of an expression product of a prostate cancer-derived gene(s) or the presence of the expression product of a prostate cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotide(s) (including a variant, a fragment, and a derivative) selected from the polynucleotide group of the present invention, to evaluate the presence or absence of prostate cancer or to detect prostate cancer. The method for detecting prostate cancer according to the present invention can also evaluate or diagnose, for example, the presence or absence of amelioration of the disease or the degree of amelioration thereof in a prostate cancer patient given a therapeutic drug for the amelioration of the disease.

The method of the present invention can comprise, for example, the following steps (a), (b), and (c):

(a) contacting a sample derived from a subject with a polynucleotide(s) in the kit or the device of the present invention in vitro;

(b) measuring an expression level(s) of the target nucleic acid(s) in the sample using the polynucleotide(s) as a nucleic acid probe(s) or a primer(s); and (c) evaluating the presence or absence of prostate cancer (cells) in the subject on the basis of the step (b).

Specifically, the present invention provides a method for detecting prostate cancer, comprising measuring an expression level(s) of a target nucleic acid(s) in a sample of a subject using a nucleic acid(s) capable of specifically binding to at least one or more (preferably at least two or more) polynucleotide(s) selected from miR-4443, miR-1908-5p, miR-4257, miR-3197, miR-3188, miR-4649-5p, miR-1343-3p, miR-6861-5p, miR-1343-5p, miR-642b-3p, miR-6741-5p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-3928-3p, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p and miR-6893-5p and evaluating in vitro the presence or absence of prostate cancer in the subject using the measured expression level(s) and a control expression level(s) of a healthy subject measured in the same way as above.

In the present specification, the term "evaluation" is evaluation support based on results of in vitro examination, not physician's judgment.

As described above, in the method of the present invention, specifically, miR-4443 is hsa-miR-4443, miR-1908-5p is hsa-miR-1908-5p, miR-4257 is hsa-miR-4257, miR-3197 is hsa-miR-3197, miR-3188 is hsa-miR-3188, miR-4649-5p is hsa-miR-4649-5p, miR-1343-3p is hsa-miR-1343-3p, miR-6861-5p is hsa-miR-6861-5p, miR-1343-5p is hsa-miR-1343-5p, miR-642b-3p is hsa-miR-642b-3p, miR-6741-5p is hsa-miR-6741-5p, miR-4745-5p is hsa-miR-4745-5p, miR-6826-5p is hsa-miR-6826-5p, miR-3663-3p is hsa-miR-3663-3p, miR-3131 is hsa-miR-3131, miR-92a-2-5p is hsa-miR-92a-2-5p, miR-4258 is hsa-miR-4258, miR-4448 is hsa-miR-4448, miR-6125 is hsa-miR-6125, miR-6880-5p is hsa-miR-6880-5p, miR-6132 is hsa-miR-6132, miR-4467 is hsa-miR-4467, miR-6749-5p is hsa-miR-6749-5p, miR-2392 is hsa-miR-2392, miR-1273g-3p is hsa-miR-1273g-3p, miR-4746-3p is hsa-miR-4746-3p, miR-1914-3p is hsa-miR-1914-3p, miR-7845-5p is hsa-miR-7845-5p, miR-6726-5p is hsa-miR-6726-5p, miR-128-2-5p is hsa-miR-128-2-5p, miR-4651 is hsa-miR-4651, miR-6765-3p is hsa-miR-6765-3p, miR-3185 is hsa-miR-3185, miR-4792 is hsa-miR-4792, miR-6887-5p is hsa-miR-6887-5p, miR-5572 is hsa-miR-5572, miR-3619-3p is hsa-miR-3619-3p, miR-6780b-5p is hsa-miR-6780b-5p, miR-4707-5p is hsa-miR-4707-5p, miR-8063 is hsa-miR-8063, miR-4454 is hsa-miR-4454, miR-4525 is hsa-miR-4525, miR-7975 is hsa-miR-7975, miR-744-5p is hsa-miR-744-5p, miR-3135b is hsa-miR-3135b, miR-4648 is hsa-miR-4648, miR-6816-5p is hsa-miR-6816-5p, miR-4741 is hsa-miR-4741, miR-7150 is hsa-miR-7150, miR-6791-5p is hsa-miR-6791-5p, miR-1247-3p is hsa-miR-1247-3p, miR-7977 is hsa-miR-7977, miR-4497 is hsa-miR-4497, miR-6090 is hsa-miR-6090, miR-6781-5p is hsa-miR-6781-5p, miR-6870-5p is hsa-miR-6870-5p, miR-6729-5p is hsa-miR-6729-5p, miR-4530 is hsa-miR-4530, miR-7847-3p is hsa-miR-7847-3p, miR-6825-5p is hsa-miR-6825-5p, miR-4674 is hsa-miR-4674, miR-3917 is hsa-miR-3917, miR-4707-3p is hsa-miR-4707-3p, miR-6885-5p is hsa-miR-6885-5p, miR-6722-3p is hsa-miR-6722-3p, miR-4516 is hsa-miR-4516, miR-6757-5p is hsa-miR-6757-5p, miR-6840-3p is hsa-miR-6840-3p, miR-5195-3p is hsa-miR-5195-3p, miR-6756-5p is hsa-miR-6756-5p, miR-6800-5p is hsa-miR-6800-5p, miR-6727-5p is hsa-miR-6727-5p, miR-6126 is hsa-miR-6126, miR-6872-3p is hsa-miR-6872-3p, miR-4446-3p is hsa-miR-4446-3p, miR-1268a is hsa-miR-1268a, miR-1908-3p is hsa-miR-1908-3p, miR-3679-5p is hsa-miR-3679-5p, miR-4534 is hsa-miR-4534, miR-4675 is hsa-miR-4675, miR-7108-5p is hsa-miR-7108-5p, miR-6799-5p is hsa-miR-6799-5p, miR-4695-5p is hsa-miR-4695-5p, miR-3178 is hsa-miR-3178, miR-5090 is hsa-miR-5090, miR-3180 is hsa-miR-3180, miR-1237-5p is hsa-miR-1237-5p, miR-4758-5p is hsa-miR-4758-5p, miR-3184-5p is hsa-miR-3184-5p, miR-4286 is hsa-miR-4286, miR-6784-5p is hsa-miR-6784-5p, miR-6768-5p is hsa-miR-6768-5p, miR-6785-5p is hsa-miR-6785-5p, miR-4706 is hsa-miR-4706, miR-711 is hsa-miR-711, miR-1260a is hsa-miR-1260a, miR-6746-5p is hsa-miR-6746-5p, miR-6089 is hsa-miR-6089, miR-6821-5p is hsa-miR-6821-5p, miR-4667-5p is hsa-miR-4667-5p, miR-8069 is hsa-miR-8069, miR-4726-5p is hsa-miR-4726-5p, miR-6124 is hsa-miR-6124, miR-4532 is hsa-miR-4532, miR-4486 is hsa-miR-4486, miR-4728-5p is hsa-miR-4728-5p, miR-4508 is hsa-miR-4508, miR-128-1-5p is hsa-miR-128-1-5p, miR-4513 is hsa-miR-4513, miR-6795-5p is hsa-miR-6795-5p, miR-4689 is hsa-miR-4689, miR-6763-5p is hsa-miR-6763-5p, miR-8072 is hsa-miR-8072, miR-6765-5p is hsa-miR-6765-5p, miR-4419b is hsa-miR-4419b, miR-7641 is hsa-miR-7641, miR-3928-3p is hsa-miR-3928-3p, miR-1227-5p is hsa-miR-1227-5p, miR-4492 is hsa-miR-4492, miR-296-3p is hsa-miR-296-3p, miR-6769a-5p is hsa-miR-6769a-5p, miR-6889-5p is hsa-miR-6889-5p, miR-4632-5p is hsa-miR-4632-5p, miR-4505 is hsa-miR-4505, miR-3154 is hsa-miR-3154, miR-3648 is hsa-miR-3648, miR-4442 is hsa-miR-4442, miR-3141 is hsa-miR-3141, miR-7113-3p is hsa-miR-7113-3p, miR-6819-5p is hsa-miR-6819-5p, miR-3195 is hsa-miR-3195, miR-1199-5p is hsa-miR-1199-5p, miR-6738-5p is hsa-miR-6738-5p, miR-4656 is hsa-miR-4656, miR-6820-5p is hsa-miR-6820-5p, miR-204-3p is hsa-miR-204-3p, miR-642a-3p is hsa-miR-642a-3p, miR-762 is hsa-miR-762, miR-1202 is hsa-miR-1202, miR-3162-5p is hsa-miR-3162-5p, miR-3196 is hsa-miR-3196, miR-3622a-5p is hsa-miR-3622a-5p, miR-3665 is hsa-miR-3665, miR-3940-5p is hsa-miR-3940-5p, miR-4294 is hsa-miR-4294, miR-4466 is hsa-miR-4466, miR-4476 is hsa-miR-4476, miR-4723-5p is hsa-miR-4723-5p, miR-4725-3p is hsa-miR-4725-3p, miR-4730 is hsa-miR-4730, miR-4739 is hsa-miR-4739, miR-4787-5p is hsa-miR-4787-5p, miR-5787 is hsa-miR-5787, miR-6085 is hsa-miR-6085, miR-6717-5p is hsa-miR-6717-5p, miR-6724-5p is hsa-miR-6724-5p, miR-6777-5p is hsa-miR-6777-5p, miR-6778-5p is hsa-miR-6778-5p, miR-6787-5p is hsa-miR-6787-5p, miR-6789-5p is hsa-miR-6789-5p, miR-6845-5p is hsa-miR-6845-5p, and miR-6893-5p is hsa-miR-6893-5p.

In the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 135 and 580 to 606, (c) a polynucleotide consisting of a nucleotide sequence complementary to a nucleotide sequence represented by any of SEQ ID NOs: 1 to 135 and 580 to 606 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 135 and 580 to 606 or a nucleotide sequence derived from the nucleotide sequence by the replacement of u with t, and (e) a polynucleotide hybridizing under stringent conditions to any of the polynucleotides (a) to (d).

The method of the present invention can further use a nucleic acid capable of specifically binding to at least one or more polynucleotide(s) selected from miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564 and miR-671-5p.

Specifically, miR-615-5p is hsa-miR-615-5p, miR-486-3p is hsa-miR-486-3p, miR-1225-3p is hsa-miR-1225-3p, miR-760 is hsa-miR-760, miR-187-5p is hsa-miR-187-5p, miR-1203 is hsa-miR-1203, miR-7110-5p is hsa-miR-7110-5p, miR-371a-5p is hsa-miR-371a-5p, miR-939-5p is hsa-miR-939-5p, miR-575 is hsa-miR-575, miR-92b-5p is hsa-miR-92b-5p, miR-887-3p is hsa-miR-887-3p, miR-920 is hsa-miR-920, miR-1915-5p is hsa-miR-1915-5p, miR-1231 is hsa-miR-1231, miR-663b is hsa-miR-663b, miR-1225-5p is hsa-miR-1225-5p, miR-16-5p is hsa-miR-16-5p, miR-423-5p is hsa-miR-423-5p, miR-451a is hsa-miR-451a, miR-564 is hsa-miR-564, and miR-671-5p is hsa-miR-671-5p.

Specifically, the nucleic acid(s) is further selected from the group consisting of the following polynucleotides (f) to (j):

(f) a polynucleotide consisting of a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 136 to 152 and 607 to 611, (h) a polynucleotide consisting of a nucleotide sequence complementary to a nucleotide sequence represented by any of SEQ ID NOs: 136 to 152 and 607 to 611 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 136 to 152 and 607 to 611 or a nucleotide sequence derived from the nucleotide sequence by the replacement of u with t, and (j) a polynucleotide hybridizing under stringent conditions to any of the polynucleotides (f) to (i).

The method of the present invention can further use a nucleic acid(s) capable of specifically binding to at least one or more polynucleotide(s) selected from miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

Specifically, miR-4763-3p is hsa-miR-4763-3p, miR-3656 is hsa-miR-3656, miR-4488 is hsa-miR-4488, miR-125a-3p is hsa-miR-125a-3p, miR-1469 is hsa-miR-1469, miR-1228-5p is hsa-miR-1228-5p, miR-6798-5p is hsa-miR-6798-5p, miR-1268b is hsa-miR-1268b, miR-6732-5p is hsa-miR-6732-5p, miR-1915-3p is hsa-miR-1915-3p, miR-4433b-3p is hsa-miR-4433b-3p, miR-1207-5p is hsa-miR-1207-5p, miR-4433-3p is hsa-miR-4433-3p, miR-6879-5p is hsa-miR-6879-5p, miR-4417 is hsa-miR-4417, miR-30c-1-3p is hsa-miR-30c-1-3p, miR-4638-5p is hsa-miR-4638-5p, miR-6088 is hsa-miR-6088, miR-4270 is hsa-miR-4270, miR-6782-5p is hsa-miR-6782-5p, miR-665 is hsa-miR-665, miR-486-5p is hsa-miR-486-5p, miR-4655-5p is hsa-miR-4655-5p, miR-1275 is hsa-miR-1275, miR-6806-5p is hsa-miR-6806-5p, miR-614 is hsa-miR-614, miR-3937 is hsa-miR-3937, miR-6752-5p is hsa-miR-6752-5p, miR-6771-5p is hsa-miR-6771-5p, miR-4450 is hsa-miR-4450, miR-211-3p is hsa-miR-211-3p, miR-663a is hsa-miR-663a, miR-6842-5p is hsa-miR-6842-5p, miR-7114-5p is hsa-miR-7114-5p, and miR-6779-5p is hsa-miR-6779-5p.

Specifically, the nucleic acid further used is a polynucleotide selected from the group consisting of the following polynucleotides (k) to (o):

(k) a polynucleotide consisting of a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 153 to 187, (m) a polynucleotide consisting of a nucleotide sequence complementary to a nucleotide sequence represented by any of SEQ ID NOs: 153 to 187 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 153 to 187 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a prostate tissue) or a body fluid such as blood, serum, plasma, or urine of the subject. The sample includes, specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

In the present specification, the subject refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of prostate cancer (cells) can comprise, for example, the following steps (a), (b), and (c):

(a) binding RNA prepared from the sample of the subject or a complementary polynucleotide (cDNA) transcribed therefrom to a polynucleotide in the kit or the device of the present invention;

(b) measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) evaluating the presence or absence of prostate cancer (or prostate cancer-derived gene expression) on the basis of the measurement results of the step (b).

For example, various hybridization methods can be used for detecting, examining, evaluating, or diagnosing prostate cancer (or prostate cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}P$, $^{33}P$, $^{35}S$, etc.), a fluorescent material, or the like, hybridizing the labeled product with the living tissue-derived RNA of the subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves preparing cDNA from the living tissue-derived RNA of the subject according to a routine method, hybridizing a pair of primers (consisting of a plus strand and a reverse strand binding to the cDNA) prepared from the polynucleotide for detection of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. Array in which a gene group immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes all of these arrays. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probe using an image detector (examples thereof can include Typhoon 9410 (GE Healthcare Japan Corp.) and 3D-Gene® scanner (Toray Industries, Inc.)).

The "stringent conditions" used in the present specification are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent conditions of washing. The hybridization conditions involves, for example, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the washing conditions, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include a treatment for approximately 15 seconds to 1 minute at 5 to 10° C. plus a Tm value calculated from the sequence of the primer, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.), LNA®-based MicroRNA PCR (Exiqon), or Ncode® miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50%, more preferably 80% or more of the number of measured samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a prostate cancer patient and a sample derived from a healthy subject as supervising samples, and determining or evaluating the presence and/or absence of the prostate cancer-derived gene in the sample.

Specifically, the present invention further provides the method comprising: a first step of measuring in vitro an expression level of a target gene in multiple samples known to be able to determine or evaluate the presence and/or absence of the prostate cancer-derived gene in the samples, using the polynucleotide, the kit, or the device (e.g., chip) for detection of the present invention, or a combination thereof; a second step of preparing a discriminant with the measurement values of the expression level of the target gene (target nucleic acid) obtained in the first step as supervising samples; a third step of measuring in vitro an expression level of the target gene in a sample derived from a subject in the same way as in the first step; and a fourth step of substituting the measurement value of the expression level of the target gene obtained in the third step into the discriminant obtained in the second step, and determining or evaluating the presence and/or absence of the prostate cancer-derived gene in the sample on the basis of the results obtained from the discriminant, wherein the target gene can be detected using the polynucleotide or using a polynucleotide for detection, a variant thereof, or a fragment thereof contained in the kit or the device (e.g., chip). In this context, the discriminant can be prepared by use of Fisher's linear discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this context, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's linear discriminant analysis, one type of linear discriminant analysis, is a dimension reduction method for selecting a dimension suitable for classification, and constructs a synthetic variable with high discriminant performance by focusing on the variance of the synthetic variables and minimizing the variance of data having the same label (Venables, W. N. et al., Modern Applied Statistics with S. Fourth edition. Springer, 2002). In the Fisher's linear discriminant analysis, direction w of projection is determined so as to maximize Formula 2. In this context, μ represents an average input, ng represents the number of data associated to class g, and μg represents an average input of the data associated to class g. The numerator and the denominator are intra-class variance and inter-class variance, respectively, when each data is projected in the direction of the vector w. Discriminant coefficient wi is determined by maximizing this ratio (Takafumi Kanamori et al., "Pattern Recognition", Kyoritsu Shuppan Co., Ltd., (2009); and Richard O. et al., Pattern Classification Second Edition, Wiley-Interscience, 2000).

Formula 2

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)}$$

$$\text{subject to } \mu = \sum_{i=1}^{n} \frac{x_i}{n}, \quad \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining, an associated cluster which has a closer Mahalanobis' distance from each cluster. In this context, μ represents a central vector of each cluster, and S-1 represents an inverse matrix of the variance-covariance matrix of the cluster. The central vector is calculated from explanatory variable x, and an average vector, a median value vector, or the like can be used.

Formula 3

$$D(x, \mu) = \{(x-\mu)^t S^{-1} (x-\mu)\}^{\frac{1}{2}}$$

SVM is a discriminant analysis method devised by V. Vapnik (The Nature of Statistical Leaning Theory, Springer, 1995). Particular data points of a data set that has known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the results of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (radial basis function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of a C-SVC discriminant that can be used in the method of the present invention will be given below. First, all subjects are divided into two groups, i.e., a prostate cancer patient group and a healthy subject group. For example, prostate tissue examination can be used for a reference under which each subject is confirmed as a prostate cancer patient or a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables, and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

Formula 4

$$\min_a \frac{1}{2} a^T Q a - e^T a$$

$$\text{subject to } y^T a = 0,\ 0 \le a_i \le C,\ i = 1, \ldots, l,$$

Formula 5 is a finally obtained discriminant, and an associated group can be determined on the basis of the sign of a value obtained according to the discriminant. In this context, x represents a support vector, y represents a label indicating the association with a group, a represents the corresponding coefficient, b represents a constant term, and K represents a kernel function.

Formula 5

$$f(x) = \operatorname{sgn}\left(\sum_{i=1}^{l} y_i a_i K(x_i, x) + b\right)$$

For example, a RBF kernel defined by Formula 6 can be used as the kernel function. In this context, x represents a support vector, and y represents a kernel parameter for adjusting the complexity of the hyperplane.

Formula 6

$$K(x_i, x_j) = \exp(-r\|x_i - x_j\|^2),\ r < 0$$

In addition, an approach such as neural network, k-nearest neighbor algorithms, decision trees, or logistic regression analysis can be selected as a method for determining or evaluating the presence and/or absence of expression of a prostate cancer-derived target gene in a sample derived from a subject, or for evaluating the expression level thereof by comparison with a control derived from a healthy subject.

The method of the present invention can comprise, for example, the following steps (a), (b), and (c):

(a) measuring an expression level of a target gene in tissues containing prostate cancer-derived genes derived from prostate cancer patients and/or samples already known to be tissues containing no prostate cancer-derived gene derived from healthy subjects, using the polynucleotide, the kit, or the device (e.g., DNA chip) for detection according to the present invention;

(b) preparing the discriminants of Formulae 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, substituting the obtained measurement value into the discriminants prepared in the step (b), and determining or evaluating the presence and/or absence of the prostate cancer-derived target gene in the sample, or evaluating the expression level thereof by comparison with a healthy subject-derived control, on the basis of the obtained results.

In this context, in the discriminants of Formulae 1 to 3, 5, and 6, x represents an explanatory variable and includes a value obtained by measuring a polynucleotide selected from the polynucleotides described above in the Section 2, or any fragment thereof. Specifically, the explanatory variable for discriminating a prostate cancer patient from a healthy subject according to the present invention is a gene expression level selected from, for example, the following expression levels (1) to (3):

(1) a gene expression level in the serum of a prostate cancer patient or a healthy subject measured by any DNA comprising 15 or more consecutive nucleotides in a nucleotide sequence represented by any of SEQ ID NOs: 1 to 135, 580 to 606 or a complementary sequence thereof, (2) a gene expression level in the serum of a prostate cancer patient or a healthy subject measured by any DNA comprising 15 or more consecutive nucleotides in a nucleotide sequence represented by any of SEQ ID NOs: 136 to 152, 607 to 611 or a complementary sequence thereof, and (3) a gene expression level in the serum of a prostate cancer patient or a healthy subject measured by any DNA comprising 15 or more consecutive nucleotides in a nucleotide sequence represented by any of SEQ ID NOs: 153 to 187 or a complementary sequence thereof.

As described above, for the method for determining or evaluating the presence and/or absence of a prostate cancer-derived gene in a sample derived from a subject, a discriminant prepared from a training cohort is required. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a prostate cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of an analytical test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by an analytical test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a prostate cancer patient group and gene expression levels of a healthy subject group may be calculated to select a gene that is used for an explanatory variable for a discriminant. Alternatively, ROC curves based on the gene expression levels of a prostate cancer patient group and a healthy subject group may be used, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of a P value, and a method of constructing a discriminant by repetitively evaluating the genes for use while adding the genes one by one in a descending order of the gene expression difference (Furey T S. et al., 2000, Bioinformatics, Vol. 16, p. 906-14). A gene expression level of another independent prostate cancer patient or healthy subject is substituted as an explanatory variable into this discriminant to calculate a result of the discriminant analysis that indicates the group to which this independent prostate cancer patient or healthy subject associated. Specifically, the found gene set for diagnosis and the discriminant constructed using the gene set for diagnosis can be evaluated in an independent sample group to find a more universal gene set for diagnosis capable of detecting prostate cancer and a more universal method for discriminating prostate cancer.

Split-sample method is preferably used for evaluating the discriminant performance (generality) of the discriminant. Specifically, a data set is divided into a training cohort and a validation cohort, and gene selection by a statistical test and construction of a discriminant are performed in the training cohort. Accuracy, sensitivity, and specificity are calculated using results of discriminant analysis in a validation cohort according to the discriminant and a true group to which the validation cohort associated, to evaluate the discriminant performance. On the other hand, instead of dividing a data set, gene selection by a statistical test and construction of a discriminant may be performed using all of samples, and accuracy, sensitivity, and specificity can be calculated by the discriminant of newly prepared samples according to the discriminant to evaluate the discriminant performance.

The present invention provides a polynucleotide for detection or for disease diagnosis useful in the diagnosis and treatment of prostate cancer, a method for detecting prostate cancer using the polynucleotide, and a kit and a device for the detection of prostate cancer, comprising the polynucleotide. Particularly, in order to select a gene for diagnosis and prepare a discriminant so as to exhibit accuracy beyond a prostate cancer diagnosis method using existing tumor markers PSA, a gene set for diagnosis and a discriminant for the method of the present invention can be constructed, which exhibit accuracy beyond PSA, for example, by comparing genes expressed in serum derived from a patient who is confirmed to be negative using PSA but finally found to have prostate cancer by detailed examination such as computed tomography using a contrast medium, with genes expressed in serum derived from a patient who has no prostate cancer.

For example, the gene set for diagnosis is set to any combination selected from one or two or more of the polynucleotides based on a nucleotide sequence represented by any of SEQ ID NOs: 1 to 135, 580 to 606, or a complementary sequence thereof as described above, optionally one or two or more of the polynucleotides based on a nucleotide sequence represented by any of SEQ ID NOs: 136 to 152, 607 to 611, or a complementary sequence thereof, and optionally one or two or more of the polynucleotides based on a nucleotide sequence represented by any of SEQ ID NOs: 153 to 187, or a complementary sequence thereof. Further, a discriminant is constructed using expression levels of the gene set for diagnosis in samples derived from class I prostate cancer patients and samples derived from class II healthy subjects as a result of tissue diagnosis. As a result, the presence or absence of prostate cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Prostate Cancer Patient and Healthy Subject>

Serum was collected after obtainment of informed consent, using VENOJECT II vacuum blood collecting tube VP-AS109K60 (Terumo Corp.) from each of 94 healthy male subjects, and 35 prostate cancer patients (30 cases with stage II, 1 case with stage III, and 4 cases with stage IV) (Table 2-1) who were confirmed to have no cancer in organs other than the prostate, and used as a training cohort. Likewise, serum was collected after obtainment of informed consent, using VENOJECT II vacuum blood collecting tube VP-AS109K60 (Terumo Corp.) from each of 47 healthy male subjects, and 17 prostate cancer patients (15 cases with stage II and 2 cases with stage III) (Table 2-2) who were confirmed to have no cancer in organs other than the prostate, and used as a validation cohort.

<Extraction of Total RNA>

Total RNA was obtained from 300 μL of the serum sample obtained from each of 193 persons in total of 141 healthy male subjects and 52 prostate cancer patients in the training cohort and the validation cohort, using a reagent for RNA extraction in 3D-Gene® RNA extraction reagent from liquid sample kit (Toray Industries, Inc.) according to the protocol provided by the manufacturer.

<Measurement of Gene Expression Level> miRNAs in the total RNA obtained from the serum sample of each of 193 persons in total of 141 healthy male subjects and 52 prostate cancer patients in the aforementioned training cohort and the validation cohort were fluorescently labeled using 3D-Gene® miRNA Labeling kit (Toray Industries, Inc.) according to the protocol (ver 2.20) provided by the manufacturer. The oligo DNA chip used was 3D-Gene® Human miRNA Oligo chip (Toray Industries, Inc.) with mounted probes having sequences complementary to 2,555 miRNAs among the miRNAs registered in miRBase Release 20. Hybridization of the miRNAs in the total RNA with the probes on the DNA chip under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 52 prostate cancer patients and the 141 healthy male subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Sample from Patients with Cancer Other than Prostate Cancer>

Serum was collected using VENOJECT II vacuum blood collecting tube VP-AS109K60 (Terumo Corp.) from each of 63 breast cancer patients who were confirmed to have no cancer in other organs after obtainment of informed consent, and used as a training cohort together with the samples of 35 prostate cancer patients and 99 healthy male subjects of Reference Example 1. Likewise, serum was collected using VENOJECT II vacuum blood collecting tube VP-AS109K60 (Terumo Corp.) from each of 30 breast cancer patients who were confirmed to have no cancer in other organs after obtainment of informed consent, and used as a validation cohort together with the samples of 17 prostate cancer patients who were confirmed to have no cancer in organs other than the prostate and 51 healthy male subjects of Reference Example 1. Subsequent operations were conducted in the same way as in Reference Example 1.

Example 1

<Selection of Gene Marker Using Samples in the Training Cohort, and Method for Evaluating Prostate Cancer Discriminant Performance with the Single Gene Marker Using Samples in the Validation Cohort>

In this Example, a gene marker for discriminating a prostate cancer patient from a healthy subject was selected from the training cohort and studied in samples of the validation cohort independent of the training cohort.

Specifically, first, the miRNA expression levels of the training cohort and the validation cohort obtained in the preceding Reference Examples 1 were combined and normalized by quantile normalization.

Next, genes for diagnosis were selected in the training cohort. Here, in order to acquire diagnostic markers with higher reliability, only genes that showed gene expression levels of $2^6$ or higher in 50% or more of the samples in either of the prostate cancer patient group in the training cohort or the healthy subject group in the training cohort were selected. In order to further acquire statistically significant genes for discriminating a prostate cancer patient group from a healthy subject group, the P value obtained by two-tailed t-test assuming equal variance as to each gene expression level was corrected by the Bonferroni method, and genes that satisfied $p<0.01$ were acquired as gene markers for use in explanatory variables of a discriminant. The obtained genes are described in Table 2.

In this way, hsa-miR-4443, hsa-miR-1908-5p, hsa-miR-4257, hsa-miR-3197, hsa-miR-3188, hsa-miR-4649-5p, hsa-miR-1343-3p, hsa-miR-6861-5p, hsa-miR-1343-5p, hsa-miR-642b-3p, hsa-miR-6741-5p, hsa-miR-4745-5p, hsa-miR-6826-5p, hsa-miR-3663-3p, hsa-miR-3131, hsa-miR-92a-2-5p, hsa-miR-4258, hsa-miR-4448, hsa-miR-6125, hsa-miR-6880-5p, hsa-miR-6132, hsa-miR-4467, hsa-miR-6749-5p, hsa-miR-2392, hsa-miR-1273g-3p, hsa-miR-4746-3p, hsa-miR-1914-3p, hsa-miR-7845-5p, hsa-miR-6726-5p, hsa-miR-128-2-5p, hsa-miR-4651, hsa-miR-6765-3p, hsa-miR-3185, hsa-miR-4792, hsa-miR-6887-5p, hsa-miR-5572, hsa-miR-3619-3p, hsa-miR-6780b-5p, hsa-miR-4707-5p, hsa-miR-8063, hsa-miR-4454, hsa-miR-4525, hsa-miR-7975, hsa-miR-744-5p, hsa-miR-3135b, hsa-miR-4648, hsa-miR-6816-5p, hsa-miR-4741, hsa-miR-7150, hsa-miR-6791-5p, hsa-miR-1247-3p, hsa-miR-7977, hsa-miR-4497, hsa-miR-6090, hsa-miR-6781-5p, hsa-miR-6870-5p, hsa-miR-6729-5p, hsa-miR-4530, hsa-miR-7847-3p, hsa-miR-6825-5p, hsa-miR-4674, hsa-miR-3917, hsa-miR-4707-3p, hsa-miR-6885-5p, hsa-miR-6722-3p, hsa-miR-4516, hsa-miR-6757-5p, hsa-miR-6840-3p, hsa-miR-5195-3p, hsa-miR-6756-5p, hsa-miR-6800-5p, hsa-miR-6727-5p, hsa-miR-6126, hsa-miR-6872-3p, hsa-miR-4446-3p, hsa-miR-1268a, hsa-miR-1908-3p, hsa-miR-3679-5p, hsa-miR-4534, hsa-miR-4675, hsa-miR-7108-5p, hsa-miR-6799-5p, hsa-miR-4695-5p, hsa-miR-3178, hsa-miR-5090, hsa-miR-3180, hsa-miR-1237-5p, hsa-miR-4758-5p, hsa-miR-3184-5p, hsa-miR-4286, hsa-miR-6784-5p, hsa-miR-6768-5p, hsa-miR-6785-5p, hsa-miR-4706, hsa-miR-711, hsa-miR-1260a, hsa-miR-6746-5p, hsa-miR-6089, hsa-miR-6821-5p, hsa-miR-4667-5p, hsa-miR-8069, hsa-miR-4726-5p, hsa-miR-6124, hsa-miR-4532, hsa-miR-4486, hsa-miR-4728-5p, hsa-miR-4508, hsa-miR-128-1-5p, hsa-miR-4513, hsa-miR-6795-5p, hsa-miR-4689, hsa-miR-6763-5p, hsa-miR-8072, hsa-miR-6765-5p, hsa-miR-4419b, hsa-miR-7641, hsa-miR-3928-3p, hsa-miR-1227-5p, hsa-miR-4492, hsa-miR-296-3p, hsa-miR-6769a-5p, hsa-miR-6889-5p, hsa-miR-4632-5p, hsa-miR-4505, hsa-miR-3154, hsa-miR-3648, hsa-miR-4442, hsa-miR-3141, hsa-miR-7113-3p, hsa-miR-6819-5p, hsa-miR-3195, hsa-miR-1199-5p, hsa-miR-6738-5p, hsa-miR-4656, hsa-miR-6820-5p, hsa-miR-615-5p, hsa-miR-486-3p, hsa-miR-1225-3p, hsa-miR-760, hsa-miR-187-5p, hsa-miR-1203, hsa-miR-7110-5p, hsa-miR-371a-5p, hsa-miR-939-5p, hsa-miR-575, hsa-miR-92b-5p, hsa-miR-887-3p, hsa-miR-920, hsa-miR-1915-5p, hsa-miR-1231, hsa-miR-663 and hsa-miR-1225-5p genes, and the nucleotide sequences of SEQ ID NOs: 1 to 152 related thereto were found.

A discriminant for determining the presence or absence of prostate cancer was further prepared by Fisher's linear discriminant analysis with the expression levels of these genes as an index. Specifically, any newly found polynucleotide consisting of a nucleotide sequence represented by any of SEQ ID NOs: 1 to 135 among the 152 genes selected in the training cohort was applied to Formula 2 to construct a discriminant. Calculated accuracy, sensitivity, and specificity are shown in Table 4. In this respect, a discriminant coefficient and a constant term are shown in Table 5.

Figure 2:
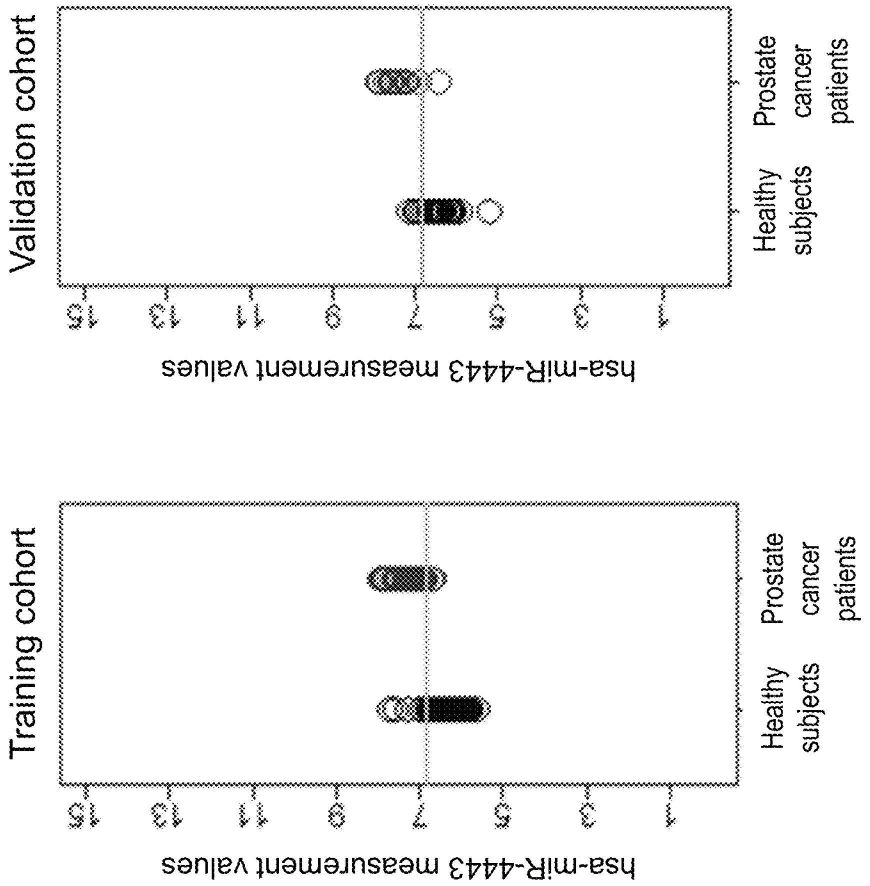
FIG. 2 Left diagram: the measurement values of hsa-miR-4443 (SEQ ID NO: 1) in healthy subjects (100 persons) and in prostate cancer patients (35 persons) selected as the training cohort were each plotted on the ordinate. The horizontal line in the diagram depicts a threshold (6.84) that was optimized by Fisher's linear discriminant analysis and discriminated between the two groups. Right diagram: the measurement values of hsa-miR-4443 (SEQ ID NO: 1) in healthy subjects (50 persons) and in prostate cancer patients (17 persons) selected as the validation cohort were each plotted on the ordinate. The horizontal line in the diagram depicts the threshold (6.84) that was set in the training cohort and discriminated between the two groups.

Next, accuracy, sensitivity, and specificity in the validation cohort were calculated using the discriminant thus prepared, and the discriminant performance of the selected polynucleotides was validated using the independent samples (Table 4). For example, the expression level measurement value of the nucleotide sequence represented by SEQ ID NO: 1 was compared between the healthy subjects (47 persons) and the prostate cancer patients (17 persons) in the validation cohort. The results showing that the gene expression level measurement values in the training cohort were significantly lower in the prostate cancer patient group than in the healthy subject group (see the left diagram of FIG. 2), were also reproducible in the validation cohort (see the right diagram of FIG. 2). Likewise, the results obtained about the other polynucleotides shown in SEQ ID NOs: 2 to 152 showed that the gene expression level measurement values were significantly lower (−) or higher (+) in the prostate cancer patient group than in the healthy subject group. These results were able to be validated in the validation cohort. For example, as for this nucleotide sequence represented by SEQ ID NO: 1, the number of samples that were correctly identified in the detection of prostate cancer was calculated using the threshold (6.84) that was set in the training cohort and discriminated between the two groups. As a result, 15 true positives, 44 true negatives, 3 false positive, and 2 false negatives were obtained. From these values, 92.2% accuracy, 88.2% sensitivity, and 93.6% specificity were obtained as detection performance. In this way, the detection performance was calculated as to all of the polynucleotides shown in SEQ ID NOs: 1 to 152, and described in Table 4.

Among the polynucleotides consisting of the nucleotide sequences represented by SEQ ID NOs: 1 to 152 shown in Table 3, for example, 141 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 103, 104, 105, 106, 107, 108, 109, 110, 111, 112, 113, 114, 116, 119, 120, 121, 123, 124, 126, 127, 128, 131, 132, 135, 136, 137, 138, 139, 140, 141, 142, 143, 144, 145, 146, 147, 148, 149, 150, 151 and 152 exhibited sensitivity of 88.2%, 94.1%, 76.5%, 88.2%, 88.2%, 94.1%, 76.5%, 64.7%, 88.2%, 76.5%, 64.7%, 82.4%, 70.6%, 88.2%, 52.9%, 47.1%, 70.6%, 94.1%, 70.6%, 76.5%, 76.5%, 70.6%, 70.6%, 29.4%, 58.8%, 88.2%, 58.8%, 76.5%, 64.7%, 76.5%, 64.7%, 47.1%, 76.5%, 82.4%, 70.6%, 47.1%, 64.7%, 58.8%, 52.9%, 82.4%, 64.7%, 70.6%, 64.7%, 70.6%, 70.6%, 76.5%, 58.8%, 58.8%, 52.9%, 64.7%, 47.1%, 41.2%, 70.6%, 52.9%, 29.4%, 35.3%, 41.2%, 58.8%, 52.9%, 41.2%, 70.6%, 52.9%, 35.3%, 64.7%, 29.4%, 70.6%, 70.6%, 76.5%, 58.8%, 70.6%, 35.3%, 58.8%, 58.8%, 47.1%, 70.6%, 76.5%, 58.8%, 82.4%, 23.5%, 52.9%, 41.2%, 47.1%, 64.7%, 41.2%, 41.2%, 35.3%, 47.1%, 47.1%, 41.2%, 29.4%, 41.2%, 64.7%, 35.3%, 70.6%, 29.4%, 47.1%, 29.4%, 52.9%, 64.7%, 47.1%, 23.5%, 35.3%, 47.1%, 35.3%, 35.3%, 52.9%, 23.5%, 35.3%, 47.1%, 52.9%, 23.5%, 23.5%, 29.4%, 52.9%, 41.2%, 23.5%, 23.5%, 41.2%, 47.1%, 29.4%, 58.8%, 29.4%, 23.5%, 29.4%, 58.8%, 88.2%, 76.5%, 58.8%, 52.9%, 47.1%, 35.3%, 52.9%, 29.4%, 47.1%, 76.5%, 58.8%, 29.4%, 29.4%, 29.4%, 41.2% and 23.5% respectively, in the validation cohort (Table 4). Non-Patent Literature 3 has reported that the existing prostate cancer marker PSA has general sensitivity of 20.5%. These results were able to demonstrate that, for example, the 141 polynucleotides consisting of the nucleotide sequences represented by SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 103, 104, 105, 106, 107, 108, 109, 110, 111, 112, 113, 114, 116, 119, 120, 121, 123, 124, 126, 127, 128, 131, 132, 135, 136, 137, 138, 139, 140, 141, 142, 143, 144, 145, 146, 147, 148, 149, 150, 151 and 152 can discriminate, each alone, prostate cancer in the validation cohort with sensitivity beyond PSA.

Example 2

<Method for Evaluating Prostate Cancer Discriminant Performance with Combination of Multiple Gene Markers Using Samples in the Validation Cohort>

In this Example, a method for evaluating prostate cancer discriminant performance with combination of the gene markers selected in Example 1 was studied.

Figure 3:
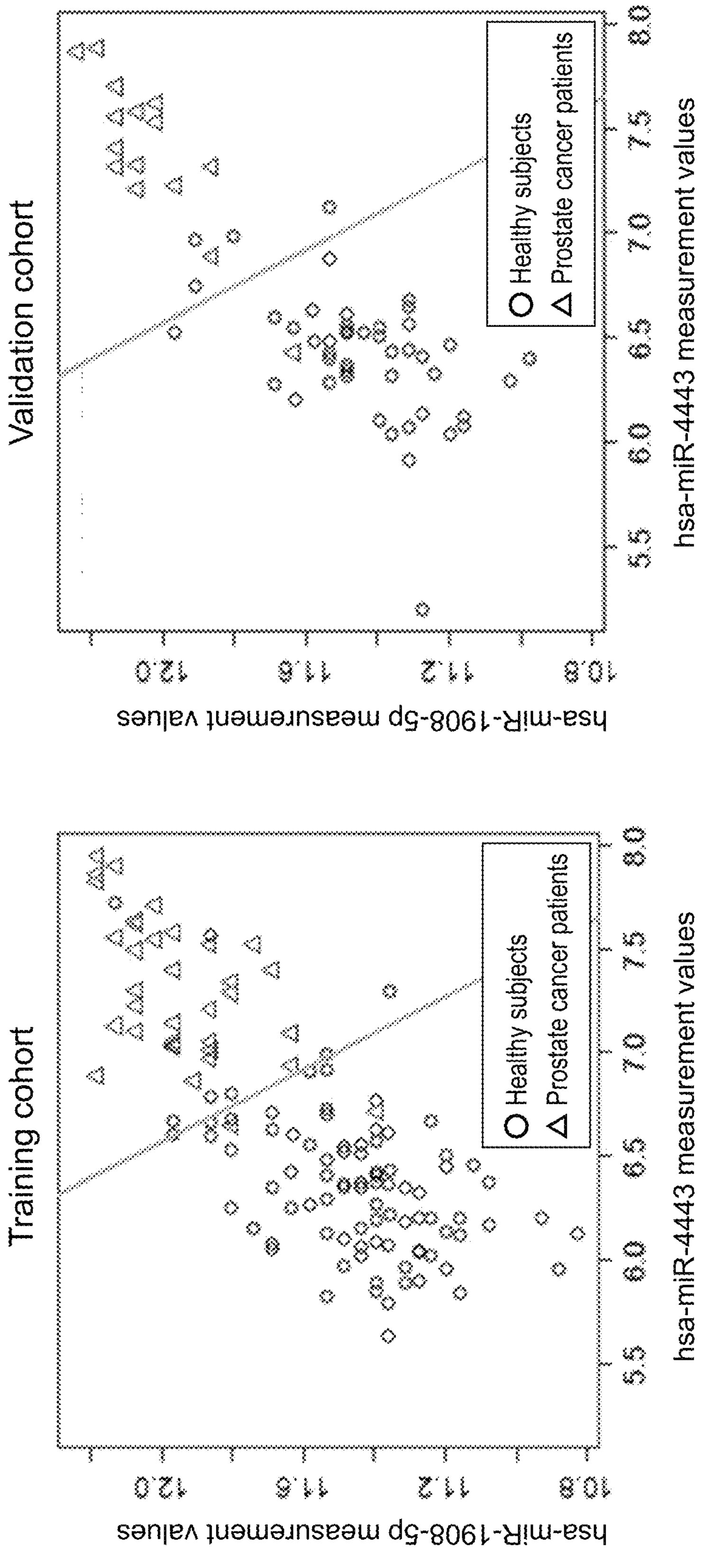
FIG. 3 Left diagram: the measurement values of hsa-miR-4443 (SEQ ID NO: 1) in healthy subjects (100 persons, circles) and in prostate cancer patients (35 persons, triangles) selected as the training cohort were each plotted on the abscissa against their measurement values of hsa-miR-1908-5p (SEQ ID NO: 2) on the ordinate. The line in the diagram depicts a discriminant function ($0=1.15x+y+19.53$) that was optimized by Fisher's linear discriminant analysis and discriminated between the two groups. Right diagram: the measurement values of hsa-miR-4443 (SEQ ID NO: 1) in healthy subjects (50 persons, circles) and in prostate cancer patients (17 persons, triangles) selected as the validation cohort were each plotted on the abscissa against their measurement values of hsa-miR-1908-5p (SEQ ID NO: 2) on the ordinate. The line in the diagram depicts the threshold ($0=1.15x+y+19.53$) that was set in the training cohort and discriminated between the two groups.

Specifically, Fisher's linear discriminant analysis was conducted as to 11,340 combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152 selected in Example 1, to construct a discriminant for determining the presence or absence of prostate cancer. Next, accuracy, sensitivity, and specificity in the validation cohort were calculated using the discriminant thus prepared, and the discriminant performance of the selected polynucleotides was validated using the independent samples. For example, the expression level measurement values of the nucleotide sequences represented by SEQ ID NO: 1 and SEQ ID NO: 2 were compared between the healthy subjects (47 persons) and the prostate cancer patients (17 persons) in the validation cohort. As a result, a scatter diagram that significantly separated the gene expression level measurement values of the prostate cancer patient group from those of the healthy subject group was obtained in the training cohort (see the left diagram of FIG. 3). These results were also reproducible for the validation cohort (see the right diagram of FIG. 3). Likewise, a scatter diagram that significantly separated the gene expression level measurement values of the prostate cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152. These results were able to be validated in the validation cohort. For example, as for these nucleotide sequences represented by SEQ ID NO: 1 and SEQ ID NO: 2, the number of samples correctly identified in the detection of prostate cancer was calculated using the threshold (0=1.15x+y+19.53) that was set in the training cohort and discriminated between the two groups. As a result, 16 true positives, 45 true negatives, 2 false positive, and 1 false negatives were obtained. From these values, 95.3% accuracy, 94.1% sensitivity, and 95.7% specificity were obtained as detection performance.

In this way, the detection performance was calculated as to all combinations (11,340 combinations) of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152. Among them, 151 combinations comprising the expression level measurement value of the polynucleotide consisting of the nucleotide sequence represented by SEQ ID NO: 1 and their detection performance are described in Table 6 as an example. For example, the combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 94.1%, 88.2%, 88.2%, and 94.1%, respectively, in the validation cohort (Table 6). In this way, 11,326 combinations of two expression level measurement values of the polynucleotides having sensitivity beyond the existing prostate cancer marker PSA (general sensitivity: 20.5%) were obtained in the validation cohort. All of the polynucleotides represented by the nucleotide sequences 1 to 152 described in Table 3 obtained in Example 1 were employed at least once in these combinations. These results were able to demonstrate that the combinations of two expression level measurement values comprising at least one or more of the expression level measurement values of the newly found polynucleotides consisting of the nucleotide sequences represented by SEQ ID NOs: 1 to 135 among the polynucleotides consisting of the nucleotide sequences represented by SEQ ID NOs: 1 to 152 has the performance of detecting prostate cancer with sensitivity beyond PSA.

Thus, markers capable of detecting prostate cancer with excellent sensitivity are obtained even if 3, 4, 5, 6, 7, 8, 9, 10 or more of the expression level measurement values of the polynucleotides consisting of the nucleotide sequences represented by SEQ ID NOs: 1 to 152 are combined. For example, the polynucleotides consisting of the nucleotide sequences represented by SEQ ID NOs: 1 to 135 newly found in Example 1 were ranked in the descending order of their P values which indicates statistical significance, and prostate cancer detection sensitivity was evaluated using combinations of one or more polynucleotides to which the polynucleotides (miRNAs) were added one by one from the top to the bottom of the rank accordingly. In short, the order to combine the polynucleotides (miRNAs) in this evaluation is in reverse in terms of SEQ ID NOs, such as SEQ ID NO: 135 to SEQ ID NOs: 134, 133, . . . , shown in Table 3. As a result, the sensitivity in the validation cohort was 29.4% for 1 polynucleotide, 47.1% for 2 polynucleotides, 76.5% for 3 polynucleotides, 82.4% for 5 polynucleotides, 82.4% for 10 polynucleotides, 88.2% for 20 polynucleotides, 100% for 50 polynucleotides, and 100% for 100 polynucleotides. These values of the sensitivity were higher than the general sensitivity (20.5%) of the existing prostate cancer marker PSA, demonstrating that even combinations of multiple (i.e., two or more) miRNAs can serve as excellent markers for the detection of prostate cancer. In this context, the combinations of multiple miRNAs are not limited to the combinations of the miRNAs added in the order of the statistically significant difference as described above, and any combination of multiple polynucleotides (miRNAs) can be used in the detection of prostate cancer.

From these results, it can be concluded that all of the polynucleotides consisting of the nucleotide sequences represented by SEQ ID NOs: 1 to 152 serve as excellent diagnostic markers.

| Sample name | Cancer stage |
|---|---|
| [Table 2-1] | |
| Training cohort | |
| PR04 | II |
| PR06 | IV |
| PR08 | II |
| PR09 | II |
| PR12 | II |
| PR19 | II |
| PR21 | II |
| PR22 | II |
| PR23 | II |
| PR29 | II |
| PR30 | II |
| PR32 | III |
| PR46 | II |
| PR48 | II |
| PR51 | II |
| PR52 | II |
| PR53 | II |
| PR64 | II |
| PR65 | II |
| PR66 | II |
| PR69 | IV |
| PR73 | II |
| PR75 | II |
| PR80 | IV |
| PR81 | II |
| PR83 | II |
| PR84 | II |
| PR85 | II |
| PR87 | II |
| PR90 | II |
| PR93 | II |
| PR94 | II |
| PR97 | II |
| PR99 | IV |
| PR101 | II |
| [Table 2-2] | |
| Validation cohort | |
| PR01 | II |
| PR17 | II |
| PR26 | III |
| PR27 | II |
| PR28 | III |
| PR33 | II |
| PR40 | II |
| PR45 | II |
| PR59 | II |
| PR62 | II |
| PR67 | II |
| PR71 | II |
| PR82 | II |
| PR91 | II |
| PR92 | II |

-continued

| Sample name | Cancer stage |
|---|---|
| PR96 | II |
| PR100 | II |

TABLE 3

| SEQ ID NO: | Gene name | P value after Bonferroni correction | Expression level in prostate cancer patient relative to healthy subject |
|---|---|---|---|
| 1 | hsa-miR-4443 | 2.10E−23 | + |
| 2 | hsa-miR-1908-5p | 7.83E−18 | + |
| 3 | hsa-miR-4257 | 2.21E−17 | − |
| 4 | hsa-miR-3197 | 5.78E−17 | + |
| 5 | hsa-miR-3188 | 5.96.E−17 | + |
| 6 | hsa-miR-4649-5p | 6.34.E−17 | − |
| 7 | hsa-miR-1343-3p | 2.48.E−16 | − |
| 8 | hsa-miR-6861-5p | 1.15.E−15 | − |
| 9 | hsa-miR-1343-5p | 3.73.E−15 | + |
| 10 | hsa-miR-642b-3p | 3.94.E−15 | − |
| 11 | hsa-miR-6741-5p | 3.03.E−14 | − |
| 12 | hsa-miR-4745-5p | 4.76.E−14 | − |
| 13 | hsa-miR-6826-5p | 1.27.E−13 | − |
| 14 | hsa-miR-3663-3p | 1.61.E−13 | − |
| 15 | hsa-miR-3131 | 5.67.E−13 | − |
| 16 | hsa-miR-92a-2-5p | 1.04.E−12 | + |
| 17 | hsa-miR-4258 | 1.59.E−12 | − |
| 18 | hsa-miR-4448 | 2.54.E−12 | + |
| 19 | hsa-miR-6125 | 4.39.E−12 | + |
| 20 | hsa-miR-6880-5p | 6.24.E−12 | + |
| 21 | hsa-miR-6132 | 8.70.E−12 | + |
| 22 | hsa-miR-4467 | 1.45.E−11 | + |
| 23 | hsa-miR-6749-5p | 1.46.E−11 | − |
| 24 | hsa-miR-2392 | 1.68.E−11 | + |
| 25 | hsa-miR-1273g-3p | 2.09.E−11 | − |
| 26 | hsa-miR-4746-3p | 2.43.E−11 | + |
| 27 | hsa-miR-1914-3p | 2.94.E−11 | − |
| 28 | hsa-miR-7845-5p | 3.03.E−11 | + |
| 29 | hsa-miR-6726-5p | 5.00.E−11 | − |
| 30 | hsa-miR-128-2-5p | 5.60.E−11 | − |
| 31 | hsa-miR-4651 | 6.14.E−11 | − |
| 32 | hsa-miR-6765-3p | 6.43.E−11 | − |
| 33 | hsa-miR-3185 | 7.07.E−11 | + |
| 34 | hsa-miR-4792 | 7.39.E−11 | + |
| 35 | hsa-miR-6887-5p | 9.57.E−11 | − |
| 36 | hsa-miR-5572 | 1.01.E−10 | + |
| 37 | hsa-miR-3619-3p | 1.89.E−10 | − |
| 38 | hsa-miR-6780b-5p | 2.55.E−10 | + |
| 39 | hsa-miR-4707-5p | 2.83.E−10 | + |
| 40 | hsa-miR-8063 | 2.93.E−10 | − |
| 41 | hsa-miR-4454 | 3.34.E−10 | − |
| 42 | hsa-miR-4525 | 3.73.E−10 | − |
| 43 | hsa-miR-7975 | 3.87.E−10 | − |
| 44 | hsa-miR-744-5p | 4.00.E−10 | + |
| 45 | hsa-miR-3135b | 4.73.E−10 | − |
| 46 | hsa-miR-4648 | 5.10.E−10 | + |
| 47 | hsa-miR-6816-5p | 6.76.E−10 | + |
| 48 | hsa-miR-4741 | 9.16.E−10 | + |
| 49 | hsa-miR-7150 | 1.34.E−09 | + |
| 50 | hsa-miR-6791-5p | 2.31.E−09 | + |
| 51 | hsa-miR-1247-3p | 3.07.E−09 | + |
| 52 | hsa-miR-7977 | 3.35.E−09 | − |
| 53 | hsa-miR-4497 | 4.19.E−09 | − |
| 54 | hsa-miR-6090 | 5.36.E−09 | + |
| 55 | hsa-miR-6781-5p | 8.00.E−09 | + |
| 56 | hsa-miR-6870-5p | 1.48.E−08 | + |
| 57 | hsa-miR-6729-5p | 1.56.E−08 | + |
| 58 | hsa-miR-4530 | 2.60.E−08 | + |
| 59 | hsa-miR-7847-3p | 3.09.E−08 | − |
| 60 | hsa-miR-6825-5p | 3.86.E−08 | + |
| 61 | hsa-miR-4674 | 3.88.E−08 | − |
| 62 | hsa-miR-3917 | 4.11.E−08 | − |
| 63 | hsa-miR-4707-3p | 4.52.E−08 | + |
| 64 | hsa-miR-6885-5p | 5.06.E−08 | − |
| 65 | hsa-miR-6722-3p | 5.76.E−08 | + |

TABLE 3-continued

| SEQ ID NO: | Gene name | P value after Bonferroni correction | Expression level in prostate cancer patient relative to healthy subject |
|---|---|---|---|
| 66 | hsa-miR-4516 | 6.32.E−08 | − |
| 67 | hsa-miR-6757-5p | 6.81.E−08 | − |
| 68 | hsa-miR-6840-3p | 1.30.E−07 | − |
| 69 | hsa-miR-5195-3p | 1.45.E−07 | − |
| 70 | hsa-miR-6756-5p | 1.48.E−07 | − |
| 71 | hsa-miR-6800-5p | 1.61.E−07 | + |
| 72 | hsa-miR-6727-5p | 1.65.E−07 | − |
| 73 | hsa-miR-6126 | 1.87.E−07 | + |
| 74 | hsa-miR-6872-3p | 2.21.E−07 | − |
| 75 | hsa-miR-4446-3p | 3.28.E−07 | − |
| 76 | hsa-miR-1268a | 4.54.E−07 | + |
| 77 | hsa-miR-1908-3p | 5.41.E−07 | − |
| 78 | hsa-miR-3679-5p | 5.53.E−07 | + |
| 79 | hsa-miR-4534 | 7.45.E−07 | + |
| 80 | hsa-miR-4675 | 7.91.E−07 | − |
| 81 | hsa-miR-7108-5p | 1.01.E−06 | + |
| 82 | hsa-miR-6799-5p | 1.57.E−06 | + |
| 83 | hsa-miR-4695-5p | 3.59.E−06 | + |
| 84 | hsa-miR-3178 | 4.54.E−06 | + |
| 85 | hsa-miR-5090 | 4.93.E−06 | − |
| 86 | hsa-miR-3180 | 6.40.E−06 | + |
| 87 | hsa-miR-1237-5p | 9.54.E−06 | + |
| 88 | hsa-miR-4758-5p | 1.50.E−05 | − |
| 89 | hsa-miR-3184-5p | 1.60.E−05 | + |
| 90 | hsa-miR-4286 | 1.96.E−05 | − |
| 91 | hsa-miR-6784-5p | 2.81.E−05 | + |
| 92 | hsa-miR-6768-5p | 3.47.E−05 | + |
| 93 | hsa-miR-6785-5p | 3.51.E−05 | − |
| 94 | hsa-miR-4706 | 3.72.E−05 | − |
| 95 | hsa-miR-711 | 4.59.E−05 | + |
| 96 | hsa-miR-1260a | 5.06.E−05 | − |
| 97 | hsa-miR-6746-5p | 5.35.E−05 | − |
| 98 | hsa-miR-6089 | 7.26.E−05 | + |
| 99 | hsa-miR-6821-5p | 7.94.E−05 | + |
| 100 | hsa-miR-4667-5p | 8.38.E−05 | + |
| 101 | hsa-miR-8069 | 9.70.E−05 | + |
| 102 | hsa-miR-4726-5p | 1.11.E−04 | − |
| 103 | hsa-miR-6124 | 1.59.E−04 | + |
| 104 | hsa-miR-4532 | 1.87.E−04 | − |
| 105 | hsa-miR-4486 | 1.92.E−04 | + |
| 106 | hsa-miR-4728-5p | 1.96.E−04 | − |
| 107 | hsa-miR-4508 | 2.20.E−04 | + |
| 108 | hsa-miR-128-1-5p | 3.56.E−04 | + |
| 109 | hsa-miR-4513 | 3.75.E−04 | − |
| 110 | hsa-miR-6795-5p | 5.28.E−04 | − |
| 111 | hsa-miR-4689 | 5.85.E−04 | − |
| 112 | hsa-miR-6763-5p | 6.01.E−04 | + |
| 113 | hsa-miR-8072 | 6.56.E−04 | + |
| 114 | hsa-miR-6765-5p | 6.67.E−04 | + |
| 115 | hsa-miR-4419b | 7.40.E−04 | − |
| 116 | hsa-miR-7641 | 8.72.E−04 | − |
| 117 | hsa-miR-3928-3p | 9.57.E−04 | + |
| 118 | hsa-miR-1227-5p | 9.66.E−04 | + |
| 119 | hsa-miR-4492 | 1.12.E−03 | − |
| 120 | hsa-miR-296-3p | 1.39.E−03 | − |
| 121 | hsa-miR-6769a-5p | 1.42.E−03 | − |
| 122 | hsa-miR-6889-5p | 1.46.E−03 | + |
| 123 | hsa-miR-4632-5p | 1.74.E−03 | + |
| 124 | hsa-miR-4505 | 1.94.E−03 | + |
| 125 | hsa-miR-3154 | 1.97.E−03 | + |
| 126 | hsa-miR-3648 | 2.03.E−03 | − |
| 127 | hsa-miR-4442 | 2.15.E−03 | − |
| 128 | hsa-miR-3141 | 3.29.E−03 | + |
| 129 | hsa-miR-7113-3p | 3.29.E−03 | + |
| 130 | hsa-miR-6819-5p | 5.95.E−03 | − |
| 131 | hsa-miR-3195 | 6.78.E−03 | + |
| 132 | hsa-miR-1199-5p | 7.39.E−03 | − |
| 133 | hsa-miR-6738-5p | 8.00.E−03 | − |
| 134 | hsa-miR-4656 | 8.53.E−03 | − |
| 135 | hsa-miR-6820-5p | 9.18.E−03 | + |
| 136 | hsa-miR-615-5p | 1.89.E−11 | − |
| 137 | hsa-miR-486-3p | 4.76.E−11 | − |
| 138 | hsa-miR-1225-3p | 8.87.E−11 | + |
| 139 | hsa-miR-760 | 1.05.E−10 | − |
| 140 | hsa-miR-187-5p | 9.50.E−09 | − |
| 141 | hsa-miR-1203 | 6.86.E−08 | + |
| 142 | hsa-miR-7110-5p | 2.08.E−07 | + |
| 143 | hsa-miR-371a-5p | 4.75.E−07 | − |
| 144 | hsa-miR-939-5p | 9.56.E−07 | + |
| 145 | hsa-miR-575 | 2.41.E−06 | + |
| 146 | hsa-miR-92b-5p | 2.89.E−06 | + |
| 147 | hsa-miR-887-3p | 1.35.E−05 | + |
| 148 | hsa-miR-920 | 3.39.E−05 | − |
| 149 | hsa-miR-1915-5p | 2.55.E−04 | − |
| 150 | hsa-miR-1231 | 3.11.E−04 | + |
| 151 | hsa-miR-663b | 1.18.E−03 | − |
| 152 | hsa-miR-1225-5p | 8.49.E−03 | + |

TABLE 4

| SEQ ID | Training cohort | | | Validation cohort | | |
|---|---|---|---|---|---|---|
| NO: | Accuracy (%) | Sensitivity (%) | Specificity (%) | Accuracy (%) | Sensitivity (%) | Specificity (%) |
| 1 | 93 | 85.7 | 95.7 | 92.2 | 88.2 | 93.6 |
| 2 | 87.6 | 85.7 | 88.3 | 92.2 | 94.1 | 91.5 |
| 3 | 89.9 | 77.1 | 94.7 | 89.1 | 76.5 | 93.6 |
| 4 | 85.3 | 71.4 | 90.4 | 95.3 | 88.2 | 97.9 |
| 5 | 89.1 | 77.1 | 93.6 | 92.2 | 88.2 | 93.6 |
| 6 | 88.4 | 77.1 | 92.6 | 92.2 | 94.1 | 91.5 |
| 7 | 86 | 74.3 | 90.4 | 82.8 | 76.5 | 85.1 |
| 8 | 86.8 | 74.3 | 91.5 | 84.4 | 64.7 | 91.5 |
| 9 | 83.7 | 74.3 | 87.2 | 92.2 | 88.2 | 93.6 |
| 10 | 86.8 | 68.6 | 93.6 | 92.2 | 76.5 | 97.9 |
| 11 | 86 | 68.6 | 92.6 | 85.9 | 64.7 | 93.6 |
| 12 | 86 | 74.3 | 90.4 | 90.6 | 82.4 | 93.6 |
| 13 | 89.1 | 77.1 | 93.6 | 89.1 | 70.6 | 95.7 |
| 14 | 79.8 | 42.9 | 93.6 | 95.3 | 88.2 | 97.9 |
| 15 | 83.7 | 68.6 | 89.4 | 76.6 | 52.9 | 85.1 |
| 16 | 87.6 | 77.1 | 91.5 | 73.4 | 47.1 | 83 |
| 17 | 82.9 | 57.1 | 92.6 | 81.2 | 70.6 | 85.1 |
| 18 | 88.4 | 65.7 | 96.8 | 93.8 | 94.1 | 93.6 |
| 19 | 88.4 | 82.9 | 90.4 | 84.4 | 70.6 | 89.4 |
| 20 | 82.9 | 57.1 | 92.6 | 92.2 | 76.5 | 97.9 |
| 21 | 87.6 | 62.9 | 96.8 | 92.2 | 76.5 | 97.9 |
| 22 | 82.2 | 60 | 90.4 | 89.1 | 70.6 | 95.7 |

TABLE 4-continued

| SEQ ID | Training cohort | | | Validation cohort | | |
|---|---|---|---|---|---|---|
| NO: | Accuracy (%) | Sensitivity (%) | Specificity (%) | Accuracy (%) | Sensitivity (%) | Specificity (%) |
| 23 | 82.2 | 60 | 90.4 | 89.1 | 70.6 | 95.7 |
| 24 | 84.5 | 57.1 | 94.7 | 71.9 | 29.4 | 87.2 |
| 25 | 87.6 | 62.9 | 96.8 | 82.8 | 58.8 | 91.5 |
| 26 | 84.5 | 65.7 | 91.5 | 93.8 | 88.2 | 95.7 |
| 27 | 82.2 | 65.7 | 88.3 | 76.6 | 58.8 | 83 |
| 28 | 81.4 | 57.1 | 90.4 | 89.1 | 76.5 | 93.6 |
| 29 | 87.6 | 68.6 | 94.7 | 85.9 | 64.7 | 93.6 |
| 30 | 85.3 | 60 | 94.7 | 87.5 | 76.5 | 91.5 |
| 31 | 82.2 | 57.1 | 91.5 | 82.8 | 64.7 | 89.4 |
| 32 | 84.5 | 60 | 93.6 | 79.7 | 47.1 | 91.5 |
| 33 | 83.7 | 65.7 | 90.4 | 90.6 | 76.5 | 95.7 |
| 34 | 89.9 | 74.3 | 95.7 | 87.5 | 82.4 | 89.4 |
| 35 | 81.4 | 57.1 | 90.4 | 85.9 | 70.6 | 91.5 |
| 36 | 79.8 | 57.1 | 88.3 | 78.1 | 47.1 | 89.4 |
| 37 | 84.5 | 60 | 93.6 | 87.5 | 64.7 | 95.7 |
| 38 | 81.4 | 54.3 | 91.5 | 82.8 | 58.8 | 91.5 |
| 39 | 79.1 | 54.3 | 88.3 | 87.5 | 52.9 | 100 |
| 40 | 83.7 | 74.3 | 87.2 | 90.6 | 82.4 | 93.6 |
| 41 | 85.3 | 60 | 94.7 | 79.7 | 64.7 | 85.1 |
| 42 | 79.1 | 48.6 | 90.4 | 89.1 | 70.6 | 95.7 |
| 43 | 81.4 | 54.3 | 91.5 | 85.9 | 64.7 | 93.6 |
| 44 | 85.3 | 54.3 | 96.8 | 90.6 | 70.6 | 97.9 |
| 45 | 89.9 | 74.3 | 95.7 | 89.1 | 70.6 | 95.7 |
| 46 | 82.9 | 60 | 91.5 | 84.4 | 76.5 | 87.2 |
| 47 | 83.7 | 60 | 92.6 | 79.7 | 58.8 | 87.2 |
| 48 | 82.9 | 54.3 | 93.6 | 82.8 | 58.8 | 91.5 |
| 49 | 84.5 | 57.1 | 94.7 | 79.7 | 52.9 | 89.4 |
| 50 | 78.3 | 48.6 | 89.4 | 87.5 | 64.7 | 95.7 |
| 51 | 82.2 | 48.6 | 94.7 | 75 | 47.1 | 85.1 |
| 52 | 80.6 | 51.4 | 91.5 | 79.7 | 41.2 | 93.6 |
| 53 | 79.8 | 60 | 87.2 | 85.9 | 70.6 | 91.5 |
| 54 | 80.6 | 42.9 | 94.7 | 87.5 | 52.9 | 100 |
| 55 | 82.9 | 57.1 | 92.6 | 76.6 | 29.4 | 93.6 |
| 56 | 80.6 | 54.3 | 90.4 | 76.6 | 35.3 | 91.5 |
| 57 | 85.3 | 51.4 | 97.9 | 81.2 | 41.2 | 95.7 |
| 58 | 80.6 | 54.3 | 90.4 | 81.2 | 58.8 | 89.4 |
| 59 | 79.1 | 51.4 | 89.4 | 81.2 | 52.9 | 91.5 |
| 60 | 78.3 | 51.4 | 88.3 | 76.6 | 41.2 | 89.4 |
| 61 | 81.4 | 48.6 | 93.6 | 85.9 | 70.6 | 91.5 |
| 62 | 82.9 | 54.3 | 93.6 | 82.8 | 52.9 | 93.6 |
| 63 | 82.9 | 60 | 91.5 | 78.1 | 35.3 | 93.6 |
| 64 | 80.6 | 42.9 | 94.7 | 89.1 | 64.7 | 97.9 |
| 65 | 78.3 | 40 | 92.6 | 79.7 | 29.4 | 97.9 |
| 66 | 80.6 | 45.7 | 93.6 | 84.4 | 70.6 | 89.4 |
| 67 | 80.6 | 57.1 | 89.4 | 84.4 | 70.6 | 89.4 |
| 68 | 79.1 | 42.9 | 92.6 | 85.9 | 76.5 | 89.4 |
| 69 | 82.2 | 48.6 | 94.7 | 81.2 | 58.8 | 89.4 |
| 70 | 79.8 | 51.4 | 90.4 | 92.2 | 70.6 | 100 |
| 71 | 79.8 | 45.7 | 92.6 | 79.7 | 35.3 | 95.7 |
| 72 | 79.8 | 51.4 | 90.4 | 78.1 | 58.8 | 85.1 |
| 73 | 77.5 | 42.9 | 90.4 | 81.2 | 58.8 | 89.4 |
| 74 | 81.4 | 51.4 | 92.6 | 73.4 | 47.1 | 83 |
| 75 | 79.1 | 54.3 | 88.3 | 82.8 | 70.6 | 87.2 |
| 76 | 76 | 42.9 | 88.3 | 84.4 | 76.5 | 87.2 |
| 77 | 78.3 | 51.4 | 88.3 | 79.7 | 58.8 | 87.2 |
| 78 | 80.6 | 51.4 | 91.5 | 92.2 | 82.4 | 95.7 |
| 79 | 78.3 | 42.9 | 91.5 | 68.8 | 23.5 | 85.1 |
| 80 | 79.1 | 40 | 93.6 | 84.4 | 52.9 | 95.7 |
| 81 | 79.1 | 45.7 | 91.5 | 81.2 | 41.2 | 95.7 |
| 82 | 79.1 | 45.7 | 91.5 | 78.1 | 47.1 | 89.4 |
| 83 | 76.7 | 42.9 | 89.4 | 89.1 | 64.7 | 97.9 |
| 84 | 80.6 | 45.7 | 93.6 | 78.1 | 41.2 | 91.5 |
| 85 | 79.8 | 37.1 | 95.7 | 84.4 | 41.2 | 100 |
| 86 | 79.8 | 45.7 | 92.6 | 75 | 35.3 | 89.4 |
| 87 | 78.1 | 32.4 | 94.7 | 85.9 | 47.1 | 100 |
| 88 | 79.1 | 31.4 | 96.8 | 84.4 | 47.1 | 97.9 |
| 89 | 75.2 | 34.3 | 90.4 | 76.6 | 41.2 | 89.4 |
| 90 | 76.7 | 37.1 | 91.5 | 76.6 | 29.4 | 93.6 |
| 91 | 74.4 | 34.3 | 89.4 | 70.3 | 17.6 | 89.4 |
| 92 | 83.7 | 51.4 | 95.7 | 79.7 | 41.2 | 93.6 |
| 93 | 77.5 | 42.9 | 90.4 | 84.4 | 64.7 | 91.5 |
| 94 | 79.8 | 42.9 | 93.6 | 76.6 | 35.3 | 91.5 |
| 95 | 82.2 | 48.6 | 94.7 | 89.1 | 70.6 | 95.7 |
| 96 | 78.3 | 45.7 | 90.4 | 73.4 | 29.4 | 89.4 |
| 97 | 76 | 34.3 | 91.5 | 75 | 47.1 | 85.1 |
| 98 | 74.4 | 25.7 | 92.6 | 76.6 | 29.4 | 93.6 |

TABLE 4-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 99 | 78.3 | 42.9 | 91.5 | 85.9 | 52.9 | 97.9 |
| 100 | 73.6 | 22.9 | 92.6 | 87.5 | 64.7 | 95.7 |
| 101 | 79.8 | 45.7 | 92.6 | 84.4 | 47.1 | 97.9 |
| 102 | 76 | 37.1 | 90.4 | 67.2 | 17.6 | 85.1 |
| 103 | 79.1 | 31.4 | 96.8 | 76.6 | 23.5 | 95.7 |
| 104 | 77.5 | 28.6 | 95.7 | 81.2 | 35.3 | 97.9 |
| 105 | 77.5 | 34.3 | 93.6 | 81.2 | 47.1 | 93.6 |
| 106 | 73.6 | 31.4 | 89.4 | 79.7 | 35.3 | 95.7 |
| 107 | 77.5 | 25.7 | 96.8 | 75 | 35.3 | 89.4 |
| 108 | 76 | 34.3 | 91.5 | 84.4 | 52.9 | 95.7 |
| 109 | 76.7 | 34.3 | 92.6 | 75 | 23.5 | 93.6 |
| 110 | 76 | 22.9 | 95.7 | 78.1 | 35.3 | 93.6 |
| 111 | 75.2 | 14.3 | 97.9 | 84.4 | 47.1 | 97.9 |
| 112 | 72.9 | 20 | 92.6 | 85.9 | 52.9 | 97.9 |
| 113 | 75.2 | 22.9 | 94.7 | 78.1 | 23.5 | 97.9 |
| 114 | 73.6 | 17.1 | 94.7 | 76.6 | 23.5 | 95.7 |
| 115 | 76.7 | 28.6 | 94.7 | 73.4 | 17.6 | 93.6 |
| 116 | 73.6 | 28.6 | 90.4 | 75 | 29.4 | 91.5 |
| 117 | 79.1 | 34.3 | 95.7 | 75 | 17.6 | 95.7 |
| 118 | 74.4 | 22.9 | 93.6 | 71.9 | 17.6 | 91.5 |
| 119 | 73.6 | 22.9 | 92.6 | 85.9 | 52.9 | 97.9 |
| 120 | 73.6 | 25.7 | 91.5 | 79.7 | 41.2 | 93.6 |
| 121 | 77.5 | 34.3 | 93.6 | 75 | 23.5 | 93.6 |
| 122 | 74.4 | 25.7 | 92.6 | 70.3 | 11.8 | 91.5 |
| 123 | 76.7 | 25.7 | 95.7 | 78.1 | 23.5 | 97.9 |
| 124 | 81.4 | 40 | 96.8 | 84.4 | 41.2 | 100 |
| 125 | 74.4 | 20 | 94.7 | 71.9 | 17.6 | 91.5 |
| 126 | 76.7 | 28.6 | 94.7 | 82.8 | 47.1 | 95.7 |
| 127 | 75.2 | 31.4 | 91.5 | 76.6 | 29.4 | 93.6 |
| 128 | 76.7 | 22.9 | 96.8 | 87.5 | 58.8 | 97.9 |
| 129 | 69.8 | 22.9 | 87.2 | 73.4 | 11.8 | 95.7 |
| 130 | 74.4 | 22.9 | 93.6 | 75 | 11.8 | 97.9 |
| 131 | 74.4 | 28.6 | 91.5 | 81.2 | 29.4 | 100 |
| 132 | 74.4 | 22.9 | 93.6 | 75 | 23.5 | 93.6 |
| 133 | 68.2 | 11.4 | 89.4 | 75 | 11.8 | 97.9 |
| 134 | 75.2 | 20 | 95.7 | 76.6 | 17.6 | 97.9 |
| 135 | 73.6 | 22.9 | 92.6 | 78.1 | 29.4 | 95.7 |
| 136 | 86.8 | 65.7 | 94.7 | 75 | 58.8 | 80.9 |
| 137 | 86 | 68.6 | 92.6 | 93.8 | 88.2 | 95.7 |
| 138 | 86.8 | 68.6 | 93.6 | 85.9 | 76.5 | 89.4 |
| 139 | 79.8 | 54.3 | 89.4 | 81.2 | 58.8 | 89.4 |
| 140 | 80.6 | 51.4 | 91.5 | 73.4 | 52.9 | 80.9 |
| 141 | 80.6 | 45.7 | 93.6 | 84.4 | 47.1 | 97.9 |
| 142 | 76 | 48.6 | 86.2 | 78.1 | 35.3 | 93.6 |
| 143 | 79.8 | 42.9 | 93.6 | 79.7 | 52.9 | 89.4 |
| 144 | 72.9 | 42.9 | 84 | 76.6 | 29.4 | 93.6 |
| 145 | 79.8 | 48.6 | 91.5 | 82.8 | 47.1 | 95.7 |
| 146 | 79.1 | 48.6 | 90.4 | 92.2 | 76.5 | 97.9 |
| 147 | 74.4 | 34.3 | 89.4 | 87.5 | 58.8 | 97.9 |
| 148 | 75.2 | 34.3 | 90.4 | 67.2 | 29.4 | 80.9 |
| 149 | 76 | 28.6 | 93.6 | 78.1 | 29.4 | 95.7 |
| 150 | 76 | 28.6 | 93.6 | 78.1 | 29.4 | 95.7 |
| 151 | 79.8 | 34.3 | 96.8 | 81.2 | 41.2 | 95.7 |
| 152 | 72.9 | 14.3 | 94.7 | 78.1 | 23.5 | 97.9 |

TABLE 5

| SEQ ID NO: | Discriminant coefficient | Constant term |
|---|---|---|
| 1 | 2.841 | 19.421 |
| 2 | 4.435 | 51.871 |
| 3 | 3.207 | 21.845 |
| 4 | 3.253 | 31.499 |
| 5 | 4.075 | 25.795 |
| 6 | 2.840 | 29.134 |
| 7 | 2.539 | 19.203 |
| 8 | 4.359 | 31.785 |
| 9 | 4.100 | 43.343 |
| 10 | 2.475 | 23.187 |
| 11 | 4.875 | 33.924 |
| 12 | 2.662 | 31.800 |
| 13 | 2.576 | 15.891 |

TABLE 5-continued

| SEQ ID NO: | Discriminant coefficient | Constant term |
|---|---|---|
| 14 | 3.758 | 45.427 |
| 15 | 3.007 | 21.322 |
| 16 | 2.086 | 20.103 |
| 17 | 2.415 | 21.597 |
| 18 | 1.386 | 8.309 |
| 19 | 5.265 | 63.510 |
| 20 | 2.601 | 20.485 |
| 21 | 3.480 | 28.174 |
| 22 | 2.098 | 21.131 |
| 23 | 5.034 | 50.773 |
| 24 | 4.361 | 26.275 |
| 25 | 2.837 | 21.020 |
| 26 | 3.180 | 21.510 |

TABLE 5-continued

| SEQ ID NO: | Discriminant coefficient | Constant term |
|---|---|---|
| 27 | 4.832 | 36.754 |
| 28 | 3.240 | 22.334 |
| 29 | 3.297 | 32.746 |
| 30 | 2.751 | 29.763 |
| 31 | 5.736 | 63.070 |
| 32 | 1.809 | 15.805 |
| 33 | 2.566 | 18.600 |
| 34 | 1.963 | 13.501 |
| 35 | 3.448 | 22.503 |
| 36 | 2.577 | 17.708 |
| 37 | 2.326 | 19.136 |
| 38 | 3.057 | 27.631 |
| 39 | 4.748 | 35.803 |
| 40 | 2.880 | 23.980 |
| 41 | 2.262 | 26.203 |
| 42 | 2.961 | 20.754 |
| 43 | 2.220 | 21.988 |
| 44 | 2.353 | 16.969 |
| 45 | 3.102 | 24.441 |
| 46 | 1.594 | 9.958 |
| 47 | 4.468 | 45.625 |
| 48 | 3.732 | 37.591 |
| 49 | 4.378 | 34.624 |
| 50 | 4.896 | 45.653 |
| 51 | 4.268 | 27.572 |
| 52 | 2.192 | 21.441 |
| 53 | 3.013 | 38.151 |
| 54 | 6.888 | 90.453 |
| 55 | 5.516 | 58.347 |
| 56 | 3.641 | 27.465 |
| 57 | 7.874 | 99.518 |
| 58 | 2.492 | 24.657 |
| 59 | 4.058 | 26.380 |
| 60 | 2.350 | 15.623 |
| 61 | 3.450 | 35.983 |
| 62 | 3.384 | 20.446 |
| 63 | 3.330 | 22.289 |
| 64 | 2.906 | 32.309 |
| 65 | 6.296 | 54.722 |
| 66 | 4.911 | 64.684 |
| 67 | 3.206 | 23.658 |
| 68 | 3.285 | 29.269 |
| 69 | 3.237 | 22.571 |
| 70 | 5.038 | 42.229 |
| 71 | 4.159 | 36.268 |
| 72 | 6.806 | 87.077 |
| 73 | 3.063 | 33.575 |
| 74 | 2.552 | 15.751 |
| 75 | 2.791 | 20.526 |
| 76 | 3.285 | 37.356 |
| 77 | 3.362 | 22.864 |
| 78 | 2.811 | 19.633 |
| 79 | 3.759 | 26.864 |
| 80 | 2.982 | 22.991 |
| 81 | 3.997 | 37.078 |
| 82 | 4.484 | 37.972 |
| 83 | 4.600 | 35.223 |
| 84 | 6.026 | 73.901 |
| 85 | 4.239 | 33.902 |
| 86 | 5.314 | 47.015 |
| 87 | 4.798 | 61.512 |
| 88 | 6.806 | 59.152 |
| 89 | 2.706 | 22.080 |
| 90 | 2.498 | 18.719 |

TABLE 5-continued

| SEQ ID NO: | Discriminant coefficient | Constant term |
|---|---|---|
| 91 | 3.833 | 48.285 |
| 92 | 3.325 | 32.674 |
| 93 | 2.793 | 25.551 |
| 94 | 3.860 | 30.344 |
| 95 | 3.878 | 32.579 |
| 96 | 2.688 | 18.916 |
| 97 | 4.301 | 28.806 |
| 98 | 6.386 | 86.216 |
| 99 | 3.660 | 32.730 |
| 100 | 4.747 | 30.458 |
| 101 | 5.928 | 76.530 |
| 102 | 4.003 | 27.083 |
| 103 | 2.947 | 21.339 |
| 104 | 3.195 | 38.076 |
| 105 | 3.103 | 22.617 |
| 106 | 5.105 | 36.656 |
| 107 | 8.087 | 105.473 |
| 108 | 2.927 | 22.240 |
| 109 | 4.111 | 25.157 |
| 110 | 4.803 | 30.149 |
| 111 | 3.332 | 31.704 |
| 112 | 3.855 | 27.615 |
| 113 | 4.606 | 57.067 |
| 114 | 4.801 | 51.079 |
| 115 | 3.144 | 19.952 |
| 116 | 1.519 | 11.331 |
| 117 | 3.217 | 19.269 |
| 118 | 6.074 | 58.552 |
| 119 | 5.508 | 57.411 |
| 120 | 2.408 | 14.813 |
| 121 | 4.332 | 28.554 |
| 122 | 3.286 | 24.338 |
| 123 | 4.276 | 34.402 |
| 124 | 3.879 | 33.369 |
| 125 | 4.935 | 30.296 |
| 126 | 2.311 | 30.293 |
| 127 | 3.246 | 31.192 |
| 128 | 4.684 | 33.975 |
| 129 | 3.468 | 20.714 |
| 130 | 6.033 | 46.013 |
| 131 | 3.614 | 30.304 |
| 132 | 2.869 | 19.654 |
| 133 | 4.117 | 30.189 |
| 134 | 3.842 | 27.896 |
| 135 | 3.012 | 23.016 |
| 136 | 2.496 | 16.713 |
| 137 | 3.062 | 24.479 |
| 138 | 3.805 | 22.035 |
| 139 | 3.410 | 30.192 |
| 140 | 2.159 | 21.828 |
| 141 | 2.667 | 17.063 |
| 142 | 1.850 | 14.572 |
| 143 | 3.628 | 27.064 |
| 144 | 2.613 | 20.101 |
| 145 | 1.927 | 12.938 |
| 146 | 3.654 | 29.801 |
| 147 | 2.419 | 17.967 |
| 148 | 2.581 | 15.080 |
| 149 | 1.552 | 10.112 |
| 150 | 3.511 | 23.568 |
| 151 | 3.078 | 27.364 |
| 152 | 3.739 | 27.780 |

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 96.1 | 91.4 | 97.9 | 95.3 | 94.1 | 95.7 |
| 1_3 | 94.6 | 94.3 | 94.7 | 96.9 | 88.2 | 100 |
| 1_4 | 94.6 | 91.4 | 95.7 | 92.2 | 88.2 | 93.6 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 1_5 | 93.8 | 88.6 | 95.7 | 95.3 | 94.1 | 95.7 |
| 1_6 | 93 | 88.6 | 94.7 | 92.2 | 88.2 | 93.6 |
| 1_7 | 96.1 | 94.3 | 96.8 | 93.8 | 88.2 | 95.7 |
| 1_8 | 94.6 | 91.4 | 95.7 | 93.8 | 88.2 | 95.7 |
| 1_9 | 93.8 | 88.6 | 95.7 | 93.8 | 88.2 | 95.7 |
| 1_10 | 93.8 | 88.6 | 95.7 | 95.3 | 94.1 | 95.7 |
| 1_11 | 96.1 | 97.1 | 95.7 | 95.3 | 94.1 | 95.7 |
| 1_12 | 94.6 | 94.3 | 94.7 | 96.9 | 94.1 | 97.9 |
| 1_13 | 96.1 | 91.4 | 97.9 | 95.3 | 88.2 | 97.9 |
| 1_14 | 93.8 | 85.7 | 96.8 | 92.2 | 88.2 | 93.6 |
| 1_15 | 94.6 | 91.4 | 95.7 | 95.3 | 88.2 | 97.9 |
| 1_16 | 96.9 | 94.3 | 97.9 | 92.2 | 88.2 | 93.6 |
| 1_17 | 93 | 85.7 | 95.7 | 92.2 | 88.2 | 93.6 |
| 1_18 | 93.8 | 88.6 | 95.7 | 95.3 | 88.2 | 97.9 |
| 1_19 | 93.8 | 88.6 | 95.7 | 92.2 | 88.2 | 93.6 |
| 1_20 | 93 | 85.7 | 95.7 | 95.3 | 94.1 | 95.7 |
| 1_21 | 91.5 | 77.1 | 96.8 | 96.9 | 88.2 | 100 |
| 1_22 | 93 | 85.7 | 95.7 | 93.8 | 94.1 | 93.6 |
| 1_23 | 91.5 | 82.9 | 94.7 | 92.2 | 88.2 | 93.6 |
| 1_24 | 93.8 | 88.6 | 95.7 | 92.2 | 88.2 | 93.6 |
| 1_25 | 93.8 | 88.6 | 95.7 | 95.3 | 94.1 | 95.7 |
| 1_26 | 93.8 | 88.6 | 95.7 | 95.3 | 94.1 | 95.7 |
| 1_27 | 92.2 | 82.9 | 95.7 | 93.8 | 94.1 | 93.6 |
| 1_28 | 93.8 | 88.6 | 95.7 | 93.8 | 88.2 | 95.7 |
| 1_29 | 93 | 88.6 | 94.7 | 95.3 | 94.1 | 95.7 |
| 1_30 | 93 | 85.7 | 95.7 | 93.8 | 88.2 | 95.7 |
| 1_31 | 94.6 | 91.4 | 95.7 | 93.8 | 94.1 | 93.6 |
| 1_32 | 93.8 | 91.4 | 94.7 | 90.6 | 88.2 | 91.5 |
| 1_33 | 94.6 | 91.4 | 95.7 | 95.3 | 94.1 | 95.7 |
| 1_34 | 96.1 | 94.3 | 96.8 | 93.8 | 88.2 | 95.7 |
| 1_35 | 94.6 | 91.4 | 95.7 | 95.3 | 88.2 | 97.9 |
| 1_36 | 93 | 85.7 | 95.7 | 90.6 | 88.2 | 91.5 |
| 1_37 | 93 | 88.6 | 94.7 | 95.3 | 88.2 | 97.9 |
| 1_38 | 93 | 82.9 | 96.8 | 93.8 | 88.2 | 95.7 |
| 1_39 | 92.2 | 82.9 | 95.7 | 95.3 | 94.1 | 95.7 |
| 1_40 | 93 | 85.7 | 95.7 | 92.2 | 88.2 | 93.6 |
| 1_41 | 94.6 | 88.6 | 96.8 | 92.2 | 88.2 | 93.6 |
| 1_42 | 95.3 | 91.4 | 96.8 | 98.4 | 94.1 | 100 |
| 1_43 | 94.6 | 91.4 | 95.7 | 92.2 | 88.2 | 93.6 |
| 1_44 | 93 | 85.7 | 95.7 | 93.8 | 88.2 | 95.7 |
| 1_45 | 94.6 | 88.6 | 96.8 | 92.2 | 88.2 | 93.6 |
| 1_46 | 93 | 85.7 | 95.7 | 93.8 | 88.2 | 95.7 |
| 1_47 | 93 | 85.7 | 95.7 | 92.2 | 88.2 | 93.6 |
| 1_48 | 94.6 | 91.4 | 95.7 | 93.8 | 88.2 | 95.7 |
| 1_49 | 93.8 | 85.7 | 96.8 | 93.8 | 88.2 | 95.7 |
| 1_50 | 95.3 | 91.4 | 96.8 | 93.8 | 94.1 | 93.6 |
| 1_51 | 93.8 | 85.7 | 96.8 | 95.3 | 88.2 | 97.9 |
| 1_52 | 93.8 | 88.6 | 95.7 | 92.2 | 88.2 | 93.6 |
| 1_53 | 92.2 | 85.7 | 94.7 | 93.8 | 94.1 | 93.6 |
| 1_54 | 92.2 | 82.9 | 95.7 | 96.9 | 94.1 | 97.9 |
| 1_55 | 92.2 | 82.9 | 95.7 | 92.2 | 88.2 | 93.6 |
| 1_56 | 92.2 | 85.7 | 94.7 | 92.2 | 88.2 | 93.6 |
| 1_57 | 93 | 85.7 | 95.7 | 96.9 | 94.1 | 97.9 |
| 1_58 | 93 | 85.7 | 95.7 | 93.8 | 88.2 | 95.7 |
| 1_59 | 92.2 | 85.7 | 94.7 | 93.8 | 88.2 | 95.7 |
| 1_60 | 92.2 | 85.7 | 94.7 | 90.6 | 88.2 | 91.5 |
| 1_61 | 93 | 85.7 | 95.7 | 93.8 | 88.2 | 95.7 |
| 1_62 | 93 | 85.7 | 95.7 | 93.8 | 88.2 | 95.7 |
| 1_63 | 93.8 | 91.4 | 94.7 | 93.8 | 88.2 | 95.7 |
| 1_64 | 93.8 | 88.6 | 95.7 | 92.2 | 88.2 | 93.6 |
| 1_65 | 93 | 85.7 | 95.7 | 92.2 | 88.2 | 93.6 |
| 1_66 | 91.5 | 82.9 | 94.7 | 95.3 | 88.2 | 97.9 |
| 1_67 | 92.2 | 85.7 | 94.7 | 93.8 | 88.2 | 95.7 |
| 1_68 | 93 | 85.7 | 95.7 | 92.2 | 88.2 | 93.6 |
| 1_69 | 93 | 82.9 | 96.8 | 93.8 | 88.2 | 95.7 |
| 1_70 | 93.8 | 94.3 | 93.6 | 95.3 | 94.1 | 95.7 |
| 1_71 | 93 | 85.7 | 95.7 | 92.2 | 88.2 | 93.6 |
| 1_72 | 91.5 | 85.7 | 93.6 | 90.6 | 88.2 | 91.5 |
| 1_73 | 93 | 85.7 | 95.7 | 92.2 | 88.2 | 93.6 |
| 1_74 | 94.6 | 88.6 | 96.8 | 92.2 | 88.2 | 93.6 |
| 1_75 | 92.2 | 85.7 | 94.7 | 92.2 | 88.2 | 93.6 |
| 1_76 | 92.2 | 82.9 | 95.7 | 93.8 | 88.2 | 95.7 |
| 1_77 | 93.8 | 88.6 | 95.7 | 92.2 | 88.2 | 93.6 |
| 1_78 | 94.6 | 91.4 | 95.7 | 93.8 | 94.1 | 93.6 |
| 1_79 | 95.3 | 91.4 | 96.8 | 96.9 | 94.1 | 97.9 |

TABLE 6-continued

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 1_80 | 93 | 85.7 | 95.7 | 92.2 | 88.2 | 93.6 |
| 1_81 | 93 | 85.7 | 95.7 | 92.2 | 88.2 | 93.6 |
| 1_82 | 93 | 85.7 | 95.7 | 92.2 | 88.2 | 93.6 |
| 1_83 | 93 | 85.7 | 95.7 | 92.2 | 88.2 | 93.6 |
| 1_84 | 94.6 | 91.4 | 95.7 | 95.3 | 94.1 | 95.7 |
| 1_85 | 94.6 | 91.4 | 95.7 | 95.3 | 88.2 | 97.9 |
| 1_86 | 93 | 85.7 | 95.7 | 92.2 | 88.2 | 93.6 |
| 1_87 | 93 | 85.3 | 95.7 | 92.2 | 88.2 | 93.6 |
| 1_88 | 91.5 | 80 | 95.7 | 96.9 | 94.1 | 97.9 |
| 1_89 | 93 | 85.7 | 95.7 | 92.2 | 94.1 | 91.5 |
| 1_90 | 94.6 | 91.4 | 95.7 | 92.2 | 88.2 | 93.6 |
| 1_91 | 92.2 | 82.9 | 95.7 | 93.8 | 88.2 | 95.7 |
| 1_92 | 92.2 | 82.9 | 95.7 | 92.2 | 88.2 | 93.6 |
| 1_93 | 93 | 85.7 | 95.7 | 92.2 | 88.2 | 93.6 |
| 1_94 | 92.2 | 85.7 | 94.7 | 93.8 | 88.2 | 95.7 |
| 1_95 | 95.3 | 91.4 | 96.8 | 93.8 | 88.2 | 95.7 |
| 1_96 | 94.6 | 88.6 | 96.8 | 90.6 | 88.2 | 91.5 |
| 1_97 | 94.6 | 91.4 | 95.7 | 92.2 | 88.2 | 93.6 |
| 1_98 | 92.2 | 82.9 | 95.7 | 93.8 | 88.2 | 95.7 |
| 1_99 | 93.8 | 91.4 | 94.7 | 95.3 | 94.1 | 95.7 |
| 1_100 | 94.6 | 88.6 | 96.8 | 90.6 | 88.2 | 91.5 |
| 1_101 | 93 | 85.7 | 95.7 | 92.2 | 88.2 | 93.6 |
| 1_102 | 94.6 | 88.6 | 96.8 | 95.3 | 94.1 | 95.7 |
| 1_103 | 93 | 85.7 | 95.7 | 93.8 | 88.2 | 95.7 |
| 1_104 | 93 | 82.9 | 96.8 | 95.3 | 88.2 | 97.9 |
| 1_105 | 92.2 | 85.7 | 94.7 | 92.2 | 88.2 | 93.6 |
| 1_106 | 93 | 88.6 | 94.7 | 95.3 | 88.2 | 97.9 |
| 1_107 | 92.2 | 85.7 | 94.7 | 92.2 | 94.1 | 91.5 |
| 1_108 | 93.8 | 88.6 | 95.7 | 92.2 | 88.2 | 93.6 |
| 1_109 | 93.8 | 85.7 | 96.8 | 92.2 | 88.2 | 93.6 |
| 1_110 | 93.8 | 88.6 | 95.7 | 95.3 | 94.1 | 95.7 |
| 1_111 | 93 | 85.7 | 95.7 | 93.8 | 88.2 | 95.7 |
| 1_112 | 91.5 | 82.9 | 94.7 | 92.2 | 88.2 | 93.6 |
| 1_113 | 93 | 85.7 | 95.7 | 92.2 | 88.2 | 93.6 |
| 1_114 | 93 | 85.7 | 95.7 | 92.2 | 88.2 | 93.6 |
| 1_115 | 92.2 | 85.7 | 94.7 | 95.3 | 88.2 | 97.9 |
| 1_116 | 93 | 88.6 | 94.7 | 93.8 | 94.1 | 93.6 |
| 1_117 | 93 | 88.6 | 94.7 | 93.8 | 88.2 | 95.7 |
| 1_118 | 93 | 85.7 | 95.7 | 93.8 | 88.2 | 95.7 |
| 1_119 | 93.8 | 85.7 | 96.8 | 93.8 | 94.1 | 93.6 |
| 1_120 | 92.2 | 82.9 | 95.7 | 95.3 | 88.2 | 97.9 |
| 1_121 | 93 | 85.7 | 95.7 | 93.8 | 88.2 | 95.7 |
| 1_122 | 93 | 85.7 | 95.7 | 92.2 | 88.2 | 93.6 |
| 1_123 | 93 | 85.7 | 95.7 | 93.8 | 88.2 | 95.7 |
| 1_124 | 91.5 | 80 | 95.7 | 92.2 | 88.2 | 93.6 |
| 1_125 | 94.6 | 88.6 | 96.8 | 93.8 | 94.1 | 93.6 |
| 1_126 | 93.8 | 85.7 | 96.8 | 92.2 | 88.2 | 93.6 |
| 1_127 | 93.8 | 88.6 | 95.7 | 93.8 | 88.2 | 95.7 |
| 1_128 | 93.8 | 91.4 | 94.7 | 92.2 | 88.2 | 93.6 |
| 1_129 | 93 | 85.7 | 95.7 | 92.2 | 88.2 | 93.6 |
| 1_130 | 93 | 82.9 | 96.8 | 95.3 | 88.2 | 97.9 |
| 1_131 | 90.7 | 82.9 | 93.6 | 93.8 | 88.2 | 95.7 |
| 1_132 | 93 | 85.7 | 95.7 | 92.2 | 88.2 | 93.6 |
| 1_133 | 94.6 | 88.6 | 96.8 | 95.3 | 88.2 | 97.9 |
| 1_134 | 93.8 | 88.6 | 95.7 | 95.3 | 94.1 | 95.7 |
| 1_135 | 93 | 85.7 | 95.7 | 93.8 | 88.2 | 95.7 |
| 1_136 | 96.9 | 97.1 | 96.8 | 93.8 | 94.1 | 93.6 |
| 1_137 | 91.5 | 80 | 95.7 | 92.2 | 88.2 | 93.6 |
| 1_138 | 93.8 | 88.6 | 95.7 | 93.8 | 94.1 | 93.6 |
| 1_139 | 92.2 | 85.7 | 94.7 | 96.9 | 94.1 | 97.9 |
| 1_140 | 94.6 | 88.6 | 96.8 | 92.2 | 88.2 | 93.6 |
| 1_141 | 95.3 | 91.4 | 96.8 | 93.8 | 88.2 | 95.7 |
| 1_142 | 93 | 85.7 | 95.7 | 92.2 | 88.2 | 93.6 |
| 1_143 | 92.2 | 82.9 | 95.7 | 92.2 | 88.2 | 93.6 |
| 1_144 | 93 | 85.7 | 95.7 | 92.2 | 88.2 | 93.6 |
| 1_145 | 93 | 85.7 | 95.7 | 92.2 | 88.2 | 93.6 |
| 1_146 | 93 | 85.7 | 95.7 | 93.8 | 88.2 | 95.7 |
| 1_147 | 93 | 85.7 | 95.7 | 92.2 | 88.2 | 93.6 |
| 1_148 | 93 | 85.7 | 95.7 | 93.8 | 88.2 | 95.7 |
| 1_149 | 92.2 | 82.9 | 95.7 | 93.8 | 88.2 | 95.7 |
| 1_150 | 93.8 | 88.6 | 95.7 | 96.9 | 94.1 | 97.9 |
| 1_151 | 93 | 85.7 | 95.7 | 93.8 | 88.2 | 95.7 |
| 1_152 | 92.2 | 85.7 | 94.7 | 92.2 | 88.2 | 93.6 |

Example 3

<Selection of Gene Marker Using all Samples and Method for Evaluating Prostate Cancer Discriminant Performance with Acquired Gene Marker>

In this Example, the samples in the training cohort and the validation cohort used in Examples 1 and 2 were integrated, and selection of a gene marker and evaluation of its prostate cancer discriminant performance were conducted using all of the samples.

Specifically, the miRNA expression levels in the serum of the 52 prostate cancer patients and the 141 healthy male subjects obtained in the preceding Reference Examples were normalized by quantile normalization. In order to acquire diagnostic markers with higher reliability, only genes that showed gene expression levels of $2^6$ or higher in 50% or more of the samples in either of the prostate cancer patient group or the healthy subject group were selected in the gene marker selection. In order to further acquire statistical significance for discriminating a prostate cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant. The obtained genes are described in Table 7. In this way, hsa-miR-4763-3p, hsa-miR-3656, hsa-miR-4488, hsa-miR-125a-3p, hsa-miR-1469, hsa-miR-1228-5p, hsa-miR-6798-5p, hsa-miR-1268b, hsa-miR-6732-5p, hsa-miR-1915-3p, hsa-miR-4433b-3p, hsa-miR-1207-5p, hsa-miR-4433-3p, hsa-miR-6879-5p, hsa-miR-4417, hsa-miR-30c-1-3p, hsa-miR-4638-5p, hsa-miR-6088, hsa-miR-4270, hsa-miR-6782-5p, hsa-miR-665, hsa-miR-486-5p, hsa-miR-4655-5p, hsa-miR-1275, hsa-miR-6806-5p, hsa-miR-614, hsa-miR-3937, hsa-miR-6752-5p, hsa-miR-6771-5p, hsa-miR-4450, hsa-miR-211-3p, hsa-miR-663a, hsa-miR-6842-5p, hsa-miR-7114-5p and hsa-miR-6779-5p genes, and the nucleotide sequences of SEQ ID NOs: 153 to 187 related thereto were found in addition to the genes described in Table 3. As with the nucleotide sequences of SEQ ID NOs: 1 to 152, the results obtained about the polynucleotides shown in the nucleotide sequences of SEQ ID NOs: 153 to 187 also showed that the measurement values were significantly lower (−) or higher (+) in the prostate cancer patient group than in the healthy subject group (Table 7). These results were able to be validated in the validation cohort. The presence or absence of prostate cancer in the newly obtained samples can be determined by the methods described in Examples 1 and 2 by using the gene expression level measurement values described in Table 7 either alone or in combination with the gene expression level measurement values described in Table 3.

TABLE 7

| SEQ ID NO: | Gene name | P value after Bonferroni correction | Expression level in prostate cancer patient with relative to healthy subject |
|---|---|---|---|
| 1 | hsa-miR-4443 | 1.11E−37 | + |
| 2 | hsa-miR-1908-5p | 1.13E−31 | + |
| 3 | hsa-miR-4257 | 6.48E−24 | − |
| 4 | hsa-miR-3197 | 1.28E−30 | + |
| 5 | hsa-miR-3188 | 5.67E−27 | + |
| 6 | hsa-miR-4649-5p | 3.70E−27 | − |
| 7 | hsa-miR-1343-3p | 7.09E−23 | − |
| 8 | hsa-miR-6861-5p | 1.80E−24 | − |
| 9 | hsa-miR-1343-5p | 2.82E−24 | + |
| 10 | hsa-miR-642b-3p | 1.07E−27 | − |
| 11 | hsa-miR-6741-5p | 6.82E−22 | − |
| 12 | hsa-miR-4745-5p | 1.13E−23 | − |
| 13 | hsa-miR-6826-5p | 3.61E−19 | − |
| 14 | hsa-miR-3663-3p | 3.08E−23 | − |
| 15 | hsa-miR-3131 | 3.50E−15 | − |
| 16 | hsa-miR-92a-2-5p | 4.74E−16 | + |
| 17 | hsa-miR-4258 | 5.92E−20 | − |
| 18 | hsa-miR-4448 | 7.18E−20 | + |
| 19 | hsa-miR-6125 | 2.60E−19 | + |
| 20 | hsa-miR-6880-5p | 4.86E−19 | + |
| 21 | hsa-miR-6132 | 2.01E−19 | + |
| 22 | hsa-miR-4467 | 7.91E−20 | + |
| 23 | hsa-miR-6749-5p | 1.81E−19 | − |
| 24 | hsa-miR-2392 | 2.70E−11 | + |
| 25 | hsa-miR-1273g-3p | 3.27E−19 | − |
| 26 | hsa-miR-4746-3p | 4.55E−21 | + |
| 27 | hsa-miR-1914-3p | 8.27E−15 | − |
| 28 | hsa-miR-7845-5p | 5.79E−19 | + |
| 29 | hsa-miR-6726-5p | 7.72E−19 | − |
| 30 | hsa-miR-128-2-5p | 5.33E−19 | − |
| 31 | hsa-miR-4651 | 5.90E−18 | − |
| 32 | hsa-miR-6765-3p | 8.39E−16 | − |
| 33 | hsa-miR-3185 | 1.60E−19 | + |
| 34 | hsa-miR-4792 | 1.45E−17 | + |
| 35 | hsa-miR-6887-5p | 1.16E−14 | − |
| 36 | hsa-miR-5572 | 4.90E−16 | + |
| 37 | hsa-miR-3619-3p | 2.51E−16 | − |
| 38 | hsa-miR-6780b-5p | 1.37E−16 | + |
| 39 | hsa-miR-4707-5p | 1.51E−17 | + |
| 40 | hsa-miR-8063 | 5.05E−20 | − |
| 41 | hsa-miR-4454 | 6.07E−14 | − |
| 42 | hsa-miR-4525 | 6.00E−19 | − |
| 43 | hsa-miR-7975 | 6.13E−15 | − |
| 44 | hsa-miR-744-5p | 5.25E−18 | + |
| 45 | hsa-miR-3135b | 1.17E−09 | − |
| 46 | hsa-miR-4648 | 9.53E−17 | + |
| 47 | hsa-miR-6816-5p | 2.60E−15 | + |
| 48 | hsa-miR-4741 | 5.52E−16 | + |
| 49 | hsa-miR-7150 | 2.35E−13 | + |
| 50 | hsa-miR-6791-5p | 6.63E−17 | + |
| 51 | hsa-miR-1247-3p | 6.77E−13 | + |
| 52 | hsa-miR-7977 | 2.22E−14 | − |
| 53 | hsa-miR-4497 | 4.39E−16 | − |
| 54 | hsa-miR-6090 | 4.58E−17 | + |
| 55 | hsa-miR-6781-5p | 1.08E−11 | + |
| 56 | hsa-miR-6870-5p | 4.41E−09 | + |
| 57 | hsa-miR-6729-5p | 6.57E−14 | + |
| 58 | hsa-miR-4530 | 1.48E−10 | + |
| 59 | hsa-miR-7847-3p | 6.31E−12 | − |
| 60 | hsa-miR-6825-5p | 3.31E−12 | + |
| 61 | hsa-miR-4674 | 7.19E−14 | − |
| 62 | hsa-miR-3917 | 1.78E−12 | − |
| 63 | hsa-miR-4707-3p | 6.32E−12 | + |
| 64 | hsa-miR-6885-5p | 1.69E−14 | − |
| 65 | hsa-miR-6722-3p | 1.09E−10 | + |
| 66 | hsa-miR-4516 | 9.57E−15 | − |
| 67 | hsa-miR-6757-5p | 1.02E−11 | − |
| 68 | hsa-miR-6840-3p | 6.73E−14 | − |
| 69 | hsa-miR-5195-3p | 1.21E−11 | − |
| 70 | hsa-miR-6756-5p | 1.46E−15 | − |
| 71 | hsa-miR-6800-5p | 3.18E−11 | + |
| 72 | hsa-miR-6727-5p | 2.88E−09 | − |
| 73 | hsa-miR-6126 | 4.50E−12 | + |
| 74 | hsa-miR-6872-3p | 4.58E−09 | − |
| 75 | hsa-miR-4446-3p | 1.90E−12 | − |
| 76 | hsa-miR-1268a | 1.09E−13 | + |
| 77 | hsa-miR-1908-3p | 2.75E−10 | − |
| 78 | hsa-miR-3679-5p | 4.14E−15 | + |
| 79 | hsa-miR-4534 | 1.65E−06 | + |
| 80 | hsa-miR-4675 | 8.56E−11 | − |
| 81 | hsa-miR-7108-5p | 5.97E−11 | + |
| 82 | hsa-miR-6799-5p | 1.21E−10 | + |
| 83 | hsa-miR-4695-5p | 2.08E−13 | + |
| 84 | hsa-miR-3178 | 1.33E−10 | + |

TABLE 7-continued

| SEQ ID NO: | Gene name | P value after Bonferroni correction | Expression level in prostate cancer patient with relative to healthy subject |
|---|---|---|---|
| 85 | hsa-miR-5090 | 6.85E−11 | − |
| 86 | hsa-miR-3180 | 1.01E−09 | + |
| 87 | hsa-miR-1237-5p | 7.78E−13 | + |
| 88 | hsa-miR-4758-5p | 1.97E−09 | − |
| 89 | hsa-miR-3184-5p | 4.70E−10 | + |
| 90 | hsa-miR-4286 | 2.39E−08 | − |
| 91 | hsa-miR-6784-5p | 1.24E−07 | + |
| 92 | hsa-miR-6768-5p | 2.85E−07 | + |
| 93 | hsa-miR-6785-5p | 2.78E−10 | − |
| 94 | hsa-miR-4706 | 3.20E−06 | − |
| 95 | hsa-miR-711 | 7.50E−11 | + |
| 96 | hsa-miR-1260a | 3.06E−07 | − |
| 97 | hsa-miR-6746-5p | 6.04E−06 | − |
| 98 | hsa-miR-6089 | 1.19E−08 | + |
| 99 | hsa-miR-6821-5p | 4.27E−10 | + |
| 100 | hsa-miR-4667-5p | 9.12E−07 | + |
| 101 | hsa-miR-8069 | 1.81E−09 | + |
| 102 | hsa-miR-4726-5p | 2.71E−05 | − |
| 103 | hsa-miR-6124 | 9.11E−05 | + |
| 104 | hsa-miR-4532 | 2.46E−09 | − |
| 105 | hsa-miR-4486 | 6.30E−09 | + |
| 106 | hsa-miR-4728-5p | 8.48E−09 | − |
| 107 | hsa-miR-4508 | 1.66E−06 | + |
| 108 | hsa-miR-128-1-5p | 2.04E−08 | + |
| 109 | hsa-miR-4513 | 1.44E−06 | − |
| 110 | hsa-miR-6795-5p | 1.12E−06 | − |
| 111 | hsa-miR-4689 | 8.95E−09 | − |
| 112 | hsa-miR-6763-5p | 2.59E−09 | + |
| 113 | hsa-miR-8072 | 1.32E−07 | + |
| 114 | hsa-miR-6765-5p | 4.48E−05 | + |
| 115 | hsa-miR-4419b | 1.22E−04 | − |
| 116 | hsa-miR-7641 | 3.99E−08 | − |
| 117 | hsa-miR-3928-3p | 7.30E−06 | + |
| 118 | hsa-miR-1227-5p | 6.47E−06 | + |
| 119 | hsa-miR-4492 | 3.11E−10 | − |
| 120 | hsa-miR-296-3p | 1.31E−06 | − |
| 121 | hsa-miR-6769a-5p | 2.26E−05 | − |
| 122 | hsa-miR-6889-5p | 5.29E−04 | + |
| 123 | hsa-miR-4632-5p | 3.39E−05 | + |
| 124 | hsa-miR-4505 | 6.21E−06 | + |
| 125 | hsa-miR-3154 | 1.41E−05 | + |
| 126 | hsa-miR-3648 | 2.83E−06 | − |
| 127 | hsa-miR-4442 | 2.03E−07 | − |
| 128 | hsa-miR-3141 | 3.73E−07 | + |
| 129 | hsa-miR-7113-3p | 4.11E−05 | + |
| 130 | hsa-miR-6819-5p | 5.08E−03 | − |
| 131 | hsa-miR-3195 | 1.18E−04 | + |
| 132 | hsa-miR-1199-5p | 8.59E−05 | − |
| 133 | hsa-miR-6738-5p | 2.49E−05 | − |
| 134 | hsa-miR-4656 | 1.45E−05 | − |
| 135 | hsa-miR-6820-5p | 3.40E−04 | + |
| 136 | hsa-miR-615-5p | 1.98E−14 | − |
| 137 | hsa-miR-486-3p | 9.28E−17 | − |
| 138 | hsa-miR-1225-3p | 3.41E−16 | + |
| 139 | hsa-miR-760 | 4.58E−15 | − |
| 140 | hsa-miR-187-5p | 7.21E−11 | − |
| 141 | hsa-miR-1203 | 8.06E−14 | + |
| 142 | hsa-miR-7110-5p | 7.39E−11 | + |
| 143 | hsa-miR-371a-5p | 3.27E−12 | − |
| 144 | hsa-miR-939-5p | 2.77E−11 | + |
| 145 | hsa-miR-575 | 1.85E−10 | + |
| 146 | hsa-miR-92b-5p | 7.45E−16 | + |
| 147 | hsa-miR-887-3p | 3.99E−12 | + |
| 148 | hsa-miR-920 | 1.63E−05 | − |
| 149 | hsa-miR-1915-5p | 1.24E−07 | − |
| 150 | hsa-miR-1231 | 1.35E−07 | + |
| 151 | hsa-miR-663b | 6.03E−07 | − |
| 152 | hsa-miR-1225-5p | 2.89E−06 | + |
| 153 | hsa-miR-4763-3p | 1.50E−07 | + |
| 154 | hsa-miR-3656 | 2.20E−06 | + |
| 155 | hsa-miR-4488 | 3.80E−06 | + |
| 156 | hsa-miR-125a-3p | 8.47E−06 | − |
| 157 | hsa-miR-1469 | 8.73E−06 | + |
| 158 | hsa-miR-1228-5p | 1.34E−05 | + |
| 159 | hsa-miR-6798-5p | 1.73E−05 | + |

TABLE 7-continued

| SEQ ID NO: | Gene name | P value after Bonferroni correction | Expression level in prostate cancer patient with relative to healthy subject |
|---|---|---|---|
| 160 | hsa-miR-1268b | 1.93E−05 | + |
| 161 | hsa-miR-6732-5p | 2.42E−05 | + |
| 162 | hsa-miR-1915-3p | 3.96E−05 | + |
| 163 | hsa-miR-4433b-3p | 4.24E−05 | + |
| 164 | hsa-miR-1207-5p | 4.14E−05 | + |
| 165 | hsa-miR-4433-3p | 4.84E−05 | + |
| 166 | hsa-miR-6879-5p | 5.79E−05 | + |
| 167 | hsa-miR-4417 | 8.44E−05 | + |
| 168 | hsa-miR-30c-1-3p | 8.49E−05 | + |
| 169 | hsa-miR-4638-5p | 7.97E−05 | + |
| 170 | hsa-miR-6088 | 2.07E−04 | − |
| 171 | hsa-miR-4270 | 2.44E−04 | − |
| 172 | hsa-miR-6782-5p | 6.53E−04 | + |
| 173 | hsa-miR-665 | 7.52E−04 | − |
| 174 | hsa-miR-486-5p | 9.25E−04 | + |
| 175 | hsa-miR-4655-5p | 1.04E−03 | + |
| 176 | hsa-miR-1275 | 1.11E−03 | + |
| 177 | hsa-miR-6806-5p | 1.78E−03 | − |
| 178 | hsa-miR-614 | 1.92E−03 | − |
| 179 | hsa-miR-3937 | 2.41E−03 | + |
| 180 | hsa-miR-6752-5p | 2.47E−03 | + |
| 181 | hsa-miR-6771-5p | 3.30E−03 | − |
| 182 | hsa-miR-4450 | 3.79E−03 | + |
| 183 | hsa-miR-211-3p | 6.22E−03 | − |
| 184 | hsa-miR-663a | 5.44E−03 | + |
| 185 | hsa-miR-6842-5p | 8.58E−03 | + |
| 186 | hsa-miR-7114-5p | 8.30E−03 | − |
| 187 | hsa-miR-6779-5p | 8.35E−03 | − |

Example 4

<Method for Evaluating Prostate Cancer-Specific Discriminant Performance with Combination of Multiple Gene Markers Using Samples in the Validation Cohort>

In this Example, gene expression levels of miRNAs in serum were compared between prostate cancer patients and a control group that consists of healthy subjects and breast cancer patients, in the same way as the method described in Example 1 in the training cohort obtained in Reference Example 2 to select a statistically significant gene for diagnosis. Polynucleotides consisting of the nucleotide sequences represented by SEQ ID NOs: 580 to 611 thus newly selected were each further combined with the gene markers selected in Example 1 to study a method for evaluating prostate cancer-specific discriminant performance.

Specifically, first, the miRNA expression levels in the training cohort and the validation cohort obtained in Reference Example 2 mentioned above were combined and normalized by quantile normalization. Next, Fisher's linear discriminant analysis was conducted as to combinations of 1 to 4 expression level measurement values comprising at least one or more of the expression level measurement values of the polynucleotides consisting of the nucleotide sequences represented by SEQ ID NOs: 1 to 187, 580 to 611, to construct a discriminant for determining the presence or absence of prostate cancer. Next, accuracy, sensitivity, and specificity in the validation cohort obtained in Reference Example 2 were calculated using the discriminant thus prepared, with the prostate cancer patient group as a positive sample group, and the healthy subject group and the breast cancer patient group as a negative sample group. The discriminant performance of the selected polynucleotides was validated using the independent samples.

Most of polynucleotides consisting of the nucleotide sequences represented by these SEQ ID NOs (SEQ ID NOs: 1 to 187, and 580 to 611 corresponding to the miRNA markers of Table 1) or complementary sequences thereof mentioned above were able to provide relatively high accuracy, sensitivity, and specificity in the determination of the presence or absence of prostate cancer, and furthermore, were able to specifically discriminate prostate cancer from the other cancers. For example, among the combinations of multiple polynucleotides selected from the group consisting of polynucleotides consisting of the nucleotide sequences represented by SEQ ID NOs: 1, 3, 4, 5, 6, 7, 9, 10, 12, 14, 15, 16, 17, 18, 20, 24, 29, 35, 37, 42, 51, 55, 58, 61, 63, 64, 67, 70, 72, 79, 82, 89, 91, 97, 98, 101, 103, 104, 112, 113, 114, 116, 119, 126, 135, 136, 139, 140, 141, 145, 147, 154, 155, 156, 158, 169, 173, 175, 178, 182, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610 and 611, or complementary sequences thereof (the cancer type-specific polynucleotide group 1) as polynucleotides capable of specifically binding to target markers, combinations comprising at least one or more polynucleotide(s) selected from the group consisting of polynucleotides of SEQ ID NOs: 1, 12, 16, 37, 42, 63, 119, 126, 139, 173, 178, 599, 609 and 611 (the cancer type-specific polynucleotide group 2) that were included in the cancer type-specific polynucleotide group 1, were able to specifically discriminate prostate cancer from the other cancers with high accuracy.

The number of the aforementioned polynucleotides with cancer type specificity in the combination can be 1, 2, 3, 4, 5, 6, 7, 8, 9, 10 or more for the combination. The combinations of 4 or more of these polynucleotides were able to exhibit discriminant accuracy of 85% or higher.

Specifically, the discriminant accuracy of the measurement using the polynucleotide consisting of the nucleotide sequence represented by SEQ ID NO: 1 or a complementary sequence thereof is shown in Table 8-1. The measurement using the combination of one polynucleotide comprising at least one polynucleotide consisting of the nucleotide sequence represented by SEQ ID NO: 1 or a complementary sequence thereof exhibited accuracy of 94.4% in the training cohort and accuracy of 91.8% in the validation cohort. Also, for example, the measurement using the combination of two polynucleotides comprising at least one polynucleotide consisting of the nucleotide sequence represented by SEQ ID NO: 1 or a complementary sequence thereof exhibited the highest accuracy of 96.4% in the training cohort and the highest accuracy of 90.8% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 98.5% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 95.4% in the training cohort and the highest accuracy of 92.9% in the validation cohort.

The discriminant accuracy of the measurement using the polynucleotide consisting of the nucleotide sequence represented by SEQ ID NO: 12 or a complementary sequence thereof is shown in Table 8-2. The measurement using the combination of one polynucleotide comprising at least one polynucleotide consisting of the nucleotide sequence represented by SEQ ID NO: 12 or a complementary sequence thereof exhibited accuracy of 65.5% in the training cohort and accuracy of 56.1% in the validation cohort. Also, for example, the measurement using the combination of two polynucleotides comprising at least one polynucleotide consisting of the nucleotide sequence represented by SEQ ID NO: 12 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 12 or a complementary sequence thereof exhibited the highest accuracy of 98.0% in the training cohort and the highest accuracy of 93.9% in the validation cohort. Furthermore, for example, the measurement using the combinations of four polynucleotides comprising at least one polynucleotide consisting of the nucleotide sequence represented by SEQ ID NO: 12 or a complementary sequence thereof exhibited the highest accuracy of 98.5% in the training cohort and the highest accuracy of 94.9% in the validation cohort.

The discriminant accuracy of the measurement using the polynucleotide consisting of the nucleotide sequence represented by SEQ ID NO: 16 or a complementary sequence thereof is shown in Table 8-3. The measurement using the combination of one polynucleotide comprising at least one polynucleotide consisting of the nucleotide sequence represented by SEQ ID NO: 16 or a complementary sequence thereof exhibited accuracy of 71.6% in the training cohort and accuracy of 74.5% in the validation cohort. Also, for example, the measurement using the combination of two polynucleotides comprising at least one polynucleotide consisting of the nucleotide sequence represented by SEQ ID NO: 16 or a complementary sequence thereof exhibited the highest accuracy of 95.4% in the training cohort and the highest accuracy of 93.9% in the validation cohort. Furthermore, for example, the measurement using the combinations of three polynucleotides comprising at least one polynucleotide consisting of the nucleotide sequence represented by SEQ ID NO: 16 or a complementary sequence thereof exhibited the highest accuracy of 97.5% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 16 or a complementary sequence thereof exhibited the highest accuracy of 98.0% in the training cohort and the highest accuracy of 88.8% in the validation cohort.

The discriminant accuracy of the measurement using the polynucleotide consisting of the nucleotide sequence represented by SEQ ID NO: 37 or a complementary sequence thereof is shown in Table 8-4. The measurement using the combination of one polynucleotide comprising at least one polynucleotide consisting of the nucleotide sequence represented by SEQ ID NO: 37 or a complementary sequence thereof exhibited accuracy of 73.6% in the training cohort and accuracy of 72.4% in the validation cohort. Also, for example, the measurement using the combination of two polynucleotides comprising at least one polynucleotide consisting of the nucleotide sequence represented by SEQ ID NO: 37 or a complementary sequence thereof exhibited the highest accuracy of 95.9% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 37 or a complementary sequence thereof exhibited the highest accuracy of 97.0% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 37 or a complementary sequence thereof exhibited the highest accuracy of 97.0% in the training cohort and the highest accuracy of 89.8% in the validation cohort.

The discriminant accuracy of the measurement using the polynucleotide consisting of the nucleotide sequence represented by SEQ ID NO: 42 or a complementary sequence thereof is shown in Table 8-5. The measurement using the combination of one polynucleotide comprising at least one polynucleotide consisting of the nucleotide sequence represented by SEQ ID NO: 42 or a complementary sequence thereof exhibited accuracy of 57.4% in the training cohort and accuracy of 59.2% in the validation cohort. Also, for example, the measurement using the combination of two polynucleotides comprising at least one polynucleotide consisting of the nucleotide sequence represented by SEQ ID NO: 42 or a complementary sequence thereof exhibited the highest accuracy of 95.4% in the training cohort and the highest accuracy of 93.9% in the validation cohort. Furthermore, for example, the measurement using the combinations of three polynucleotides comprising at least one polynucleotide consisting of the nucleotide sequence represented by SEQ ID NO: 42 or a complementary sequence thereof exhibited the highest accuracy of 97.5% in the training cohort and the highest accuracy of 95.9% in the validation cohort. Furthermore, for example, the measurement using the combinations of four polynucleotides comprising at least one polynucleotide consisting of the nucleotide sequence represented by SEQ ID NO: 42 or a complementary sequence thereof exhibited the highest accuracy of 96.9% in the training cohort and the highest accuracy of 94.9% in the validation cohort.

The discriminant accuracy of the measurement using the polynucleotide consisting of the nucleotide sequence represented by SEQ ID NO: 63 or a complementary sequence thereof is shown in Table 8-6. The measurement using the combination of one polynucleotide comprising at least one polynucleotide consisting of the nucleotide sequence represented by SEQ ID NO: 63 or a complementary sequence thereof exhibited accuracy of 72.6% in the training cohort and accuracy of 73.5% in the validation cohort. Also, for example, the measurement using the combination of two polynucleotides comprising at least one polynucleotide consisting of the nucleotide sequence represented by SEQ ID NO: 63 or a complementary sequence thereof exhibited the highest accuracy of 94.9% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 63 or a complementary sequence thereof exhibited the highest accuracy of 95.9% in the training cohort and the highest accuracy of 95.9% in the validation cohort. Furthermore, for example, the measurement using the combinations of four polynucleotides comprising at least one polynucleotide consisting of the nucleotide sequence represented by SEQ ID NO: 63 or a complementary sequence thereof exhibited the highest accuracy of 94.4% in the training cohort and the highest accuracy of 89.8% in the validation cohort.

The discriminant accuracy of the measurement using the polynucleotide consisting of the nucleotide sequence represented by SEQ ID NO: 119 or a complementary sequence thereof is shown in Table 8-7. The measurement using the combination of one polynucleotide comprising at least one polynucleotide consisting of the nucleotide sequence represented by SEQ ID NO: 119 or a complementary sequence thereof exhibited accuracy of 46.9% in the training cohort and accuracy of 48.0% in the validation cohort. Also, for example, the measurement using the combination of two polynucleotides comprising at least one polynucleotide consisting of the nucleotide sequence represented by SEQ ID NO: 119 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 119 or a complementary sequence thereof exhibited the highest accuracy of 97.4% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 119 or a complementary sequence thereof exhibited the highest accuracy of 96.4% in the training cohort and the highest accuracy of 89.8% in the validation cohort.

The discriminant accuracy of the measurement using the polynucleotide consisting of the nucleotide sequence represented by SEQ ID NO: 126 or a complementary sequence thereof is shown in Table 8-8. The measurement using the combination of one polynucleotide comprising at least one polynucleotide consisting of the nucleotide sequence represented by SEQ ID NO: 126 or a complementary sequence thereof exhibited accuracy of 66.0% in the training cohort and accuracy of 53.1% in the validation cohort. Also, for example, the measurement using the combination of two polynucleotides comprising at least one polynucleotide consisting of the nucleotide sequence represented by SEQ ID NO: 126 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited the highest accuracy of 96.4% in the training cohort and the highest accuracy of 90.8% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited the highest accuracy of 93.9% in the training cohort and the highest accuracy of 91.8% in the validation cohort.

The discriminant accuracy of the measurement using the polynucleotide consisting of the nucleotide sequence represented by SEQ ID NO: 139 or a complementary sequence thereof is shown in Table 8-9. The measurement using the combination of one polynucleotide comprising at least one polynucleotide consisting of the nucleotide sequence represented by SEQ ID NO: 139 or a complementary sequence thereof exhibited accuracy of 43.7% in the training cohort and accuracy of 40.8% in the validation cohort. Also, for example, the measurement using the combination of two polynucleotides comprising at least one polynucleotide consisting of the nucleotide sequence represented by SEQ ID NO: 139 or a complementary sequence thereof exhibited the highest accuracy of 94.4% in the training cohort and the highest accuracy of 92.9% in the validation cohort. Furthermore, for example, the measurement using the combinations of three polynucleotides comprising at least one polynucleotide consisting of the nucleotide sequence represented by SEQ ID NO: 139 or a complementary sequence thereof exhibited the highest accuracy of 96.4% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 139 or a complementary sequence thereof exhibited the highest accuracy of 92.4% in the training cohort and the highest accuracy of 91.8% in the validation cohort.

The discriminant accuracy of the measurement using the polynucleotide consisting of the nucleotide sequence represented by SEQ ID NO: 173 or a complementary sequence thereof is shown in Table 8-10. The measurement using the combination of one polynucleotide comprising at least one polynucleotide consisting of the nucleotide sequence represented by SEQ ID NO: 173 or a complementary sequence thereof exhibited accuracy of 43.7% in the training cohort and accuracy of 55.1% in the validation cohort. Also, for example, the measurement using the combination of two polynucleotides comprising at least one polynucleotide consisting of the nucleotide sequence represented by SEQ ID NO: 173 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 173 or a complementary sequence thereof exhibited the highest accuracy of 97.0% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 173 or a complementary sequence thereof exhibited the highest accuracy of 92.4% in the training cohort and the highest accuracy of 95.9% in the validation cohort.

The discriminant accuracy of the measurement using the polynucleotide consisting of the nucleotide sequence represented by SEQ ID NO: 178 or a complementary sequence thereof is shown in Table 8-11. The measurement using the combination of one polynucleotide comprising at least one polynucleotide consisting of the nucleotide sequence represented by SEQ ID NO: 178 or a complementary sequence thereof exhibited accuracy of 68.0% in the training cohort and the highest accuracy of 72.4% in the validation cohort. Also, for example, the measurement using the combination of two polynucleotides comprising at least one polynucleotide consisting of the nucleotide sequence represented by SEQ ID NO: 178 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 178 or a complementary sequence thereof exhibited the highest accuracy of 96.4% in the training cohort and the highest accuracy of 94.9% in the validation cohort. Furthermore, for example, the measurement using the combinations of four polynucleotides comprising at least one polynucleotide consisting of the nucleotide sequence represented by SEQ ID NO: 178 or a complementary sequence thereof exhibited the highest accuracy of 96.4% in the training cohort and the highest accuracy of 93.9% in the validation cohort.

The discriminant accuracy of the measurement using the polynucleotide consisting of the nucleotide sequence represented by SEQ ID NO: 599 or a complementary sequence thereof is shown in Table 8-12. The measurement using the combination of one polynucleotide comprising at least one polynucleotide consisting of the nucleotide sequence represented by SEQ ID NO: 599 or a complementary sequence thereof exhibited accuracy of 61.4% in the training cohort and the highest accuracy of 65.3% in the validation cohort. Also, for example, the measurement using the combination of two polynucleotides comprising at least one polynucleotide consisting of the nucleotide sequence represented by SEQ ID NO: 599 or a complementary sequence thereof exhibited the highest accuracy of 94.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 599 or a complementary sequence thereof exhibited the highest accuracy of 97.5% in the training cohort and the highest accuracy of 92.9% in the validation cohort. Furthermore, for example, the measurement using the combinations of four polynucleotides comprising at least one polynucleotide consisting of the nucleotide sequence represented by SEQ ID NO: 599 or a complementary sequence thereof exhibited the highest accuracy of 96.4% in the training cohort and the highest accuracy of 94.9% in the validation cohort.

The discriminant accuracy of the measurement using the polynucleotide consisting of the nucleotide sequence represented by SEQ ID NO: 609 or a complementary sequence thereof is shown in Table 8-13. The measurement using the combination of one polynucleotide comprising at least one polynucleotide consisting of the nucleotide sequence represented by SEQ ID NO: 609 or a complementary sequence thereof exhibited accuracy of 59.7% in the training cohort and accuracy of 65.3% in the validation cohort. Also, for example, the measurement using the combination of two polynucleotides comprising at least one polynucleotide consisting of the nucleotide sequence represented by SEQ ID NO: 609 or a complementary sequence thereof exhibited the highest accuracy of 95.4% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 609 or a complementary sequence thereof exhibited the highest accuracy of 96.4% in the training cohort and the highest accuracy of 91.8% in the validation cohort. Furthermore, for example, the measurement using the combinations of four polynucleotides comprising at least one polynucleotide consisting of the nucleotide sequence represented by SEQ ID NO: 609 or a complementary sequence thereof exhibited the highest accuracy of 96.4% in the training cohort and the highest accuracy of 88.8% in the validation cohort.

The discriminant accuracy of the measurement using the polynucleotide consisting of the nucleotide sequence represented by SEQ ID NO: 611 or a complementary sequence thereof is shown in Table 8-14. The measurement using the combination of one polynucleotide comprising at least one polynucleotide consisting of the nucleotide sequence represented by SEQ ID NO: 611 or a complementary sequence thereof exhibited accuracy of 55.8% in the training cohort and accuracy of 62.2% in the validation cohort. Also, for example, the measurement using the combination of two polynucleotides comprising at least one polynucleotide consisting of the nucleotide sequence represented by SEQ ID NO: 611 or a complementary sequence thereof exhibited the highest accuracy of 94.9% in the training cohort and the highest accuracy of 91.8% in the validation cohort. Furthermore, for example, the measurement using the combinations of three polynucleotides comprising at least one polynucleotide consisting of the nucleotide sequence represented by SEQ ID NO: 611 or a complementary sequence thereof exhibited the highest accuracy of 98.0% in the training cohort and the highest accuracy of 90.8% in the validation cohort. Furthermore, for example, the measurement using the combinations of four polynucleotides comprising at least one polynucleotide consisting of the nucleotide sequence represented by SEQ ID NO: 611 or a complementary sequence thereof exhibited the highest accuracy of 96.4% in the training cohort and the highest accuracy of 90.8% in the validation cohort.

Figure 4:
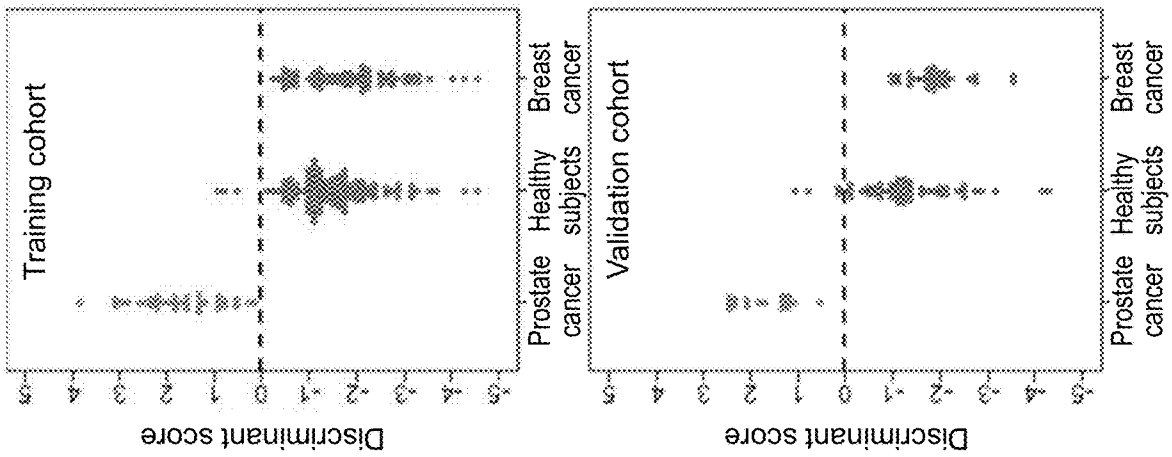
FIG. 4 Upper diagram: a discriminant ($1.34\times$miR-92a-2-5p$+1.56\times$miR-6820-5p$-1.29\times$miR-4745-5p$-0.76\times$miR-125a-3p$-4.31$) was prepared by use of Fisher's linear discriminant analysis from the measurement values of hsa-miR-4745-5p (SEQ ID NO: 12), hsa-miR-92a-2-5p (SEQ ID NO: 16), hsa-miR-6820-5p (SEQ ID NO: 135), and hsa-miR-125a-3p (SEQ ID NO: 156) in 35 prostate cancer patients, 99 healthy subjects, and 63 breast cancer patients selected as the training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared in the training cohort as to the measurement values of hsa-miR-4745-5p (SEQ ID NO: 12), hsa-miR-92a-2-5p (SEQ ID NO: 16), hsa-miR-6820-5p (SEQ ID NO: 135), and hsa-miR-125a-3p (SEQ ID NO: 156) in 17 prostate cancer patients, 51 healthy subjects, and 30 breast cancer patients selected as the validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 12, 16, 135, and 156 were compared among 35 prostate cancer patients, 99 healthy subjects, and 63 breast cancer patients in the training cohort. As a result, a scatter diagram that significantly separated the discriminant score of the prostate cancer patient group from the discriminant scores of the other groups was obtained in the training cohort (see the upper diagram of FIG. 4). These results were also reproducible in the validation cohort (see the lower diagram of FIG. 4).

TABLE 8-1

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 94.4 | 91.4 | 95.1 | 91.8 | 94.1 | 91.4 |
| 1_597 | 96.4 | 97.1 | 96.3 | 90.8 | 88.2 | 91.4 |
| 1_7_29 | 98.5 | 100 | 98.1 | 92.9 | 94.1 | 92.6 |
| 1_63_139_600 | 94.9 | 91.4 | 95.7 | 91.8 | 88.2 | 92.6 |
| 1_12_63_599 | 95.4 | 100 | 94.4 | 91.8 | 94.1 | 91.4 |
| 1_141_173_599 | 95.4 | 97.1 | 95.1 | 91.8 | 94.1 | 91.4 |
| 1_16_139_178 | 95.4 | 100 | 94.4 | 92.9 | 94.1 | 92.6 |
| 1_63_173_599 | 93.9 | 94.3 | 93.8 | 90.8 | 94.1 | 90.1 |

TABLE 8-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 12 | 65.5 | 74.3 | 63.6 | 56.1 | 70.6 | 53.1 |
| 1_12 | 94.9 | 94.3 | 95.1 | 91.8 | 94.1 | 91.4 |
| 1_7_12 | 98 | 100 | 97.5 | 93.9 | 94.1 | 93.8 |
| 12_42_63_609 | 92.3 | 97.1 | 91.3 | 89.8 | 100 | 87.7 |
| 12_16_135_156 | 98.5 | 100 | 98.1 | 94.9 | 100 | 93.8 |
| 12_16_169_178 | 94.9 | 100 | 93.8 | 88.8 | 100 | 86.4 |
| 12_16_139_601 | 94.9 | 100 | 93.8 | 91.8 | 100 | 90.1 |
| 12_16_42_607 | 97 | 100 | 96.3 | 93.9 | 100 | 92.6 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 16 | 71.6 | 97.1 | 66 | 74.5 | 100 | 69.1 |
| 1_16 | 95.4 | 94.3 | 95.7 | 93.9 | 94.1 | 93.8 |
| 1_16_42 | 97.5 | 97.1 | 97.5 | 94.9 | 94.1 | 95.1 |
| 16_18_139_178 | 94.4 | 97.1 | 93.8 | 92.9 | 94.1 | 92.6 |
| 12_16_37_178 | 98 | 100 | 97.5 | 88.8 | 100 | 86.4 |
| 12_16_37_599 | 97.5 | 100 | 96.9 | 89.8 | 100 | 87.7 |
| 12_16_37_97 | 96.4 | 100 | 95.7 | 89.8 | 100 | 87.7 |
| 12_14_16_599 | 95.4 | 100 | 94.4 | 87.8 | 94.1 | 86.4 |

TABLE 8-4

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 37 | 73.6 | 77.1 | 72.8 | 72.4 | 82.4 | 70.4 |
| 1_37 | 95.9 | 97.1 | 95.7 | 92.9 | 88.2 | 93.8 |
| 1_37_135 | 97 | 97.1 | 96.9 | 92.9 | 88.2 | 93.8 |
| 37_63_139_611 | 93.4 | 88.6 | 94.4 | 88.8 | 94.1 | 87.7 |
| 37_42_63_178 | 91.4 | 94.3 | 90.7 | 90.8 | 94.1 | 90.1 |
| 37_42_63_599 | 91.4 | 91.4 | 91.4 | 91.8 | 94.1 | 91.4 |
| 37_42_63_139 | 91.9 | 91.4 | 92 | 91.8 | 94.1 | 91.4 |
| 12_16_37_603 | 97 | 100 | 96.3 | 89.8 | 100 | 87.7 |

TABLE 8-5

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 42 | 57.4 | 48.6 | 59.3 | 59.2 | 52.9 | 60.5 |
| 1_42 | 95.4 | 94.3 | 95.7 | 93.9 | 94.1 | 93.8 |
| 1_3_42 | 97.5 | 94.3 | 98.1 | 95.9 | 94.1 | 96.3 |
| 42_63_607_611 | 90.4 | 88.6 | 90.7 | 90.8 | 100 | 88.9 |
| 42_63_609_611 | 90.8 | 88.6 | 91.3 | 91.8 | 100 | 90.1 |
| 42_63_173_599 | 89.3 | 91.4 | 88.9 | 90.8 | 100 | 88.9 |
| 12_16_42_609 | 96.9 | 100 | 96.3 | 94.9 | 100 | 93.8 |
| 42_63_91_609 | 88.3 | 91.4 | 87.6 | 90.8 | 100 | 88.9 |

TABLE 8-6

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 63 | 72.6 | 88.6 | 69.1 | 73.5 | 88.2 | 70.4 |
| 1_63 | 94.9 | 91.4 | 95.7 | 92.9 | 94.1 | 92.6 |
| 1_42_63 | 95.9 | 94.3 | 96.3 | 95.9 | 94.1 | 96.3 |
| 10_42_63_599 | 92.9 | 97.1 | 92 | 91.8 | 100 | 90.1 |
| 42_63_599_609 | 88.8 | 91.4 | 88.2 | 91.8 | 100 | 90.1 |
| 42_63_583_609 | 94.4 | 91.4 | 95 | 89.8 | 100 | 87.7 |
| 37_42_63_611 | 93.9 | 91.4 | 94.4 | 94.9 | 100 | 93.8 |
| 12_63_70_599 | 90.9 | 100 | 88.9 | 89.8 | 94.1 | 88.9 |

TABLE 8-7

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 119 | 46.9 | 62.9 | 43.5 | 48 | 58.8 | 45.7 |
| 1_119 | 94.9 | 91.4 | 95.7 | 91.8 | 94.1 | 91.4 |
| 1_16_119 | 97.4 | 100 | 96.9 | 91.8 | 88.2 | 92.6 |
| 12_16_37_119 | 96.4 | 100 | 95.7 | 89.8 | 100 | 87.7 |
| 37_63_119_584 | 93.4 | 88.6 | 94.4 | 87.8 | 94.1 | 86.4 |
| 63_119_173_178 | 87.2 | 88.6 | 87 | 82.7 | 94.1 | 80.2 |
| 63_119_158_173 | 85.7 | 88.6 | 85.1 | 84.7 | 88.2 | 84 |
| 63_119_173_605 | 87.2 | 88.6 | 87 | 82.7 | 88.2 | 81.5 |

TABLE 8-8

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 126 | 66 | 71.4 | 64.8 | 53.1 | 64.7 | 50.6 |
| 1_126 | 94.4 | 94.3 | 94.4 | 91.8 | 94.1 | 91.4 |
| 1_126_597 | 96.4 | 97.1 | 96.3 | 90.8 | 88.2 | 91.4 |
| 16_126_597_599 | 90.9 | 100 | 88.9 | 81.6 | 88.2 | 80.2 |
| 16_42_126_599 | 92.9 | 94.3 | 92.6 | 92.9 | 100 | 91.4 |
| 16_126_139_601 | 93.9 | 100 | 92.6 | 91.8 | 100 | 90.1 |
| 16_126_593_599 | 89.8 | 97.1 | 88.3 | 85.7 | 94.1 | 84 |
| 15_16_126_599 | 91.4 | 97.1 | 90.1 | 81.6 | 94.1 | 79 |

TABLE 8-9

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 139 | 43.7 | 62.9 | 39.5 | 40.8 | 64.7 | 35.8 |
| 1_139 | 94.4 | 91.4 | 95.1 | 92.9 | 94.1 | 92.6 |
| 1_139_141 | 96.4 | 97.1 | 96.3 | 94.9 | 94.1 | 95.1 |
| 37_63_139_584 | 92.4 | 91.4 | 92.6 | 90.8 | 94.1 | 90.1 |
| 63_139_173_178 | 85.3 | 91.4 | 84 | 89.8 | 94.1 | 88.9 |
| 16_63_139_601 | 92.4 | 97.1 | 91.4 | 91.8 | 94.1 | 91.4 |
| 37_63_139_600 | 89.8 | 91.4 | 89.5 | 88.8 | 94.1 | 87.7 |
| 16_139_178_586 | 91.4 | 100 | 89.5 | 92.9 | 100 | 91.4 |

TABLE 8-10

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 173 | 43.7 | 51.4 | 42 | 55.1 | 58.8 | 54.3 |
| 1_173 | 94.9 | 94.3 | 95.1 | 91.8 | 94.1 | 91.4 |
| 1_15_173 | 97 | 97.1 | 96.9 | 91.8 | 94.1 | 91.4 |
| 63_139_173_599 | 84.8 | 88.6 | 84 | 89.8 | 94.1 | 88.9 |
| 63_119_173_581 | 90.3 | 91.4 | 90.1 | 89.8 | 94.1 | 88.9 |
| 63_173_582_599 | 88.3 | 91.4 | 87.7 | 84.5 | 88.2 | 83.8 |
| 63_136_173_599 | 92.4 | 94.3 | 92 | 95.9 | 94.1 | 96.3 |
| 29_63_173_178 | 87.8 | 91.4 | 87 | 88.8 | 88.2 | 88.9 |

TABLE 8-11

| SEQ ID NO: | Training cohort Accuracy (%) | Sensitivity (%) | Specificity (%) | Validation cohort Accuracy (%) | Sensitivity (%) | Specificity (%) |
|---|---|---|---|---|---|---|
| 178 | 68 | 68.6 | 67.9 | 72.4 | 82.4 | 70.4 |
| 1_178 | 94.4 | 91.4 | 95.1 | 91.8 | 94.1 | 91.4 |
| 1_15_178 | 96.4 | 97.1 | 96.3 | 94.9 | 94.1 | 95.1 |
| 16_139_178_601 | 93.4 | 100 | 92 | 90.8 | 100 | 88.9 |
| 16_37_139_178 | 93.4 | 94.3 | 93.2 | 91.8 | 94.1 | 91.4 |
| 1_12_16_178 | 96.4 | 100 | 95.7 | 93.9 | 100 | 92.6 |
| 1_63_173_178 | 94.9 | 94.3 | 95.1 | 91.8 | 94.1 | 91.4 |
| 16_139_178_597 | 93.9 | 100 | 92.6 | 89.8 | 100 | 87.7 |

TABLE 8-12

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 599 | 61.4 | 74.3 | 58.6 | 65.3 | 82.4 | 61.7 |
| 1_599 | 94.4 | 91.4 | 95.1 | 91.8 | 94.1 | 91.4 |
| 3_112_599 | 97.5 | 97.1 | 97.5 | 92.9 | 94.1 | 92.6 |
| 12_37_63_599 | 91.9 | 97.1 | 90.7 | 88.8 | 94.1 | 87.7 |
| 42_58_63_599 | 90.9 | 94.3 | 90.1 | 87.8 | 94.1 | 86.4 |
| 1_12_16_599 | 96.4 | 100 | 95.7 | 94.9 | 100 | 93.8 |
| 63_119_173_599 | 87.2 | 88.6 | 87 | 80.6 | 88.2 | 79 |
| 16_18_139_599 | 94.9 | 97.1 | 94.4 | 92.9 | 94.1 | 92.6 |

TABLE 8-13

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 609 | 59.7 | 77.1 | 55.9 | 65.3 | 82.4 | 61.7 |
| 1_609 | 95.4 | 94.3 | 95.7 | 91.8 | 94.1 | 91.4 |
| 1_10_609 | 96.4 | 94.3 | 96.9 | 91.8 | 94.1 | 91.4 |
| 42_63_585_609 | 89.8 | 91.4 | 89.4 | 91.8 | 100 | 90.1 |
| 42_63_592_609 | 88.8 | 88.6 | 88.8 | 89.8 | 100 | 87.7 |
| 18_42_581_609 | 93.4 | 94.3 | 93.2 | 90.8 | 94.1 | 90.1 |
| 12_16_599_609 | 96.4 | 100 | 95.7 | 88.8 | 100 | 86.4 |
| 16_126_599_609 | 87.2 | 97.1 | 85.1 | 84.7 | 88.2 | 84.0 |

TABLE 8-14

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 611 | 55.8 | 54.3 | 56.2 | 62.2 | 58.8 | 63 |
| 1_611 | 94.9 | 94.3 | 95.1 | 91.8 | 94.1 | 91.4 |
| 10_15_611 | 98 | 100 | 97.5 | 90.8 | 100 | 88.9 |
| 12_16_37_611 | 96.4 | 100 | 95.7 | 90.8 | 100 | 88.9 |
| 1_63_139_611 | 94.4 | 88.6 | 95.7 | 91.8 | 88.2 | 92.6 |
| 63_158_173_611 | 87.8 | 88.6 | 87.7 | 83.7 | 88.2 | 82.7 |
| 16_37_139_611 | 93.9 | 97.1 | 93.2 | 90.8 | 100 | 88.9 |
| 16_37_595_611 | 91.9 | 97.1 | 90.7 | 84.7 | 82.4 | 85.2 |

As shown in these Examples, the kit, device and the method of the present invention can detect prostate cancer more sensitively than the existing tumor markers and therefore permit early decision to carry out the surgical resection of the cancer site. As a result, improvement in 5-year survival rate and reduction in the rate of recurrence can be achieved.

INDUSTRIAL APPLICABILITY

According to the present invention, prostate cancer can be effectively detected by a simple and inexpensive method. This permits early detection, diagnosis and treatment of prostate cancer. The method of the present invention can detect prostate cancer with limited invasiveness using the blood of a patient and therefore allows prostate cancer to be detected conveniently and rapidly.

All publications, patents, and patent applications cited herein are incorporated herein by reference in their entirety.

The invention claimed is:

1. A method for detecting prostate cancer in a human subject, comprising:

measuring an expression level of hsa-miR-6741-5p in a blood, serum, or plasma sample from the subject;

comparing the measured expression level of hsa-miR-6741-5p to a control expression level in a sample from a healthy subject;

detecting a decreased level of hsa-miR-6741-5p in the sample from the subject as compared to the control expression level from the sample from the healthy subject;

wherein the decreased level of hsa-miR-6741-5p indicates that the subject has prostate cancer; and wherein the method further comprises treating the subject for the prostate cancer or performing a diagnostic procedure on the subject with the prostate cancer;

wherein the treating comprises surgery, radiotherapy, chemotherapy or the combination thereof, and wherein the diagnostic procedure comprises rectal examination, transrectal ultrasonography of the prostate, or imaging of prostate tissue.

2. The method according to claim 1, wherein the expression level of hsa-miR-6741-5p in the sample is measured by using a kit comprising a nucleic acid(s) that specifically binds to hsa-miR-6741-5p.

3. The method according to claim 2, wherein the kit further comprises at least one nucleic acid capable of specifically binding to at least one polynucleotide selected from the group consisting of other prostate cancer markers: miR-1908-5p, miR-4257, miR-3197, miR-3188, miR-4649-5p, miR-1343-3p, miR-6861-5p, miR-1343-5p, miR-642b-3p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p miR-6893-5p, and/or miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564, miR-671-5p, miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

4. The method according to claim 3, comprising performing the diagnostic procedure on the subject.

5. The method according to claim 1, wherein the expression level of hsa-miR-6741-5p in the sample is measured by using a device comprising a nucleic acid(s) that specifically binds to hsa-miR-6741-5p.

6. The method according to claim 5, wherein the device further comprises at least one nucleic acid capable of specifically binding to at least one polynucleotide selected from the group consisting of other prostate cancer markers: miR-1908-5p, miR-4257, miR-3197, miR-3188, miR-4649-5p, miR-1343-3p, miR-6861-5p, miR-1343-5p, miR-642b-3p, miR-4745-5p, miR-6826-5p, miR-3663-3p, miR-3131, miR-92a-2-5p, miR-4258, miR-4448, miR-6125, miR-6880-5p, miR-6132, miR-4467, miR-6749-5p, miR-2392, miR-1273g-3p, miR-4746-3p, miR-1914-3p, miR-7845-5p, miR-6726-5p, miR-128-2-5p, miR-4651, miR-6765-3p, miR-3185, miR-4792, miR-6887-5p, miR-5572, miR-3619-3p, miR-6780b-5p, miR-4707-5p, miR-8063, miR-4454, miR-4525, miR-7975, miR-744-5p, miR-3135b, miR-4648, miR-6816-5p, miR-4741, miR-7150, miR-6791-5p, miR-1247-3p, miR-7977, miR-4497, miR-6090, miR-6781-5p, miR-6870-5p, miR-6729-5p, miR-4530, miR-7847-3p, miR-6825-5p, miR-4674, miR-3917, miR-4707-3p, miR-6885-5p, miR-6722-3p, miR-4516, miR-6757-5p, miR-6840-3p, miR-5195-3p, miR-6756-5p, miR-6800-5p, miR-6727-5p, miR-6126, miR-6872-3p, miR-4446-3p, miR-1268a, miR-1908-3p, miR-3679-5p, miR-4534, miR-4675, miR-7108-5p, miR-6799-5p, miR-4695-5p, miR-3178, miR-5090, miR-3180, miR-1237-5p, miR-4758-5p, miR-3184-5p, miR-4286, miR-6784-5p, miR-6768-5p, miR-6785-5p, miR-4706, miR-711, miR-1260a, miR-6746-5p, miR-6089, miR-6821-5p, miR-4667-5p, miR-8069, miR-4726-5p, miR-6124, miR-4532, miR-4486, miR-4728-5p, miR-4508, miR-128-1-5p, miR-4513, miR-6795-5p, miR-4689, miR-6763-5p, miR-8072, miR-6765-5p, miR-4419b, miR-7641, miR-1227-5p, miR-4492, miR-296-3p, miR-6769a-5p, miR-6889-5p, miR-4632-5p, miR-4505, miR-3154, miR-3648, miR-4442, miR-3141, miR-7113-3p, miR-6819-5p, miR-3195, miR-1199-5p, miR-6738-5p, miR-4656, miR-6820-5p, miR-204-3p, miR-642a-3p, miR-762, miR-1202, miR-3162-5p, miR-3196, miR-3622a-5p, miR-3665, miR-3940-5p, miR-4294, miR-4466, miR-4476, miR-4723-5p, miR-4725-3p, miR-4730, miR-4739, miR-4787-5p, miR-5787, miR-6085, miR-6717-5p, miR-6724-5p, miR-6777-5p, miR-6778-5p, miR-6787-5p, miR-6789-5p, miR-6845-5p miR-6893-5p, and/or miR-615-5p, miR-486-3p, miR-1225-3p, miR-760, miR-187-5p, miR-1203, miR-7110-5p, miR-371a-5p, miR-939-5p, miR-575, miR-92b-5p, miR-887-3p, miR-920, miR-1915-5p, miR-1231, miR-663b, miR-1225-5p, miR-16-5p, miR-423-5p, miR-451a, miR-564, miR-671-5p, miR-4763-3p, miR-3656, miR-4488, miR-125a-3p, miR-1469, miR-1228-5p, miR-6798-5p, miR-1268b, miR-6732-5p, miR-1915-3p, miR-4433b-3p, miR-1207-5p, miR-4433-3p, miR-6879-5p, miR-4417, miR-30c-1-3p, miR-4638-5p, miR-6088, miR-4270, miR-6782-5p, miR-665, miR-486-5p, miR-4655-5p, miR-1275, miR-6806-5p, miR-614, miR-3937, miR-6752-5p, miR-6771-5p, miR-4450, miR-211-3p, miR-663a, miR-6842-5p, miR-7114-5p and miR-6779-5p.

* * * * *